US012006361B2

(12) United States Patent
Cini et al.

(10) Patent No.: US 12,006,361 B2
(45) Date of Patent: Jun. 11, 2024

(54) ALBUMIN BINDING DOMAIN FUSION PROTEINS

(71) Applicant: Sonnet BioTherapeutics, Inc., Princeton, NJ (US)

(72) Inventors: John K. Cini, Blairstown, NJ (US); Haomin Huang, Yardley, PA (US)

(73) Assignee: SONNET BIOTHERAPEUTICS, INC., Princeton, NJ (US)

(*) Notice: Subject to any disclaimer, the term of this patent is extended or adjusted under 35 U.S.C. 154(b) by 325 days.

(21) Appl. No.: 17/307,884

(22) Filed: May 4, 2021

(65) Prior Publication Data

US 2022/0106392 A1 Apr. 7, 2022

Related U.S. Application Data

(63) Continuation of application No. 15/932,387, filed on Feb. 20, 2018, now Pat. No. 11,028,166.

(60) Provisional application No. 62/459,975, filed on Feb. 16, 2017, provisional application No. 62/459,981, filed on Feb. 16, 2017.

(51) Int. Cl.
| | | |
|---|---|---|
| *C07K 16/24* | (2006.01) | |
| *A61K 39/00* | (2006.01) | |
| *A61K 39/395* | (2006.01) | |
| *A61P 35/00* | (2006.01) | |
| *C07K 14/715* | (2006.01) | |
| *C07K 14/76* | (2006.01) | |
| *C07K 16/18* | (2006.01) | |
| *C07K 16/22* | (2006.01) | |
| *C07K 16/28* | (2006.01) | |
| *C07K 16/46* | (2006.01) | |
| *C12N 15/00* | (2006.01) | |
| *C12N 15/10* | (2006.01) | |
| *C12N 15/13* | (2006.01) | |
| *C12N 15/62* | (2006.01) | |
| *A61K 38/00* | (2006.01) | |
| *C12N 15/63* | (2006.01) | |

(52) U.S. Cl.
CPC .... *C07K 16/244* (2013.01); *A61K 39/001138* (2018.08); *A61K 39/00114* (2018.08); *A61K 39/3955* (2013.01); *A61P 35/00* (2018.01); *C07K 14/7155* (2013.01); *C07K 16/18* (2013.01); *C07K 16/22* (2013.01); *C07K 16/2818* (2013.01); *C07K 16/468* (2013.01); *A61K 38/00* (2013.01); *A61K 2039/6081* (2013.01); *C07K 14/76* (2013.01); *C07K 2317/31* (2013.01); *C07K 2317/33* (2013.01); *C07K 2317/622* (2013.01); *C07K 2317/76* (2013.01); *C07K 2319/00* (2013.01); *C12N 15/62* (2013.01); *C12N 15/63* (2013.01); *C12N 2510/00* (2013.01); *C12N 2800/00* (2013.01)

(58) Field of Classification Search
CPC .. C07K 16/244; C07K 14/7155; C07K 14/76; C07K 16/18; C07K 2317/622; C07K 2319/00; A61K 39/00114; A61K 2039/6081; A61K 39/3955
See application file for complete search history.

(56) References Cited

U.S. PATENT DOCUMENTS

| | | | |
|---|---|---|---|
| 8,188,223 B2 | 5/2012 | Beirnaert et al. | |
| 8,679,496 B2 | 3/2014 | Coulstock et al. | |
| 8,921,528 B2 | 12/2014 | Holt et al. | |
| 9,012,609 B2 | 4/2015 | Arulanantham et al. | |
| 9,175,071 B2 | 11/2015 | De Angelis et al. | |
| 9,321,832 B2 | 4/2016 | Tomlinson et al. | |
| 9,790,475 B2 | 10/2017 | Buller et al. | |
| 9,803,004 B2 | 10/2017 | Adams et al. | |
| 9,897,077 B2 | 2/2018 | Chen et al. | |
| 2005/0238649 A1 | 10/2005 | Doronina et al. | |
| 2006/0024317 A1 | 2/2006 | Boyd et al. | |
| 2006/0074008 A1 | 4/2006 | Senter et al. | |
| 2014/0170109 A1* | 6/2014 | Wulhfard | A61K 47/6813 424/85.2 |
| 2015/0307629 A1 | 10/2015 | Bernett et al. | |
| 2016/0215063 A1 | 7/2016 | Bernett et al. | |
| 2017/0369563 A1 | 12/2017 | Dubridge et al. | |

FOREIGN PATENT DOCUMENTS

| | | |
|---|---|---|
| CN | 102875675 A | 1/2013 |
| CN | 105051069 A | 11/2015 |
| JP | 20145364978 T | 12/2014 |
| WO | WO 2004/010957 A2 | 2/2004 |
| WO | WO 2005/118642 A2 | 12/2005 |
| WO | WO 2006/005910 A2 | 1/2006 |
| WO | WO 2013/068571 A1 | 5/2013 |
| WO | WO 2014110601 A1 | 7/2014 |

OTHER PUBLICATIONS

Zoller, M J, and M Smith, Nucleic Acids Research, vol. 10, No. 20, 1982, p. 6487-6500.
Bessard et al., "High Antitumor Activity of RLI, and Interleukin-15 (IL-15)-IL-15 Receptor α Fusion Protein, in Metastatic Melanoma and Colorectal Cancer", *Molecular Cancer Therapeutics* v. 8, issue 9, p. 2736-45 (2009).
Boggio, K., et al., "Interleukin 12-Mediated Prevention of Spontaneous Mammary Adenocarcinomas in Two Lines of Her-2/neu Transgenic Mice", *J. Exper. Med.* v. 188, n. 3, p. 589-96 (1998).
Brunda, M.J., et al., "Antitumor and Antimetastatic Activity of Interleukin 12 Against Murine tumors" *J. Exper Med* v. 178, n 4, p. 1223-30 (1993).
Cavallo et al., "Immune Events Associated with the Cure of Established Tumors and Spontaneous Metastases by Local and Systemic Interleukin 12", *Cancer Res.* v. 59, issue 2, p. 414-21 (1999).

(Continued)

*Primary Examiner* — Hong Sang

(57) ABSTRACT

Compositions that include an albumin binding domain and a fusion partner (e.g., a cytokine or a binding moiety) are provided. Such therapeutics have increased serum half-life and find use in applications where one or more such therapeutics are needed, for example, in oncology applications.

5 Claims, 94 Drawing Sheets

Specification includes a Sequence Listing.

(56) References Cited

OTHER PUBLICATIONS

Coughlin et al., "Interleukin-12 and Interleukin-18 Synergistically Induce Murine Tumor Regression which Involves Inhibition of Angiogenesis" *J. Clinical Invest.* v. 101, n. 6, p. 1441-1452 (1998).

Croce et al., "Sequential Immunogene Therapy with Interleukin-12- and Interleukin-15-Engineered Neuroblastoma Cells Cures Metastatic Disease in Syngeneic Mice", *Clin Cancer Res.*, v. 11(2), p. 735-742 (2005).

Cundall, M., "Production of Single-Chain Anti-Albumin Antibodies for Use in Protein Stabilization", Natl. Library of Canada, (Jan. 1, 1998), XP055476205, http://citeseerx.ist.psu.edu/viewdoc/download?doi=10.1.1628.9353&rep=rep1&type=pdf.

Dave, E. et al., "Fab-dsFv: A bispecific antibody format with extended serum half-life through albumin binding", *MABS*, v. 8, n. 7, (Aug. 17, 2016).

Dietrich et al., "Complex Cancer Gene Therapy in Mice Melanoma" Langenbeck's Archives of Surgery, v. 387, issue 3-4, p. 177-182 (Jul. 2002).

Gao et al., "Mechanism of Action of IL-7 nd its Potential Applications and Limitations in Cancer Immunotherapy", *Int. J. Mol. Sci.* v. 16, n. 5: 10267-10280 (2015).

Gu, Xin, et al., "Molecular Modeling and Affinity Determination of scFv Antibody: Proper linker Peptide Enhances its Activity", Annals of Biomedical Engineering, Kluwer academic Publishers-Plenum Publishers, NE, v. 38, n. 2, p. 537-549 (Oct. 9, 2009).

Kilinc et al., "Reversing Tumor Immune Suppression with Intratumoral IL-12: Activation of Tumor-Associated T Effector/Memory Cells, Induction of T Suppressor Apoptosis, and Infiltration of CD8+ T Effectors", *J Immunol* 177(10):6962-6973 (2006).

Lieschke et al., "Bioactive Murine and Human Interleukin-12 Fusion Proteins which Retain Antitumor Activity in vivo" *Nature Biotechnology*, v. 15, p. 35-40 (1997).

Mlecnik, B., et al., "Functional Network Pipeline Reveals Genetic Determinants Associated with in Situ Lymphocyte Proliferation and Survival of Cancer Patents", *Sci Transl Med.*,v. 6, n. 228, p. 228ra37 (2014).

Muraoka, J. "Selection and Characterization of Human Serum Albumin-Specific Porcine scFv Antibodies Using a Phage Display Library", Monoclonal Antibodies in *Immunodiagnosis and Immunotherapy*, v. 33, n. 1, p. 42-48 (Feb. 1, 2014).

Nastala et al., "Recombinant IL-12 Administration Induces Tumor Regression in Association with IFN-Gamma Production", *J Immunol.*, v. 153, n. 4, p. 1697-1706 (1994).

Rubinstein et al., "Converting IL-15 to a Superagaonist by Binding to Soluble IL-15Rα", *Proc Natl Acad Sci U.S.A.*, v.103, n. 24, p. 9166-71 (2006).

Subleski et al., "Enhanced Antitumor Response by Divergent Modulation of Natural Killer and Natural Killer T Cells in the Liver", Cancer Res v. 66, n. 22, p. 11005-11012 (2006).

Thyrell, L. et al., "Mechanisms of Interferon-Alpha Induced Apoptosis in Malignant Cells" *Oncogene*, v. 21, p. 1251-1262 (2002).

Weiner, G.J., "Building Better Monoclonal Antibody-Based Therapeutics", *Nat Rev Cancer*, v. 15(6): 361-370 (2015).

Wu, J., "IL-15 Agonists: The Cancer Cure Cytokine", *J. Mol Genet Med*, v. 7(4), 85 (2013).

Yu, W-G, et al., "Molecular Mechanisms Underlying IFN-γ-Mediated Tumor Growth Inhibition Induced during Tumor Immunotherapy with rIL-12", *Inter. Immunol*, v. 8, n. 6, p. 855-865 (1996).

Yusakul, Gorawit et al., "Effect of Linker Length Between Variable Domains of Single Chain Variable Fragment Antibody Against Daidzin on its Reactivity", Bioscience Biotechnology Biochemistry, v. 80, n. 7 p. 1306-1312 (Jul. 2, 2016).

Zhu, X. et al., "Novel Human Interleukin-15 Agonists", *Journal of Immunology* 183:3598-6007 (2009).

\* cited by examiner

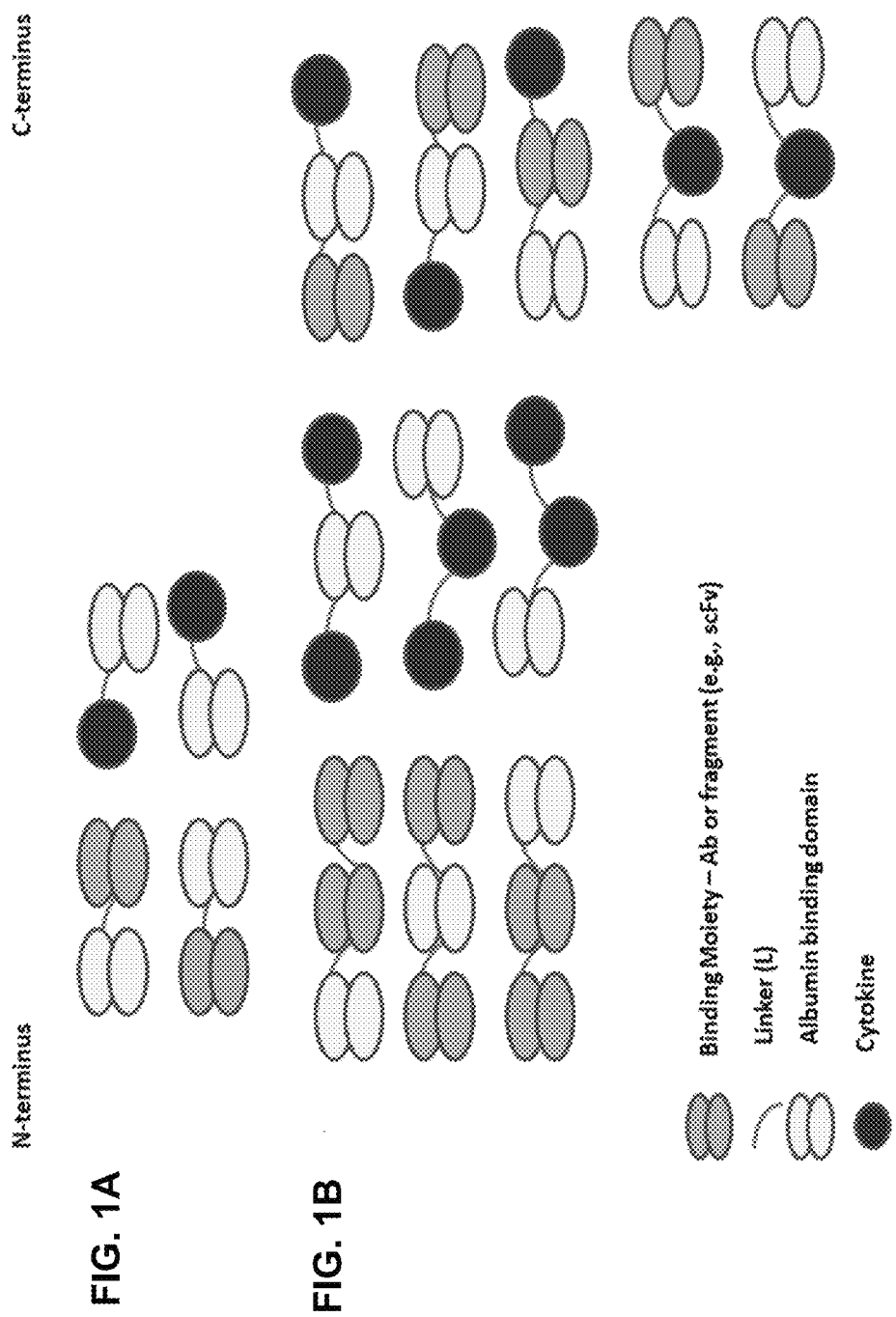

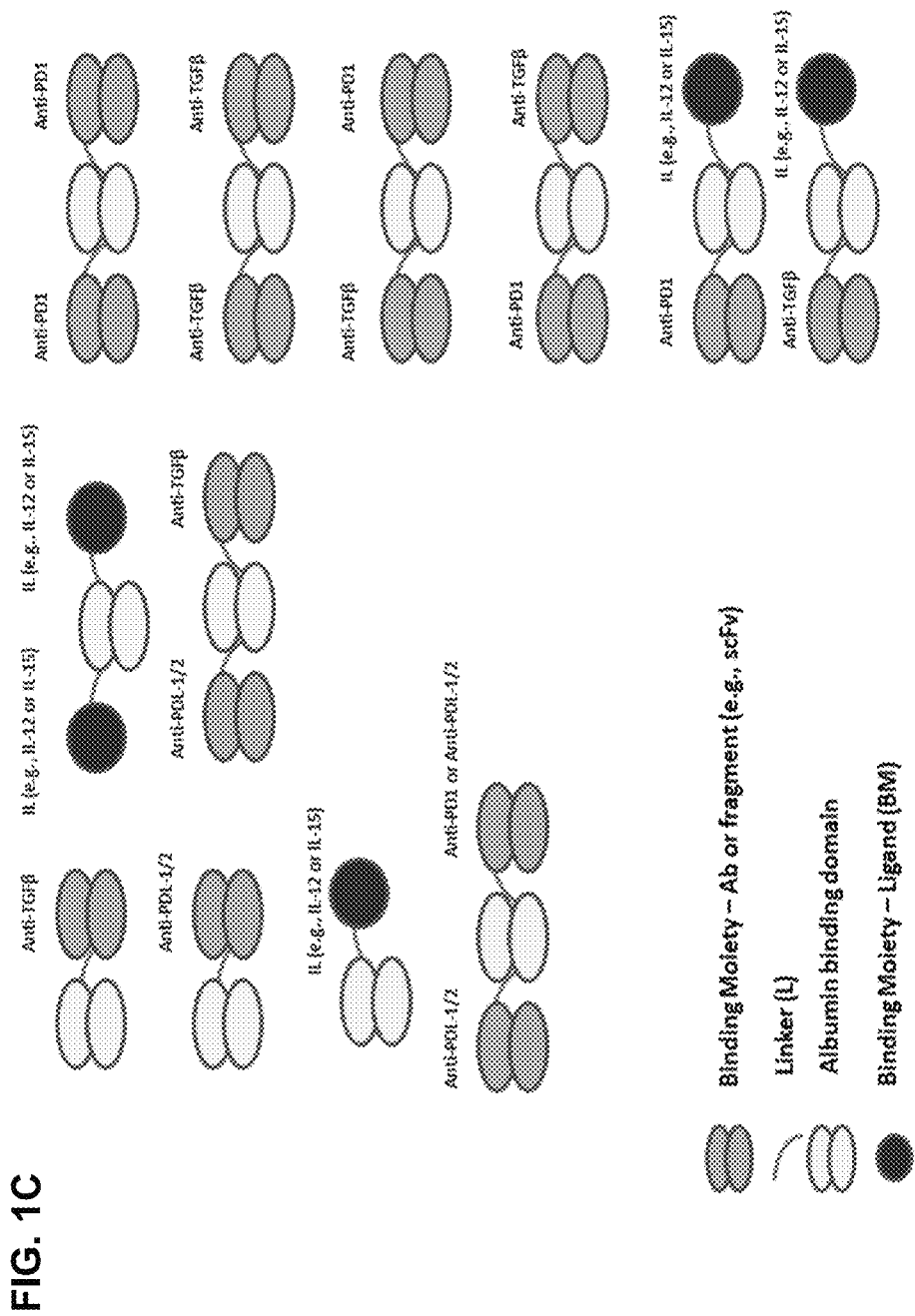

| | Sequence | SEQ ID NO: |
|---|---|---|
| Variable heavy (vh) chain | EVQLVESGGGLIQPGRSLRLSCAASGITFDDYVMHWVRQAPGKGLEWVAGI SSNSGYIGYADSVRGRFTISRDNAKNSLFLQMNRLRPEDTALYYCVKGLYSNP RGGAFDIWGQGTMVTVSS | 1 |
| vhCDR1 | GITFDDYV | 2 |
| vhCDR2 | ISSNSGYI | 3 |
| vhCDR3 | VKGLYSNPRGGAFDI | 4 |
| Variable light (vl) chain | SYVLTQPPSVSVAPGQTATITCGGNNIGTKSVHWYQQKPGQAPVLVVYADS DRPSGIPERVSGSNSGNTATLTISRVEAGDEADYYCQVWDSRSDHLWVFGG GTKLTVLG | 5 |
| vlCDR1 | NIGTKS | 6 |
| vlCDR2 | ADS | 7 |
| vlCDR3 | QVWDSRSDHLWV | 8 |

| | Sequence | SEQ ID NO: |
|---|---|---|
| Variable heavy (vh) chain | EVQLVESGGGLIQPGRSLRLSCAASGITFDDHVMHWVRQAPGKGLEWVAG ISSNSGYIGYADSVKGRFTISRDNAKNSLYLQMNRLRAEDTAVYYCVKGLYSN PRGGAFDIWGQGTMVTVSS | 9 |
| vhCDR1 | GITFDDHV | 10 |
| vhCDR2 | ISSNSGYI | 11 |
| vhCDR3 | VKGLYSNPRGGAFDI | 12 |
| Variable light (vl) chain | SYVLTQPPSVSVAPGQTATITCGGNNIGTKSVHWYQQKPGQAPVLVVYADS DRPSGIPERVSGSNSGNTATLTISRVEAGDEADYYCQVWDSRSDHLWVFGG GTKLTVLG | 13 |
| vlCDR1 | NIGTKS | 14 |
| vlCDR2 | ADS | 15 |
| vlCDR3 | QVWDSRSDHLWV | 16 |

| | Sequence | SEQ ID NO: |
|---|---|---|
| Variable heavy (vh) chain | EVQLVESGGGLIQPGRSLRLSCAASGITFDDYAMHWVRQAPGKGLEWVAGI SSNSGYIGYADSVKGRFTISRDNAKNSLYLQMNRLRAEDTAVYYCVKGLYSN PRGGAFDIWGQGTMVTVSS | 17 |
| vhCDR1 | GITFDDYA | 18 |
| vhCDR2 | ISSNSGYI | 19 |
| vhCDR3 | VKGLYSNPRGGAFDI | 20 |
| Variable light (vl) chain | SYVLTQPPSVSVAPGQTATITCGGNNIGTKSVHWYQQKPGQAPVLVVYADS DRPSGIPERVSGSNSGNTATLTISRVEAGDEADYYCQVWDSRSDHLWVFGG GTKLTVLG | 21 |
| vlCDR1 | NIGTKS | 22 |
| vlCDR2 | ADS | 23 |
| vlCDR3 | QVWDSRSDHLWV | 24 |

| | Sequence | SEQ ID NO: |
|---|---|---|
| Variable heavy (vh) chain | EVQLVESGGGLIQPGRSLRLSCAASGITFDDAVMHWVRQAPGKGLEWVAG ISSNSGYIGYADSVKGRFTISRDNAKNSLYLQMNRLRAEDTAVYYCVKGLYSN PRGGAFDIWGQGTMVTVSS | 25 |
| vhCDR1 | GITFDDAV | 26 |
| vhCDR2 | ISSNSGYI | 27 |
| vhCDR3 | VKGLYSNPRGGAFDI | 28 |
| Variable light (vl) chain | SYVLTQPPSVSVAPGQTATITCGGNNIGTKSVHWYQQKPGQAPVLVVYADS DRPSGIPERVSGSNSGNTATLTISRVEAGDEADYYCQVWDSRSDHLWVFGG GTKLTVLG | 29 |
| vlCDR1 | NIGTKS | 30 |
| vlCDR2 | ADS | 31 |
| vlCDR3 | QVWDSRSDHLWV | 32 |

| | Sequence | SEQ ID NO: |
|---|---|---|
| Variable heavy (vh) chain | EVQLVQSGAEVKKPGESLKISCKGSGYSFNSYWIGWVRQMPGKGLEWMAII YPGDSDTRYSPSFQGQVTFSVDKSINTAYLVWTSLKASDTAIYYCARQRWGS SSFDLWGQGTLVTVSS | 33 |
| vhCDR1 | GYSFNSYW | 34 |
| vhCDR2 | IYPGDSDT | 35 |
| vhCDR3 | ARQRWGSSSFDL | 36 |
| Variable light (vl) chain | QSVLTQPPSVSAAPGQKVTISCSGSSSNIGNNYVSWYQQLPGTAPKLLIYEN NKRPSGIPDRFSGSKSGTSATLGITGLQTGDEADYYCGTWDSSLSAGVFGGG TQLTVLG | 37 |
| vlCDR1 | SSNIGNNY | 38 |
| vlCDR2 | ENN | 39 |
| vlCDR3 | GTWDSSLSAGV | 40 |

| | Sequence | SEQ ID NO: |
|---|---|---|
| Variable heavy (vh) chain | EVQLVQSGAEVKKPGESLKISCKGSGYSFNSYWIGWVRQMPGKGLEWMGII YPGDSDTRYSPSFQGQVTFSVDKSINTAYLQWSSLKASDAAMYYCARQRW GSSSFDAWGQGTLVTVSS | 41 |
| vhCDR1 | GYSFNSYW | 42 |
| vhCDR2 | IYPGDSDT | 43 |
| vhCDR3 | ARQRWGSSSFDA | 44 |
| Variable light (vl) chain | QSVLTQPPSVSAAPGQKVTISCSGSSSNIGNNYVSWYQQLPGTAPKLLIYEN NKRPSGIPDRFSGSKSGTSATLGITGLQTGDEADYYCGTWDSSLSAGVFGGG TQLTVLG | 45 |
| vlCDR1 | SSNIGNNY | 46 |
| vlCDR2 | ENN | 47 |
| vlCDR3 | GTWDSSLSAGV | 48 |

| | Sequence | SEQ ID NO: |
|---|---|---|
| Variable heavy (vh) chain | EVQLVQSGAEVKKPGESLKISCKGSGYSFTSYWIGWVRQMPGKGLEWMGII YPGDSDTRYSPSPSFEGQVTISADKSISTAYLQWSSLKASDTAMYYCARLHGVVS RGDYWGQGTLVTVSS | 49 |
| vhCDR1 | GYSFTSYW | 50 |
| vhCDR2 | IYPGDSDT | 51 |
| vhCDR3 | ARLHGVVSRGDY | 52 |
| Variable light (vl) chain | QSALTQPASVSGSPGQSITISCSGGISSLAGSYNLVSWYQQYPGKAPKLIIYEVT KRPSGVSNRFSGSKSGNTASLTISGLQADDEAEYSCSSYAGRNAVAVFGGGT QLTVLG | 53 |
| vlCDR1 | SSLAGSYNL | 54 |
| vlCDR2 | EVT | 55 |
| vlCDR3 | SSYAGRNAVAV | 56 |

| | Sequence | SEQ ID NO: |
|---|---|---|
| Variable heavy (vh) chain | EVQLVQSGAEVKKPGESLKISCKGSGYSFTSYWIGWVRQMPGKGLEWMGII YPGDSDTRYSPSFEGQVTISADKSISTAYLQWSSLKASDTAAYYCARLHGVVS RGDYWGQGTLVTVSS | 57 |
| vhCDR1 | GYSFTSYW | 58 |
| vhCDR2 | IYPGDSDT | 59 |
| vhCDR3 | ARLHGVVSRGDY | 60 |
| Variable light (vl) chain | QSALTQPASVSGSPGQSITISCSGISSLAGSYNLVSWYQQYPGKAPKLIIYEVT KRPSGVSNRFSGSKSGNTASLTISGLQADDEAEYSCSSYAGRNAVAVFGGGT QLTVLG | 61 |
| vlCDR1 | SSLAGSYNL | 62 |
| vlCDR2 | EVT | 63 |
| vlCDR3 | SSYAGRNAVAV | 64 |

| | Sequence | SEQ ID NO: |
|---|---|---|
| Variable heavy (vh) chain | EVQLVETGGGVVRPGGSLRLSCAASGFTFSSYAMSWVRQAPGKGLEWVSAI SGSGGSTYYADSVKGRFTISRDNSKNTLSLQMNSLRAEDTAVYYCAKSSGWY PYYYGMDVWGQGTTVTVSS | 65 |
| vhCDR1 | GFTFSSYA | 66 |
| vhCDR2 | ISGSGGST | 67 |
| vhCDR3 | AKSSGWYPYYYGMDV | 68 |
| Variable light (vl) chain | SYELMQPPSVSVSPGQTARITCSGNNLGDKYTSWYQHKPGQSPVMVIYQD TKRPSGIAERFSGSNSGNTATLTISGTQALDEADYYCQAWDTGTAVFGGGT QLTVLG | 69 |
| vlCDR1 | NLGDKY | 70 |
| vlCDR2 | QDT | 71 |
| vlCDR3 | QAWDTGTAV | 72 |

| | Sequence | SEQ ID NO: |
|---|---|---|
| Variable heavy (vh) chain | EVQLVETGGGVVRPGGSLRLSCAASGFTFSSYAMSWVRQAPGKGLEWVSAI SGSGGSTYYADSVKGRFTISRDNSKNTLSLQMNSLRAEDTAAYYCAKSSGWY PYYYGMDVWGQGTTVTVSS | 73 |
| vhCDR1 | GFTFSSYA | 74 |
| vhCDR2 | ISGSGGST | 75 |
| vhCDR3 | AKSSGWYPYYYGMDV | 76 |
| Variable light (vl) chain | SYELMQPPSVSVSPGQTARITCSGNNLGDKYTSWYQHKPGQSPVMVIYQD TKRPSGIAERFSGSNSGNTATLTISGTQALDEADYYCQAWDTGTAVFGGGT QLTVLG | 77 |
| vlCDR1 | NLGDKY | 78 |
| vlCDR2 | QDT | 79 |
| vlCDR3 | QAWDTGTAV | 80 |

| | Sequence | SEQ ID NO: |
|---|---|---|
| Variable heavy (vh) chain | EVQLVQSGAEVKKPGESLKISCQAFGYNFNNYWIGWVRQMPGKGLEWMG IIYPGDSDTRYSPSFQGQVTISADKSISTAYLQWSSLKASDTAMYYCARRSTVT KSFDIWGQGTMVTVSS | 81 |
| vhCDR1 | GYNFNNYW | 82 |
| vhCDR2 | IYPGDSDT | 83 |
| vhCDR3 | ARRSTVTKSFDI | 84 |
| Variable light (vl) chain | QAGLTQPPSVSKGLRQTATLTCTGNSNNVGKQGAAWLQQHQGHPPKLLSY SSINRPVGISERFSASRSGNTASLTITGLQPEDEADYYCSAWDSSLSAWVFGG GTKLTVLG | 85 |
| vlCDR1 | SNNVGKQG | 86 |
| vlCDR2 | SSI | 87 |
| vlCDR3 | SAWDSSLSAWV | 88 |

| | Sequence | SEQ ID NO: |
|---|---|---|
| Variable heavy (vh) chain | QVQLQESGPGLVKPSETLSLTCTVSGGSISSSSYYWGWIRQPPGKGLEWIGSIYYSGSTYYNPSLKSRVTISVDTSKNQFSLKLSSVTAADTAVYYCARRSAWSSGWSTLRYYYYGMDVWGQGTTVTVSS | 89 |
| vhCDR1 | GGSISSSSYY | 90 |
| vhCDR2 | IYYSGST | 91 |
| vhCDR3 | ARRSAWSSGWSTLRYYYYGMDV | 92 |
| Variable light (vl) chain | EIVLTQSPATLSLSPGERATLSCRASQSIATYLAWYQQNPGQAPRLLIYDASTRATGIPARFSGSGSGTDFTLTISSLEPEDFAVYYCQERSNWSRLTFGGGTKVEIKR | 93 |
| vlCDR1 | QSIATY | 94 |
| vlCDR2 | DAS | 95 |
| vlCDR3 | QERSNWSRLT | 96 |

| | Sequence | SEQ ID NO: |
|---|---|---|
| Variable heavy (vh) chain | EVQLVQSGAEVKKPGESLKISCKGSGYSFTNYWIGWVRQVPGRGLEWLAIIYPGDSDTRYSPSFEGQVTISADKSISTAYLQWSSLKASDTAMYYCARLHGVVSRGDYWGQGTLVTVSS | 97 |
| vhCDR1 | GYSFTNYW | 98 |
| vhCDR2 | IYPGDSDT | 99 |
| vhCDR3 | ARLHGVVSRGDY | 100 |
| Variable light (vl) chain | QSALTQPASVSGSPGQSITISCSGGISSLAGSYNLVSWYQQYPGKAPKLIIYEVTKRPSGVSNRFSGSKSGNTASLTISGLQADDEAEYCSSYAGRNAVAVFGGGTQLTVLG | 101 |
| vlCDR1 | SSLAGSYNL | 102 |
| vlCDR2 | EVT | 103 |
| vlCDR3 | SSYAGRNAVAV | 104 |

| | Sequence | SEQ ID NO: |
|---|---|---|
| Variable heavy (vh) chain | EVQLVQSGAEVKKPGESLKISCKGSGYSFTNYWIGWVRQMPGEGLEWMGII YPGDSDTRYSPSPSFEGQVTISADKSISTAYLQWSSLKASDTAMYYCARLHGVVS RGDYWGQGTLVTVSS | 105 |
| vhCDR1 | GYSFTNYW | 106 |
| vhCDR2 | IYPGDSDT | 107 |
| vhCDR3 | ARLHGVVSRGDY | 108 |
| Variable light (vl) chain | QSALTQPASVSGSPGQSITISCSGISSLAGSYNLVSWYQQYPGKAPKLIIYEVT KRPSGVSNRFSGSKSGNTASLTISGLQADDEAEYSCSSYAGRNAVAVFGGGT QLTVLG | 109 |
| vlCDR1 | SSLAGSYNL | 110 |
| vlCDR2 | EVT | 111 |
| vlCDR3 | SSYAGRNAVAV | 112 |

| | Sequence | SEQ ID NO: |
|---|---|---|
| Variable heavy (vh) chain | EVQLVQSGAEVKKPGESLKISCKGSGYSFTNYWIGWVRQMPGEGLEWMGII YPGDSDTRYSPSPSFEGQVTISADKSISTAYLQWNSLKASDTAMYYCARLHGVV SRGDYWGQGTLVTVSS | 113 |
| vhCDR1 | GYSFTNYW | 114 |
| vhCDR2 | IYPGDSDT | 115 |
| vhCDR3 | ARLHGVVSRGDY | 116 |
| Variable light (vl) chain | QSALTQPASVSGSPGQSITISCSGISSLAGSYNLVSWYQQYPGKAPKLIIYEVT KRPSGVSNRFSGSKSGNTASLTISGLQADDEAEYSCSSYAGRNAVAVFGGGT QLTVLG | 117 |
| vlCDR1 | SSLAGSYNL | 118 |
| vlCDR2 | EVT | 119 |
| vlCDR3 | SSYAGRNAVAV | 120 |

| | Sequence | SEQ ID NO: |
|---|---|---|
| Variable heavy (vh) chain | EVQLVETGGGVVQPGGSLRLSCAASGFTFSNYAMSWVRQAPGKGLEWVS GISGSSNSIYYADSVKGRFTIARDNAKNTLFLQVNSLRAEDTAVYYCARHHGR LYYYYGMDVWGQGTTVTVSS | 121 |
| vhCDR1 | GFTFSNYA | 122 |
| vhCDR2 | ISGSSNSI | 123 |
| vhCDR3 | ARHHGRLYYYYGMDV | 124 |
| Variable light (vl) chain | SYELTQPPSVSVSPGQTASITCSGDKLGEKYASWYQQKPGQSPVMVIYQDR KRPSGIPERFSGSNSGNTATLTISGTQAMDEADYYCQAWDTTTPGFGGGTK VTVLG | 125 |
| vlCDR1 | KLGEKY | 126 |
| vlCDR2 | QDR | 127 |
| vlCDR3 | QAWDTTTPG | 128 |

| | Sequence | SEQ ID NO: |
|---|---|---|
| Variable heavy (vh) chain | EVQLVESGGGLIQPGRSLRLSCAASGITFDDYVMHWVRQAPGKGLEWVAGI SSNSGYIGYADSVRGRFTISRDNAKNTLFLQVNRLRPEDTAVYYCARHHGRLY YYGMDVWGQGTTVTVSS | 129 |
| vhCDR1 | GITFDDYV | 130 |
| vhCDR2 | ISSNSGYI | 131 |
| vhCDR3 | ARHHGRLYYYGMDV | 132 |
| Variable light (vl) chain | SYELTQPPSVSVSPGQTASITCSGDKLGEKYASWYQQKPGQSPVMVIYQDR KRPSGIPERFSGSNSGNTATLTISGTQAMDEADYYCQAWDTTTPGFGGGTK VTVLG | 133 |
| vlCDR1 | KLGEKY | 134 |
| vlCDR2 | QDR | 135 |
| vlCDR3 | QAWDTTTPG | 136 |

| | Sequence | SEQ ID NO: |
|---|---|---|
| Variable heavy (vh) chain | EVQLVQSGAEVKKPGESLKISCKGSGYSFSSYWIGWVRQMPGKGLEWMGII YPGDSDTRYSPSPSFEGQVTISADKSISTAYLQWSSLKASDTAMYYCARLHGVVS RGDYWGQGTLVTVSS | 137 |
| vhCDR1 | GYSFSSYW | 138 |
| vhCDR2 | IYPGDSDT | 139 |
| vhCDR3 | ARLHGVVSRGDY | 140 |
| Variable light (vl) chain | QSALTQPASVSGSPGQSITISCSGISSLAGSYNLVSWYQQYPGKAPKLIIYEVT KRPSGVSNRFSGSKSGNTASLTISGLQADDEAEYSCSSYAGRNAVAVFGGGT QLTVLG | 141 |
| vlCDR1 | SSLAGSYNL | 142 |
| vlCDR2 | EVT | 143 |
| vlCDR3 | SSYAGRNAVAV | 144 |

| | Sequence | SEQ ID NO: |
|---|---|---|
| Variable heavy (vh) chain | EVQLVQSGAEVKKPGESLKISCKGSGYNFNSYWIAWVRQMPGKGLEWMGI IYPGDSDTRYGPPFKGQATISADKSINTAYLQWSSLRPSDTAIYYCARLVGEG RSIQYWGQGTLVTVSS | 145 |
| vhCDR1 | GYNFNSYW | 146 |
| vhCDR2 | IYPGDSDT | 147 |
| vhCDR3 | ARLVGEGRSIQY | 148 |
| Variable light (vl) chain | QPVLTQPPSASASLGASVTLTCTLTSGYRNYKVDWYQQRPGKGPRFVMRVG TGGIVGSKGDGIPDRFSALGSGLNRYLTIKDIQEEDESDYYCGADYGSGSNFL VVFGGGTKLTVLG | 149 |
| vlCDR1 | SGYRNYK | 150 |
| vlCDR2 | VGTGGIVG | 151 |
| vlCDR3 | GADYGSGSNFLVV | 152 |

| | Sequence | SEQ ID NO: |
|---|---|---|
| Variable heavy (vh) chain | EVQLVQSGAEVKKPGESLKISCKASGYDFTRYWIVWVRQMPGKGLEYMGII YPGDSDTRYGPPFKGQATISADKSINTAYLQWSSLRPSDTAIYYCARLVGEGR SIQYWGQGTLVTVSS | 153 |
| vhCDR1 | GYDFTRYW | 154 |
| vhCDR2 | IYPGDSDT | 155 |
| vhCDR3 | ARLVGEGRSIQY | 156 |
| Variable light (vl) chain | QPVLTQPPSASASLGASVTLTCTLTSGYRNYKVDWYQQRPGKGPRFVMRVG TGGIVGSKGDGIPDRFSALGSGLNRYLTIKDIQEEDESDYYCGADYGSGSNFL VVFGGGTKVTVLG | 157 |
| vlCDR1 | SGYRNYK | 158 |
| vlCDR2 | VGTGGIVG | 159 |
| vlCDR3 | GADYGSGSNFLVV | 160 |

| | Sequence | SEQ ID NO: |
|---|---|---|
| Variable heavy (vh) chain | EVQLVQSGAEVKKPGESLKISCKGSGYSFTRSWIAWVRQMPGKGLEWMGII YPGDSDTRYSPSPSFEGQVTISADKSISTAYLQWSSLKASDTAMYYCARLHGVVS RGDYWGQGTLVTVSS | 161 |
| vhCDR1 | GYSFTRSW | 162 |
| vhCDR2 | IYPGDSDT | 163 |
| vhCDR3 | ARLHGVVSRGDY | 164 |
| Variable light (vl) chain | QSALTQPASVSGSPGQSITISCSGISSLAGSYNLVSWYQQYPGKAPKLIIYEVT KRPSGVSNRFSGSKSGNTASLTISGLQADDEAEYSCSSYAGRNAVAVFGGGT QLTVLG | 165 |
| vlCDR1 | SSLAGSYNL | 166 |
| vlCDR2 | EVT | 167 |
| vlCDR3 | SSYAGRNAVAV | 168 |

| | Sequence | SEQ ID NO: |
|---|---|---|
| Variable heavy (vh) chain | EVQLVQSGAEVKKPGESPKISCKGSGYSFTNYWIGWVRQMPGEGLEWMGI IYPGDSDTRYSPSFEGQVTISADKSISTAYLQWSSLKASDTAMYYCARLHGVV SRGDYWGQGTLVTVSS | 169 |
| vhCDR1 | GYSFTNYW | 170 |
| vhCDR2 | IYPGDSDT | 171 |
| vhCDR3 | ARLHGVVSRGDY | 172 |
| Variable light (vl) chain | QSALTQPASVSGSPGQSITISCSGISSLAGSYNLVSWYQQYPGKAPKLIIYEVT KRPSGVSNRFSGSKSGNTASLTISGLQADDEAEYSCSSYAGRNAVAVFGGGT QLTVLG | 173 |
| vlCDR1 | SSLAGSYNL | 174 |
| vlCDR2 | EVT | 175 |
| vlCDR3 | SSYAGRNAVAV | 176 |

| | Sequence | SEQ ID NO: |
|---|---|---|
| Variable heavy (vh) chain | EVQLVETGGGVVRPGRSLRLSCAASGFTFDDYAMHWVRQAPGKGLEWVS AISGSGGSTYYADSVKGRFTISRDNSKNTLSLQMNSLRAEDTAVYYCAKSSG WYPYYYGMDVWGQGTTVTVSS | 177 |
| vhCDR1 | GFTFDDYA | 178 |
| vhCDR2 | ISGSGGST | 179 |
| vhCDR3 | AKSSGWYPYYYGMDV | 180 |
| Variable light (vl) chain | SYELMQPPSVSVSPGQTARITCSGNNLGDKYTSWYQHKPGQSPVMVIYQD TKRPSGIAERFSGSNSGNTATLTISGTQALDEADYYCQAWDTGTAVFGGGT QLTVLG | 181 |
| vlCDR1 | NLGDKY | 182 |
| vlCDR2 | QDT | 183 |
| vlCDR3 | QAWDTGTAV | 184 |

| | Sequence | SEQ ID NO: |
|---|---|---|
| Variable heavy (vh) chain | EVQLVETGGGVVQPGGSLRLSCAASGFTFSNYAMSWVRQAPGKGLEWVS GISGSSGSIGYADSVKGRFTIARDNAKNTLFLQVNSLRAEDTALYYCARHHGR LYYYYGMDVWGQGTTVTVSS | 185 |
| vhCDR1 | GFTFSNYA | 186 |
| vhCDR2 | ISGSSGSI | 187 |
| vhCDR3 | ARHHGRLYYYYGMDV | 188 |
| Variable light (vl) chain | SYELTQDPAVSVALGQTVRITCQGDSLRSYYASWYQQKPGQAPVLVIYGKN NRPSGIPDRFSGSSSGNTASLTITGAQAEDEADYYCNSRDSSGTVVFGGGTKL TVLG | 189 |
| vlCDR1 | SLRSYY | 190 |
| vlCDR2 | GKN | 191 |
| vlCDR3 | NSRDSSGTVV | 192 |

| | Sequence | SEQ ID NO: |
|---|---|---|
| Variable heavy (vh) chain | EVQLVETGGGVVRPGGSLRLSCAASGFTFSSYAMSWVRQAPGKGLEWVSAISGSGGSTYYADSVKGRFTISRDNSKNTLSLQMNSLRAEDTAVYYCAKSSGWYPYYYGMDVWGQGTTVTVSS | 193 |
| vhCDR1 | GYSFTSYW | 194 |
| vhCDR2 | IYPGDSDT | 195 |
| vhCDR3 | VKGLYSNPRGGAFDI | 196 |
| Variable light (vl) chain | SYELMQPPSVSVSPGQTARITCSGNNLGDKYTSWYQHKPGQSPVMVIYQDTKRPSGIAERFSGSNSGNTATLTISGTQALDEADYYCQAWDTGTAVFGGGTQLTVLGLGG | 197 |
| vlCDR1 | NLGDKY | 198 |
| vlCDR2 | QDT | 199 |
| vlCDR3 | QAWDTGTAV | 200 |

FIG. 2Z

A10m3 amino acid sequence
EVQLVESGGGLIQPGRSLRLSCAASG<u>ITFDDAVMH</u>WVRQAPGKGLEWVA<u>GISSN</u><u>S</u>
<u>GYIGYADSVKG</u>RFTISRDNAKNSLYLQMNRLRAEDTAVYYC<u>VKGLYSNPRGGAFD</u>
<u>I</u>WGQGTMVTVSSASTGGGGSGGGGSGGGGSVHSSYVLTQPPSVSVAPGQTATITC
<u>GGNNIGTKSVH</u>WYQQKPGQAPVLVVY<u>ADSDRPS</u>GIPERVSGSNSGNTATLTISRV
EAGDEADYYC<u>QVWDSRSDHLWV</u>FGGGTKLTVLG (SEQ ID NO: 201)

Variable heavy chain
EVQLVESGGGLIQPGRSLRLSCAASG<u>ITFDDAVMH</u>WVRQAPGKGLEWVA<u>GISSN</u><u>S</u>
<u>GYIGYADSVKG</u>RFTISRDNAKNSLYLQMNRLRAEDTAVYYC<u>VKGLYSNPRGGAFD</u>
<u>I</u>WGQGTMVTVSSAST (SEQ ID NO: 202)

Variable light chain
VHSSYVLTQPPSVSVAPGQTATITC<u>GGNNIGTKSVH</u>WYQQKPGQAPVLVVY<u>ADSD</u>
<u>RPS</u>GIPERVSGSNSGNTATLTISRVEAGDEADYYC<u>QVWDSRSDHLWV</u>FGGGTKLT
VLG (SEQ ID NO: 203)

FIG. 3
Variant IL-15

Parental IL15
NWVNVISDLKKIEDLIQSMHIDATLYTESDVHPSCKVTAMKCFLLELQVISLESGDASIHDTVENLIILANNSLSSNGNVTESGCKECEELEE
KNIKEFLQSFVHIVQMFINTS (SEQ ID NO: 204)

IL15 K86A
NWVNVISDLKKIEDLIQSMHIDATLYTESDVHPSCKVTAMKCFLLELQVISLESGDASIHDTVENLIILANNSLSSNGNVTESGCAECEELEE
KNIKEFLQSFVHIVQMFINTS (SEQ ID NO: 205)

IL15 K86R
NWVNVISDLKKIEDLIQSMHIDATLYTESDVHPSCKVTAMKCFLLELQVISLESGDASIHDTVENLIILANNSLSSNGNVTESGCRECEELEE
KNIKEFLQSFVHIVQMFINTS (SEQ ID NO: 206)

IL15 N112A
NWVNVISDLKKIEDLIQSMHIDATLYTESDVHPSCKVTAMKCFLLELQVISLESGDASIHDTVENLIILANNSLSSNGNVTESGCKECEELEE
KNIKEFLQSFVHIVQMFIATS (SEQ ID NO: 207)

IL15 N112S
NWVNVISDLKKIEDLIQSMHIDATLYTESDVHPSCKVTAMKCFLLELQVISLESGDASIHDTVENLIILANNSLSSNGNVTESGCKECEELEE
KNIKEFLQSFVHIVQMFISTS (SEQ ID NO: 208)

IL15 N112Q
NWVNVISDLKKIEDLIQSMHIDATLYTESDVHPSCKVTAMKCFLLELQVISLESGDASIHDTVENLIILANNSLSSNGNVTESGCKECEELEE
KNIKEFLQSFVHIVQMFIQTS (SEQ ID NO: 209)

IL15 K86R/N112A
NWVNVISDLKKIEDLIQSMHIDATLYTESDVHPSCKVTAMKCFLLELQVISLESGDASIHDTVENLIILANNSLSSNGNVTESGCRECEELEE
KNIKEFLQSFVHIVQMFIATS (SEQ ID NO: 210)

FIG. 4

Parental IL15–A10m3
NWVNVISDLKKIEDLIQSMHIDATLYTESDVHPSCKVTAMKCFLLELQVISLESGDASIHDTVENLIILANNSLSSNGNVTESGCKECEEL
EEKNIKEFLQSFVHIVQMFINTSGGGGSGGGGSGGGGSGGGGSEVQLVESGGGLIQPGRSLRLSCAASGITFDDAVMHWVRQA
PGKGLEWVAGISSNSGYIGYADSVKGRFTISRDNAKNSLYLQMNRLRAEDTAVYYCVKGLYSNPRGGAFDIWGQGTMVTVSSASTGG
GGSGGGGSGGGGSVHSSYVLTQPPSVSVAPGQTATITCGGNNIGTKSVHWYQQKPGQAPVLVVYADSDRPSGIPERVSGSNSGNTATL
TISRVEAGDEADYYCQVWDSRSDHLWVFGGGTKLTVLG (SEQ ID NO: 211)

IL15 K86A–A10M3 K86A
NWVNVISDLKKIEDLIQSMHIDATLYTESDVHPSCKVTAMKCFLLELQVISLESGDASIHDTVENLIILANNSLSSNGNVTESGCAECEEL
EEKNIKEFLQSFVHIVQMFINTSGGGGSGGGGSGGGGSGGGGSEVQLVESGGGLIQPGRSLRLSCAASGITFDDAVMHWVRQA
PGKGLEWVAGISSNSGYIGYADSVKGRFTISRDNAKNSLYLQMNRLRAEDTAVYYCVKGLYSNPRGGAFDIWGQGTMVTVSSASTGG
GGSGGGGSGGGGSVHSSYVLTQPPSVSVAPGQTATITCGGNNIGTKSVHWYQQKPGQAPVLVVYADSDRPSGIPERVSGSNSGNTATL
TISRVEAGDEADYYCQVWDSRSDHLWVFGGGTKLTVLG (SEQ ID NO: 212)

IL15 K86R–A10M3
NWVNVISDLKKIEDLIQSMHIDATLYTESDVHPSCKVTAMKCFLLELQVISLESGDASIHDTVENLIILANNSLSSNGNVTESGCRECEEL
EEKNIKEFLQSFVHIVQMFINTSGGGGSGGGGSGGGGSGGGGSEVQLVESGGGLIQPGRSLRLSCAASGITFDDAVMHWVRQA
PGKGLEWVAGISSNSGYIGYADSVKGRFTISRDNAKNSLYLQMNRLRAEDTAVYYCVKGLYSNPRGGAFDIWGQGTMVTVSSASTGG
GGSGGGGSGGGGSVHSSYVLTQPPSVSVAPGQTATITCGGNNIGTKSVHWYQQKPGQAPVLVVYADSDRPSGIPERVSGSNSGNTATL
TISRVEAGDEADYYCQVWDSRSDHLWVFGGGTKLTVLG (SEQ ID NO: 213)

IL15R K86R/ N112A–A10M3
NWVNVISDLKKIEDLIQSMHIDATLYTESDVHPSCKVTAMKCFLLELQVISLESGDASIHDTVENLIILANNSLSSNGNVTESGCRECEEL
EEKNIKEFLQSFVHIVQMFIATSGGGGSGGGGSGGGGSGGGGSEVQLVESGGGLIQPGRSLRLSCAASGITFDDAVMHWVRQA
PGKGLEWVAGISSNSGYIGYADSVKGRFTISRDNAKNSLYLQMNRLRAEDTAVYYCVKGLYSNPRGGAFDIWGQGTMVTVSSASTGG
GGSGGGGSGGGGSVHSSYVLTQPPSVSVAPGQTATITCGGNNIGTKSVHWYQQKPGQAPVLVVYADSDRPSGIPERVSGSNSGNTATL
TISRVEAGDEADYYCQVWDSRSDHLWVFGGGTKLTVLG (SEQ ID NO: 214)

FIG. 6A

```
1  - NWVNVISDLKKIEDLIQSMHIDATLYTESDVHPSCKVT    SEQ ID NO: 215
39 - AMKCFLLELQVISLESGDASIHDTVENLIILANNSLSS    SEQ ID NO: 216
77 - NGNVTESGCKECEELEEKNIKEFLQSFVHIVQMFINTS    SEQ ID NO: 217
              +   ++              +
```

FIG. 6B

Output:

| Residue | Score | Ubiquitinated |
|---------|-------|---------------|
| 10 | 0.41 | No |
| 11 | 0.43 | No |
| 36 | 0.43 | No |
| 41 | 0.36 | No |
| 86 | 0.68 | Yes  Low confidence |
| 94 | 0.53 | No |
| 97 | 0.51 | No |

Legend:

| Label | Score range | Sensitivity | Specificity |
|-------|-------------|-------------|-------------|
| Low confidence | $0.62 \leq s \leq 0.69$ | 0.464 | 0.903 |
| Medium confidence | $0.69 \leq s \leq 0.84$ | 0.346 | 0.950 |
| High confidence | $0.84 \leq s \leq 1.00$ | 0.197 | 0.989 |

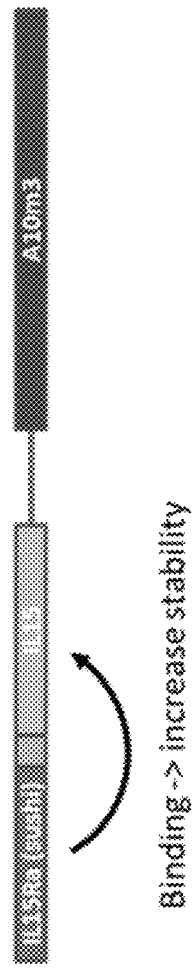
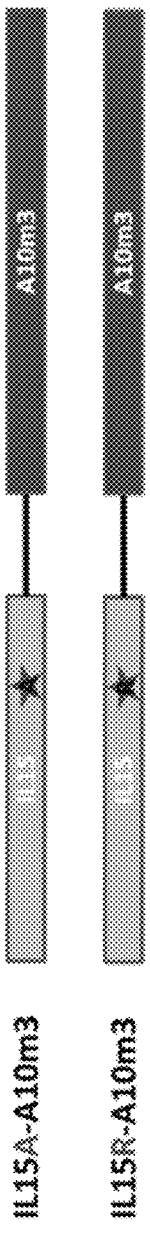
FIG. 7A Improving stability via IL15 alpha receptor sushi domain
FIG. 7B Improving stability by preventing ubiquitin-dependent degradation

FIG. 14

| Time for IV (6 mice for each group) N=30 | T=5 ? day ~50mm³ | 7 day | 9 day | 11 Day | 14 day End? |
|---|---|---|---|---|---|
| 1 Placebo | PBS | - | - | - | Wgt tumor & size/homogenate & serum |
| 2 IL15-ABD 1 ug/mice | 1 ug | 1 ug | 1 ug | 1 ug | Wgt tumor & size/homogenate & serum |
| 3 IL15-ABD 10 ug/mice | 10 ug | 10 ug | 10 ug | 10 ug | Wgt tumor & size/homogenate & serum |
| 4 IL15-ABD 25 ug/mice | 25 ug | 25 ug | 25 ug | 25 ug | Wgt tumor & size/homogenate & serum |
|  | Dose 1 | Dose 2 | Dose 3 | Dose 4 Final | Dose every 48 hrs |

Vehicle Control

FIG. 17

| Sample ID | Tissue | Treatment | Live Cells | CD45+CD3+ | CD45+CD3- | CD45+CD3-CD11+ | CD27+ | CD27 median | CD49b | CD49b median | CD49b+ NK1.1+ | CD122 | CD122 median |
|---|---|---|---|---|---|---|---|---|---|---|---|---|---|
| | | | | | | | | | CD45+CD3-CD11+ | | | | |
| 31 | Spleen | Vehicle | 94 | 22.6 | 57.6 | 14.5 | 1.4 | 66608 | 35.4 | 38208 | 20.3 | 40.5 | 46562 |
| 32 | | | 94.6 | 29.1 | 67.4 | 11.7 | 5.3 | 38600 | 34.9 | 36208 | 28.4 | 38.2 | 29334 |
| 33 | | | 92.5 | 29 | 63.3 | 13.5 | 6.17 | 36208 | 30.3 | 31808 | 18.1 | 27.5 | 30464 |
| | | Mean | 93.7 | 27.6 | 62.8 | 13.2 | 8.3 | 46805.3 | 33.7 | 33480.0 | 19.6 | 38.8 | 35413.3 |
| 34 | | IL-15 ABD 25ug/mouse | 92 | 38.6 | 59 | 12.9 | 19 | 91264 | 35.1 | 62720 | 20 | 36 | 65368 |
| 35 | | | 93.2 | 29.7 | 63.4 | 17.2 | 11.8 | 54848 | 37.3 | 44224 | 19.5 | 38.3 | 44032 |
| 36 | | | 94.1 | 31.6 | 63.4 | 17.8 | 18.7 | 65872 | 43.8 | 48464 | 24.7 | 44.9 | 49512 |
| | | Mean | 93.1 | 30.8 | 61.9 | 16.0 | 16.5 | 66928.0 | 38.7 | 51136.0 | 21.4 | 39.1 | 52497.3 |
| 30 | Tumor | Vehicle | 38.6 | 0.6 | 3.1 | 83.2 | 3.9 | 126768 | 3.1 | 128832.0 | 5.0 | 5.8 | 137216 |
| 38 | | | 31.2 | 0.6 | 1.4 | 77.3 | 4.8 | 86640 | 6.3 | 42384.0 | 4.2 | 8.7 | 65472 |
| 39 | | | 37.6 | 0.7 | 3.6 | 83.9 | 3.0 | 153320 | 3.6 | 177544.0 | 2.3 | 4.9 | 85408 |
| | | Mean | 38.1 | 0.7 | 2.7 | 78.1 | 3.8 | 117909.3 | 4.3 | 143960.0 | 3.8 | 6.4 | 117696.0 |
| 40 | | IL-15 ABD 25ug/mouse | 34.3 | 1.3 | 2.8 | 84.4 | 24.1 | 99071 | 19.1 | 56616.0 | 17.3 | 32.8 | 83024 |
| 41 | | | 31.1 | 3.0 | 3.0 | 73.4 | 31.0 | 109068 | 11.4 | 59712.0 | 28.6 | 35.8 | 112008 |
| 42 | | | 41.3 | 0.4 | 0.5 | 78.6 | 11.8 | 102720 | 8.8 | 53832.0 | 10.3 | 17.1 | 94976 |
| | | Mean | 35.5 | 2.2 | 2.1 | 72.1 | 22.3 | 103893.3 | 12.8 | 56593.0 | 16.1 | 28.6 | 96000.0 |
| | | | | Cytotoxic T-Cell | | 6X NK-CD70 Highly Act | | | 3X NK-T Cells | | 4x NK- INF produce | 4X NK – IL2+IL-15 recp | | |

FIG. 18
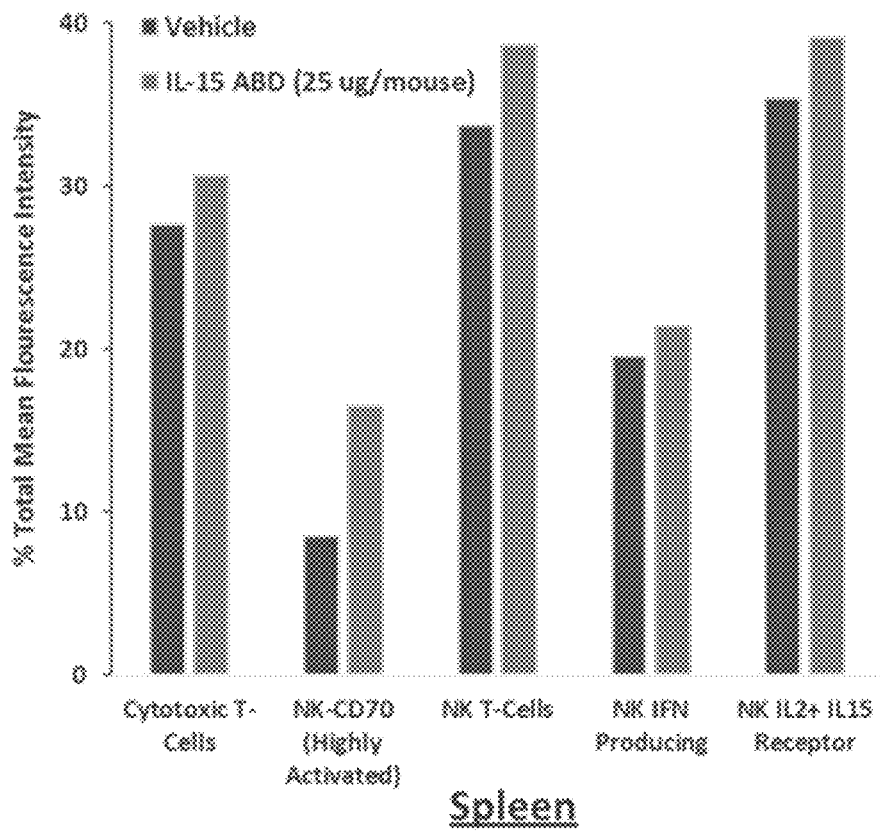
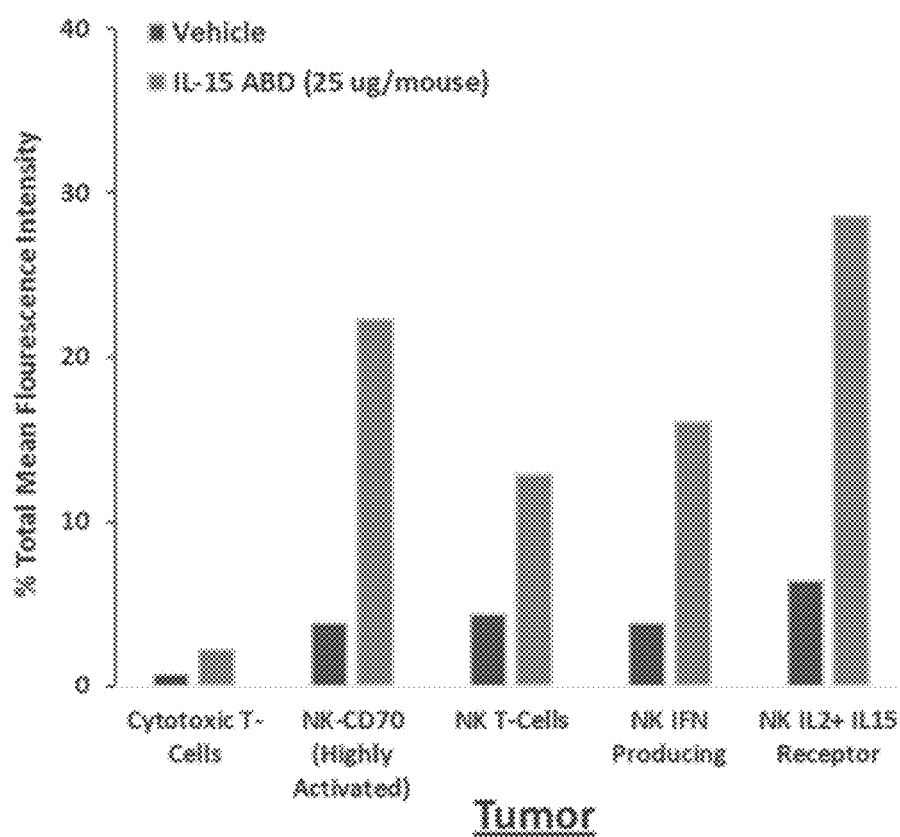

FIG. 20 mIL12sc-A10m3

MWELEKDVYVVEVDWTPDAPGETVNLTCDTPEEDDITWTSDQRHGVIGSGKTLTI
TVKEFLDAGQYTCHKGGETLSHSHLLLHKKENGIWSTEILKNFKNKTFLKCEAPN
YSGRFTCSWLVQRNMDLKFNIKSSSSSPDSRAVTCGMASLSAEKVTLDQRDYEKYS
VSCQEDVTCPTAEETLPIELALEARQQNKYENYSTSFFIRDIIKPDPPKNLQMKPLK
NSQVEVSWEYPDSWSTPHSYFSLKFFVRIQRKKEKMKETEEGCNQKGAFLVEKTS
TEVQCKGGNVCVQAQDRYYNSSCSKWACVPCRVRSGGGGSGGGGSGGGGSRVIPVS
GPARCLSQSRNLLKTTDDMVKTAREKLKHYSCTAEDIDHEDITRDQTSTLKTCLPLELH
KNESCLATRETSSTTRGSCLPPQKTSLMMTLCLGSIYEDLKMYQTEFQAINAALQNHNH
QQIILDKGMLVAIDELMQSLNHNGETLRQKPPVGEADPYRVKMKLCILLHAFSTRVVTI
NRVMGYLSSA<u>GGGGSGGGGSGGGGSGGGGSGGGGS</u>EVQLVESGGGLIQPGRSLRLSCA
ASGITFDDAVMHWVRQAPGKGLEWVAGISSNSGYIGYADSVKGRFTISRDNAKNSLYL
QMNRLRAEDTAVYYCVKGLYSNPRGGAFDIWGQGTMVTVSSASTGGGGSGGGGSGG
GGSVHSSYVLTQPPSVSVAPGQTATITCGGNNIGTKSVHWYQQKPGQAPVLVVYADSD
RPSGIPERVSGSNSGNTATLTISRVEAGDEADYYCQVWDSRSDHLWVFGGGTKLTVLG
(SEQ ID NO: 218)

Human IL-12sc-A10m3

IWELKKDVYVVELDWYPDAPGEMVVLTCDTPEEDGITWTLDQSSEVLGSGKTLTI
QVKEFGDAGQYTCHKGGEVLSHSLLLLHKKEDGIWSTDILKDQKEPKNKTFLRCE
AKNYSGRFTCWWLTTISTDLTFSVKSSRGSSDPQGVTCGAATLSAERVRGDNKEYE
YSVECQEDSACPAAEESLPIEVMVDAVHKLKYENYTSSFFIRDIIKPDPPKNLQLKPL
KNSRQVEVSWEYPDTWSTPHSYFSLTFCVQVQGKSKREKKDRVFTDKTSATVICR
KNASISVRAQDRYYSSSWSEWASVPCS<u>GGGGGGS</u>RNLPVATPDPGMFPCLHHSQNLL
RAVSNMLQKARQTLEFYPCTSEEIDHEDITKDKTSTVEACLPLELTKNESCLNSRETSFIT
NGSCLASRKTSFMMALCLSSIYEDLKMYQVEFKTMNAKLLMDPKRQIFLDQNMLAVID
ELMQALNFNSETVPQKSSLEEPDFYKTKIKLCILLHAFRIRAVTIDRVTSYLNAS<u>GGGGSG
GGGSGGGGSGGGGSGGGGS</u>EVQLVESGGGLIQPGRSLRLSCAASGITFDDAVMHWVRQ
APGKGLEWVAGISSNSGYIGYADSVKGRFTISRDNAKNSLYLQMNRLRAEDTAVYYCV
KGLYSNPRGGAFDIWGQGTMVTVSSASTGGGGSGGGGSGGGGSVHSSYVLTQPPSVSV
APGQTATITCGGNNIGTKSVHWYQQKPGQAPVLVVYADSDRPSGIPERVSGSNSGNTAT
LTISRVEAGDEADYYCQVWDSRSDHLWVFGGGTKLTVLG (SEQ ID NO: 219)

| Group | Treatment | Animals per group | Dose Schedule and Route | Takedown at 24 hrs after Dosing | Tumor Growth and Body Weight Monitoring | Forwards Study End |
|---|---|---|---|---|---|---|
| 1 | Placebo | 9 mice* | 7 days after tumor inoculation (tumor = 100m$^3$) | 3 mice* | Every 2 days | Monitor tumor growth daily until 50% of tumor sin the last remain group reach 2000mm^3. |
| 2 | IL12 (3 ug) | 6 mice | | | | |
| 3 | IL12-ABD (4.5 ug) | 6 mice | | | | |
| 4 | IL12 (10 ug) | 6 mice | | | | |
| 5 | IL12-ABD (15 ug) | 6 mice | | | | |
| 6 | IL12 (20 ug) | 9 mice* | | 3 mice* | | |
| 7 | IL12-ABD (30 ug) | 9 mice* | | 3 mice* | | |

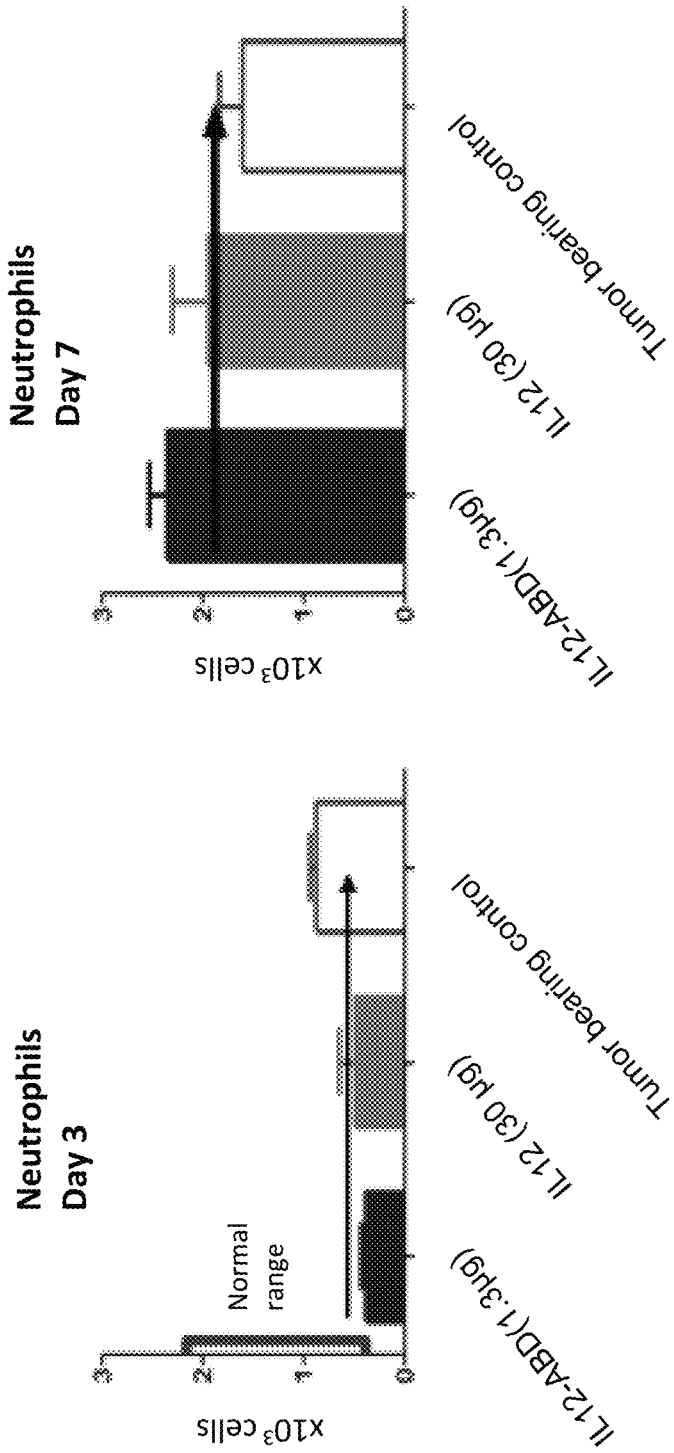

FIG. 34 hIL15RA-A10m3-mIL-12sc
NWVNVISDLKKIEDLIQSMHIDATLYTESDVHPSCKVTAMKCFLLELQVISLESGDASIHDTVENLIILA
NNSLSSNGNVTESGCRECEELEEKNIKEFLQSFVHIVQMFIATSGGGGSGGGGSGGGGSGGGGSGGGG
SEVQLVESGGGLIQPGRSLRLSCAASGITFDDAVMHWVRQAPGKGLEWVAGISSNSGYIGYADSVKG
RFTISRDNAKNSLYLQMNRLRAEDTAVYYCVKGLYSNPRGGAFDIWGQGTMVTVSSASTGGGGSGG
GGSGGGGSVHSSYVLTQPPSVSVAPGQTATITCGGNNIGTKSVHWYQQKPGQAPVLVVYADSDRPSG
IPERVSGSNSGNTATLTISRVEAGDEADYYCQVWDSRSDHLWVFGGGTKLTVLGGGGSGGGGSGG
GGSGGGGSGGGGSMWELEKDVYVVEVDWTPDAPGETVNLTCDTPEEDDITWTSDQRHGVIGSG
KTLTITVKEFLDAGQYTCHKGGETLSHSHLLLHKKENGIWSTEILKNFKNKTFLKCEAPNYSGR
FTCSWLVQRNMDLKFNIKSSSSSPDSRAVTCGMASLSAEKVTLDQRDYEKYSVSCQEDVTCPTA
EETLPIELALEARQQNKYENYSTSFFIRDIIKPDPPKNLQMKPLKNSQVEVSWEYPDSWSTPHSYF
SLKFFVRIQRKKEKMKETEEGCNQKGAFLVEKTSTEVQCKGGNVCVQAQDRYYNSSCSKWAC
VPCRVRSGGGGSGGGGSGGGGSRVIPVSGPARCLSQSRNLLKTTDDMVKTAREKLKHYSCTAEDIDH
EDITRDQTSTLKTCLPLELHKNESCLATRETSSTTRGSCLPPQKTSLMMTLCLGSIYEDLKMYQTEFQA
INAALQNHNHQQIILDKGMLVAIDELMQSLNHNGETLRQKPPVGEADPYRVKMKLCILLHAFSTRVV
TINRVMGYLSSA (SEQ ID NO: 220)

mIL-12sc-A10m3-hIL15R
MWELEKDVYVVEVDWTPDAPGETVNLTCDTPEEDDITWTSDQRHGVIGSGKTLTITVKEFLDA
GQYTCHKGGETLSHSHLLLHKKENGIWSTEILKNFKNKTFLKCEAPNYSGRFTCSWLVQRNMD
LKFNIKSSSSSPDSRAVTCGMASLSAEKVTLDQRDYEKYSVSCQEDVTCPTAEETLPIELALEARQ
QNKYENYSTSFFIRDIIKPDPPKNLQMKPLKNSQVEVSWEYPDSWSTPHSYFSLKFFVRIQRKKE
KMKETEEGCNQKGAFLVEKTSTEVQCKGGNVCVQAQDRYYNSSCSKWACVPCRVRSGGGGSG
GGGSGGGGSRVIPVSGPARCLSQSRNLLKTTDDMVKTAREKLKHYSCTAEDIDHEDITRDQTSTLKTC
LPLELHKNESCLATRETSSTTRGSCLPPQKTSLMMTLCLGSIYEDLKMYQTEFQAINAALQNHNHQQII
LDKGMLVAIDELMQSLNHNGETLRQKPPVGEADPYRVKMKLCILLHAFSTRVVTINRVMGYLSSAG
GGGSGGGGSGGGGSGGGGSGGGGSEVQLVESGGGLIQPGRSLRLSCAASGITFDDAVMHWVRQAPG
KGLEWVAGISSNSGYIGYADSVKGRFTISRDNAKNSLYLQMNRLRAEDTAVYYCVKGLYSNPRGGA
FDIWGQGTMVTVSSASTGGGGSGGGGSGGGGSVHSSYVLTQPPSVSVAPGQTATITCGGNNIGTKSV
HWYQQKPGQAPVLVVYADSDRPSGIPERVSGSNSGNTATLTISRVEAGDEADYYCQVWDSRSDHLW
VFGGGTKLTVLGGGGSGGGGSGGGGSGGGGSGGGGSNWVNVISDLKKIEDLIQSMHIDATLYTESD
VHPSCKVTAMKCFLLELQVISLESGDASIHDTVENLIILANNSLSSNGNVTESGCRECEELEEKNIKEFL
QSFVHIVQMFINTS (SEQ ID NO: 221)

mIL-12sc-A10m3-hIL15RA
MWELEKDVYVVEVDWTPDAPGETVNLTCDTPEEDDITWTSDQRHGVIGSGKTLTITVKEFLDA
GQYTCHKGGETLSHSHLLLHKKENGIWSTEILKNFKNKTFLKCEAPNYSGRFTCSWLVQRNMD
LKFNIKSSSSSPDSRAVTCGMASLSAEKVTLDQRDYEKYSVSCQEDVTCPTAEETLPIELALEARQ
QNKYENYSTSFFIRDIIKPDPPKNLQMKPLKNSQVEVSWEYPDSWSTPHSYFSLKFFVRIQRKKE
KMKETEEGCNQKGAFLVEKTSTEVQCKGGNVCVQAQDRYYNSSCSKWACVPCRVRSGGGGSG
GGGSGGGGSRVIPVSGPARCLSQSRNLLKTTDDMVKTAREKLKHYSCTAEDIDHEDITRDQTSTLKTC
LPLELHKNESCLATRETSSTTRGSCLPPQKTSLMMTLCLGSIYEDLKMYQTEFQAINAALQNHNHQQII
LDKGMLVAIDELMQSLNHNGETLRQKPPVGEADPYRVKMKLCILLHAFSTRVVTINRVMGYLSSAG
GGGSGGGGSGGGGSGGGGSGGGGSEVQLVESGGGLIQPGRSLRLSCAASGITFDDAVMHWVRQAPG
KGLEWVAGISSNSGYIGYADSVKGRFTISRDNAKNSLYLQMNRLRAEDTAVYYCVKGLYSNPRGGA
FDIWGQGTMVTVSSASTGGGGSGGGGSGGGGSVHSSYVLTQPPSVSVAPGQTATITCGGNNIGTKSV
HWYQQKPGQAPVLVVYADSDRPSGIPERVSGSNSGNTATLTISRVEAGDEADYYCQVWDSRSDHLW
VFGGGTKLTVLGGGGSGGGGSGGGGSGGGGSGGGGSNWVNVISDLKKIEDLIQSMHIDATLYTESD
VHPSCKVTAMKCFLLELQVISLESGDASIHDTVENLIILANNSLSSNGNVTESGCRECEELEEKNIKEFL
QSFVHIVQMFIATS (SEQ ID NO: 222)

FIG. 36 hIL15RA-A10m3-hIL-12sc

NWVNVISDLKKIEDLIQSMHIDATLYTESDVHPSCKVTAMKCFLLELQVISLESGDASIHDTVENLI
ILANNSLSSNGNVTESGCRECEELEEKNIKEFLQSFVHIVQMFIATSGGGGSGGGGSGGGGSGGGG
SGGGGSEVQLVESGGGLIQPGRSLRLSCAASGITFDDAVMHWVRQAPGKGLEWVAGISSNSGYIG
YADSVKGRFTISRDNAKNSLYLQMNRLRAEDTAVYYCVKGLYSNPRGGAFDIWGQGTMVTVSS
ASTGGGGSGGGGSGGGGSVHSSYVLTQPPSVSVAPGQTATITCGGNNIGTKSVHWYQQKPGQAP
VLVVYADSDRPSGIPERVSGSNSGNTATLTISRVEAGDEADYYCQVWDSRSDHLWVFGGGTKLT
VLGGGGSGGGGSGGGGSGGGGSGGGGSIWELKKDVYVVELDWYPDAPGEMVVLTCDTPEE
DGITWTLDQSSEVLGSGKTLTIQVKEFGDAGQYTCHKGGEVLSHSLLLLHKKEDGIWSTDIL
KDQKEPKNKTFLRCEAKNYSGRFTCWWLTTISTDLTFSVKSSRGSSDPQGVTCGAATLSAER
VRGDNKEYEYSVECQEDSACPAAEESLPIEVMVDAVHKLKYENYTSSFFIRDIIKPDPPKNLQ
LKPLKNSRQVEVSWEYPDTWSTPHSYFSLTFCVQVQGKSKREKKDRVFTDKTSATVICRKN
ASISVRAQDRYYSSSWSEWASVPCSGGGGGGSRNLPVATPDPGMFPCLHHSQNLLRAVSNMLQ
KARQTLEFYPCTSEEIDHEDITKDKTSTVEACLPLELTKNESCLNSRETSFITNGSCLASRKTSFMM
ALCLSSIYEDLKMYQVEFKTMNAKLLMDPKRQIFLDQNMLAVIDELMQALNFNSETVPQKSSLEE
PDFYKTKIKLCILLHAFRIRAVTIDRVTSYLNAS (SEQ ID NO: 223)

Human IL-12sc-A10m3-hIL15R

IWELKKDVYVVELDWYPDAPGEMVVLTCDTPEEDGITWTLDQSSEVLGSGKTLTIQVKEFG
DAGQYTCHKGGEVLSHSLLLLHKKEDGIWSTDILKDQKEPKNKTFLRCEAKNYSGRFTCW
WLTTISTDLTFSVKSSRGSSDPQGVTCGAATLSAERVRGDNKEYEYSVECQEDSACPAAEESL
PIEVMVDAVHKLKYENYTSSFFIRDIIKPDPPKNLQLKPLKNSRQVEVSWEYPDTWSTPHSYF
SLTFCVQVQGKSKREKKDRVFTDKTSATVICRKNASISVRAQDRYYSSSWSEWASVPCSGGG
GGGSRNLPVATPDPGMFPCLHHSQNLLRAVSNMLQKARQTLEFYPCTSEEIDHEDITKDKTSTVE
ACLPLELTKNESCLNSRETSFITNGSCLASRKTSFMMALCLSSIYEDLKMYQVEFKTMNAKLLMD
PKRQIFLDQNMLAVIDELMQALNFNSETVPQKSSLEEPDFYKTKIKLCILLHAFRIRAVTIDRVTSY
LNASGGGGSGGGGSGGGGSGGGGSGGGGSEVQLVESGGGLIQPGRSLRLSCAASGITFDDAVMH
WVRQAPGKGLEWVAGISSNSGYIGYADSVKGRFTISRDNAKNSLYLQMNRLRAEDTAVYYCVK
GLYSNPRGGAFDIWGQGTMVTVSSASTGGGGSGGGGSGGGGSVHSSYVLTQPPSVSVAPGQTATI
TCGGNNIGTKSVHWYQQKPGQAPVLVVYADSDRPSGIPERVSGSNSGNTATLTISRVEAGDEADY
YCQVWDSRSDHLWVFGGGTKLTVLGGGGSGGGGSGGGGSGGGGSGGGGSNWVNVISDLKKI
EDLIQSMHIDATLYTESDVHPSCKVTAMKCFLLELQVISLESGDASIHDTVENLILANNSLSSNGN
VTESGCRECEELEEKNIKEFLQSFVHIVQMFINTS (SEQ ID NO: 224)

Human IL-12sc-A10m3-hIL15RA

IWELKKDVYVVELDWYPDAPGEMVVLTCDTPEEDGITWTLDQSSEVLGSGKTLTIQVKEFG
DAGQYTCHKGGEVLSHSLLLLHKKEDGIWSTDILKDQKEPKNKTFLRCEAKNYSGRFTCW
WLTTISTDLTFSVKSSRGSSDPQGVTCGAATLSAERVRGDNKEYEYSVECQEDSACPAAEESL
PIEVMVDAVHKLKYENYTSSFFIRDIIKPDPPKNLQLKPLKNSRQVEVSWEYPDTWSTPHSYF
SLTFCVQVQGKSKREKKDRVFTDKTSATVICRKNASISVRAQDRYYSSSWSEWASVPCSGGG
GGGSRNLPVATPDPGMFPCLHHSQNLLRAVSNMLQKARQTLEFYPCTSEEIDHEDITKDKTSTVE
ACLPLELTKNESCLNSRETSFITNGSCLASRKTSFMMALCLSSIYEDLKMYQVEFKTMNAKLLMD
PKRQIFLDQNMLAVIDELMQALNFNSETVPQKSSLEEPDFYKTKIKLCILLHAFRIRAVTIDRVTSY
LNASGGGGSGGGGSGGGGSGGGGSGGGGSEVQLVESGGGLIQPGRSLRLSCAASGITFDDAVMH
WVRQAPGKGLEWVAGISSNSGYIGYADSVKGRFTISRDNAKNSLYLQMNRLRAEDTAVYYCVK
GLYSNPRGGAFDIWGQGTMVTVSSASTGGGGSGGGGSGGGGSVHSSYVLTQPPSVSVAPGQTATI
TCGGNNIGTKSVHWYQQKPGQAPVLVVYADSDRPSGIPERVSGSNSGNTATLTISRVEAGDEADY
YCQVWDSRSDHLWVFGGGTKLTVLGGGGSGGGGSGGGGSGGGGSGGGGSNWVNVISDLKKI
EDLIQSMHIDATLYTESDVHPSCKVTAMKCFLLELQVISLESGDASIHDTVENLILANNSLSSNGN
VTESGCRECEELEEKNIKEFLQSFVHIVQMFIATS (SEQ ID NO: 225)

| | Sequence | SEQ ID NO: |
|---|---|---|
| Variable heavy (vh) chain | QVQLVESGGGLVKPGRSLRLSCAASGFTFSSYAMHWVRQAPGKGLEWVAVISYDGSNKYYADSVKGRFTISRDNSKNTLYLQMNSLRAEDTAVYYCAKEMRYCSGGSCYPYAYYMDVWGQGTTVTVSSAST | 226 |
| Variable light (vl) chain | VHSSSELTQDPAVSVALGQTVRITCQGDSLRSYYASWYQQKPGQAPVLVIYGKNNRPSGIPDRFSGSSSGNTASLTITGAQAEDEADYYCNSRDSSGNLVFGGGTKLTVLGLGG | 227 |
| scFv | QVQLVESGGGLVKPGRSLRLSCAASGFTFSSYAMHWVRQAPGKGLEWVAVISYDGSNKYYADSVKGRFTISRDNSKNTLYLQMNSLRAEDTAVYYCAKEMRYCSGGSCYPYAYYMDVWGQGTTVTVSSASTGGGGSGGGGSGGGGSVHSSSELTQDPAVSVALGQTVRITCQGDSLRSYYASWYQQKPGQAPVLVIYGKNNRPSGIPDRFSGSSSGNTASLTITGAQAEDEADYYCNSRDSSGNLVFGGGTKLTVLGLGG | 228 |

| | Sequence | SEQ ID NO: |
|---|---|---|
| Variable heavy (vh) chain | VQLVESGGGLVQPGGSLRLSCAASGFTFSSYAISWVRQAPGKGLEWVSAISG SGGSTYYADSVKGRFTISRDNSKNTLYLQMNSLRAEDTAAYYCAKEISGSYLG LVAFDIWGQGTMVTVSSAST | 229 |
| Variable light (vl) chain | VHSSYVLTQPLSVSVAPGQTARMTCGGDNVGAKSVHWYQQKPGQAPVLLI YYDHDRPSGIPERFSGSNSGNTATLTITRVEAGDEADYYCQVWDPSSDVVFG GGTQLTVLGLGG | 230 |
| scFv | EVQLVESGGGLVQPGGSLRLSCAASGFTFSSYAISWVRQAPGKGLEWVSAIS GSGGSTYYADSVKGRFTISRDNSKNTLYLQMNSLRAEDTAAYYCAKEISGSYL GLVAFDIWGQGTMVTVSSASTGGGGSGGGGSGGGGSVHSSYVLTQPLSVS VAPGQTARMTCGGDNVGAKSVHWYQQKPGQAPVLLIYYDHDRPSGIPERF SGSNSGNTATLTITRVEAGDEADYYCQVWDPSSDVVFGGGTQLTVLGLGG | 231 |

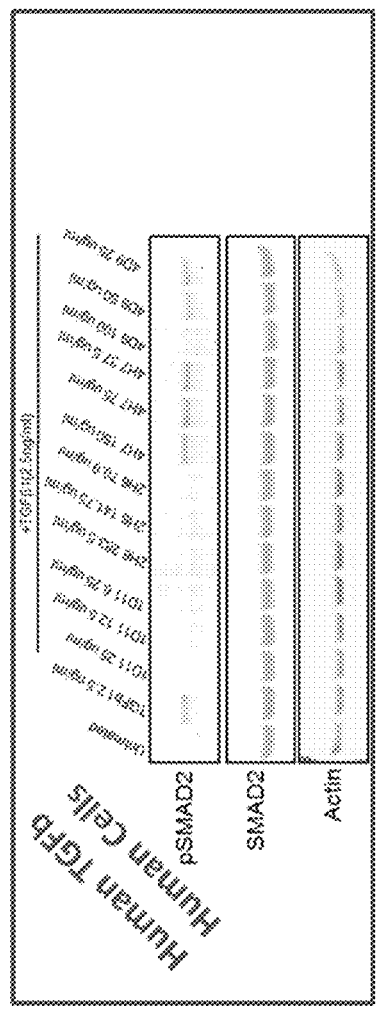
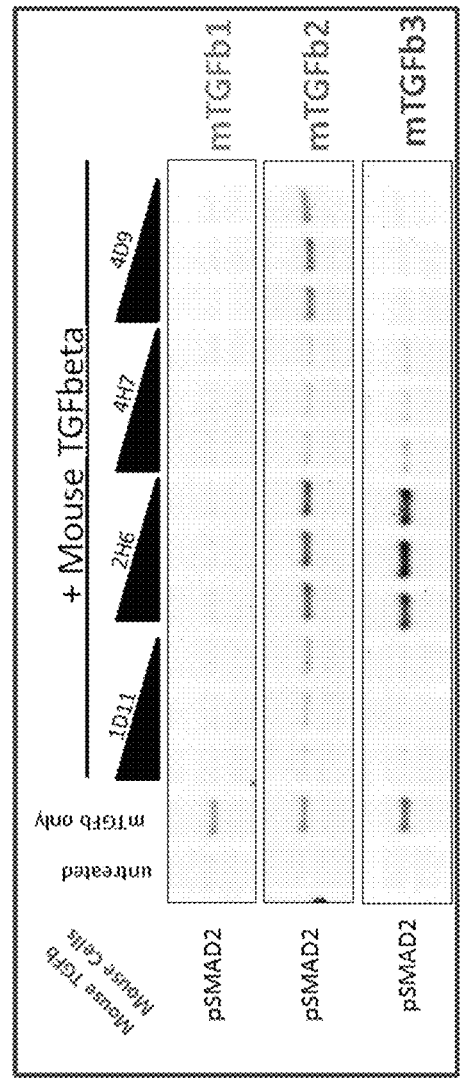
FIG. 44A
FIG. 44B

FIG. 45A

4H7m scFv
QVQLVESGGGLVKPGRSLRLSCAASGFTFSSYAMHWVRQAPGKGLEWVAVISYDGSNKYYADS
VKGRFTISRDNSKNTLYLQMNSLRAEDTAVYYCAKEMRYCSGGSCYPYAYYMDVWGQGTTVT
VSSASTGGGGSGGGGSGGGGSVHSSSELTQDPAVSVALGQTVRITCQGDSLRSYYASWYQQKPG
QAPVLVIYGKNNRPSGIPDRFSGSSSGNTASLTITGAQAEDEADYYCNSRDSSGNLVVFGGGTKL
TVLGLGG (SEQ ID NO: 232)

4H7m scFV-A6m
QVQLVESGGGLVKPGRSLRLSCAASGFTFSSYAMHWVRQAPGKGLEWVAVISYDGSNKYYADS
VKGRFTISRDNSKNTLYLQMNSLRAEDTAVYYCAKEMRYCSGGSCYPYAYYMDVWGQGTTVT
VSSASTGGGGSGGGGSGGGGSVHSSSELTQDPAVSVALGQTVRITCQGDSLRSYYASWYQQKPG
QAPVLVIYGKNNRPSGIPDRFSGSSSGNTASLTITGAQAEDEADYYCNSRDSSGNLVVFGGGTKL
TVLGLGGGGGSGGGGSGGGGSGGGGSGGGGSEVQLVQSGAEVKKPGESLKISCKGSGYSFNS
YWIGWVRQMPGKGLEWMGIIYPGDSDTRYSPSFQGQVTFSVDKSINTAYLQWSSLKASDAAMY
YCARQRWGSSSFDAWGQGTLVTVSSASTGGGGSGGGGSGGGGSVHSQSVLTQPPSVSAAPGQK
VTISCSGSSSNIGNNYVSWYQQLPGTAPKLLIYENNKRPSGIPDRFSGSKSGTSATLGITGLQTGDE
ADYYCGTWDSSLSAGVFGGGTQLTVLG (SEQ ID NO: 233)

4D9m scFV
EVQLVESGGGLVQPGGSLRLSCAAS<u>GFTFSSYAIS</u>WVRQAPGKGLEWVSA<u>ISGSGGST</u>YYADSV
KGRFTISRDNSKNTLYLQMNSLR<u>AEDTAAYYCAKEISGSYLGLVAFDI</u>WGQGTMVTVSSASTGG
GGSGGGGSGGGGSVHSSYVLTQPLSVSVAPGQTARMTCGGD<u>NVGAKS</u>VHWYQQKPGQAPVLL
IY<u>YDH</u>DRPSGIPERFSGSNSGNTATLTITRVEAGDEADYYC<u>QVWDPSSDVV</u>FGGGTQLTVLGLGG
(SEQ ID NO: 234)

VH
EVQLVESGGGLVQPGGSLRLSCAAS<u>GFTFSSYAIS</u>WVRQAPGKGLEWVSA<u>ISGSGGST</u>YYADSV
KGRFTISRDNSKNTLYLQMNSLR<u>AEDTAAYYCAKEISGSYLGLVAFDI</u>WGQGTMVTVSSAST
(SEQ ID NO: 235)

vhCDR1: GFTFSSYA (SEQ ID NO: 236)   vhCDR2: SGSGGST (SEQ ID NO: 237)
vhCDR3: AEDTAAYYCAKEISGSYLGLVAFD (SEQ ID NO: 238)

VL
VHSSYVLTQPLSVSVAPGQTARMTCGGD<u>NVGAKS</u>VHWYQQKPGQAPVLLIY<u>YDH</u>DRPSGIPER
FSGSNSGNTATLTITRVEAGDEADYYC<u>QVWDPSSDVV</u>FGGGTQLTVLGLGG (SEQ ID NO: 239)

vlCDR1: NVGAKS (SEQ ID NO: 240)  vlCDR2: YDH (SEQ ID NO: 241)
vlCDR3: QVWDPSSDVV (SEQ ID NO: 242)

4D9m scFV-A6m
EVQLVESGGGLVQPGGSLRLSCAASGFTFSSYAISWVRQAPGKGLEWVSAISGSGGSTYYADSV
KGRFTISRDNSKNTLYLQMNSLRAEDTAAYYCAKEISGSYLGLVAFDIWGQGTMVTVSSASTGG
GGSGGGGSGGGGSVHSSYVLTQPLSVSVAPGQTARMTCGGDNVGAKSVHWYQQKPGQAPVLL
IYYDHDRPSGIPERFSGSNSGNTATLTITRVEAGDEADYYCQVWDPSSDVVFGGGTQLTVLGLGG
<u>GGGGSGGGGSGGGGSGGGGSGGGGS</u>EVQLVQSGAEVKKPGESLKISCKGSGYSFNSYWIGWVR
QMPGKGLEWMGIIYPGDSDTRYSPSFQGQVTFSVDKSINTAYLQWSSLKASDAAMYYCARQRW
GSSSFDAWGQGTLVTVSSASTGGGGSGGGGSGGGGSVHSQSVLTQPPSVSAAPGQKVTISCSGSS
SNIGNNYVSWYQQLPGTAPKLLIYENNKRPSGIPDRFSGSKSGTSATLGITGLQTGDEADYYCGT
WDSSLSAGVFGGGTQLTVLG (SEQ ID NO: 243)

EC50 values mouse T cell proliferation assay with m/h TGF 1 & 3 @ 1 ng and m/h TGF 2 @ 10 ng— EC50 inhibition

| | Mouse TGFb1 (1ng/ml) EC50 (ug/ml) | Mouse TGFb2 (10ng/ml) EC50 (ug/ml) | Mouse TGFb3 (1ng/ml) EC50 (ug/ml) | Human TGFb1 (1ng/ml) EC50 (ug/ml) | Human TGFb2 (10ng/ml) EC50 (ug/ml) | Human TGFb3 (1ng/ml) EC50 (ug/ml) |
|---|---|---|---|---|---|---|
| 4D9M-A6M | 1.914 | 2.549 | 1.552 | 2.094 | 2.134 | 2.131 |
| 4H7M-A6M | 7.505 | 5.495 | 5.969 | 5.297 | 4.949 | 5.435 |

FIG. 48A

Positively Changed Linkers

| Name | Sequence | | Length | Charge |
|---|---|---|---|---|
| Gly-Ser 15 | GGGGSGGGGSGGGGS | (SEQ ID NO: 244) | 15 | 0 |
| Whitlow linker | GSTSGSGKPGSGEGSTKG | (SEQ ID NO: 245) | 18 | +1 |
| 6paxA_1 (+A) | IRPRAIGGSKPRVA | (SEQ ID NO: 246) | 14 | +4 |
| +B | GKGGSGKGGSGKGGS | (SEQ ID NO: 247) | 15 | +3 |
| +C | GGKGSGGKGSGGKGS | (SEQ ID NO: 248) | 15 | +3 |
| +D | GGGKSGGGKSGGGKS | (SEQ ID NO: 249) | 15 | +3 |
| +E | GKGKSGKGKSGKGKS | (SEQ ID NO: 250) | 15 | +6 |
| +F | GGGKSGGKGSGKGGS | (SEQ ID NO: 251) | 15 | +3 |
| +G | GKPGSGKPGSGKPGS | (SEQ ID NO: 252) | 15 | +3 |
| +H | GKPGSGKPGSGKPGSGKPGS | (SEQ ID NO: 253) | 20 | +4 |
| +I | GKGKSGKGKSGKGKSGKGKS | (SEQ ID NO: 254) | 20 | +8 |

FIG. 48B

Negatively Charged Linkers

| Name | Sequence | | Length | Charge |
|---|---|---|---|---|
| Gly-Ser 15 | GGGGSGGGGSGGGGSGGGGS | (SEQ ID NO: 255) | 20 | 0 |
| 3hsc_2 (-A) | STAGDTHLGGEDFD | (SEQ ID NO: 256) | 14 | -4 |
| -B | GEGGSGEGGSGEGGS | (SEQ ID NO: 257) | 15 | -3 |
| -C | GGEGSGGEGSGGEGS | (SEQ ID NO: 258) | 15 | -3 |
| -D | GGGESGGGESGGGES | (SEQ ID NO: 259) | 15 | -3 |
| -E | GEGESGEGESGEGES | (SEQ ID NO: 260) | 15 | -6 |
| -F | GGGESGGEGSGEGGS | (SEQ ID NO: 261) | 15 | -3 |
| -G | GEGESGEGESGEGESGEGES | (SEQ ID NO: 262) | 20 | -8 |

Additional Linkers

| Sequence | |
|---|---|
| GGGGSGGGGSGGGGS | (SEQ ID NO: 263) |
| GGGGSGGGGSGGGGSGGGGS | (SEQ ID NO: 264) |
| GSTSGSGKPGSGEGSTKG | (SEQ ID NO: 265) |
| PRGASKSGSASQTGSAPGS | (SEQ ID NO: 266) |
| GTAAAGAGAAGGAAAGAAG | (SEQ ID NO: 267) |
| GTSGSSGSGSGGSGSGGGG | (SEQ ID NO: 268) |
| GKPGSGKPGSGKPGSGKPGS | (SEQ ID NO: 269) |
| GGGGGGS | (SEQ ID NO: 270) |

Human hIL-2
APTSSSTKKTQLQLEHLLLDLQMILNGINNYKNPKLTRMLTFKFYMPKKATELKHLQCL
EEELKPLEEVLNLAQSKNFHLRPRDLISNINVIVLELKGSETTFMCEYADETATIVEFLNR
WITFCQSIISTLT (SEQ ID NO: 271)

Human hIL-2-A10m3
APTSSSTKKTQLQLEHLLLDLQMILNGINNYKNPKLTRMLTFKFYMPKKATELKHLQCL
EEELKPLEEVLNLAQSKNFHLRPRDLISNINVIVLELKGSETTFMCEYADETATIVEFLNR
WITFCQSIISTLTGGGGSGGGGSGGGGSGGGGSGGGGSEVQLVESGGGLIQPGRSLRLSC
AASGITFDDAVMHWVRQAPGKGLEWVAGISSNSGYIGYADSVKGRFTISRDNAKNSLY
LQMNRLRAEDTAVYYCVKGLYSNPRGGAFDIWGQGTMVTVSSASTGGGGSGGGGSGG
GGSVHSSYVLTQPPSVSVAPGQTATITCGGNNIGTKSVHWYQQKPGQAPVLVVYADSD
RPSGIPERVSGSNSGNTATLTISRVEAGDEADYYCQVWDSRSDHLWVFGGGTKLTVLG
(SEQ ID NO: 272)

Mouse mIL-2
APTSSSTSSSTAEAQQQQQQQQQQQQHLEQLLMDLQELLSRMENYRNLKLPRMLTFKF
YLPKQATELKDLQCLEDELGPLRHVLDLTQSKSFQLEDAENFISNIRVTVVKLKGSDNTF
ECQFDDESATVVDFLRRWIAFCQSIISTSPQ (SEQ ID NO: 273)

Mouse mIL2-A10m3
APTSSSTSSSTAEAQQQQQQQQQQQQHLEQLLMDLQELLSRMENYRNLKLPRMLTFKF
YLPKQATELKDLQCLEDELGPLRHVLDLTQSKSFQLEDAENFISNIRVTVVKLKGSDNTF
ECQFDDESATVVDFLRRWIAFCQSIISTSPQGGGGSGGGGSGGGGSGGGGSGGGGSEVQ
LVESGGGLIQPGRSLRLSCAASGITFDDAVMHWVRQAPGKGLEWVAGISSNSGYIGYAD
SVKGRFTISRDNAKNSLYLQMNRLRAEDTAVYYCVKGLYSNPRGGAFDIWGQGTMVT
VSSASTGGGGSGGGGSGGGGSVHSSYVLTQPPSVSVAPGQTATITCGGNNIGTKSVHWY
QQKPGQAPVLVVYADSDRPSGIPERVSGSNSGNTATLTISRVEAGDEADYYCQVWDSRS
DHLWVFGGGTKLTVLG (SEQ ID NO: 274)

Human hIL-7
DCDIEGKDGKQYESVLMVSIDQLLDSMKEIGSNCLNNEFNFFKRHICDANKEGMFLFRA
ARKLRQFLKMNSTGDFDLHLLKVSEGTTILLNCTGQVKGRKPAALGEAQPTKSLEENKS
LKEQKKLNDLCFLKRLLQEIKTCWNKILMGTKEH (SEQ ID NO: 275)

Human hIL-7-A10m3
DCDIEGKDGKQYESVLMVSIDQLLDSMKEIGSNCLNNEFNFFKRHICDANKEGMFLFRA
ARKLRQFLKMNSTGDFDLHLLKVSEGTTILLNCTGQVKGRKPAALGEAQPTKSLEENKS
LKEQKKLNDLCFLKRLLQEIKTCWNKILMGTKEHGGGGSGGGGSGGGGSGGGGSGGG
GSEVQLVESGGGLIQPGRSLRLSCAASGITFDDAVMHWVRQAPGKGLEWVAGISSNSG
YIGYADSVKGRFTISRDNAKNSLYLQMNRLRAEDTAVYYCVKGLYSNPRGGAFDIWGQ
GTMVTVSSASTGGGGSGGGGSGGGGSVHSSYVLTQPPSVSVAPGQTATITCGGNNIGTK
SVHWYQQKPGQAPVLVVYADSDRPSGIPERVSGSNSGNTATLTISRVEAGDEADYYCQ
VWDSRSDHLWVFGGGTKLTVLG (SEQ ID NO: 276)

Mouse mIL-7
ECHIKDKEGKAYESVLMISIDELDKMTGTDSNCPNNEPNFFRKHVCDDTKEAAFLNRAA
RKLKQFLKMNISEEFNVHLLTVSQGTQTLVNCTSKEEKNVKEQKKNDACFLKRLLREIK
TCWNKILKGSI (SEQ ID NO: 277)

Mouse mIL-7-A10m3
ECHIKDKEGKAYESVLMISIDELDKMTGTDSNCPNNEPNFFRKHVCDDTKEAAFLNRAA
RKLKQFLKMNISEEFNVHLLTVSQGTQTLVNCTSKEEKNVKEQKKNDACFLKRLLREIK
TCWNKILKGSIGGGGSGGGGSGGGGSGGGGSGGGGSEVQLVESGGGLIQPGRSLRLSCA
ASGITFDDAVMHWVRQAPGKGLEWVAGISSNSGYIGYADSVKGRFTISRDNAKNSLYL
QMNRLRAEDTAVYYCVKGLYSNPRGGAFDIWGQGTMVTVSSASTGGGGSGGGGSGG
GGSVHSSYVLTQPPSVSVAPGQTATITCGGNNIGTKSVHWYQQKPGQAPVLVVYADSD
RPSGIPERVSGSNSGNTATLTISRVEAGDEADYYCQVWDSRSDHLWVFGGGTKLTVLG
(SEQ ID NO: 278)

Human hIL-12sc

IWELKKDVYVVELDWYPDAPGEMVVLTCDTPEEDGITWTLDQSSEVLGSGKTLTI
QVKEFGDAGQYTCHKGGEVLSHSLLLLHKKEDGIWSTDILKDQKEPKNKTFLRCE
AKNYSGRFTCWWLTTISTDLTFSVKSSRGSSDPQGVTCGAATLSAERVRGDNKEYE
YSVECQEDSACPAAEESLPIEVMVDAVHKLKYENYTSSFFIRDIIKPDPPKNLQLKPL
KNSRQVEVSWEYPDTWSTPHSYFSLTFCVQVQGKSKREKKDRVFTDKTSATVICR
KNASISVRAQDRYYSSSWSEWASVPCSGGGGGGSRNLPVATPDPGMFPCLHHSQNLL
RAVSNMLQKARQTLEFYPCTSEEIDHEDITKDKTSTVEACLPLELTKNESCLNSRETSFIT
NGSCLASRKTSFMMALCLSSIYEDLKMYQVEFKTMNAKLLMDPKRQIFLDQNMLAVID
ELMQALNFNSETVPQKSSLEEPDFYKTKIKLCILLHAFRIRAVTIDRVTSYLNAS (SEQ
ID NO: 279)

Human hIL-12sc-A10m3

IWELKKDVYVVELDWYPDAPGEMVVLTCDTPEEDGITWTLDQSSEVLGSGKTLTI
QVKEFGDAGQYTCHKGGEVLSHSLLLLHKKEDGIWSTDILKDQKEPKNKTFLRCE
AKNYSGRFTCWWLTTISTDLTFSVKSSRGSSDPQGVTCGAATLSAERVRGDNKEYE
YSVECQEDSACPAAEESLPIEVMVDAVHKLKYENYTSSFFIRDIIKPDPPKNLQLKPL
KNSRQVEVSWEYPDTWSTPHSYFSLTFCVQVQGKSKREKKDRVFTDKTSATVICR
KNASISVRAQDRYYSSSWSEWASVPCSGGGGGGSRNLPVATPDPGMFPCLHHSQNLL
RAVSNMLQKARQTLEFYPCTSEEIDHEDITKDKTSTVEACLPLELTKNESCLNSRETSFIT
NGSCLASRKTSFMMALCLSSIYEDLKMYQVEFKTMNAKLLMDPKRQIFLDQNMLAVID
ELMQALNFNSETVPQKSSLEEPDFYKTKIKLCILLHAFRIRAVTIDRVTSYLNASGGGGSG
GGGSGGGGSGGGGSGGGGSEVQLVESGGGLIQPGRSLRLSCAASGITFDDAVMHWVRQ
APGKGLEWVAGISSNSGYIGYADSVKGRFTISRDNAKNSLYLQMNRLRAEDTAVYYCV
KGLYSNPRGGAFDIWGQGTMVTVSSASTGGGGSGGGGSGGGGSVHSSYVLTQPPSVSV
APGQTATITCGGNNIGTKSVHWYQQKPGQAPVLVVYADSDRPSGIPERVSGSNSGNTAT
LTISRVEAGDEADYYCQVWDSRSDHLWVFGGGTKLTVLG (SEQ ID NO: 280)

Human hIL-18-A10m3

YFGKLESKLSVIRNLNDQVLFIDQGNRPLFEDMTDSDCRDNAPRTIFIISMYKDSQPRGM
AVTISVKCEKISTLSCENKIISFKEMNPPDNIKDTKSDIIFFQRSVPGHDNKMQFESSSYEG
YFLACEKERDLFKLILKKEDELGDRSIMFTVQNED (SEQ ID NO: 281)

Human hIL-18-A10m3

YFGKLESKLSVIRNLNDQVLFIDQGNRPLFEDMTDSDCRDNAPRTIFIISMYKDSQPRGM
AVTISVKCEKISTLSCENKIISFKEMNPPDNIKDTKSDIIFFQRSVPGHDNKMQFESSSYEG
YFLACEKERDLFKLILKKEDELGDRSIMFTVQNEDGGGGSGGGGSGGGGSGGGGSGGG
GSEVQLVESGGGLIQPGRSLRLSCAASGITFDDAVMHWVRQAPGKGLEWVAGISSNSG
YIGYADSVKGRFTISRDNAKNSLYLQMNRLRAEDTAVYYCVKGLYSNPRGGAFDIWGQ
GTMVTVSSASTGGGGSGGGGSGGGGSVHSSYVLTQPPSVSVAPGQTATITCGGNNIGTK
SVHWYQQKPGQAPVLVVYADSDRPSGIPERVSGSNSGNTATLTISRVEAGDEADYYCQ
VWDSRSDHLWVFGGGTKLTVLG (SEQ ID NO: 282)

Mouse mIL-18-A10m3

NFGRLHCTTAVIRNINDQVLFVDKRQPVFEDMTDIDQSASEPQTRLIIYMYKDSEVRGLA
VTLSVKDSKMSTLSCKNKIISFEEMDPPENIDDIQSDLIFFQKRVPGHNKMEFESSLYEGH
FLACQKEDDAFKLILKKKDENGDKSVMFTLTNLHQSGGGGSGGGGSGGGGSGGGGSG
GGGSEVQLVESGGGLIQPGRSLRLSCAASGITFDDAVMHWVRQAPGKGLEWVAGISSN
SGYIGYADSVKGRFTISRDNAKNSLYLQMNRLRAEDTAVYYCVKGLYSNPRGGAFDIW
GQGTMVTVSSASTGGGGSGGGGSGGGGSVHSSYVLTQPPSVSVAPGQTATITCGGNNIG
TKSVHWYQQKPGQAPVLVVYADSDRPSGIPERVSGSNSGNTATLTISRVEAGDEADYY
CQVWDSRSDHLWVFGGGTKLTVLG (SEQ ID NO: 283)

Human hIL-21
QGQDRHMIRMRQLIDIVDQLKNYVNDLVPEFLPAPEDVETNCEWSAFSCFQKAQLKSA
NTGNNERIINVSIKKLKRKPPSTNAGRRQKHRLTCPSCDSYEKKPPKEFLERFKSLLQKMI
HQHLSSRTHGSEDS (SEQ ID NO: 284)

Human hIL-21-A10m3
QGQDRHMIRMRQLIDIVDQLKNYVNDLVPEFLPAPEDVETNCEWSAFSCFQKAQLKSA
NTGNNERIINVSIKKLKRKPPSTNAGRRQKHRLTCPSCDSYEKKPPKEFLERFKSLLQKMI
HQHLSSRTHGSEDSGGGGSGGGGSGGGGSGGGGSGGGGSEVQLVESGGGLIQPGRSLR
LSCAASGITFDDAVMHWVRQAPGKGLEWVAGISSNSGYIGYADSVKGRFTISRDNAKN
SLYLQMNRLRAEDTAVYYCVKGLYSNPRGGAFDIWGQGTMVTVSSASTGGGGSGGGG
SGGGGSVHSSYVLTQPPSVSVAPGQTATITCGGNNIGTKSVHWYQQKPGQAPVLVVYA
DSDRPSGIPERVSGSNSGNTATLTISRVEAGDEADYYCQVWDSRSDHLWVFGGGTKLTV
LG (SEQ ID NO: 285)

Mouse mIL-21
PDRLLIRLRHLIDIVEQLKIYENDLDPELLSAPQDVKGHCEHAAFACFQKAKLKPSNPGN
NKTFIIDLVAQLRRRLPARRGGKKQKHIAKCPSCDSYEKRTPKEFLERLKWLLQKMIHQ
HLS (SEQ ID NO: 286)

Mouse mIL-21-A10m3
PDRLLIRLRHLIDIVEQLKIYENDLDPELLSAPQDVKGHCEHAAFACFQKAKLKPSNPGN
NKTFIIDLVAQLRRRLPARRGGKKQKHIAKCPSCDSYEKRTPKEFLERLKWLLQKMIHQ
HLSGGGGSGGGGSGGGGSGGGGSGGGGSEVQLVESGGGLIQPGRSLRLSCAASGITFDD
AVMHWVRQAPGKGLEWVAGISSNSGYIGYADSVKGRFTISRDNAKNSLYLQMNRLRA
EDTAVYYCVKGLYSNPRGGAFDIWGQGTMVTVSSASTGGGGSGGGGSGGGGSVHSSY
VLTQPPSVSVAPGQTATITCGGNNIGTKSVHWYQQKPGQAPVLVVYADSDRPSGIPERV
SGSNSGNTATLTISRVEAGDEADYYCQVWDSRSDHLWVFGGGTKLTVLG (SEQ ID
NO: 287)

Human hIL-27sc
RKGPPAALTLPRVQCRASRYPIAVDCSWTLPPAPNSTSPVSFIATYRLGMAARGHSWPC
LQQTPTSTSCTITDVQLFSMAPYVLNVTAVHPWGSSSSFVPFITEHIIKPDPPEGVRLSPLA
ERQLQVQWEPPGSWPFPEIFSLKYWIRYKRQGAARFHRVGPIEATSFILRAVRPRARYYV
QVAAQDLTDYGELSDWSLPATATMSLGK (SEQ ID NO: 288)

Human hIL-27sc-A10m3
RKGPPAALTLPRVQCRASRYPIAVDCSWTLPPAPNSTSPVSFIATYRLGMAARGHSWPC
LQQTPTSTSCTITDVQLFSMAPYVLNVTAVHPWGSSSSFVPFITEHIIKPDPPEGVRLSPLA
ERQLQVQWEPPGSWPFPEIFSLKYWIRYKRQGAARFHRVGPIEATSFILRAVRPRARYYV
QVAAQDLTDYGELSDWSLPATATMSLGK<u>GGGGSGGGGSGGGGS</u>FPRPPGRPQLSLQEL
RREFTVSLHLARKLLSEVRGQAHRFAESHLPGVNLYLLPLGEQLPDVSLTFQAWRRLSD
PERLCFISTTLQPFHAPLGGLGTQGRWTNMERMQLWAMRLDLRDLQRHLRFQVLAAGF
NLPEEEEEEEEEEEERKGLLPGALGSALQGPAQVSWPQLLSTYRLLHSLELVLSRAVRE
LLLLSKAGHSVWPLGFPTLSPQP<u>GGGGSGGGGSGGGGSGGGGSGGGGS</u>EVQLVESGGG
LIQPGRSLRLSCAASGITFDDAVMHWVRQAPGKGLEWVAGISSNSGYIGYADSVKGRFT
ISRDNAKNSLYLQMNRLRAEDTAVYYCVKGLYSNPRGGAFDIWGQGTMVTVSSASTG
GGGSGGGGSGGGGSVHSSYVLTQPPSVSVAPGQTATITCGGNNIGTKSVHWYQQKPGQ
APVLVVYADSDRPSGIPERVSGSNSGNTATLTISRVEAGDEADYYCQVWDSRSDHLWV
FGGGTKLTVLG (SEQ ID NO: 289)

Mouse mIL-27sc
YTETALVALSQPRVQCHASRYPVAVDCSWTPLQAPNSTRSTSFIATYRLGVATQQQSQP
CLQRSPQASRCTIPDVHLFSTVPYMLNVTAVHPGGASSSLLAFVAERIIKPDPPEGVRLRT
AGQRLQVLWHPPASWPFPDIFSLKYRLRYRRGASHFRQVGPIEATTFTLRNSKPHAKY
CIQVSAQDLTDYGKPSDWSLPGQVESAPHKP (SEQ ID NO: 290)

Mouse mIL-27sc-A10m3
YTETALVALSQPRVQCHASRYPVAVDCSWTPLQAPNSTRSTSFIATYRLGVATQQQSQP
CLQRSPQASRCTIPDVHLFSTVPYMLNVTAVHPGGASSSLLAFVAERIIKPDPPEGVRLRT
AGQRLQVLWHPPASWPFPDIFSLKYRLRYRRGASHFRQVGPIEATTFTLRNSKPHAKY
CIQVSAQDLTDYGKPSDWSLPGQVESAPHKP<u>GGGGSGGGGSGGGGS</u>FPTDPLSLQELRR
EFTVSLYLARKLLSEVQGYVHSFAESRLPGVNLDLLPLGYHLPNVSLTFQAWHHLSDSE
RLCFLATTLRPFPAMLGGLGTQGTWTSSEREQLWAMRLDLRDLHRHLRFQVLAAGFKC
SKEEEDKEEEEEEEEEEKKLPLGALGGPNQVSSQVSWPQLLYTYQLLHSLELVLSRAVR
DLLLLSLPRRPGSAWD<u>GGGGSGGGGSGGGGSGGGGSGGGGS</u>EVQLVESGGGLIQPGR
SLRLSCAASGITFDDAVMHWVRQAPGKGLEWVAGISSNSGYIGYADSVKGRFTISRDNA
KNSLYLQMNRLRAEDTAVYYCVKGLYSNPRGGAFDIWGQGTMVTVSSASTGGGGSGG
GGSGGGGSVHSSYVLTQPPSVSVAPGQTATITCGGNNIGTKSVHWYQQKPGQAPVLVV
YADSDRPSGIPERVSGSNSGNTATLTISRVEAGDEADYYCQVWDSRSDHLWVFGGGTK
LTVLG (SEQ ID NO: 291)

FIG. 49G

GM-CSF-ABD

Human GM-CSF
MWLQSLLLLGTVACSISAPARSPSPSTQPWEHVNAIQEARRLLNLSRDTAAEMNETVEVI
SEMFDLQEPTCLQTRLELYKQGLRGSLTKLKGPLTMMASHYKQHCPPTPETSCATQIITF
ESFKENLKDFLLVIPFDCWEPVQE (SEQ ID NO: 292)

Human GM-CSF-A10m3
MWLQSLLLLGTVACSISAPARSPSPSTQPWEHVNAIQEARRLLNLSRDTAAEMNETVEVI
SEMFDLQEPTCLQTRLELYKQGLRGSLTKLKGPLTMMASHYKQHCPPTPETSCATQIITF
ESFKENLKDFLLVIPFDCWEPVQEGGGGSGGGGSGGGGSGGGGSGGGGSEVQLVESGG
GLIQPGRSLRLSCAASGITFDDAVMHWVRQAPGKGLEWVAGISSNSGYIGYADSVKGRF
TISRDNAKNSLYLQMNRLRAEDTAVYYCVKGLYSNPRGGAFDIWGQGTMVTVSSASTG
GGGSGGGGSGGGGSVHSSYVLTQPPSVSVAPGQTATITCGGNNIGTKSVHWYQQKPGQ
APVLVVYADSDRPSGIPERVSGSNSGNTATLTISRVEAGDEADYYCQVWDSRSDHLWV
FGGGTKLTVLG (SEQ ID NO: 293)

IFN-α1

Human IFN-α
CDLPETHSLDNRRTLMLLAQMSRISPSSCLMDRHDFGFPQEEFDGNQFQKAPAISVLHEL
IQQIFNLFTTKDSSAAWDEDLLDKFCTELYQQLNDLEACVMQEERVGETPLMNADSILA
VKKYFRRITLYLTEKKYSPCAWEVVRAEIMRSLSLSTNLQERLRRKE (SEQ ID NO: 294)

Human IFN-α-A10m3
CDLPETHSLDNRRTLMLLAQMSRISPSSCLMDRHDFGFPQEEFDGNQFQKAPAISVLHEL
IQQIFNLFTTKDSSAAWDEDLLDKFCTELYQQLNDLEACVMQEERVGETPLMNADSILA
VKKYFRRITLYLTEKKYSPCAWEVVRAEIMRSLSLSTNLQERLRRKEGGGGSGGGGSGG
GGSGGGGSGGGGSEVQLVESGGGLIQPGRSLRLSCAASGITFDDAVMHWVRQAPGKGL
EWVAGISSNSGYIGYADSVKGRFTISRDNAKNSLYLQMNRLRAEDTAVYYCVKGLYSN
PRGGAFDIWGQGTMVTVSSASTGGGGSGGGGSGGGGSVHSSYVLTQPPSVSVAPGQTA
TITCGGNNIGTKSVHWYQQKPGQAPVLVVYADSDRPSGIPERVSGSNSGNTATLTISRVE
AGDEADYYCQVWDSRSDHLWVFGGGTKLTVLG (SEQ ID NO: 295)

FIG. 50

Anti-PD-L1 10D12
Variable Heavy Domain
VQLVESGGGLVKPGGSLRLSCAAS<u>GFTFSDYY</u>MSWIRQAPGKGLEWVSY<u>ISSSGSTI</u>YY
ADSVKGRFTISRDNAKNSLYLQMNSLRAEDTAVYYC<u>ASRSSMAQH</u>WGQGTLVTVSSAS
T (SEQ ID NO: 296)

vhCDR1: GFTFSDYY (SEQ ID NO: 297)
vhCDR2: ISSSGSTI (SEQ ID NO: 298)
vhCDR3: ASRSSMAQH (SEQ ID NO: 299)

Variable Light Domain
SNFMLTQPHSVSESPGKTVTISCTRS<u>SGSIASYY</u>VQWYQQRPGSAPTTVIY<u>EDN</u>QRPSGVP
DRFSGSIDSSSNSASLTISGLKTEDEADYYC<u>QSYDSNNQV</u>FGGGTKVTVLG (SEQ ID
NO: 300)

vlCDR1: SGSIASYY (SEQ ID NO: 301)
vlCDR2: EDN (SEQ ID NO: 302)
vlCDR3: QSYDSNNQV (SEQ ID NO: 303)

scFv
QVQLVESGGGLVKPGGSLRLSCAASGFTFSDYYMSWIRQAPGKGLEWVSYISSSGSTIY
YADSVKGRFTISRDNAKNSLYLQMNSLRAEDTAVYYCASRSSMAQHWGQGTLVTVSS
ASTGGGGSGGGGSGGGGSNFMLTQPHSVSESPGKTVTISCTRSSGSIASYYVQWYQQRP
GSAPTTVIYEDNQRPSGVPDRFSGSIDSSSNSASLTISGLKTEDEADYYCQSYDSNNQVFG
GGTKVTVLG (SEQ ID NO: 304)

FIG. 51A

A-linker-ABD-linker-B

| A | B |
| --- | --- |
| IL-2 | IL-12 |
| IL-2 | IL-15 |
| IL-7 | IL-12 |
| IL-7 | IL-15 |
| IL-12 | IL-21 |
| IL-12 | IL-18 |
| IL-15 | IL-12 |
| IL-18 | GM-CSF |
| IL-21 | IL-15 |
| GM-CSF | IL-12 |
| GM-CSF | IL-21 |
| IFN-α | IL-15 | linker-ABD-linker

GGGGSGGGGSGGGGSGGGGSGGGGSEVQLVESGGGLIQPGRSLRLSCAASGITFDDAVMHWVRQAPGKGLEWVAGISSNSGYIGYADSVKGRFTISRDNAKNSLYLQMNRLRAEDTAVYYCVKGLYSNPRGGAFDIWGQGTMVTVSSASTGGGGSGGGGSGGGGSVHSSYVLTQPPSVSVAPGQTATITCGGNNIGTKSVHWYQQKPGQAPVLVVYADSDRPSGIPERVSGSNSGNTATLTISRVEAGDEADYYCQVWDSRSDHLWVFGGGTKLTVLGGGGSGGGGSGGGGSGGGGSGGGGS (SEQ ID NO: 305)

FIG. 51B

A-linker-ABD-linker-B

| A | B |
|---|---|
| Anti-TGF-β scFv* | Anti-TGF-β scFv |
| Anti-TGF-β scFv | Anti-PD-L1 scFv** |
| Anti-TGF-β scFv | IL-15 |
| Anti-TGF-β scFv | IL-12 |
| Anti-PD-L1 scFv | Anti-PD-L1 scFv |
| Anti-PD-L1 scFv | IL-12 |
| Anti-PD-L1 scFv | IL-15 |
| Anti-TNF scFv | Anti-IL-1 scFv |
| Anti-TNF scFv | Anti-IL-6 scFv |
| Anti-TNF scFv | Anti-IL-17 scFv |
| Anti-TNF scFv | Anti-IL-23 scFv |

*Anti-TGF-β scFv, *e.g.*, 4D9 scFv

**Anti-PD-L1 scFv, *e.g.*, 10D12 scFv linker-ABD-linker

GGGGSGGGGSGGGGSGGGGSGGGGSEVQLVESGGGLIQPGRSLRLSCAASGITF
DDAVMHWVRQAPGKGLEWVAGISSNSGYIGYADSVKGRFTISRDNAKNSLYLQ
MNRLRAEDTAVYYCVKGLYSNPRGGAFDIWGQGTMVTVSSASTGGGGSGGGG
SGGGGSVHSSYVLTQPPSVSVAPGQTATITCGGNNIGTKSVHWYQQKPGQAPVL
VVYADSDRPSGIPERVSGSNSGNTATLTISRVEAGDEADYYCQVWDSRSDHLWV
FGGGTKLTVLGGGGSGGGGSGGGGSGGGGSGGGGS (SEQ ID NO: 306)

ALBUMIN BINDING DOMAIN FUSION PROTEINS

CROSS-REFERENCE TO RELATED APPLICATIONS

This application is a continuation of U.S. patent application Ser. No. 15/932,387 filed Feb. 20, 2018 which claims priority under 35 U.S.C. § 119(e) to U.S. Provisional Patent Application No. 62/459,975 filed Feb. 16, 2017 and U.S. Provisional Patent Application No. 62/459,981 filed Feb. 16, 2017 which are herein incorporated by reference in their entirety for all purposes.

REFERENCE TO SEQUENCE LISTING

The Sequence Listing text copy submitted herewith via EFS-Web was created on May 4, 2021, is entitled 1160765007US01_ST25.txt, is 286 kilobytes in size and is herein incorporated by reference in its entirety.

BACKGROUND

While biologics have been useful in the treatment of many diseases, including cancers, the short circulatory half-life of such molecules represent a major obstacle.

Biologics are useful for the treatment of cancers in a variety of ways. Cytokine-based therapies can work directly on cancer cells by interfering with how such cells grow and multiply. Cytokines may also stimulate the immune system, by encouraging the growth of killer T cells and other cells that attack cancer cells. Further, cytokines can promote cancer cells to send out chemicals that attract immune system cells. See, e.g., Dranoff, Nature Reviews Cancer 4: 11-22 (2004); and Zhang et al., Proc Natl Acad Sci U.S.A. 106(18): 7513-7518 (2009). Antibodies are desirable as therapeutics due to their ability to recognize targets with both specificity and high affinity. Monoclonal antibody based therapies, including those that target tumor surface antigens and inhibitory signals that limit T-cell activation, have been a standard component of cancer therapeutics for over 20 years. See, e.g., Weiner, Nat Rev Cancer 15(6): 361-370 (2015).

Short circulatory half-life represents a major obstacle for many biologics. See, e.g., Perdreau et al., European Cytokine Network 21: 297-307 (2010). Such short-acting therapeutics require frequent dosing profiles that can reduce applicability to the clinic, particular for chronic conditions. Long serum half-life is desirable as it would decrease the need for repetitive injections of the molecule to achieve a therapeutically relevant serum concentration. Methods of extending the half-life of therapeutic proteins include PEGylation, fusion to human serum albumin (HSA), fusion to the constant fragment (Fc) of a human immunoglobulin IgG, and fusion to non-structured polypeptides such as XTEN. See, e.g., Stohl, BioDrugs 29(4): 215-239 (2015). Half-life extension technologies enable new and improved biologic therapies that reduce the cost and burden of frequent dosing. Thus, there remains a continued need for novel reagents and methods useful for extending the half-lives of protein and peptide based therapeutics.

SUMMARY

Compositions that include albumin binding domain (ABD) are provided herein. As described herein, biologics that include the subject albumin binding domains (i.e., albumin binding domain fusion proteins) advantageously exhibit extended half-lives and better in vivo pharmacokinetics as compared to biologics without the ABD.

In one aspect, provided herein is a composition that includes an albumin binding domain (ABD). The ABD includes: a) a variable heavy chain that includes a vhCDR1, a vhCDR2 and a vhCDR3 of any one of the variable heavy chains depicted in FIG. 2; and b) a variable light chain that includes a vlCDR1, a vlCDR2 and a vlCDR3 of any one of the variable light chains depicted in FIG. 2.

In some embodiments the vhCDR1 includes a vhCDR1 sequence, the vhCDR2 comprises a vhCDR2 sequence, and the vhCDR3 includes a vhCDR3 sequence according to any of the vhCDR1, vhCDR2, and vhCDR3 sequences depicted in FIG. 2. In one embodiment, the variable heavy chain includes the sequence of any one of the variable heavy chains depicted in FIG. 2. In some embodiments, the vlCDR1 includes a vlCDR1 sequence, the vlCDR2 includes a vlCDR2 sequence, and the vlCDR3 includes a vlCDR3 sequence according to any of the vlCDR1, vlCDR2, and vhCDR3 sequences depicted in FIG. 2. In one embodiment, the variable light chain includes the sequence of any one of the variable light chains depicted in FIG. 2. In an exemplary embodiment, the albumin binding domain comprises the variable heavy chain and variable light chain of A10m3 (FIG. 2D).

In another aspect, provided herein is a composition that includes a variant IL-15. The variant IL-15 includes one or more amino acid substitutions selected from the group consisting of K86A, K86R, N112A, N112S, N112Q, K86A/N112A, K86R/N112A, K86A/N112S, K86R/N112S, K86A/N112Q, K86R/N112Q, K86A/N112A/N79A, K86R/N112A/N79A, K86A/N112A/N79D, K86R/N112A/N79D, K86A/N112A/N79Q, K86R/N112A/N79Q, K86A/N112A/N71D, K86R/N112A/N71D, K86A/N112A/N71Q, K86R/N112A/N71Q, K86A/N112A/N71D/N79A, K86A/N112A/N71D/N79D, K86A/N112A/N71Q/N79A, K86A/N112A/N71Q/N79D, K86R/N112A/N71D/N79A, K86R/N112A/N71D/N79D, K86R/N112A/N71D/N79Q, K86R/N112A/N71Q/N79A, K86R/N112A/N71Q/N79D, and K86R/N112A/N71Q/N79Q, as compared o a parental IL-15.

In some embodiments, the variant IL-15 includes an amino acid sequence of any one of the variant IL-15s depicted in FIG. 3. In certain embodiments, the variant IL-15 further includes an IL-15 receptor alpha (IL-15Ra) attached to said IL-15.

In one aspect, provided herein is an albumin binding domain (ABD) fusion protein that includes an ABD attached to a fusion partner. The ABD includes a variable heavy chain that includes a vhCDR1, a vhCDR2 and a vhCDR3 of any one of the variable heavy chains depicted in FIG. 2, and a variable light chain that includes a vlCDR1, a vlCDR2 and a vlCDR3 of any one of the variable light chains depicted in FIG. 2.

In some embodiments, the vhCDR1 includes a vhCDR1 sequence, the vhCDR2 includes a vhCDR2 sequence, and the vhCDR3 includes a vhCDR3 sequence according to any of the vhCDR1, vhCDR2, and vhCDR3 sequences depicted in FIG. 2. In some embodiments, the variable heavy chain includes the sequence of any one of the variable heavy chain sequences depicted in FIG. 2.

In certain embodiments, the vlCDR1 includes a vlCDR1 sequence, the vlCDR2 includes a vlCDR2 sequence, and the vlCDR3 includes a vlCDR3 sequence according to any of the vlCDR1, vlCDR2, and vhCDR3 sequences depicted in FIG. 2. In certain embodiments, the variable light chain includes the sequence of any one of the variable light chain sequences depicted in FIG. 2.

In an exemplary embodiment, the variable heavy chain and the variable light chain include the variable heavy chain and variable light chain of A10m3, respectively (FIG. 2D).

In some embodiments, the fusion partner is a cytokine. In certain embodiments, the cytokine is selected from: IL-2, IL-7, IL-12, IL-15, IL-18, IL-21, GM-CSF and IFN-α.

In certain embodiments, the fusion partner is a binding moiety. In some embodiments, the binding moiety is an scFv that includes an scFv variable heavy chain and an scFv variable light chain. In some embodiments, the scFv is selected from: an anti-TGFβ scFv, an anti-PD-L1 scFv, and an anti-TNF scFv. In some embodiments, the scFv is an anti-interleukin scFv. In exemplary embodiments, the scFv is an anti-IL-1, IL-6, IL-8, IL-17(A-F) or IL-23 scFv.

In some embodiments, the ABD is attached to said fusion partner by a linker. In an exemplary embodiment, the linker is $(GGGGS)_x$ [SEQ ID NO: 307], wherein x is an integer from 1-10

In another aspect, provided herein is an IL15-albumin binding domain (ABD) fusion protein according to the formula (IL-15)-L-(ABD). The ABD includes a variable heavy chain that includes a vhCDR1, a vhCDR2 and a vhCDR3 of any one of the variable heavy chains depicted in FIG. 2, and a variable light chain that includes a vlCDR1, a vlCDR2 and a vlCDR3 of any one of the variable light chains depicted in FIG. 2, and L is a linker.

In some embodiments, the vhCDR1 includes a vhCDR1 sequence, the vhCDR2 includes a vhCDR2 sequence, and the vhCDR3 includes a vhCDR3 sequence according to any of the vhCDR1, vhCDR2, and vhCDR3 sequences depicted in FIG. 2. In some embodiments, the variable heavy chain includes the sequence of any one of the variable heavy chain sequences depicted in FIG. 2.

In certain embodiments, the vlCDR1 includes a vlCDR1 sequence, the vlCDR2 includes a vlCDR2 sequence, and the vlCDR3 includes a vlCDR3 sequence according to any of the vlCDR1, vlCDR2, and vhCDR3 sequences depicted in FIG. 2. In certain embodiments, the variable light chain includes the sequence of any one of the variable light chain sequences depicted in FIG. 2.

In an exemplary embodiment, the variable heavy chain and the variable light chain include the variable heavy chain and variable light chain of A10m3, respectively (FIG. 2D).

An IL15-ABD fusion protein, wherein said IL-15 is a variant IL-15 comprising one or more amino acid substitutions selected from the group consisting of K86A, K86R, N112A, N112S, N112Q, K86A/N112A, K86R/N112A, K86A/N112S, K86R/N112S, K86A/N112Q, K86R/N112Q, K86A/N112A/N79A, K86R/N112A/N79A, K86A/N112A/N79D, K86R/N112A/N79D, K86A/N112A/N79Q, K86R/N112A/N79Q, K86A/N112A/N71D, K86R/N112A/N71D, K86A/N112A/N71Q, K86R/N112A/N71Q, K86A/N112A/N71D/N79A, K86A/N112A/N71D/N79D, K86A/N112A/N71Q/N79A, K86A/N112A/N71Q/N79D, K86R/N112A/N71D/N79A, K86R/N112A/N71D/N79D, K86R/N112A/N71D/N79Q, K86R/N112A/N71Q/N79A, K86R/N112A/N71Q/N79D, and K86R/N112A/N71Q/N79Q, as compared to a parental IL-15. In some embodiments, the variant IL-15 includes an amino acid sequence of any one of the variant IL-15s depicted in FIG. 3. In an exemplary embodiment, the variant IL-15 includes the amino acid sequence of IL15 K86R/N112A.

In certain embodiments, the IL-15 is a wild-type IL-15. In some embodiments, the IL-15 comprises a wild-type IL-15 attached to a IL-15 receptor alpha (IL-15Rα).

In certain embodiments, the linker is selected from any of the linkers depicted in FIG. 48. In some embodiments, the linker is $(GGGGS)_x$ [SEQ ID NO: 307], wherein x is an integer from 1-10.

In one embodiment, the IL15-ABD fusion protein has an amino acid sequence according to any one of the amino acid sequences depicted in FIG. 4.

In another aspect, provided herein is an IL12-albumin binding domain (ABD) fusion protein according to the formula (IL-12)-L-(ABD). The ABD includes a variable heavy chain that includes a vhCDR1, a vhCDR2 and a vhCDR3 of any one of the variable heavy chains depicted in FIG. 2, and a variable light chain that includes a vlCDR1, a vlCDR2 and a vlCDR3 of any one of the variable light chains depicted in FIG. 2, and L is a linker.

In some embodiments, the vhCDR1 includes a vhCDR1 sequence, the vhCDR2 includes a vhCDR2 sequence, and the vhCDR3 includes a vhCDR3 sequence according to any of the vhCDR1, vhCDR2, and vhCDR3 sequences depicted in FIG. 2. In some embodiments, the variable heavy chain includes the sequence of any one of the variable heavy chain sequences depicted in FIG. 2.

In certain embodiments, the vlCDR1 includes a vlCDR1 sequence, the vlCDR2 includes a vlCDR2 sequence, and the vlCDR3 includes a vlCDR3 sequence according to any of the vlCDR1, vlCDR2, and vhCDR3 sequences depicted in FIG. 2. In certain embodiments, the variable light chain includes the sequence of any one of the variable light chain sequences depicted in FIG. 2.

In an exemplary embodiment, the variable heavy chain and the variable light chain include the variable heavy chain and variable light chain of A10m3, respectively (FIG. 2D).

In one embodiment, the IL-12 is a single chain IL-12 that includes a p35 subunit, a p40 subunit and an IL-12 linker, and the IL-12 linker covalently attaches the p35 subunit to the p40 subunit. In certain embodiments, the linker is selected from any of the linkers depicted in FIG. 48. In an exemplary embodiment, the linker is $(GGGGS)_x$ [SEQ ID NO: 307], where x is an integer from 1-10.

In an exemplary embodiment, the IL12-ABD fusion protein includes an amino acid sequence according to any one of the amino acid sequences of FIG. 20.

In another aspect, provided herein is n albumin binding domain (ABD) fusion protein having a formula, from N-terminus to C-terminus, selected from: a) (IL-12)-L1-(ABD)-L2-(IL-15); and b) (IL-15)-L1-(ABD)-L2-(IL-12). The ABD includes a variable heavy chain that includes a vhCDR1, a vhCDR2 and a vhCDR3 of any one of the variable heavy chains depicted in FIG. 2, and a variable light chain that includes a vlCDR1, a vlCDR2 and a vlCDR3 of any one of the variable light chains depicted in FIG. 2, and L1 and L2 are a first and second linker, respectively.

In some embodiments, the vhCDR1 includes a vhCDR1 sequence, the vhCDR2 includes a vhCDR2 sequence, and the vhCDR3 includes a vhCDR3 sequence according to any of the vhCDR1, vhCDR2, and vhCDR3 sequences depicted in FIG. 2. In some embodiments, the variable heavy chain includes the sequence of any one of the variable heavy chain sequences depicted in FIG. 2.

In certain embodiments, the vlCDR1 includes a vlCDR1 sequence, the vlCDR2 includes a vlCDR2 sequence, and the vlCDR3 includes a vlCDR3 sequence according to any of the vlCDR1, vlCDR2, and vhCDR3 sequences depicted in FIG. 2. In certain embodiments, the variable light chain includes the sequence of any one of the variable light chain sequences depicted in FIG. 2.

In an exemplary embodiment, the variable heavy chain and the variable light chain include the variable heavy chain and variable light chain of A10m3, respectively (FIG. 2D).

In some embodiment, the IL-15 includes a wild-type IL-15 polypeptide. In certain embodiments, the wild-type IL-15 is attached to an IL-15 receptor alpha (IL-15Rα).

In one embodiment, the IL-15 is a variant IL-15 that includes one or more amino acid substitutions selected from: K86A, K86R, N112A, N112S, N112Q, K86A/N112A, K86R/N112A, K86A/N112S, K86R/N112S, K86A/N112Q, K86R/N112Q, K86A/N112A/N79A, K86R/N112A/N79A, K86A/N112A/N79D, K86R/N112A/N79D, K86A/N112A/N79Q, K86R/N112A/N79Q, K86A/N112A/N71D, K86R/N112A/N71D, K86A/N112A/N71Q, K86R/N112A/N71Q, K86A/N112A/N71D/N79A, K86A/N112A/N71D/N79D, K86A/N112A/N71Q/N79A, K86A/N112A/N71Q/N79D, K86R/N112A/N71D/N79A, K86R/N112A/N71D/N79D, K86R/N112A/N71D/N79Q, K86R/N112A/N71Q/N79A, K86R/N112A/N71Q/N79D, and K86R/N112A/N71Q/N79Q, as compared to a parental IL-15. In one embodiment, the IL-15 includes an amino acid sequence according to any of the amino acid sequences depicted in FIG. 3.

In certain embodiments, the IL-12 is a single chain IL-12 that includes a p35 subunit, a p40 subunit and an IL-12 linker, and where the IL-12 linker attaches the p35 subunit to the p40 subunit.

In some embodiments, the first linker and second linker are each independently selected from any of the linkers depicted in FIG. 48. In an exemplary embodiment, the linker is (GGGGS)$_x$ [SEQ ID NO: 307], where x is an integer from 1-10.

In another aspect, provided herein is an ABD fusion protein that includes an albumin binding domain (ABD), a cytokine, and a linker (L), according to the formula (cytokine)-L-(ABD). The ABD includes a variable heavy chain that includes a vhCDR1, a vhCDR2 and a vhCDR3 of any one of the variable heavy chains depicted in FIG. 2, and a variable light chain that includes a vlCDR1, a vlCDR2 and a vlCDR3 of any one of the variable light chains depicted in FIG. 2, and L is a linker. The cytokine is selected from: IL-2, IL-7, IL-12, IL-15, IL-18, IL-21, GM-CSF and IFN-α.

In some embodiments, the vhCDR1 includes a vhCDR1 sequence, the vhCDR2 includes a vhCDR2 sequence, and the vhCDR3 includes a vhCDR3 sequence according to any of the vhCDR1, vhCDR2, and vhCDR3 sequences depicted in FIG. 2. In some embodiments, the variable heavy chain includes the sequence of any one of the variable heavy chain sequences depicted in FIG. 2.

In certain embodiments, the vlCDR1 includes a vlCDR1 sequence, the vlCDR2 includes a vlCDR2 sequence, and the vlCDR3 includes a vlCDR3 sequence according to any of the vlCDR1, vlCDR2, and vhCDR3 sequences depicted in FIG. 2. In certain embodiments, the variable light chain includes the sequence of any one of the variable light chain sequences depicted in FIG. 2.

In an exemplary embodiment, the variable heavy chain and the variable light chain include the variable heavy chain and variable light chain of A10m3, respectively (FIG. 2D).

In some embodiments, the linker is selected from any of the linkers depicted in FIG. 48. In an exemplary embodiment, the linker is (GGGGS)$_x$ [SEQ ID NO: 307], where x is an integer from 1-10.

In another aspect, provided herein is an ABD fusion protein according to the formula: (FP1)-L1-(ABD)-L2-(FP2), where ABD is an albumin binding domain that includes a variable heavy chain and a variable light chain; where FP1 and FP2 are a first fusion protein and a second fusion protein, respectively; and where L1 and L2 are a first and second linker, respectively. The ABD includes a variable heavy chain that includes a vhCDR1, a vhCDR2 and a vhCDR3 of any one of the variable heavy chains depicted in FIG. 2, and a variable light chain that includes a vlCDR1, a vlCDR2 and a vlCDR3 of any one of the variable light chains depicted in FIG. 2.

In some embodiments, the vhCDR1 includes a vhCDR1 sequence, the vhCDR2 includes a vhCDR2 sequence, and the vhCDR3 includes a vhCDR3 sequence according to any of the vhCDR1, vhCDR2, and vhCDR3 sequences depicted in FIG. 2. In some embodiments, the variable heavy chain includes the sequence of any one of the variable heavy chain sequences depicted in FIG. 2.

In certain embodiments, the vlCDR1 includes a vlCDR1 sequence, the vlCDR2 includes a vlCDR2 sequence, and the vlCDR3 includes a vlCDR3 sequence according to any of the vlCDR1, vlCDR2, and vhCDR3 sequences depicted in FIG. 2. In certain embodiments, the variable light chain includes the sequence of any one of the variable light chain sequences depicted in FIG. 2.

In an exemplary embodiment, the variable heavy chain and the variable light chain include the variable heavy chain and variable light chain of A10m3, respectively (FIG. 2D).

In some embodiments, FP1 and FP2 are a first cytokine and a second cytokine respectively. In an exemplary embodiment, the first cytokine and said second cytokine are selected from IL-2 and IL-12; IL-7 and IL-15; IL-15 and IL-12; IL-18 and GM-CSF; IL-21 and IL-15; GM-CSF and IL-12; GM-CSF and IL-21; and IFN-α and IL-15.

In some embodiments, the first and second fusion partner are selected from: an anti-PD-L1 scFv and an IL-12; an anti-PD-L1 scFv and an IL-15; an anti-PD-L1 scFv and a anti-TGFβ scFv; a first anti-PD-L1 scFv and a second PD-L1 scFv; an anti-TGFβ scFv and an IL-12; an anti-TGFβ scFv and an IL-15; a anti-TGFβ scFv and a PD-L1 scFv; and a first anti-TGFβ scFv and a second anti-TGFβ scFv.

An ABD fusion protein, wherein FP1 and FP2 are a first binding moiety and a second binding moiety, respectively. In certain embodiments, the first binding moiety and the second binding moiety are each an scFv. In an exemplary embodiment, the first binding moiety and the second binding moiety are selected from: a TNF scFv and an IL-1 scFv; a TNF scFv and an IL-6 scFv; a TNF scFv and an IL-8 scFv; a TNF scFv and an IL-17 (isoforms A-F) scFv; TNF scFv and an IL-23 scFv; and a first TNF scFv and a second TNF scFv.

In some embodiments, the first linker and second linker are each independently selected from any of the linkers depicted in FIG. 48. In one embodiment, the first linker and second linker are each independently (GGGGS)$_x$ [SEQ ID NO: 307], where x is an integer from 1-10.

In another aspect, provided herein is an albumin binding domain (ABD) fusion protein that includes a TGFβ binding domain and an albumin binding domain. The albumin binding domain includes a ABD variable heavy chain and a ABD variable light chain having the amino acid sequences of any of the variable heavy chains and variable light chains in FIG. 2.

In an exemplary embodiment, the ABD variable heavy chain and said ABD variable light chain comprises the amino acid sequence of the variable heavy chain and variable light chain of A10m3.

In one embodiment, the TGFβ binding domain is an scFv that includes a variable heavy chain and a variable light chain of 4D9 (FIG. 40B). In some embodiments, the ABD further includes an IL-12, an IL-15, a PD-L1 binding domain, or a second TGFβ binding domain.

In another aspect, provided herein is an albumin binding domain (ABD) fusion protein that includes a PD-L1 binding domain and an albumin binding domain. The albumin binding domain includes a ABD variable heavy chain and a ABD variable light chain having the amino acid sequences of any of the variable heavy chains and variable light chains in FIG. 2.

In some embodiments, the ABD variable heavy chain and the ABD variable light chain comprises the amino acid sequence of the variable heavy chain and variable light chain of A10m3 (FIG. 2D). In certain embodiments, the PD-L1 binding domain is an scFv comprising a variable heavy chain and a variable light chain of 10D12 (FIG. 50).

In some embodiments, the ABD further includes an IL-12, an IL-15, a TGFβ binding domain, or a second PD-L1 binding domain.

In another aspect, provided herein is a nucleic acid that encodes any of the albumin binding domains, variant IL-15s or ABD fusion proteins described herein, host cells that include any such nucleic acids, and methods of making such ABDs, variant IL-15s or ABD fusion proteins.

In yet another aspect, provided herein is a method of inhibiting or reducing a tumor in a subject in need thereof, the method includes administering to the subject a ABD fusion protein.

BRIEF DESCRIPTION OF THE DRAWINGS

FIG. 1A-FIG. 1C illustrates several exemplary albumin binding domain fusion proteins disclosed herein, including fusion proteins where an albumin binding domain is attached to a cytokine (e.g., IL-12 or IL-15) and fusion proteins where an albumin bind domain is attached to 1) two cytokines; 2) two binding moieties (e.g., scFvs); 3) a binding moiety and a cytokine.

FIG. 2A-FIG. 2Z shows the sequences of exemplary albumin binding domains included in certain embodiments of the subject albumin binding domain fusion proteins described herein. Included in these figures are the variable heavy domain and variable light domain sequences, as well as particular vhCDR1-3 and vlCDR1-3 sequences.

FIG. 3 shows the sequences of exemplary IL-15 variants described herein.

FIG. 4 shows exemplary embodiments of the IL-15-ABD fusion proteins described herein. The IL-15-ABD fusion proteins depicted in FIG. 4 include A10m3 ABD.

FIG. 6A and FIG. 6B depicts the identification of the potential IL-15 ubiquitination sites that are putatively protected by IL-15 receptor alpha (IL-15Rα) binding to IL-15. (A) K86 in red is a putative ubiquitination site which is next to the IL-15Rα binding sites (marked by stars); (B) K86 is a hit for ubiquitination from UbPred, an online ubiquitination site database.

FIG. 7A and FIG. 7B provides schematic illustrations of various IL-15-ABD fusion proteins with improved stability described herein, including an IL-15-ABD with a IL-15Rα/IL15 "sushi domain" fusion partner (A) and IL-15-ABD fusion proteins that include IL-15 variant fusion partners having amino acid substitutions at putative ubiquitination site K86 (B).

FIG. 14 depicts the experimental set up of a study to assess the in vivo effects of IL-15 and IL-15-ABD on tumor growth in a B16-F10 mouse melanoma model.

FIG. 17 and FIG. 18 provide a summary of the effects of IL-15-ABD treatment on lymphocyte populations in spleens and tumors.

FIG. 20 depicts the sequences of exemplary IL-12-ABDs described herein: mIL-12sc-A10m3 and human IL-12sc-A10m3.

FIG. 23 depicts the experimental set up of a study to assess the in vivo effects of IL-12 and IL-12-ABD on tumor growth in a B16-F10 mouse melanoma model. Similar molar concentrations of IL-12 and IL-12 were used at three different concentrations. For example, 3 µg of IL-12 is the same molar concentration as 4.5 µg of IL-12-ABD, 10 µg of IL-12 is the same molar concentration as 15 µg of IL-12-ABD, and 20 µg of IL-12 is the same molar concentration as 30 µg of IL-12-ABD. The molecular weight of IL-12 is 70 kD and the molecular weight of IL-12-ABD is 107 kD.

FIG. 24A shows the results of tumor size assessments in IL-12 and IL-12-ABD groups, FIG. 24B shows IL-12 treatment groups separately and FIG. 24C shows IL-12-ABD treatment groups separately.

FIG. 31A-FIG. 31D further depicts the hematopoietic effects of IL-12-ABD and IL-12 in mice from the study depicted in FIG. 32 at 3 and 7 days.

FIG. 34 depicts the sequences of exemplary subject IL-15-ABD-IL-12 described herein: 1) hIL-15 (K86R/N112A)-A10m3-mIL-12sc; 2) mIL-12sc-A10m3-hIL-15 (K86R); and 3) mIL-12sc-A10m3-hIL-15 (K86R/N112A).

FIG. 36 depicts the sequences of additional exemplary subject IL-15-ABD-IL-12 described herein: 1) hIL-15 (K86R)-A10m3-hIL-12sc; 2) hIL-12sc-A10m3-hIL-15 (K86R); and 3) hIL-12sc-A10m3-hIL-15 (K86R/N112A).

FIG. 40A and FIG. 40B depict the sequences of two exemplary TGFβ binding domains described herein: 4H7 and 4D9, including variable heavy chain, variable light chain and scFv format sequences.

(FIG. 42A) Schematic representation of the loss of E-cadherin and induced expression of vimentin during EMT. (FIG. 44B) Mouse 4T1 cells were cultured in growth media supplemented with TGF-β1 alone or with 1D11 (panel 3) or anti-TGF-β1 scFv (panel 4), then fixed and stained with E-cadherin antibody (green) and vimentin antibody (purple). Nuclei were counterstained with DAPI (blue). Treatment with TGF-β1 induced loss of E-cadherin from cell-cell junctions and increased expression of vimentin. This effect is reversed by the addition of 1D11 or subject anti-TGF-β1 scFv described herein. FIG. 43 further shows that subject anti-TGF-β1 scFvs described herein block TGF-β1-mediated carcinoma cell migration.

FIG. 44A and FIG. 44B provides a summary of studies showing that subject anti-TGF-β1 scFvs described herein are capable of inhibiting TGF-β-mediated Smad2 phosphorylation in human (A) and mouse cells (B). In A, subject anti-TGF-β1 scFvs were capable of inhibiting human TGF-β1 mediated Smad2 phosphorylation in human cells in a dose dependent manner. In B, subject anti-TGF-β1 scFvs were capable of inhibiting mouse TGF-β1, -β2 and -β3 mediated Smad2 phosphorylation in mouse cells.

FIG. 45A depicts the sequences of exemplary TGF-β1 scFv-ABD constructs (4D9M-A6m and 4H7-A6m).

FIG. 48A and FIG. 48B depicts exemplary linkers that can be used with the subject fusion proteins. Such linkers can be used as scFv linkers for ABD variable heavy chain and variable light chains. Such linkers can also be used to attach the albumin binding domains described herein to IL-12 and IL-15 fusion partners or to connect components of IL-12 fusion partners (p35 and p40) or IL-15 fusion partners (IL-15 and IL-15Rα) to each other.

FIG. 49A-FIG. 49G provides the amino acid sequence of exemplary cytokines that can be included in the ABD fusion proteins described herein. Also depicted in FIGS. 49A-G are exemplary cytokine-ABD fusion proteins where the ABD is A10m3. Although such cytokines-ABD fusion proteins are depicted with A10m3 ABD, any ABD, including ABD described herein can be included in the cytokine-ABD fusion proteins.

FIG. 50 provides the amino sequence of an exemplary anti-PD-L1 binding domain, 10D12 that can be used with the ABD fusion proteins described herein. 10D12 binds to hPD-L1 at low pH and is crossreactive with mPD-L1. 10D12 does not bind to hPD-L2 or mPD-L2. Further, 10D12 blocks PD-1/PD-L1 interaction, as well as B71/PD-L1 interaction.

FIG. 51A and FIG. 51B depict several useful cytokine-ABD-cytokine (A) and binding moiety-ABD-cytokine/binding moiety (B) combinations. "A" and "B" in each combination can be switched to the opposite orientation. Also depicted in these figures is an linker-A10m3-linker backbone that can be included in the cytokine-ABD-cytokine and binding moiety-ABD-cytokine/binding moiety combinations. Although A10m3 ABD is depicted, any ABD, include any of those depicted herein (e.g., FIG. 2) can be used in such constructs.

DETAILED DESCRIPTION

A. Overview

Figure 5A:
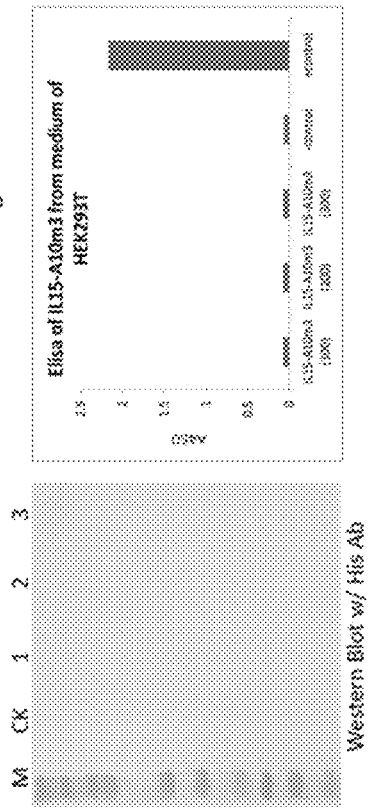
FIG. 5A and FIG. 5B depicts the results of studies showing that transcription does not account for the low expression of IL-15-A10m3 in HEK293T cells. Verification of IL15-A10m3 mRNA in transfected cells. A) Expression of IL15-A10m3 in HEK293 cannot be detected by Western blotting using either anti-His tag antibody (left), or by functional ELISA binding to MSA (right). M: Marker, CK: non-transfected culture medium as control, 1-3: media from 3 independently transfected cell cultures (100, 200 and 250=100, 200, 250 ug/ml Zeocin respectfully). 10 ug/ml E. coli produced IL15-A10m3 was served as the positive control. B) mRNA was prepared from 4 independently IL15-A10m3 transfected cells and RT-PCR was performed to quantify the mRNA level of IL15-A10m3 mRNA in comparison with that of a house-keeping gene, GAPDH. Lane1) untransfected cell control; 2-5) Transcription of IL15-A10m3 mRNA appears to be normal in all transfected cells; 6) GAPDH mRNA positive control.

Biologics, including cytokine and antibody based therapeutics are useful for the treatment of cancers.

Current and potential cytokine based therapeutics include those utilizing IL-2, IL-7, IL-12, IL-15, IL-18, IL-21 GM-CSF and IFN-α.

IL-12 is capable of mediating immune effector functions in a manner compatible to enhancing pro-inflammatory, endogenous anti-tumor immune response. (See, e.g., Boggio et al., *J Exp Med* 188:589-96 (1998); Cavallo et al., *Cancer Res* 59:414-21 (1999); Yu et al. *Int Immunol* 8:855-65 (1996); Nastala et al., *J Immunol* 153:1697:706 (1994); Brunda et al., *J Exp Med* 178: 1223-30 (1993). IL-12 is known to induce an inflammatory Th1 CD4+ T cell response as well as enhance CD8+ T cell cytotoxicity. Studies have also shown that T cell secretion of IFNγ mediated by IL-12 may reverse T cell anergy and confer effector T cell resistance to immune suppressive regulatory T cells. The ability of IL-12 to not only activate the adaptive and the innate immune systems, but also further modulate the otherwise immune-hostile tumor microenvironment makes IL-12 an ideal candidate for tumor immunotherapy.

IL-15 is capable of stimulating T cell proliferation inside tumors (see, e.g., Miecnik et al., *Sci Transl Med* 6(228): 228ra37 (2014) as well as extend the survivability of effector memory CD8+ T cells and is critical for the development of NK cells. Thus, it is believed that IL-15 can boost the potency of checkpoint inhibitors and other immunotherapies that harness T cells to attack cancer cells. IL-15 monomer, however, has a short half-life of less than 40 minutes in vivo. Modifications to IL-15 monomer can improve its in vivo pharmacokinetics in the treatment of cancers. These modifications have generally centered on improving the transpresentation of IL-15 with the alpha subunit of IL-15 receptor, IL-15Rα. Such modifications include: 1) preassociation of IL-15 and its soluble receptor a-subunit-Fc fusion to form IL-15: IL-15Rα-Fc complex (see, e.g., Rubinstein et al., *Proc Natl Acad Sci U.S.A.* 103:9166-71 (2006)); 2) expression of the hyperagonists IL-15-sIL-15Rα-sushi protein (see, e.g., Bessard et al., *Molecular cancer therapeutics* 8: 2736-45 (2009)); and 3) pre-association of human IL-15 mutant IL-15N72D with IL-15Rα-Fc sushi-Fc fusion complex (see, e.g., Zhu et al., *Journal of Immunology* 183: 3598-6007 (2009)).

Monoclonal antibody based therapies, including those that target tumor surface antigens and inhibitory signals that limit T-cell activation, have been a standard component of cancer therapeutics for over 20 years. See, e.g., Weiner, *Nat Rev Cancer* 15(6): 361-370 (2015).

Short circulatory half-life represents a major obstacle for many biologics, including cytokine and antibody based therapeutics. See, e.g., Herrington-Symes et al., *Advances in Bioscience and Biotechnology* 4: 689-698 (2013) and Perdreau et al., *European Cytokine Network* 21: 297-307 (2010). Such short-acting therapeutics require frequent dosing profiles that can reduce applicability to the clinic, particular for chronic conditions. Long serum half-life is desirable as it would decrease the need for repetitive injections of the molecule to achieve a therapeutically relevant serum concentration. Methods of extending the half-life of therapeutic proteins include PEGylation, fusion to human serum albumin (HSA), fusion to the constant fragment (Fc) of a human immunoglobulin IgG, and fusion to non-structured fusion proteins such as XTEN. See, e.g., Stohl, *BioDrugs* 29(4): 215-239 (2015). Half-life extension technologies enable improved or new biologic therapies that reduce the cost and burden of frequent dosing. Thus, there remains a continued need for novel reagents and methods that can extend the half-lives of protein and peptide based therapeutics.

Provided herein are novel albumin binding domain (ABD) fusion proteins, useful for extending the half-lives of biologics (e.g., interleukins and antibodies). Serum albumin possess a long half-life in the range of 2-4 weeks due to recycling through the neonatal Fc receptor (FcRn). Albumin is taken up by endothelial cells through macropinocytosis and binds to the FcRn in a pH-dependent manner in the acidic environment of the early endosome. Albumin-FcRn binding diverts albumin molecules from degradation in the lysosomal compartment and redirects the albumin molecules to the plasma membrane, where they are released back into the blood plasma due to the neutral pH.

Albumin binding domains (ABDs) described herein do not compete with FcRN for albumin binding and bind albumin at a pH range that allows for the ABD to also undergo FcRn-driven endosomal albumin recycling when bound to albumin. As such, biologics that include the subject albumin binding domain (ABD) are capable of evading lysosomal degradation using the albumin-FcRn pathway and, consequently, exhibit longer serum half-lives than counterparts lacking ABDs.

Moreover, such ABD containing therapeutics advantageously localize to tumors, which are known to contain high levels of serum albumin. Thus, such ABD containing therapeutics are particularly useful for the treatment of cancers.

B. Albumin Binding Domains

In one aspect, provided herein are compositions that include an albumin binding domain. As used herein, "serum albumin" refers to a member of a family of globular proteins produced by the liver that functions primarily as a carrier protein of steroids, fatty acids, and thyroid hormones in the blood. Serum albumin also plays a major role in stabilizing extracellular fluid volume by contributing to oncotic pressure of plasma, and includes, but is not limited to, human serum albumin (HSA, Genbank Accession numbers: NM_000477 and NP_000468) and mouse serum albumin (MSA, Genbank accession numbers: NM_009654 and NP_0033784). The structure of albumin is characterized by several long a helices and contains eleven distinct binding domains for hydrophobic compounds. In humans, serum albumin is encoded by the ALB gene.

Fusion proteins that include the subject albumin binding domain (ABD) can bind serum albumin (SA), which allows the fusion protein to be taken in by cells by macropinocytosis. In certain embodiments, the ABDs described herein bind at a pH range of about pH 5.5 to about pH 7.2. In the early endosome, such SA bound ABD fusion proteins bind to FcRn via SA at an acidic pH (e.g., pH 5.5), which in turn diverts the SA bound ABD fusion protein from the lysosome compartment of the cell and back to the plasma membrane. At the plasma membrane, the SA dissociates from FcRn due to the neutral pH (e.g., pH 7.1-7.5) and the SA and ABD fusion protein are released back into the bloodstream. As therapeutics that include the subject ABD are capable of binding to albumin at a pH range of about pH 5.5 to about pH 7.2, such therapeutics advantageously also undergo FcRn-driven endosomal albumin recycling and, thus, evade lysosomal degradation. Accordingly, therapeutics that include such ABDs advantageously exhibit longer serum half-lives than counterparts lacking ABDs. Such therapeutics are particular useful for the treatment of cancers, which are known to contain high levels of serum albumin.

In some embodiments, the albumin binding domain binds albumin at a site that does not interfere with SA binding to a neonatal Fc receptor (FcRn). By "FcRn" or "neonatal Fc Receptor" as used herein is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two fusion proteins, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin.

In some embodiments, the albumin binding domain described or exemplified herein preferably specifically binds to serum albumin (e.g., HSA) at an epitope on the serum albumin molecule that does not participate in the interaction of the serum albumin molecule with the FcRn. Binding of the SA binding moiety to the serum albumin molecule thus preferably does not substantially interfere with, inhibit, prevent, or otherwise reduce binding of the serum albumin molecule (e.g., HSA) with the FcRn. Preferably, the albumin binding domain does not compete with the FcRn for binding to the serum albumin molecule. Preferably, the albumin binding domain does not sterically inhibit binding of serum albumin to the FcRn. Preferably, the SA binding moiety does not change the conformation of the serum albumin molecule such that the albumin cannot interact with the FcRn.

In some embodiments, the albumin binding domain binds SA (e.g., HSA) at a pH of 5.0±0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0. 2.1, 2.2, 0.2.3, 0.2.4, 0.2.5, 0.2.6, 2.7, 2.8, 2.9, or 3.0. In some embodiments, the albumin binding domain binds SA at a range of pH of about pH 5.5-about pH 7.2. In some embodiments, the SA binding moiety binds SA at a pH of 5.5.

In certain embodiments, the albumin binding domain is a human serum albumin (HSA) binding domain. HSA binding domains include, but are not limited to, albumin binding domains that can bind to an HSA molecule such as a whole HSA molecule or a fragment of an HSA. In some embodiments, the HSA binding domain also binds mouse serum albumin. In some embodiments, the HSA binding domain also binds cyno monkey albumin. In certain embodiments, the HSA binding domain does not bind to bovine serum albumin (BSA).

Albumin binding domains provided herein can include a variable heavy chain alone or a variable heavy chain in association with a variable light chain. In some embodiments, the albumin binding domain includes a variable heavy chain. In certain embodiments, the variable heavy chain includes a vhCDR1, vhCDR2, and vhCDR3 (variable heavy chain Complementary Determining Regions 1-3). In certain embodiments, the antigen binding domain also includes a variable light chain. In certain embodiments, the variable light chain includes a vlCDR1, vlCDR2 and vlCDR3 (variable light chain Complementary Determining Regions 1-3).

In some embodiments the albumin binding domain includes a variable heavy chain that includes the vhCDR1, vhCDR2, and vhCDR3 of any of the variable heavy chains depicted in FIG. 2 In some embodiments, the albumin binding domain includes the vhCDR1, vhCDR2, and vhCDR3 of an A10m3 variable heavy chain, as shown in FIG. 2D. In certain embodiments, the albumin binding domain includes the vhCDR1, vhCDR2, and vhCDR3 of A10m3 as shown in FIG. 2D.

In certain embodiments the albumin binding domain also includes a variable light chain. In an exemplary embodiment, the albumin binding domain includes a variable light chain that includes the vlCDR1, vlCDR2, and vlCDR3 of any of the variable light chains depicted in FIG. 2. In some embodiments, the albumin binding domain includes the vlCDR1, vlCDR2, and vlCDR3 of an A10m3 variable light chain, as shown in FIG. 2D. In certain embodiments, the albumin binding domain includes the vlCDR1, vlCDR2, and vlCDR3 of A10m3 as shown in FIG. 2D.

In certain embodiments, the albumin binding domain (e.g., HSA binding domain) is an antibody or an antibody fragment. In some embodiments, the albumin binding domain (e.g., HSA binding domain) is an scFv.

In some embodiments where the ABD includes both a variable heavy chain and a variable light chain, the variable heavy chain and the variable light chain are attached to each other by a linker (e.g., an scFv linker). In certain embodiments, the linker is attached to the variable heavy chain at its C-terminus and the variable light chain at its N-terminus. Suitable linkers are described herein and in FIG. 48. In some embodiments, the linker is a (Gly4Ser)$_x$ linker, where x is 1, 2, 3, 4, 5, 6, 7, or 8. In certain embodiments, the linker is a (Gly4Ser)$_5$ linker.

In certain embodiments, the albumin binding domain also includes a variable heavy chain that includes the vhCDR1, vhCDR2 and vhCDR3 of A10m3 and a variable light chain that includes the vlCDR1, vlCDR2 and vlCDR3 of A10m3 (FIG. 2D). In one embodiment, the albumin binding domain includes the variable heavy sequence and variable light sequence of the A10m3 ABD depicted in FIG. 2D.

C. Interleukin-15 Variants

In another aspect, provided herein are compositions that include variant IL-15s with improved in vivo stability and/or biological activity as compared to wildtype IL-15.

As used herein, "interleukin 15", "IL-15" and "IL15" all refer to an interleukin that binds to and signals through a complex composed of an IL-15 specific receptor alpha chain, an IL-2/IL-15 receptor beta chain (CD122) and the common gamma chain (gamma-C, CD132) (Genbank Accession numbers: NM_00000585 and NP_000576 (human); and NM_001254747 and NP_001241676 (mouse)).

IL-15 has been shown to stimulate T cell proliferation inside tumors (see, e.g., Miecnik et al., *Sci Transl Med* 6(228):228ra37 (2014). IL-15 also is able to extend the survivability of effector memory CD8+ T cells and is critical for the development of NK cells. It is believed that IL-15 can boost the potency of checkpoint inhibitors and other immunotherapies that harness T cells to attack cancer cells. Therefore, without being bound by any particular theory of operation, it is believed that the IL-15s described herein are useful for the treatment of cancers.

IL-15 monomer, however, has a short half-life of less than 40 minutes in vivo. Modifications to IL-15 monomer can improve its in vivo pharmacokinetics in the treatment of cancers. These modifications have generally centered on improving the trans-presentation of IL-15 with the alpha subunit of IL-15 receptor, IL-15Rα. Such modifications include: 1) pre-association of IL-15 and its soluble receptor a-subunit-Fc fusion to form IL-15: IL-15Rα-Fc complex (see, e.g., Rubinstein et al., *Proc Natl Acad Sci U.S.A.* 103:9166-71 (2006)); 2) expression of the hyperagonists IL-15-sIL-15Rα-sushi protein (see, e.g., Bessard et al., *Molecular cancer therapeutics* 8: 2736-45 (2009)); and 3) pre-association of human IL-15 mutant IL-15N72D with IL-15Rα-Fc sushi-Fc fusion complex (see, e.g., Zhu et al., *Journal of Immunology* 183: 3598-6007 (2009)).

In some embodiments, the IL-15 is a variant of a parental IL-15 with increased stability as compared to wildtype IL-15. In particular embodiments, the variant IL-15 is a variant of a wildtype human IL-15. In an exemplary embodiment, the variant IL-15 includes an amino acid substitution at position K86 of the parental IL-15 shown in FIG. 3. As described herein, K86 is a putative site for ubiquitin-dependent degradation (See Example 2) when made using particular cell types (e.g., HEK293 T cells). Therefore, without being bound by any particular theory of operation, it is believed that removal of the K86 ubiquitination site by amino acid substitution improves the stability of IL-15 (See Examples 2 and 3).

In certain embodiments, the IL-15 is a variant IL-15 having an amino acid substitution at position N112. Amino acid position N112 is a key site for IL-15 bioactivity, as it is critical for a proper IL-15/IL-15 receptor gamma interaction, particularly when IL-15 is attached to an ABD. Therefore, without being bound by any particular theory of operation, it is believed that mutations at position N112 can enhance one or more functions of IL-15 including, but not limited to, promoting T cell proliferation in tumor environments, enhancing survivability of CD8+ T cells and promoting NK cell development.

Particular amino acid substitutions that can improve IL-15 in vivo stability and/or biological activity include, but are not limited to: K86A, K86R, N112A, N112S, N112Q, K86A/N112A, K86R/N112A, K86A/N112S, K86R/N112S, K86A/N112Q, K86R/N112Q, K86A/N112A/N79A, K86R/N112A/N79A, K86A/N112A/N79D, K86R/N112A/N79D, K86A/N112A/N79Q, K86R/N112A/N79Q, K86A/N112A/N71D, K86R/N112A/N71D, K86A/N112A/N71Q, K86R/N112A/N71Q, K86A/N112A/N71D/N79A, K86A/N112A/N71D/N79D, K86A/N112A/N71Q/N79A, K86A/N112A/N71Q/N79D, K86R/N112A/N71D/N79A, K86R/N112A/N71D/N79D, K86R/N112A/N71D/N79Q, K86R/N112A/N71Q/N79A, K86R/N112A/N71Q/N79D, and K86R/N112A/N71Q/N79Q. Exemplary variant IL-15s that include one or more of such amino acid substitutions are depicted in FIG. 3. In an exemplary embodiment, the variant IL-15 includes the amino acid substitutions K86A and N112A.

In one embodiment, the IL-15 described herein (wild-type and variant IL-15s) is attached to IL-15R alpha. Such IL-15 presented in trans with its receptor has been shown to have a prolonged half-life and higher potency as compared to native 11-15 alone. See, e.g., Wu, *J Mol Genet* Med 7, 85 (2013).

D. IL-12

In another aspect, provided herein are compositions that include IL-12. As used herein, "interleukin 12", "IL-12" and "IL12" all refer to an interleukin that is a heterodimeric cytokine encoded by the IL-12A and IL-12B genes (Genbank Accession numbers: NM_000882 (IL-12A) and NM_002187 (IL-12B)). IL-12 is composed of a bundle of four alpha helices and is involved in the differentiation of native T cells into TH1 cells. IL-12 binds to the IL-12 receptor, which is a heterodimeric receptor formed by IL-12R-β1 and IL-12R-β2. IL-12 is known as a T cell-stimulating factor that can stimulate the growth and function of T cells. In particular, IL-12 can stimulate the production of interferon gamma (IFN-γ), and tumor necrosis factor-alpha (TNF-α) from T cells and natural killer (NK) cells and reduce IL-4 mediated suppression of IFN-γ. IL-12 can further mediate enhancement of the cytotoxic activity of NK cells and CD8+ cytotoxic T lymphocytes. Moreover, IL-12 can also have anti-angiogenic activity by increasing production of interferon gamma, which in turn increases the production of the chemokine inducible protein-10 (IP-10 or CXCL10). IP-10 then mediates this anti-angiogenic effect. Without being bound by any particular theory of operation, it is believed that IL-12 through its ability to induce immune responses and its anti-angiogenic activity can be used to treat cancers.

In some embodiments, the IL-12 is a mouse IL-12. In other embodiments, the IL-12 is a human IL-12.

In certain embodiments, the IL-12 is a single chain IL-12 polypeptide comprising an IL-12 p35 subunit attached to an IL-12 p40 subunit. Such IL-12 single chain polypeptides advantageously retain one or more of the biological activities of wildtype IL-12. In some embodiments, the single chain IL-12 polypeptide described herein is according to the formula, from N-terminus to C-terminus, (p40)-(L)-(p35), wherein "p40" is an IL-12 p40 subunit, "p35" is IL-12 p35 subunit and L is a linker. In other embodiments, the single chain IL-12 is according to the formula from N-terminus to C-terminus, (p35)-(L)-(p40). Any suitable linker can be used in the single chain IL-12 polypeptide including those described herein and disclosed in FIG. 49C. Suitable linkers can include, for example, linkers having the amino acid sequence (GGGGS)$_x$ [SEQ ID NO: 307] wherein x is an integer from 1-10. Other suitable linkers include, for example, the amino acid sequence GGGGGGS [SEQ ID NO: 270]. Exemplary single chain IL-12 linkers than can be used with the subject single chain IL-12 polypeptides are also described in Lieschke et al., *Nature Biotechnology* 15: 35-40 (1997), which is incorporated herein in its entirety by reference and particularly for its teaching of IL-12 polypeptide linkers.

In an exemplary embodiment, the single chain IL-12 polypeptide is a single chain human IL-12 polypeptide (i.e., it includes a human p35 and p40 IL-12 subunit). In certain embodiments, the single chain IL-12 polypeptide is a single chain mouse IL-12 polypeptide. Exemplary single chain human and mouse IL-12s are depicted in FIG. 20 (shown as fusion peptide with ABD) and 49C.

E. ABD Fusion Proteins

In one aspect, provided herein are ABD compositions that include an albumin binding domain attached to one or more fusion partners (e.g., a first fusion partner, a second fusion partner, etc.) via a linker. As discussed herein, subject ABD fusion proteins are able to under FcRn mediated endosomal recycling and, thus, advantageously exhibit extended half life compared to counterparts that do not include such ABDs.

ABDs useful for such ABD fusion proteins include, but are not limited to, those described herein. The amino acids sequences of such ABDs, including vhCDR1-3, vlCDR1-3, variable heavy chain and variable light chain sequences, are disclosed, for example, in FIG. 2. In some embodiments, the ABD fusion protein includes a variable heavy chain that includes the vhCDR1, vhCDR2 and vhCDR3 of any of the ABD variable heavy chains in FIG. 2, and a variable light chain that includes the v1CDR1, v1CDR2 and vCDR3 of any of the ABD variable light chains in FIG. 2. In certain embodiments, the ABD includes a variable heavy chain having a vhCDR1, a vhCDR2 and a vhCDR3 of an ABD disclosed in FIG. 2 and a variable light chain having a vhCDR1, a vhCDR2 and a vhCDR3 of an ABD disclosed in FIG. 2. In some embodiments, the ABD fusion protein includes the variable heavy chain and variable light chain of an ABD disclosed in FIG. 2.

In an exemplary embodiment, the ABD fusion protein includes a variable heavy chain that includes the vhCDR1, vhCDR2 and vhCDR3 of the A10m3 variable heavy chain, and a variable light chain that includes the v1CDR1, v1CDR2 and vCDR3 of the A10m3 variable light chain (FIG. 2D). In certain embodiments, the ABD includes a variable heavy chain having a vhCDR1, a vhCDR2 and a vhCDR3 of A10m3 and a variable light chain having a vhCDR1, a vhCDR2 and a vhCDR3 of A10m3 (FIG. 2D). In some embodiments, the ABD fusion protein includes the variable heavy chain and variable light chain of A10m3 (FIG. 2D).

ABD fusion proteins described herein include a fusion partner. In some embodiments, the fusion partner include two fusion partners (a first fusion partner (FP 1) and a second fusion partner (FP2). In embodiments that include two fusion partners, the fusion partners can be attached to the ABD in several orientations. In some embodiments, the ABD fusion protein is according to the formula, from N-terminus to C-terminus: FP1-ABD-FP2, FP1-PF2-ABD or ABD-FP1-FP2, wherein FP1 is a first fusion partner and FP2 is a second fusion partner.

Any suitable fusion partner wherein half-life extension of the fusion partner is desired, can be included in the subject ABD fusion proteins. Fusion partners may include, for example, cytokines (e.g., interferons and interleukins), growth factors, polypeptides, proteins, and hormones (e.g., growth hormones, parathyroid hormone).

In certain embodiments, the fusion partner is an antibody-based binding moiety that includes a variable heavy chain and a variable light chain. Such binding moieties can bind to any target of interest including, for example, tumor specific targets or cytokines. In an exemplary embodiment, the fusion partner is a single chain variable fragment (scFv). Antibody-based fusion partners also include, but are not limited to, ds-scFv, single domain antibodies (sdAb), diabodies, dsFvs, ds-scFvs, Fabs, and full length antibodies. Antibody-based fusion partners also include multispecific (e.g., bispecific) antibodies and fragments.

The subject ABD fusion proteins described herein utilize linkers between components (ABD and fusion partners) and within components. For example, scFv fusion partners utilize standard peptide linkers, generally based on glycine and serine, to attach the variant heavy and light chains to form the scFv. Further, standard peptide linkers are utilize to attached ABDs to fusion partners (e.g., cytokine fusion partners). Moreover, linkers are used to attach components of particular moieties, for example, the p35 and p40 subunit of IL-12 and IL-15 with IL-15Rα. In some embodiments, the linker is a (Gly4Ser)$_x$ linker, where x is 1, 2, 3,4 ,6, 7 or 8. In particular embodiments, the ABD is connected to fusion partners by (Gly4Ser)$_5$ linkers.

As shown herein, there are a number of suitable linkers that can be used, including traditional peptide bonds, generated by recombinant techniques. The linker peptide may predominantly include the following amino acid residues: Gly, Ser, Ala, or Thr. The linker peptide should have a length that is adequate to link two molecules in such a way that they assume the correct conformation relative to one another so that they retain the desired activity. In one embodiment, the linker is from about 1 to 50 amino acids in length, preferably about 1 to 30 amino acids in length. In one embodiment, linkers of 1 to 20 amino acids in length may be used, with from about 5 to about 10 amino acids finding use in some embodiments. Useful linkers include glycine-serine polymers, including for example (GS)n, (GSGGS)n [SEQ ID NO: 309], (GGGGS)n [SEQ ID NO: 307], and (GGGS)n [SEQ ID NO: 310], where n is an integer of at least one (and generally from 3 to 4), glycine-alanine polymers, alanine-serine polymers, and other flexible linkers. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers, that is may find use as linkers.

Other linker sequences may include any sequence of any length of CL/CH1 domain but not all residues of CL/CH1 domain; for example the first 5-12 amino acid residues of the CL/CH1 domains. Linkers can be derived from immunoglobulin light chain, for example Cκ or Cλ. Linkers can be derived from immunoglobulin heavy chains of any isotype, including for example Cγ1, Cγ2, Cγ3, Cγ4, Cα1, Cα2, Cδ, Cε, and Cμ. Linker sequences may also be derived from other proteins such as Ig-like proteins (e.g., TCR, FcR, KIR), hinge region-derived sequences, and other natural sequences from other proteins.

Often the linker is not substantially sensitive to the extracellular environment. As used herein, "not substantially sensitive to the extracellular environment," in the context of a linker, means that no more than about 20%, 15%, 10%, 5%, 3%, or no more than about 1% of the linkers, in a sample of antibody-drug conjugate compound, are cleaved when the antibody-drug conjugate compound presents in an extracellular environment (for example, in plasma).

Whether a linker is not substantially sensitive to the extracellular environment can be determined, for example, by incubating with plasma the antibody-drug conjugate compound for a predetermined time period (for example, 2, 4, 8, 16, or 24 hours) and then quantitating the amount of free drug present in the plasma.

In other, non-mutually exclusive embodiments, the linker promotes cellular internalization. In certain embodiments, the linker promotes cellular internalization when conjugated to the therapeutic agent (that is, in the milieu of the linker-therapeutic agent moiety of the antibody-drug conjugate compound as described herein). In yet other embodiments, the linker promotes cellular internalization when conjugated to both the auristatin compound and the ABD fusion proteins of the invention.

A variety of exemplary linkers that can be used with the present compositions and methods are described in WO 2004-010957, U.S. Publication No. 2006/0074008, U.S. Publication No. 20050238649, and U.S. Publication No. 2006/0024317 (each of which is incorporated by reference herein in its entirety and for all purposes).

Exemplary linkers that can be utilized with the subject ABDs as domain linkers, scFv linkers, as well as attach components of particular fusion partners are further depicted in FIG. 48.

In some embodiments, the linker is a "domain linker", used to link any two domains as outlined herein together (e.g., a cytokine fusion partner (e.g., an interleukin) and an ABD). While any suitable linker can be used, many embodiments utilize a glycine-serine polymer, including for example (GS)n, (GSGGS)n [SEQ ID NO: 309], (GGGGS)n [SEQ ID NO: 307], and (GGGS)n [SEQ ID NO: 310], where n is an integer of at least one (and generally from 3 to 4 to 5) as well as any peptide sequence that allows for recombinant attachment of the two domains with sufficient length and flexibility to allow each domain to retain its biological function.

In some embodiments, the fusion partner is an scFv that includes a variable heavy chain and a variable light chain. In such embodiments, the ABD variable heavy chain is attached to the variable light chain with an scFv linker.

Exemplary ABD fusion proteins are further discussed below.

1. Cytokine-ABD Fusion Proteins

In some embodiments, the ABD fusion protein includes a cytokine fusion partner, i.e., a cytokine-albumin binding domain (cytokine-ABD) fusion proteins (FIG. 1). In some embodiments, the cytokine-ABD fusion protein includes an IL-2, IL-7, IL-12, IL-15, IL-18, IL-21, IL-27, GM-CSF or IFN-α. Subject cytokine-ABD fusion proteins are useful for immunomodulatory effects in a subject where such immunomodulatory effects are needed (e.g., treatment of a cancer or an autoimmune disease). Moreover, subject cytokine-ABDs exhibit a longer half-life and improved pharmacokinetic properties as compared to interleukin therapeutics alone.

Any ABD can be used with the subject cytokine-ABD fusion proteins described herein. In some embodiments, the ABD includes a ABD variable heavy chain. In certain embodiments the ABD includes a ABD variable light chain. In exemplary embodiments, the ABD is an scFv that includes a variable heavy chain attached to a variable light chain by a linker (e.g., any one of the linkers disclosed herein and in FIG. 48).

In certain embodiments, the variable heavy chain includes the vhCDR1-3 of any of the ABD variable heavy chains described herein, including those ABD variable heavy chains depicted in FIG. 2. In certain embodiments, the ABD variable heavy chain includes the vhCDR1-3 of the A10m3 variable heavy chain (FIG. 2D). In some embodiments, the ABD variable heavy chain includes the A10m3 vhCDR1-3 as depicted in FIG. 2D. In exemplary embodiments, the ABD variable heavy chain has the amino acid sequence of A10m3 variable heavy chain.

In certain embodiments, the ABD includes a ABD variable light chain. In some embodiments, the ABD variable light chain includes the vlCDR1-3 of any of the ABD variable light chains described herein, including those ABD variable light chains depicted in FIG. 2. In certain embodiments, the ABD variable light chain includes the vlCDR1-3 of the A10m3 variable light chain (FIG. 2D). In some embodiments, the ABD variable light chain includes the A10m3 vlCDR1-3 as depicted in FIG. 2D. In exemplary embodiments, the ABD variable light chain has the sequence of A10m3 variable light chain.

The amino acid sequences of exemplary cytokines that can be used in the subject cytokine-ABD fusions, as well as exemplary cytokine-ABD fusion proteins, where the ABD is A10m3 are depicted in FIG. 49A-G.

In some embodiments, the IL-ABD is according to the formula, from N-terminus to C-terminus, cytokine-L-ABD or ABD-L-cytokine, where L is a linker that attaches the cytokine to the ABD (e.g., a peptide linker). In certain embodiments, the cytokine-ABD includes a variable heavy chain and the cytokine is attached to the N-terminal of the ABD variable heavy chain. In some embodiments, the cytokine is attached to the C-terminal of the ABD variable heavy chain. In an exemplary embodiment, the interleukin-ABD includes an ABD that also includes a variable light chain (e.g., an ABD scFv). In some embodiments, the cytokine is attached to the C-terminal of the variable light chain. In certain embodiment, the N-terminal of the cytokine is attached to the ABD. In other embodiments, the C-terminal of the cytokine is attached to the ABD.

In certain embodiments, the cytokine is cytokine selected from IL-2, IL-7, IL-12, IL-15, IL-18, IL-21, IL-27, GM-CSF and IFN-α. Cytokine molecules include, for example, full length cytokine and cytokine fragments, for example, a part that is important for the particular cytokine's function (e.g., a part of the interleukin that binds to its receptor).

In some embodiments, the cytokine-ABD includes an IL-2 molecule or fragment thereof. As used herein, "interleukin 2," "IL-2,", and "IL2" are refer to a member of the cytokine having four alpha helix bundles and signals through the IL-2 receptor (Genbank Accession numbers: NM_000586 and NP_000577 (human) and NM_008366 and NP_032392 (mouse)). IL-2 plays key roles in immune system function, tolerance and immunity, primarily via its direct effects on T cells. In the thymus, IL-2 prevents autoimmune diseases by promoting the differentiation of certain immature T cells into regulatory T cells, which kill off other T cells that are primed to attack normal healthy cells in the body. IL-2 has been used for the treatment of cancers (malignant melanoma, renal cell cancer) in large intermittent doses and has been extensively used in continuous doses. Exemplary IL-2-ABDs are shown in FIG. 49A.

In some embodiments, the cytokine-ABD fusion protein includes an IL-7 molecule or fragment thereof. As used herein, "interleukin 7" "IL-7", and "IL7" (Genbank Accession numbers: NM_000880 and NP_000871 (human); and NM_008371 and NP_032397 (mouse)) all refer to a member of a cytokine that is a hematopoietic growth factor secreted by stromal cells in the bone marrow and thymus and binds to IL-7 receptor. Interleukin-7 (IL-7) is a non-hematopoietic cell-derived cytokine with a central role in the adaptive immune system. It promotes lymphocyte development in the thymus maintains survival of naive and memory T cell homeostasis in the periphery. Moreover, it is important for the organogenesis of lymph nodes (LN) and for the maintenance of activated T cells recruited into the secondary lymphoid organs (SLOs). IL-7 is an ideal solution for the immune reconstitution of immunosuppressed cancer patients by promoting peripheral T cell expansion. In animal models, IL-7 has been proven to prolong the survival of tumor-bearing hosts. Exemplary IL-7-ABDs are shown in FIG. 49B.

In certain embodiments, cytokine-ABD includes a an IL-12 molecule or fragment thereof. In some embodiments, the IL-12 is a single chain IL-12 as described herein and as depicted in FIG. 20 (shown as a fusion peptide with ABD) and 49C.

In certain embodiments, the cytokine-ABD includes an IL-15 molecule or fragment thereof. In some embodiments, the IL-15-ABD includes a variant IL-15 as described herein and at FIGS. 3 and 4. In some embodiments, the IL-15 is a wildtype IL-15, as shown in FIG. 3 (e.g., "parental IL-15"). In certain embodiments, the wild-type IL-15 is attached to an IL-15 receptor alpha (IL-15Rα).

In certain embodiments, the cytokine-ABD includes an IL-21 molecule or fragment thereof. As used herein, "interleukin 21" "IL-21", and "IL21" (Genbank Accession numbers: NM_001207006 and NP_001193935 (human); and NM_0001291041 and NP_001277970 (mouse)) all refer to a member of a cytokine that binds to IL-21 receptor and has potent regulatory effects on cells of the immune system, including natural killer (NK) cells and cytotoxic cells and binds to IL-21 receptor that can destroy virally infected or cancerous cells. Therefore, without being bound by any particular theory of operation, it is believed that the subject cytokine-ABD having an IL-21 are useful for the treatment of various cancers. Exemplary IL-21-ABDs are shown in FIG. 49E.

Other useful cytokines that may be included in the subject cytokine-ABDs includes, not are not limited to IL-27, IFN-α and GM-CSF. In certain embodiments, the interleukin-ABD polypeptide also includes an interferon-alpha, interferon-beta or GM-CSF molecule. Such molecules are useful for delivery into tumors and reduction of toxicity.

In some embodiments, the cytokine-ABD includes two cytokines attached to an ABD selected from the following: IL-2 and IL-12; IL-7 and IL-15; IL-15 and IL-12; IL-18 and GMC SF; IL-21 and IL-15; GMC-SF and IL-12; GMC-SF and IL-21; and IFN-α and IL-15. FIG. 1 depicts several exemplary orientations in which two cytokines can be attached to the ABD. Any ABD can be used in such fusion protein, including those that include any of the ABD variable heavy domains and variable light domains shown in FIG. 2. In some embodiments, the ABD is A10m3.

Any linker can be used to attached each cytokine to the ABD, including any linker depicted in FIG. 48. An exemplary backbone linker-A10m3-linker sequence for use in such fusion proteins is depicted in FIG. 50. Exemplary linkers than can be used include (GGGGS)$_x$ [SEQ ID NO: 307] linkers wherein X is 1-10. In certain embodiments, a (GGGGS)$_5$ [SEQ ID NO: 307] is used to attach the cytokine to the ABD.

In some embodiments, the cytokine-ABD is according to a formula selected from the following: (from N-terminus to C-terminus): Cytokine 1-L1-ABD-L2-Cytokine 2; Cytokine 1-L1-Cytokine 2-L2-ABD; and ABD-L1-Cytokine 1-L2-Cytokine 2, where L1 and L2 are linkers that connect the cytokines and ABD components and Cytokine 1 and Cytokine 2 are selected from the following cytokine pairs: IL-2 and IL-12; IL-7 and IL-15; IL-15 and IL-12; IL-18 and GM-CSF; IL-21 and IL-15; GM-CSF and IL-12; GM-CSF and IL-21; and IFN-α and IL-15. In some embodiments, the ABD is A10m3 (FIG. 2D).

In such cytokine-ABDs, either cytokine can be "Cytokine 1" and the other cytokine can be "Cytokine 2". For example, in one embodiment of the IL-2 and IL-12 cytokine pair, IL-2 is "Cytokine 1" and IL-12 is "Cytokine 2". In another embodiment of the IL-2 and IL-12 cytokine pair, IL-12 is "Cytokine 1" and IL-2 is "Cytokine 2".

In some embodiments, the cytokine-ABD include two of the same interleukins. In other embodiments, the interleukin-ABD polypeptide includes two different interleukins (e.g., an IL-12 and an IL-15), as described above. ABD fusion proteins that include particular cytokine combinations are disclosed in FIG. 51. Exemplary cytokine-ABD fusion proteins that include a combination of different cytokines are further discussed in detail below.

a. IL-12 and IL-15

In certain embodiments, the cytokine-ABD fusion protein includes an IL-12 and an IL-15. Exemplary IL-12 and IL-15 sequences that can be included in such embodiments are depicted in FIGS. 3 and 49C. It is believed that cytokine-ABDs that include both an IL-12 and IL-15 fusion partner exhibit the anti-tumor effects of both interleukins. The combination of IL-12 and IL-15 was shown to induce enhanced anti-tumor activity as compared to either cytokine alone. Such enhanced anti-tumor activity was correlated with the reciprocal upregulation of each cytokine's receptors through the synergistic induction of IFN-γ. IL-12 in combination with IL-15 was further shown to promote anti-tumor activity in peritoneal macrophages through the synthesis of nitric oxide. Without being bound by any particular theory of operation, it is believed that polypeptides having both an IL-12 and an IL-15 fusion partner are capable of rapidly activate the innate response (IL-12) as well as potently stimulate the proliferation of T cells and maintain memory CD8+ T cells (IL-15). Animal studies show that sequential delivery of IL-12 and IL-15 expressing cells also cured mice in a therapeutic setting of established tumor. Depleting CD8+ cells eliminated the protection of this therapy, suggesting clonal expansion of tumor CTL. See, e.g., Croce et al., *Clin Cancer Res* 11(2 Pt 1):735-742 (2005).

In some embodiments, the cytokine-ABD is according to the formula, from N-terminus to C-terminus:

a) (IL-12)-L1-(ABD)-L2-(IL-15); or b) (IL-15)-L1-(ABD)-L2-(IL-12).

Any suitable ABD can be used including, for example, an ABD having a ABD variable heavy chain that includes the vhCDR1-3 of any of the ABD variable heavy chains listed in FIG. 2. In an exemplary embodiment, the variable heavy chain includes the vhCDR1-3 of a A10m3 variable heavy chain (FIG. 2D). In certain embodiments, the ABD includes a ABD variable light chain that includes the v1CDR1-3 of a A10m3 variable light chain. In an exemplary embodiment, the ABD is an A10m3 scFv.

Any suitable IL-12 and IL-15 can be used. In some embodiments, the IL-15 is a variant IL-15 as described herein (see, e.g., FIG. 3). The IL-15 can also be a wild-type IL-15 or a wild-type IL-15 that is attached to an IL-15Rα. In one embodiment, the IL-15 is a variant IL-15 selected from those depicted in FIG. 3. In an exemplary embodiment, the Il-15 is a variant IL-15 having amino acid substitutions K86R and N112A.

IL-12s that can be used include those IL-12s that have a p35 and p40 domain. In some embodiments, the IL-12 is a single chain IL-12 as described herein (see, e.g., FIG. 20, as shown as part of an IL-12-ABD fusion polypeptide and FIG. 49C).

In such embodiments, L1 and L2 are a first and second linker, respectively, L1 and L2 can be any linker that is suitable for attaching the IL-15 and IL-12 domains to the ABD domain (e.g., the linkers listed in FIG. 48). Exemplary linkers than can be used include (GGGGS), [SEQ ID NO: 307] linkers wherein X is 1-10. In certain embodiments, L1 and L2 are each (GGGGS)$_5$ [SEQ ID NO: 307].

Sequences of exemplary ABD polypeptides that include an IL-12 and an IL-15 are shown in FIGS. 34 and 36.

b. IL-2 and IL-12

In certain embodiments, the cytokine-ABD includes an IL-2 and an IL-12.

IL-2 and IL-12 reciprocally upregulate each other's receptors and use separate signaling pathways to induce different but complementary biological effects. Both IL-2 and IL-12 can stimulate mitogen or CD3-activated T cells to proliferate & produce IFN-γ. Moreover, studies show that the delivery of both IL-2 and IL-12 genes into mice bearing B16 melanoma elicited a significant reduction in tumor burden and enhancement in overall survival (see, e.g., Dietrich et al., *Arch Surg* 387(34):177-182 (2002)). Thus, it is believed that cytokine-ABD fusion proteins having both an IL-2 and an IL- are useful for the reduction of tumors and treatment of cancers.

c. IL-2 and IL-15

In certain embodiments, the cytokine-ABD fusion protein includes an IL-2 and an IL-15. Both IL-2 and IL-15 are capable of stimulating the proliferation of NK cells and activated T cells, as well as supporting the expansion of effector T cells. It is believed that cytokine-ABD fusion proteins that include both an IL-2 and IL-15 are useful for the reduction of tumors and treatment of cancers.

d. IL-7 and IL-12

In certain embodiments, the cytokine-ABD fusion protein includes an IL-7 and an IL-12 fusion partner.

Interleukin-7 (IL-7) is a non-hematopoietic cell-derived cytokine with a central role in the adaptive immune system. It promotes lymphocyte development in the thymus maintains survival of naive and memory T cell homeostasis in the periphery. Moreover, it is important for the organogenesis of lymph nodes (LN) and for the maintenance of activated T cells recruited into the secondary lymphoid organs (SLOs). The immune capacity of cancer patients is suppressed and is characterized by lower T cell counts, less effector immune cells infiltration, higher levels of exhausted effector cells and higher levels of immunosuppressive cytokines, such as transforming growth factor β (TGF-β). IL-7 is an ideal solution for the immune reconstitution of immunosuppressed cancer patients by promoting peripheral T cell expansion. In animal models, IL-7 has been proven to prolong the survival of tumor-bearing hosts. See Gao et al., *Int. J. Mol. Sci.* 16: 10267-10280 (2015).

IL-12 acts directly on CD8+ T cells to enhance their IL-7 mediated proliferation. It is believed that cytokine-ABD fusion proteins that include an IL-7 and IL-12 binding domain advantageously promote the proliferation of CD8+ T cells and enhance cytolytic activity against tumors.

e. IL-7 and IL-15

In certain embodiments, the cytokine-ABD fusion protein includes an IL-7 and an IL-15. As mentioned above, interleukin 7 and 15 are considered powerful pro-inflammatory cytokines that have the ability to reduce tumorgenesis. It is believed that cytokine ABD fusion proteins that include both an IL-7 and IL-15 are useful for the reduction of tumors and treatment of cancers.

f. IL-12 and IL-21

In certain embodiments, the cytokine-ABD includes an IL-12 and an IL-21.

As mentioned above, IL-12 is capable of stimulating the proliferation of NK cells and activated T cells and supporting the expansion of effector T cells. IL-21 is a regulator of NK and T cell function that bridges innate and adaptive immune systems. IL-21 promotes the maturation of NK cells from bone marrow progenitors, activates human peripheral NK cells, promotes NK expansion and maturation, and enhances CD8+ T cell-mediated effector functions.

It is believed that cytokine-ABD fusion proteins that include both an IL-12 and an IL-21 are useful for the reduction of tumors and treatment of cancers.

g. IL-12 and IL-18

In certain embodiments, the cytokine-ABD includes an IL-12 and an IL-18.

IL-18 is known to induce IFN-γ production, promote Th1 cell development and NK activation. IL-12 is known to induce the upregulation of the IL-18 receptor in an IFN-γ-dependent manner. Administration of SCK murine mammary carcinoma cells co-expressing IL-18 and IL-12 to mice reduced tumor burden and inhibited angiogenesis (See, e.g., Coughlin et al., *J Clin Invest* 101 (6):1441-1452 (1998)). IL-18 in combination with IL-12 to tumor bearing mice synergistically induced a prolonged serum level of IFN-γ, while tumor bearing mice treated with IL-18 or IL-12 alone induced minimal serum IFN-γ that was rapidly attenuated (See, e.g., Subleski et al., *Cancer Res* 66(22):11005-11012 (2006)). Exemplary IL-18-ABDs are shown in FIG. 37.

It is believed that cytokine-ABD fusion proteins that include both an IL-12 and IL-18 fusion partner are useful for the reduction of tumors and treatment of cancers.

h. GM-CSF and IL-12

In certain embodiments, the cytokine-ABD includes a GM-CSF and an IL-18. GM-CSF regulates hematopoietic progenitor cell differentiation and proliferation. GM-CSF also enhances the capacity of APC to process and present antigen, which in turn leads to the activation of cytotoxic T cells, increased IFN-γ production and, ultimately, tumor regression. Both GM-CSF and IL-12 are able to elicit significant anti-tumor responses in several different preclinical tumor models, including a liver tumor model and a lung tumor model. (See, e.g., Kilinc et al., *J Immunol* 177(10): 6962-6973 (2006)).

It is believed that cytokine-ABD fusion proteins that include both a GM-CSFand IL-12 fusion partner are useful for the reduction of tumors and treatment of cancers.

i. IFN alpha and IL-12

Cooperative nature of these two cytokines extends beyond mere similar biological effects. For example, IL-12, which is well known to induce IFN-γ production, can lead to the production of additional soluble factors that enhance IFN-α signaling. Interferons, including, interferon alpha, are known to induce apoptosis in malignant cells. See, e.g., Thyrell, L. et al., *Oncogene* 21,1251-1262 (2002).

It is believed that cytokine-ABD fusion proteins that include both an IFN alpha and IL-12 are useful for the reduction of tumors and treatment of cancers.

Additional cytokine-cytokine combinations that can be included in the subject cytokine-ABD fusion proteins are depicted in FIG. 51A.

2. Binding Moiety-ABD Fusion Proteins

In some embodiments, the ABD fusion proteins includes a binding moiety (e.g., an scFv) fusion partner, i.e., a BM-ABD fusion protein. In some embodiments, the BM-ABD includes one binding moiety. In certain embodiments, the BM-ABD includes two binding moieties (e.g., scFvs). In other embodiments, the BM-ABD includes a cytokine and a binding moiety (FIG. 1B). FIG. 1 depicts several exemplary orientations in which the binding moiety or binding moiety-cytokine/binding moiety-binding moiety combinations can be attached to the ABD.

Binding moieties that are useful for practice with the subject BM-ABDs binding moieties that are based on antibody variable heavy domain and variable light domain. In some embodiments, the binding moiety includes a variable heavy domain and a variable light domain. In some embodiments, the binding moiety is a single chain variable fragment (scFv).

Any ABD can be used in such fusion protein, including those that include any of the ABD variable heavy domains and variable light domains shown in FIG. 2. In certain embodiments, the ABD includes the variable heavy and light domains of A10m3. In some embodiments, the ABD is A10m3 scFv.

Any linker can be used to attached the cytokine and/or binding moiety to the ABD, including any linker depicted in FIG. 48. In an exemplary embodiment, the linker is (GGGGS)$_5$ [SEQ ID NO: 307]. An exemplary backbone linker-A10m3-linker sequence for use in such fusion proteins is depicted in FIG. 48.

Exemplary combinations of two binding moieties (e.g., scFvs) or a cytokine and a binding moiety that can be such ABD fusion proteins are depicted in FIG. 51B.

In some embodiments, the BM-ABD includes an anti-TGFβ binding domain (e.g., an anti-TGF(3 scFv). Exemplary anti-TGFβ scFv sequences are depicted in FIG. 45. In some embodiments, the anti-TGFβ scFv includes the variable heavy and variable light domain of 4D9 anti-TGFβ scFv. In some embodiments, the ABD fusion protein includes an anti-TGFβ scFv and a cytokine or additional binding moiety, where the cytokine or additional binding moiety is a second anti-TGFβ scFv, IL-15, IL-12, or an anti-PD-L1 binding domain (10D12). See FIG. 51B.

In some embodiments, the BM-ABD includes an anti-PD-L1 binding domain (e.g., an anti-T PD-L1 scFv). In some embodiments, the anti-PD-L1 scFv includes the variable heavy and variable light domain of 4D9 anti-PD-L1 10D12 scFv. In some embodiments, the ABD fusion protein includes an anti-PD-L1 scFv and a cytokine or additional binding moiety, where the cytokine or additional binding moiety is a second anti-anti-PD-L1 scFv, IL-15, IL-12, or an anti-TGFβ binding domain (4D9). See FIG. 51B.

a. TGF-β binding moieties

In certain embodiments, the BM-ABD provided herein includes a TGF-β binding moiety. As used herein, "TGF-β," "TGFβ," "TGFb," and "transforming growth factor beta" all refer to a member of a family of cytokines that are involved that controls proliferation, cellular differentiation, and other functions in most cells and exist in at least three isoforms: TGFβ1 (Genbank Accession numbers: NM_000660 and NP_000651 (human); and NM_011577 and NP_035707 (mouse)), TGFβ2 (Genbank Accession numbers NM_001135599 and NP_001129071 (human)) and NM_009367 and NP_33393 (mouse)), and TGFβ3 (Genbank Accession number: NM_003239). TGFβ family members have an N-terminal signal peptide of 20-30 amino acids that are required for secretion from cells, a pro-region, and a 112-113 amino acid C-terminal region that becomes the mature TGFβ molecule following its release form the pro-region by proteolytic cleavage. In certain embodiments, the mature TGFβ protein can dimerize to produce a 25 kDa active molecule with many conserved structural motifs, include nine cysteine residues, eight of which form disulfide bonds within the TGFβ molecule to create a cysteine knot structure. The ninth conserved cysteine forms a bond with the ninth cysteine of another TGFβ to produce the dimer.

Without being bound by any particular theory of operation, it is believed that subject BM-ABD that bind TGFβ can be used to treat subjects having cancers (e.g., a late stage cancer). In certain embodiments, the BM-ABD includes a TGFβ1 binding moiety. In certain embodiments, the BM-ABD includes a TGFβ2 binding moiety. In certain embodiments, the BM-ABD includes a TGFβ3 binding moiety. In some embodiments, the multivalent binding polypeptide includes a binding moiety that can bind TGFβ1, TGFβ2, and/or TGFβ3 or any combination thereof (e.g., binds TGFβ1 and TGFβ2; binds TGFβ2 and TGFβ3; binds TGFβ1 and TGFβ3; or binds TGFβ1, TGFβ2 and TGFβ3). In some embodiments, the TGFβ binding moiety binds TGFβ1, TGFβ2 and TGFβ3. In some embodiments, the TGFβ binding moiety that includes the variable heavy domain and variable light domain of a TGFβ binding moiety in FIG. 40. In one embodiment, the TGFβ binding moiety includes the variable heavy domain and variable light domain of TGFβ binding moiety 4D9 (FIG. 40B). In a particular embodiment, the TGFβ binding moiety is the 4D9 scFv. 4D9 has been shown to prevent the expansion of CD4$^+$FoxP3$^+$ regulatory T cell, prevent Smad activation (e.g., Smad2 phosphorylation), as well as prevent cellular epithelial-to-mesenchymal transition and/or cancer cell migration.

In some embodiments, the TGFβ binding moiety-ABD fusion protein is further attached to another binding moiety or cytokine. In certain embodiments, the other binding moiety is a PD-L1 binding moiety or another TGFβ binding moiety. In some embodiments, the cytokine is IL-15 or IL-12 (See FIG. 51B).

b. PD-L1 Binding Moieties

In certain embodiments, the BM-ABD provided herein includes a Programmed Cell Death 1 Ligand 1 (PD-L1) binding moiety. As used herein, "Programmed Cell Death 1 Ligand 1," "Programmed Death Ligand 1," "PDL1," and "PD-L1" (Genbank Accession numbers NM_001267706 and NP_001254635 (human) and NM_021893 and NP_068693 (mouse)) all refer to a member of a 40 kDa type 1 transmembrane protein that has binds to PD1 receptor, found on activated T cells, B cells, and myeloid cells, to modulate activation or inhibition. PD-L1 upregulation allows cancers to evade the immune system. See, e.g., Hamanishi et al., Proc Natl Acad Sci USA 104(9): 3360-5 (2007). As such, it is believed that subject BM-ABDs that include a PD-L1 binding moiety may be useful in the treatment of cancers.

In one embodiment, the PD-L1 binding moiety includes the variable heavy domain and variable light domain of PD-L1 binding moiety 10D12 (FIG. 50). In a particular embodiment, the PD-L1 binding moiety is the 10D12 scFv (FIG. 50). 10D12 binds to hPD-L1 at low pH and is crossreactive with mPD-L1. 10D12 does not bind to hPD-L2 or mPD-L2. Further, 10D12 blocks PD-1/PD-L1 interaction, as well as B71/PD-L1 interaction.

In some embodiments, the PD-L1 binding moiety-ABD fusion protein is further attached to another binding moiety or cytokine. In certain embodiments, the other binding moiety is a TGFβ binding moiety or another PD-L1 binding moiety. In some embodiments, the cytokine is IL-15 or IL-12 (See FIG. 51B).

c. TNF and Other Binding Moieties

In one embodiment, the ABD fusion protein provided herein includes a tumor nercosis factor (TNF) binding moiety. With out being bound by any particular theory of operation, it is believe that such ABD fusion proteins are useful as anti-inflammation and/or cancer therapeutics. In some embodiments, the TNF binding moiety is an scFv. In particular embodiments, the TNF binding moiety-ABD fusion protein is further attached to another fusion partner that is a binding moiety or an inhibitor peptide. In certain embodiments, the second binding moiety is a second TNF binding moiety, an IL-1 binding moiety, an IL-6 binding moiety, an IL-8 binding moiety, an IL-17 (isoforms A-F) binding moiety, or an IL-23 binding moiety.

In another embodiment, the ABD fusion protein includes a binding moiety selected from an IL-1, IL-6, IL-8, IL-17 (A-F) and IL-23 binding moiety.

In some embodiments, such TNF and interleukin binding moieties-ABDs are useful for the treatment of diseases such as rheumatoid arthritis, Crohn's disease, psoriatic arthritis, ankylosing spondylitis, ulcerative colitis, chronic plaque psoriasis and TNF based diseases.

F. Diagnostic Uses

In another aspect, provided herein are methods for imaging and/or detecting tumors. In some aspects, the methods comprise contacting a tumor cell, tumor cell culture, tumor vasculature cell, tumor vasculature cell culture, tumor tissue, and other tissues and cells with a subject ABD fusion protein of the invention that is labeled.

The ABD fusion protein also find use in the in vitro or in vivo imaging of tumors or autoimmune disease states associated with the antigen binding partners of the ABD fusion protein herein. In some embodiments, the fusion protein described herein are used for both diagnosis and treatment, or for diagnosis alone. In some embodiments, a subject ABD fusion protein is labeled.

Diagnosis can be done either in vivo, by administration of a diagnostic protein that allows whole body imaging as described below, or in vitro, on samples removed from a patient. "Sample" in this context includes any number of things, including, but not limited to, bodily fluids (including, but not limited to, blood, urine, serum, lymph, saliva, anal and vaginal secretions, perspiration and semen), as well as tissue samples such as result from biopsies of relevant tissues.

By "labeled" herein is meant that the ABD fusion protein disclosed herein have one or more elements, isotopes, or chemical compounds attached to enable the detection in a screen or diagnostic procedure. In general, labels fall into several classes: a) immune labels, which may be an epitope incorporated as a fusion partner that is recognized by an antibody, b) isotopic labels, which may be radioactive or heavy isotopes, c) small molecule labels, which may include fluorescent and colorimetric dyes, or molecules such as biotin that enable other labeling methods, and d) labels such as particles (including bubbles for ultrasound labeling) or paramagnetic labels that allow body imagining. Labels may be incorporated into the proteins at any position (for example, through one or more of the linkers described herein) and may be incorporated in vitro or in vivo during protein expression, as is known in the art. Specific labels include optical dyes, including, but not limited to, chromophores, phosphors and fluorophores, with the latter being specific in many instances. Fluorophores can be either "small molecule" fluores, or proteinaceous fluores.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.).

Suitable optical dyes, including fluorophores, are described in Molecular Probes Handbook by Richard P. Haugland, entirely incorporated by reference.

Suitable proteinaceous fluorescent labels also include, but are not limited to, green fluorescent protein, including a *Renilla, Ptilosarcus,* or *Aequorea* species of GFP (Chalfie et al., *Science* 263:802-805 (1994)), EGFP (Clontech Laboratories, Inc., Genbank Accession Number U55762), blue fluorescent protein (BFP, Quantum Biotechnologies, Inc. 1801 de Maisonneuve Blvd. West, 8th Floor, Montreal, Quebec, Canada H3H 1J9; Stauber, 1998, Biotechniques 24:462-471; Heim et al., 1996, Curr. Biol. 6:178-182), enhanced yellow fluorescent protein (EYFP, Clontech Laboratories, Inc.), luciferase (Ichiki et al., *J. Immunol.* 150: 5408-5417 (1993)), .beta galactosidase (Nolan et al., *Proc. Natl. Acad. Sci. U.S.A.* 85:2603-2607 (1998)) and *Renilla* (WO92/15673, WO95/07463, WO98/14605, WO98/26277, WO99/49019, U.S. Pat. Nos. 5,292,658, 5,418,155, 5,683,888, 5,741,668, 5,777,079, 5,804,387, 5,874,304, 5,876,995, 5,925,558). All of the above-cited references in this paragraph are expressly incorporated herein by reference.

G. Production of Albumin Binding Domains and Fusion Proteins

As will be appreciated by those in the art, standard protocols are used to make the subject ABDs. General methods for antibody molecular biology, expression, purification, and screening are described in Antibody Engineering, edited by Kontermann & Dubel, Springer, Heidelberg, 2001; and Hayhurst & Georgiou, *Curr Opin Chem Biol* 5:683-689 (2001); Maynard & Georgiou, *Annu Rev Biomed Eng* 2:339-76 (2000).

In one embodiment disclosed herein, nucleic acids are created that encode the ABD fusion protein, and that may then be cloned into host cells, expressed and assayed, if desired. Thus, nucleic acids, and particularly DNA, may be made that encode each protein sequence. These practices are carried out using well-known procedures. For example, a variety of methods that may find use in generating ABD fusion proteins, similar to the production of antibodies, are disclosed herein are described in Molecular Cloning—A Laboratory Manual, 3rd Ed. (Maniatis, Cold Spring Harbor Laboratory Press, New York, 2001), and Current Protocols in Molecular Biology (John Wiley & Sons), both incorporated entirely by reference. There are a variety of techniques that may be used to efficiently generate DNA encoding ABDs disclosed herein. Such methods include, but are not limited to, gene assembly methods, PCR-based method and methods which use variations of PCR, ligase chain reaction-based methods, pooled oligo methods such as those used in synthetic shuffling, error-prone amplification methods and methods which use oligos with random mutations, classical site-directed mutagenesis methods, cassette mutagenesis, and other amplification and gene synthesis methods. As is known in the art, there are a variety of commercially available kits and methods for gene assembly, mutagenesis, vector subcloning, and the like, and such commercial products find use in for generating nucleic acids that encode ABD fusion proteins.

The ABDs disclosed herein may be produced by culturing a host cell transformed with nucleic acid, e.g., an expression vector, containing nucleic acid encoding the ABD fusion proteins, under the appropriate conditions to induce or cause expression of the protein. The conditions appropriate for expression will vary with the choice of the expression vector and the host cell, and will be easily ascertained by one skilled in the art through routine experimentation. A wide variety of appropriate host cells may be used, including but not limited to mammalian cells, bacteria, insect cells, yeast, and plant cells. For example, a variety of cell lines that may find use in generating ABD fusion proteins disclosed herein are described in the ATCC® cell line catalog, available from the American Type Culture Collection.

In one embodiment, the ABDs are expressed in mammalian expression systems, including systems in which the expression constructs are introduced into the mammalian cells using virus such as retrovirus or adenovirus. Any mammalian cells may be used, e.g., human, mouse, rat, hamster, and primate cells. Suitable cells also include known research cells, including but not limited to Jurkat T cells, NIH3T3, CHO, BHK, COS, HEK293, PER C.6, HeLa, Sp2/0, NSO cells and variants thereof. In an alternate embodiment, library proteins are expressed in bacterial cells. Bacterial expression systems are well known in the art, and include *Escherichia coli* (*E. coli*), *Bacillus subtilis, Streptococcus cremoris*, and *Streptococcus lividans*. In alternate embodiments, the ABD fusion proteins are produced in insect cells (e.g., Sf21/Sf9, *Trichoplusia ni* Bti-Tn5b1-4) or yeast cells (e.g., *S. cerevisiae, Pichia*, etc). In an alternate embodiment, the ABD polypetides are expressed in vitro using cell free translation systems. In vitro translation systems derived from both prokaryotic (e.g., *E. coli*) and eukaryotic (e.g., wheat germ, rabbit reticulocytes) cells are available and may be chosen based on the expression levels and functional properties of the protein of interest. For example, as appreciated by those skilled in the art, in vitro translation is required for some display technologies, for example ribosome display. In addition, the ABD fusion proteins may be produced by chemical synthesis methods. Also transgenic expression systems both animal (e.g., cow, sheep or goat milk, embryonated hen's eggs, whole insect larvae, etc.) and plant (e.g., corn, tobacco, duckweed, etc.).

The nucleic acids that encode ABD fusion proteins disclosed herein may be incorporated into an expression vector in order to express the protein. A variety of expression vectors may be utilized for protein expression. Expression vectors may comprise self-replicating extra-chromosomal vectors or vectors which integrate into a host genome. Expression vectors are constructed to be compatible with the host cell type. Thus expression vectors which find use in generating antibodies disclosed herein include, but are not limited to, those which enable protein expression in mammalian cells, bacteria, insect cells, yeast, and in in vitro systems. As is known in the art, a variety of expression vectors are available, commercially or otherwise, that may find use for expressing antibodies disclosed herein.

The disclosed ABD fusion proteins can be encoded by multiple nucleic acid molecules. For example, the variable heavy and light chains can be introduced into a host cell independently. Though present on separate nucleic acids, their expression yields a single polypeptide.

Expression vectors typically comprise a protein operably linked with control or regulatory sequences, selectable markers, any fusion partners, and/or additional elements. By "operably linked" herein is meant that the nucleic acid is placed into a functional relationship with another nucleic acid sequence. Generally, these expression vectors include transcriptional and translational regulatory nucleic acid operably linked to the nucleic acid encoding the multivalent ABD fusion proteins, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used.

In one embodiment, ABDs are purified or isolated after expression. ABDs and ABD fusion proteins may be isolated or purified in a variety of ways known to those skilled in the art. Purification may be particularly useful for separating heterodimeric heavy chain species from homodimeric heavy chain species, as described herein. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, isoelectric focusing, immunological, precipitation, dialysis, and chromatofocusing techniques. Ultrafiltration and diafiltration techniques, in conjunction with protein concentration, are also useful. Fusion is employed, Ni+2 affinity chromatography if a His-tag is employed, or immobilized anti-flag antibody if a flag-tag is used. For general guidance in suitable purification techniques, see, e.g., incorporated entirely by reference Protein Purification: Principles and Practice, 3rd Ed., Scopes, Springer-Verlag, NY, 1994, incorporated entirely by reference. The degree of purification necessary will vary depending on the screen or use of the antibodies. In some instances no purification is needed.

H. Therapeutic Uses of Albumin Binding Domains and ABD Fusion Proteins

The subject ABDs and ABD fusion proteins find use in a variety of therapeutic uses as described herein.

In one aspect, provided herein is a method of inhibiting tumor growth in a subject in need thereof by administering to the subject albumin binding domain (ABD) fusion proteins described herein. Useful ABD fusion proteins include, but are not limited to, those disclosed in FIGS. 4, 20, 34, 36, 40, 45, 50-51.

In some embodiments, the ABD fusion protein includes an IL-12 or IL-15 (e.g., an IL-12-ABD or IL-15-ABD fusion protein). As described herein, IL-15 ABD fusion proteins are capable of inhibiting tumor growth in a dose dependent manner. Such IL-15 mediated tumor growth inhibition is accompanied by an increase in tumor infiltrating lymphocytes, including cytotoxic T lymphocytes (CTLs) and activated natural killer (NK) cells. In certain embodiments, the ABD fusion protein includes an IL-12 molecule. In some embodiments, the ABD fusion protein includes an IL-15. In yet other embodiments, the cytokine-ABD includes an IL-12 and an IL-15. In some embodiments, the IL-15-ABD includes a variant IL-15 as described herein (see, e.g., FIG. 3).

Also provided herein is a method of treating a subject having cancer by administering to the subject albumin binding domain (ABD) fusion protein. In some embodiments, the ABD fusion protein includes an IL-12 or IL-15 (e.g., an IL-12-ABD or IL-15-ABD fusion protein). IL-12 and IL-15 are cytokines for immunomodulation of the tumor microenvironment owing to its ability to proliferate and extend survivability of CD8+ T cells. Other useful ABD fusion proteins include, but are not limited to, those disclosed in FIGS. 4, 20, 34, 36, 40, 45, 50-51.

Examples of cancer to be treated herein include, but are not limited to, carcinoma, blastoma, sarcoma, certain leukemia or lymphoid malignancies. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, skin cancer/melanoma, as well as head and neck cancer and metasteses associated with any of the primary tumors.

In another aspect provided herein, is a method of increasing proliferation and/or survivability of a CD8+ T cell. In certain embodiments, the method comprises contacting the cell with an albumin binding domain fusion protein that includes in IL-12 and/or IL-15 (e.g., an IL-12-ABD or IL-15-ABD fusion protein). In certain embodiments, the ABD fusion protein includes an IL-12 molecule. In some embodiments, the ABD fusion protein includes an IL-15 molecule. In yet other embodiments, the fusion protein the ABD fusion protein includes an IL-12 and an IL-15.

Pharmaceutical Formulations, Administration and Dosing

In another aspect, provided herein is a therapeutic composition comprising any subject albumin binding domain (ABD) polypeptide and a carrier. Subject therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16th Edition, A. Osal., Ed., 1980).

1. Compositions for In Vivo Administration

Formulations of the albumin binding domain (ABD) fusion protein used in accordance with the present invention are prepared for storage by mixing an ABD fusion protein having the desired degree of purity with optional pharmaceutically acceptable carriers, excipients or stabilizers (Remington's Pharmaceutical Sciences 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) fusion proteins; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA or DPTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG) of various molecular weights.

The formulation herein may also contain more than one active compound as necessary for the particular indication being treated, preferably those with complementary activities that do not adversely affect each other. For example, it may be desirable to provide ABD fusion proteins with other specificities. Alternatively, or in addition, the composition may comprise a cytotoxic agent, cytokine, growth inhibitory agent and/or small molecule antagonist. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration should be sterile, or nearly so. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

When encapsulated albumin binding domain fusion proteins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

2. Administrative Modalities

The subject albumin binding domain fusion proteins and therapeutic agents are administered to a subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred.

3. Treatment Modalities

In the methods provided herein, therapy is used to provide a positive therapeutic response with respect to a disease or condition. By "positive therapeutic response" is intended an improvement in the disease or condition, and/or an improvement in the symptoms associated with the disease or condition. For example, a positive therapeutic response would refer to one or more of the following improvements in the disease: (1) a reduction in the number of tumor cells; (2) an increase in tumor cell death; (3) inhibition of tumor cell survival; (5) inhibition (i.e., slowing to some extent, preferably halting) of tumor growth; (6) an increased patient survival rate; and (7) some relief from one or more symptoms associated with the disease or condition.

Positive therapeutic responses in any given disease or condition can be determined by standardized response criteria specific to that disease or condition. Tumor response can be assessed for changes in tumor morphology (i.e., overall tumor burden, tumor size, and the like) using screening techniques such as magnetic resonance imaging (MM) scan, x-radiographic imaging, computed tomographic (CT) scan, bone scan imaging, endoscopy, and tumor biopsy sampling including bone marrow aspiration (BMA) and counting of tumor cells in the circulation.

In addition to these positive therapeutic responses, the subject undergoing therapy may experience the beneficial effect of an improvement in the symptoms associated with the disease.

Thus, for B cell tumors, for example, the subject may experience a decrease in the so-called B symptoms, i.e., night sweats, fever, weight loss, and/or urticaria. For pre-malignant conditions, therapy with an multivalent therapeutic agent may block and/or prolong the time before development of a related malignant condition, for example, development of multiple myeloma in subjects suffering from monoclonal gammopathy of undetermined significance (MGUS).

An improvement in the disease may be characterized as a complete response. By "complete response" is intended an absence of clinically detectable disease with normalization of any previously abnormal radiographic studies, bone marrow, and cerebrospinal fluid (CSF) or abnormal monoclonal protein in the case of myeloma.

Such a response may persist for at least 4 to 8 weeks, or sometimes 6 to 8 weeks, following treatment according to the subject methods. Alternatively, an improvement in the disease may be categorized as being a partial response. By "partial response" is intended at least about a 50% decrease in all measurable tumor burden (i.e., the number of malignant cells present in the subject, or the measured bulk of tumor masses or the quantity of abnormal monoclonal protein) in the absence of new lesions, which may persist for 4 to 8 weeks, or 6 to 8 weeks.

Treatment includes a "therapeutically effective amount" of the medicaments used. A "therapeutically effective amount" refers to an amount effective, at dosages and for periods of time necessary, to achieve a desired therapeutic result.

A therapeutically effective amount may vary according to factors such as the disease state, age, sex, and weight of the individual, and the ability of the medicaments to elicit a desired response in the individual. A therapeutically effective amount is also one in which any toxic or detrimental effects of the antibody or antibody portion are outweighed by the therapeutically beneficial effects.

A "therapeutically effective amount" for tumor therapy may also be measured by its ability to stabilize the progression of disease. The ability of a compound to inhibit cancer may be evaluated in an animal model system predictive of efficacy in human tumors.

Alternatively, this property of a composition may be evaluated by examining the ability of the compound to inhibit cell growth or to induce apoptosis by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

EXAMPLES

Example 1: Screening and Identification of Human Serum Albumin Binding Domains

Solid phase panning and solution panning methods were carried out to identify phage scFv albumin binding domains (ABD). Albumin binding domains that were selected from a primary screen for human serum albumin binding domains were subsequently screened for cross-reactivity to mouse serum albumin using standard ELISA techniques. Primary albumin binding domain candidates obtained using the screening methods were sequenced and subsequently assayed for target concentration-dependent binding, pH stability, FcRn binding interference and kinetic binding. In particular, candidate ABDs were chosen for their ability to bind human serum albumin (kD ~20-60 nM), mouse serum albumin (kD ~10-30 nM) and cyno serum albumin (kD ~20-60 nM) at low pH (pH5.5) and neutral pH (pH 7.7). Candidate ABDs were assayed to ensure that they did not compete with FcRn binding to serum albumin. As explained herein, ABDs that bind at such pH and did not compete with FcRn binding are capable of undergoing FcRn mediated endosomal recycling. Thus, biologics (e.g., cytokines and antibody based biologics) that include such ABDs are also capable of undergoing such FcRn mediated recycling and, thus, exhibit a longer half-life compared to counterparts that do not include such ABDs.

Five albumin binding clones were selected based on these criteria: A9, A10, A6, 2B4, 2H10. Of these five clones, A10 was selected based on high expression level and best activity profile. A10 was then mutated to eliminate regions that could putatively cause immunogenicity. From these A10 variants, A10m3 was selected as the lead based on its high affinity for serum albumin.

The sequences of exemplary human serum albumin bind domains are shown in FIG. 2 including A10m3 (FIG. 2D).

Example 2: Variant IL-15 and IL-15-ABDs

Figure 5B:
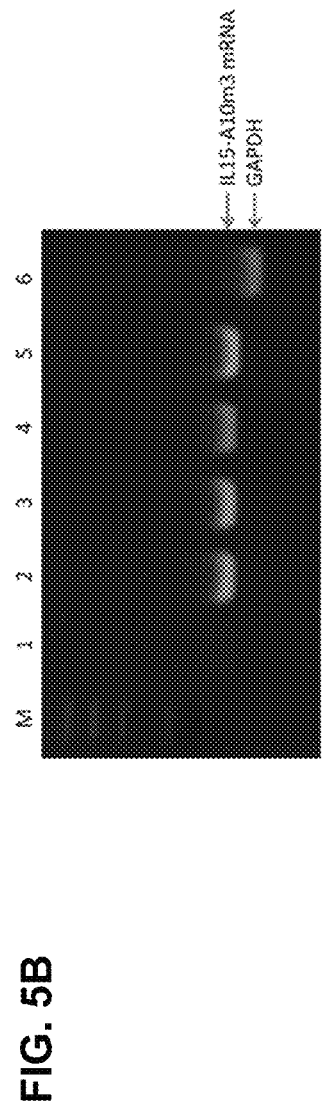
Figure 8A:
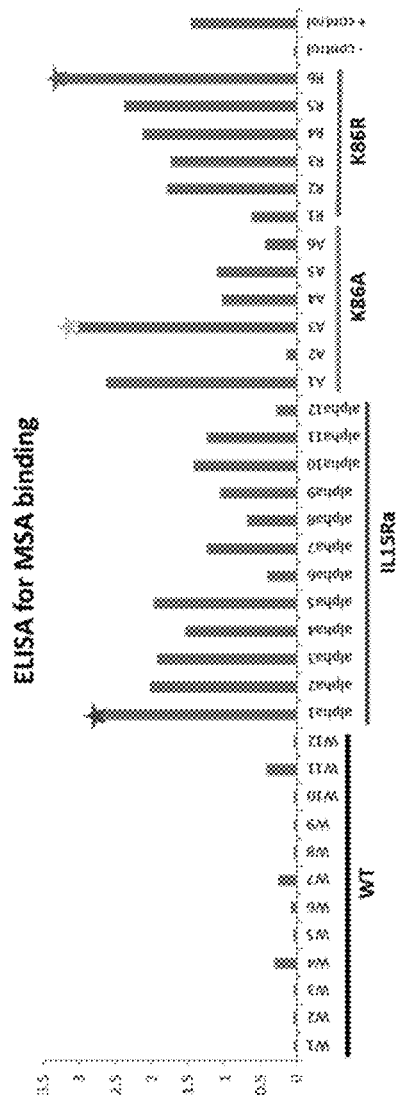
FIG. 8A and FIG. 8B depicts studies assessing the expression level (FIG. 8A) and ability of HEK293 cell-produced IL-15-ABD K86R and K86A variants and IL-15Rα/IL-15-ABD to bind mouse serum albumin (FIG. 8A) and IL-15Rα (FIG. 8B). A) ELISA readout for IL15-ABD binding to mouse serum albumin (MSA) of 12 WT IL15-A10m3 clones (WT), 12 IL-15Rα/IL-15-A10m3 clones (IL15Ra), 6 IL-15 K86A-A10m3 mutant clones (K86A) and 6 IL-15 K86R-A10m3 mutant clones (K86R). Culture medium of each sample well from 24-well plates was added to ELISA plates coated with MSA. B) ELISA for binding of IL-15 to IL-15 receptor alpha (IL-15Rα) which was coated on the plate was used to confirm that K86A (clone A3, yellow star) and K86R (clone R6, green star) mutations had no impact on the binding activity of IL-15 to IL-15Rα. The internal IL-15Rα in IL-15Rα-IL-15-A10m3 (clone alpha1, red star) could bind to internal IL15 and thus block its binding to IL-15Rα coated on the plate. 10 ug/ml of E. coli produced WT IL-15-A10m3 was used as positive control.
Figure 8B:
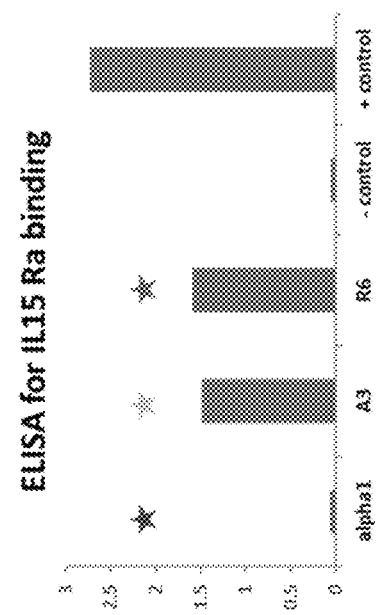
Figure 9A:
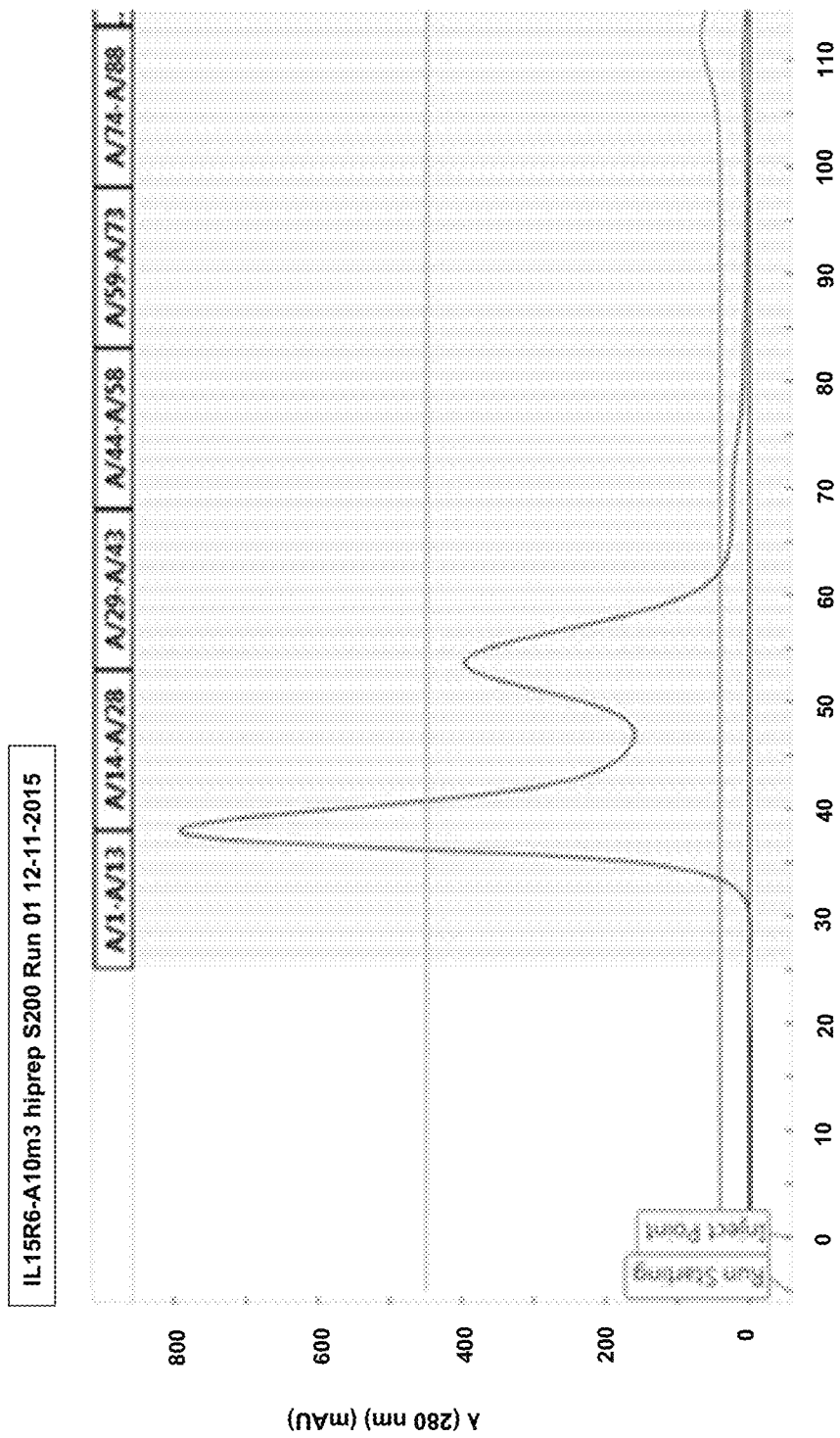
FIG. 9A-FIG. 9C depicts the scaled-up production of IL15K86R-A10m3 clone #6. A) Chromatograph of IL15K86R-A10m3 by a size exclusion column; B) SDS-PAGE analysis of the SEC fractions from 14 to 42; C) Final products (1: IL15K86R-A10m3, 2: IL15Ra-IL15-A10m3) were final confirmed by SDS-PAGE (left) and Western blotting with anti-His tag antibody (right).
Figure 9C:
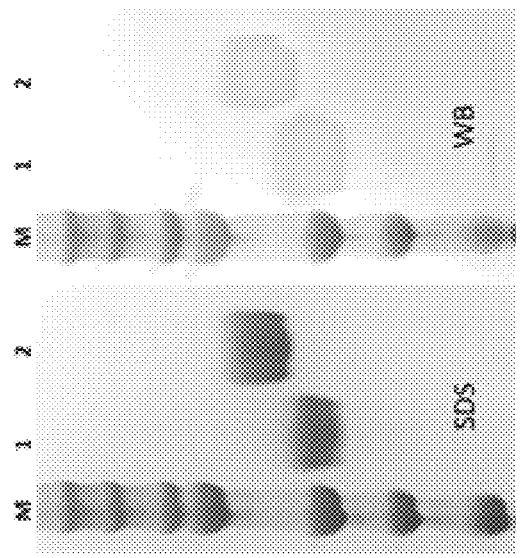
Figure 9B:
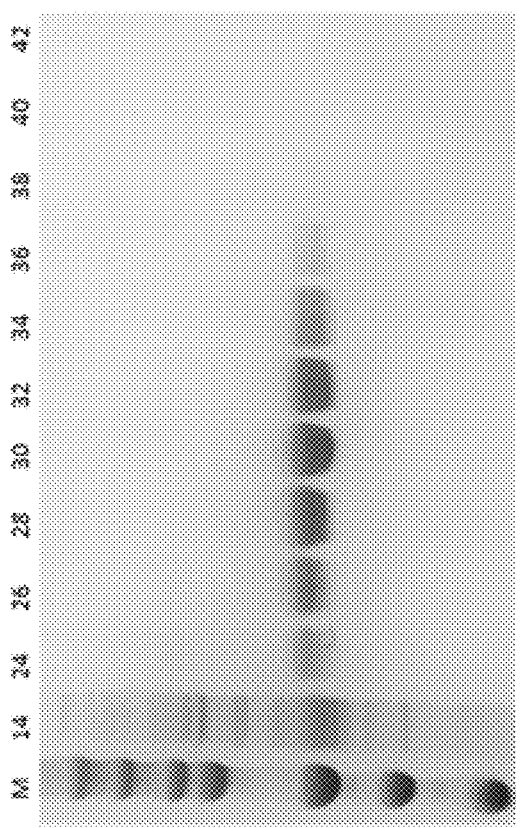
Figure 10:
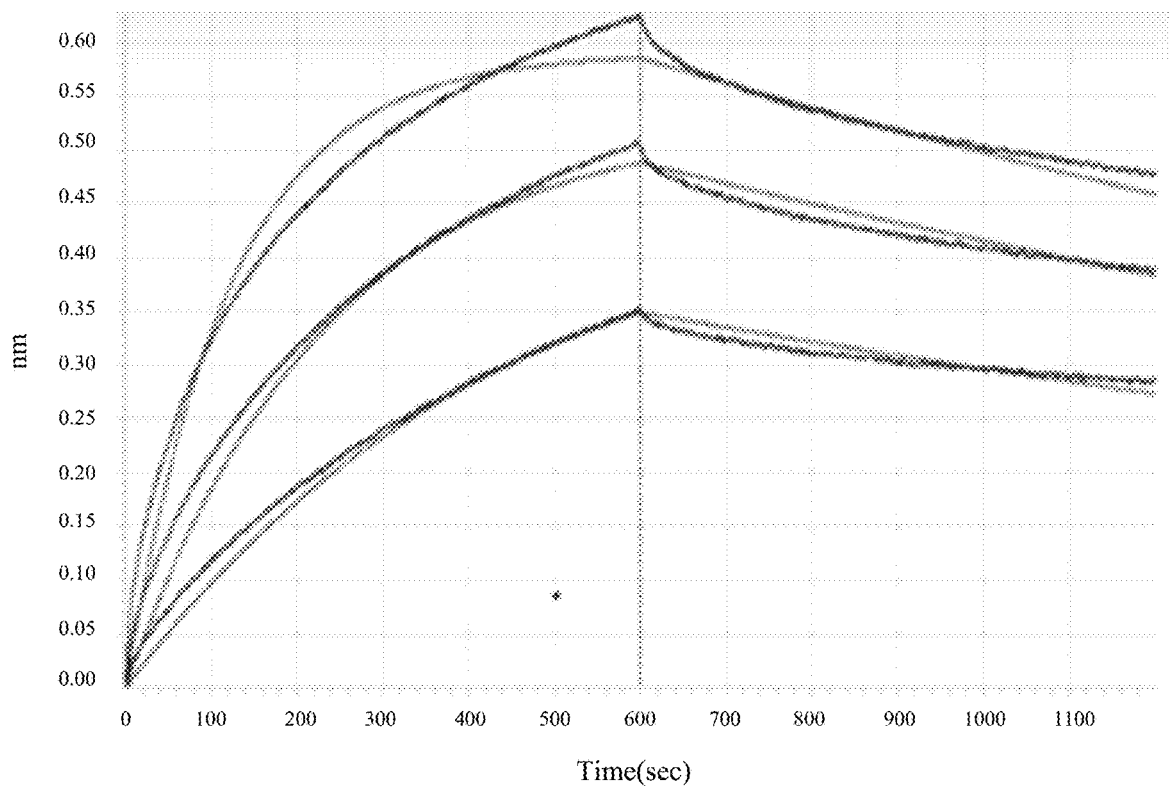
FIG. 10 depicts the results of in vitro binding assays, confirming the ability of IL-15 K86R-A10m3 to bind mouse serum albumin (MSA).
Figure 11:
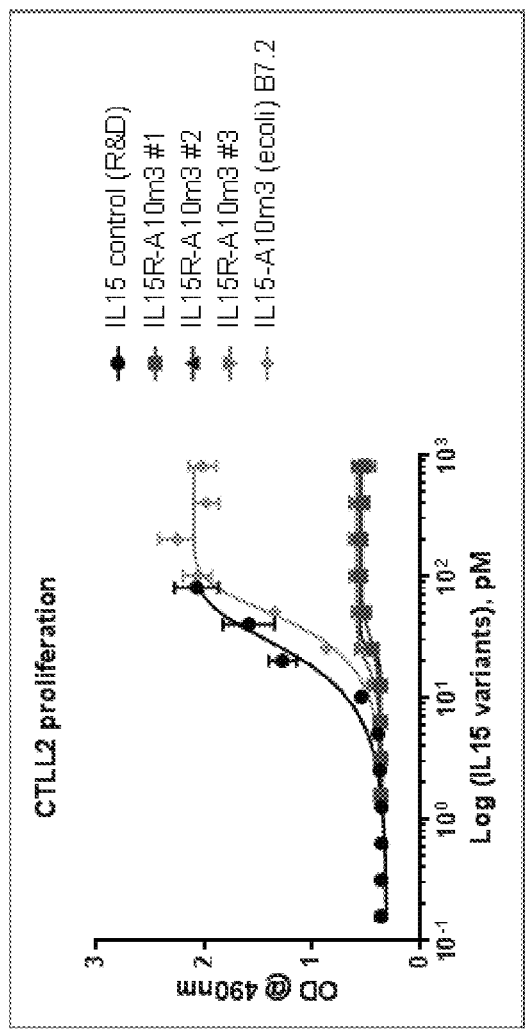
FIG. 11 depicts the results of CTLL2 proliferation assays, showing that IL-15 K86R-A10m3 polypetides produced form HEK293T cells have reduced bioactivity compared to wildtype IL-15 and IL-15-A10m3 produced from E. coli.
Figure 12A:
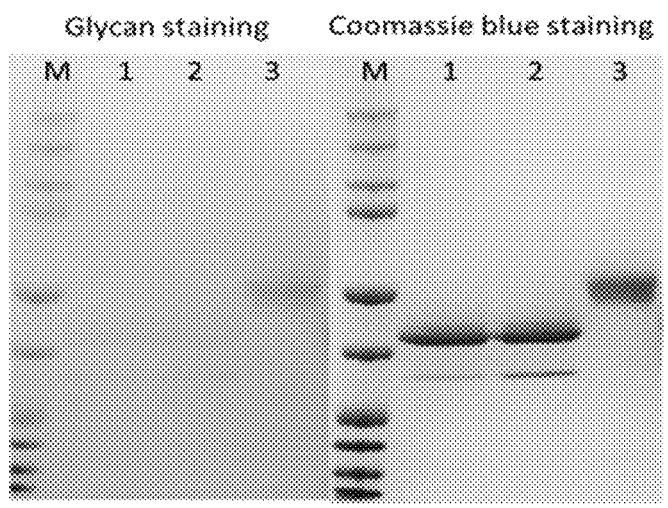
FIG. 12A and FIG. 12B depicts results of studies showing that the reduced bioactivity of HEK cell produced IL-15 K86R-A10m3 is at least partially due to its glycosylation.
Figure 12B:
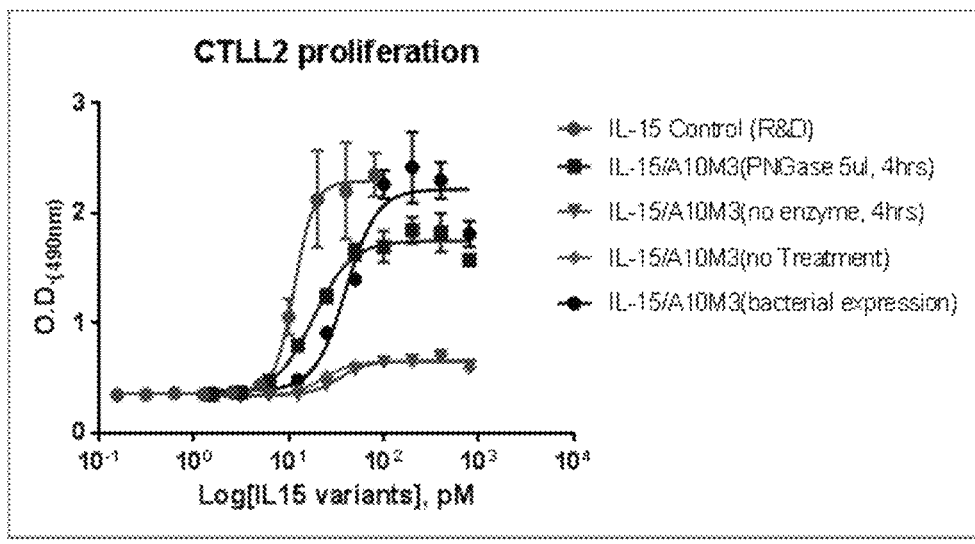

Expression of IL15-A10m3 Protein is Extremely Poor by HEK293T Cells, which Cannot be Accounted by Transcription IL-15-ABD (IL-15-A10m3) constructs were produced in HEK293 cells in three independently transfected cell cultures and assessed by Western blotting using either anti-His tag antibody (FIG. 5A, left) or by functional ELISA binding to mouse serum albumin (FIG. 5A, right). As shown in FIG. 5A, expression of IL-15-A10m3 could not be assessed by either of these methods. To assess whether the lack of IL-15-A10m3 expression in HEK293 cells was due to low transcription levels, mRNA was prepared from four independently IL-15-A10m3 transfected cells and RT-PCR was performed to quantify the mRNA level of IL15-A10m3 mRNA (FIG. 5B, lanes 2-5) in comparison with that of a house-keeping gene, GAPDH (FIG. 5B, lane 6). As shown in FIG. 5B, IL15-A10m3 mRNA was detected in significant quantities from the transfected cells relative to that control GAPDH, suggesting that the low expression levels of IL-15-A10m3 produced in HEK293 cells is not due to transcription, but most likely due associated with the translational or post-translational process.

Identification of a putative ubiquitination site in IL15 that is adjacent to the IL15 receptor alpha binding site Studies have shown that IL15 protein were expressed in the cells but are very unstable with a short half-life. Co-expression of IL15Rα with IL15 in the same cell greatly increased the amount of cell surface IL15Rα as well as IL15. Further studies confirmed that IL15Rα acts as a chaperon of IL15 and binds IL15 intracellularly to protect and stabilize IL15 before secretion. These findings suggest that translation may not account for the low productivity of IL15. Rather, post-translational modification (PTM) might play a role in IL15 intracellular instability, and that the intracellular instability of IL15 can be overcome by IL15Rα blocking the specific yet-not-known post-translational modification. Ubiquitination is a well-documented mechanism that allows cells to mark intracellular proteins for degradation.

Given that IL15 is a very potent proinflammatory cytokine, whose expression is tightly controlled by cells, it is possible that cells utilize ubiquitination to actively control IL15 protein levels. Potential ubiquitination sites on IL-15 that are putatively protected upon binding to IL-15Rα were identified (FIG. 6). In particular, amino acid K86 is a putative ubiquitination site that is next to the IL-15/IL-15Rα binding site (FIG. 6A), suggesting the possibility that the binding of IL15Rα to IL15 blocks the accessibility of ubiquitin ligase (e.g., E3) to K86 on the IL15 protein. K86 was further confirmed as a ubiquitination site using UbPred, an online ubiquitination site database FIG. 6B.

Mutation of K86 on IL15 Restores the Expression of the IL15-A10m3 Protein by HEK293T Cells To assess whether ubiquitination at K86 affects the intracellular stability of IL-15, IL-15 variants containing amino acid substitutions at K86, including K86A and K86R, were made. The sequences of several of these IL-15 variants are shown in FIG. 3. Without being bound by any particular theory of operation, it is believed that amino acid substitutions at these particular ubiquitination sites lead to ubiquitination resistant IL-15 that exhibit increased stability over wildtype IL-15. Such IL-15 variants were attached to an ABD (A10m3) for further half-life extension (FIG. 4). FIG. 7 provides schematic illustrations of such IL-15-ABD fusion proteins including an IL-15-ABD with a IL-15Rα/IL15 "sushi domain" (A) and IL-15-ABD fusion proteins that include IL-15 variants having amino acid substitutions at ubiquitination site K86 (B).

HEK293 cell-produced IL-15-ABD K86R and K86A variants and IL-15Rα/IL15-ABD were assessed for their ability to bind mouse serum albumin (MSA) and IL-15Rα. As shown in FIG. 8A, HEK293-produced IL-15-ABD K86R and K86A variants (12 clones) and IL-15Rα/IL15-ABD (12 clones) exhibited higher expression as compared to HEK-293-produced wildtype IL-15-ABD (12 clones). Such constructs also were capable of binding to MSA. Moreover, as shown FIG. 8B, the K86R (clone R6, green star) and K86A (clone A3, yellow star) substitutions did not interfere with the ability of the variants to bind to IL-15Rα. Interestingly, IL15Rα-fused IL15-A10m3 failed to show any binding to IL15Rα, suggesting that the internal IL15Rα sushi domain bound to IL15 intra-molecularly and thus blocked the binding to external IL15Rα coated on the plate. This is consistent with our and others' finding that binding of IL15 to IL15Rα sushi domain increases the IL15 expression (FIG. 7B).

A scaled up production of one particular variant HEK293 cell-produced IL-15-ABD containing amino acid substitution K86R (IL-15 K86R-A10m3) was carried out and the IL-15 K86R-A10m3 construct was assessed for serum albumin binding in vitro. As shown in FIG. 9, IL-15-ABD having a K86 mutation (IL-15 K86R-A10m3) and IL-15Rα/IL15-ABD (IL-15Rα/IL15-A10m3) were capable of being produced in HEK 293 cells in scaled up quantities, as confirmed by SDS-PAGE (FIG. 9C, left) and Western blotting with an anti-His tag antibody (right). Further, as shown in FIG. 10, K86R-A10m3 exhibited binding to mouse serum albumin (MSA).

The Bioactivity of IL15 K86R-A10m3 Produced from HEK293T Cells is Impaired, which can be Rescued by De-Glycosylation.

Bioactivity of various IL-15-ABDs were tested using CTLL2 proliferation assays. IL-15-ABDs tested include wildtype IL-15-A10m3 and three different IL-15 K86R-A10m3s produced in HEK293T cells. Commercially available IL-15 and in-house produced IL-15-ABD, both made using *E. coli*, were used as controls. As shown in FIG. 11, IL-15 K86R-A10m3 produced from HEK293T showed a significantly reduced ability to promote CTLL2 proliferation compared to controls produced in *E. coli*, including commercial wildtype IL-15 (R&D) and IL-15-A10m3 produced in-house. Given the difference in CTLL2 proliferation assays between IL15 K86R-A10m3 from HEK293T and IL15-A10m3 from *E. coli*, it was hypothesized that since IL15-A10m3 produced from *E. coli* does not undergo the classic N-glycosylation as it does in mammalian cells, it is possible that glycosylation of IL15 K86R-A10m3 in HEK293 T cells may interfere in the interaction of IL15 K86R-A10m3 with its receptors.

To assess whether the reduced bioactivity of HEK cell-produced IL-15 K86R-A10m3 is due to glycosylation, IL-15 K86R-A10m3 was deglycosylated using PNGase and CTLL2 proliferation assays were carried out to assess bioactivity of the deglycosylated IL15 K86R-A10m3. After PNGase mix treatment of IL-15 K86R-A10m3 under native conditions, glycan was completely removed and visualized by SDS-PAGE followed by glycan staining (FIG. 12A, left) and coomassie blue staining (FIG. 12A, right). 1) IL-15R-A10m3+5 ul PNGase mix; 2) protein+10 ul PNGase mix; 3) no enzyme control. As shown in FIG. 12B, deglycosylation of IL-15 K86R-A10m3 (blue) nearly completely rescued activity in CTLL2 proliferation assays, in comparison with non-treated samples (purple, yellow). WT IL-15 from R&D systems (red) and in-house *E. coli* produced IL-15-A10m3 (black) were used as positive controls.

N112 of IL-15 K86R A10m3 is Critical for its Bioactivity to Promote CTLL2 Proliferation Amino acid position N112 of IL-15 K86R-A10m3 is a key site for IL-15 bioactivity, particularly in the context of IL-15-ABD, as it is critical for a proper establishment of the interaction between IL-15 and IL15 receptor gamma. Variant IL-15 K86R was further mutated at N112A to determine whether mutations at this site could restore IL-15 bioactivity, similar to deglycosylated IL-15. In particular, IL15 K86R-A10m3 were mutated to further include a N112Q, N112A or N112S IL-15 amino acid substitution and CTTLL2 proliferation assays were carried out to test bioactivity. As shown in FIG. 13A, introducing amino acid substitution N112A into IL-15 K86R-A10m3 (blue) restored its bioactivity comparable to that of deglycosylated IL-15 K86R-A10m3 (green) in CTLL2 proliferation assays, while N112Q mutation (red) has no effect on bioactivity relative to the parental IL-15R-A10m3 without deglycosylation (yellow). WT IL-15 (Black) from R&D systems served as positive control.

Figure 13A:
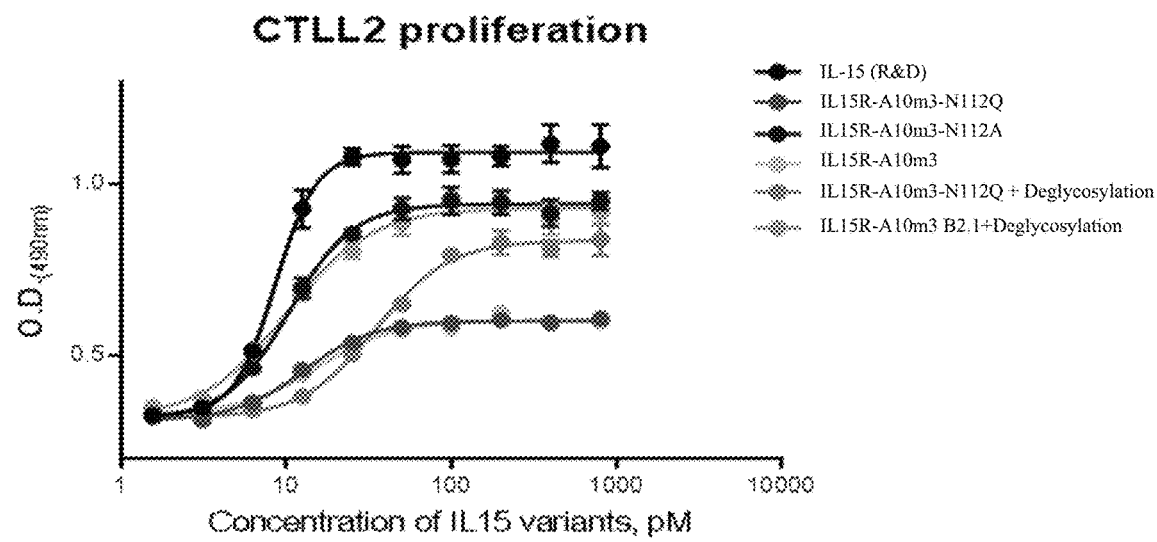
FIG. 13A and FIG. 13B provides the results of studies, showing that N112A mutation introduced into IL15 K86R-A10m3 can restore IL-15 bioactivity comparable to that of deglycosylated IL-15R-A10m3 in CTLL2 proliferation assays (A). (B) further shows that IL-15R-A10m3 fusion proteins with IL-15 amino acid substitutions N112A, N112Q and N112S displayed increased bioactivity inversely proportional to the size of the substituted side chain.
Figure 13B:
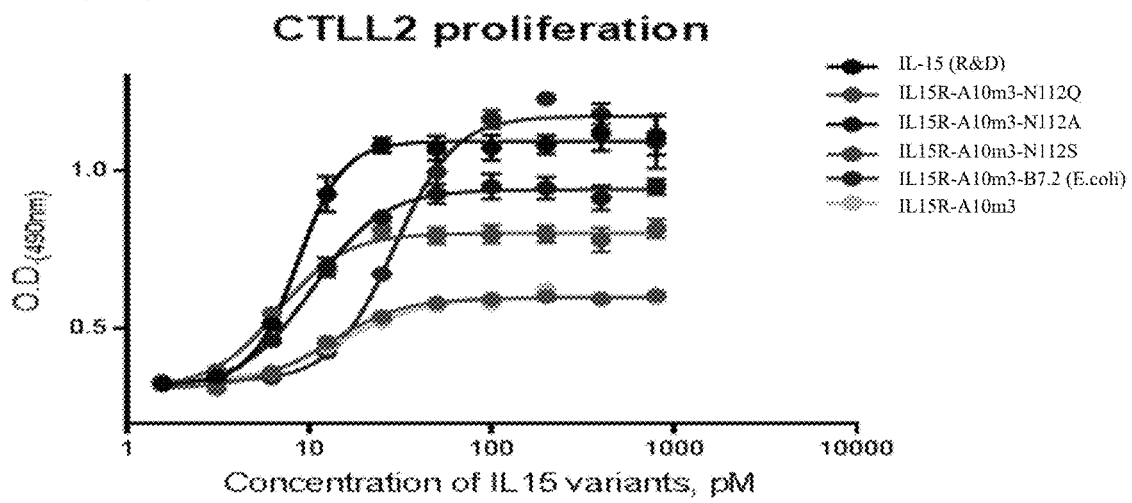
Figure 15:
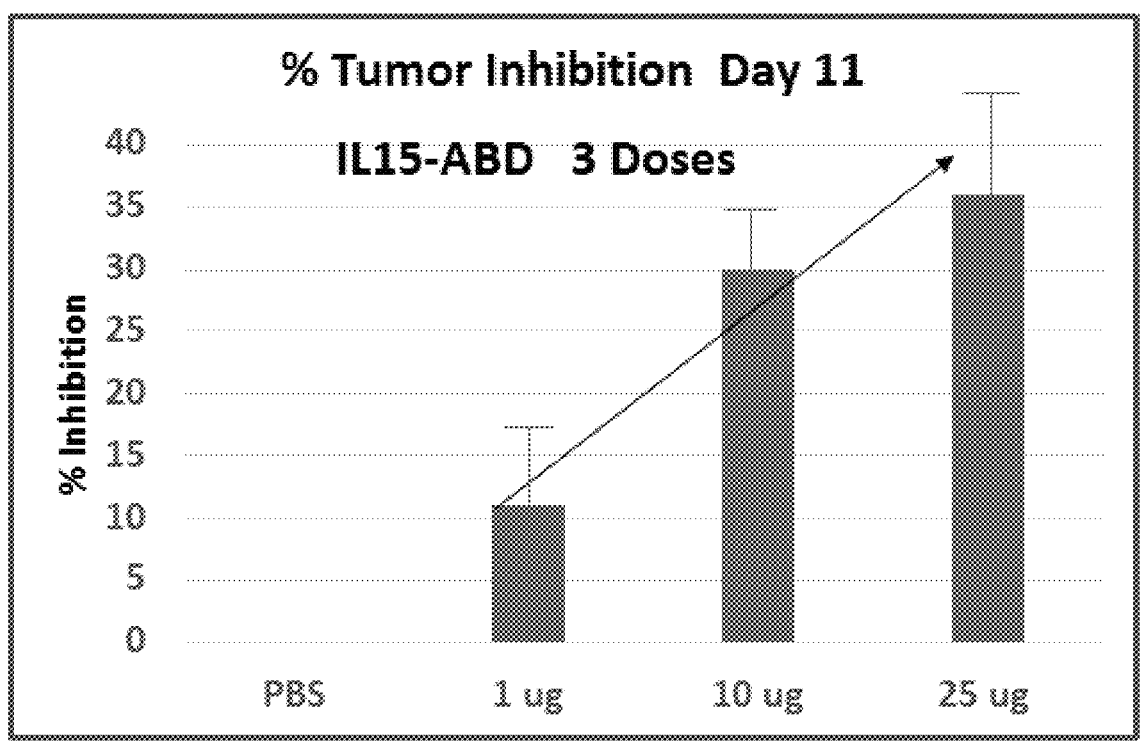
FIG. 15 is a graph, showing the amount of B16-F10 tumor growth inhibition in C57BL/6 mice treated with IL-15-ABD fusion protein, 11 days after treatment.

Mutations with different side chains at N112 were tested to further demonstrate the size effect on the bioactivity. As show in FIG. 13B, N112Q (big, red), N112S (medium, green) and N112A (small, blue) displayed an increased bioactivity inversely proportional to the size of the side chains. Moreover, the suggested hydrogen bond established by N112 of IL-15 and Y103 of IL15 receptor gamma does not seem to be important for this activity, as N112A cannot form such a bond. WT IL-15 from R&D systems (black) and in-house E. coli produced IL-15-A10m3 (purple) were used as the positive control; parental IL15 K86R-A10m3 without deglycosylation (yellow) was used as the negative control.

Example 3: In Vivo Activity of Variant IL-15 and IL-15-ABDs

Figure 16A:
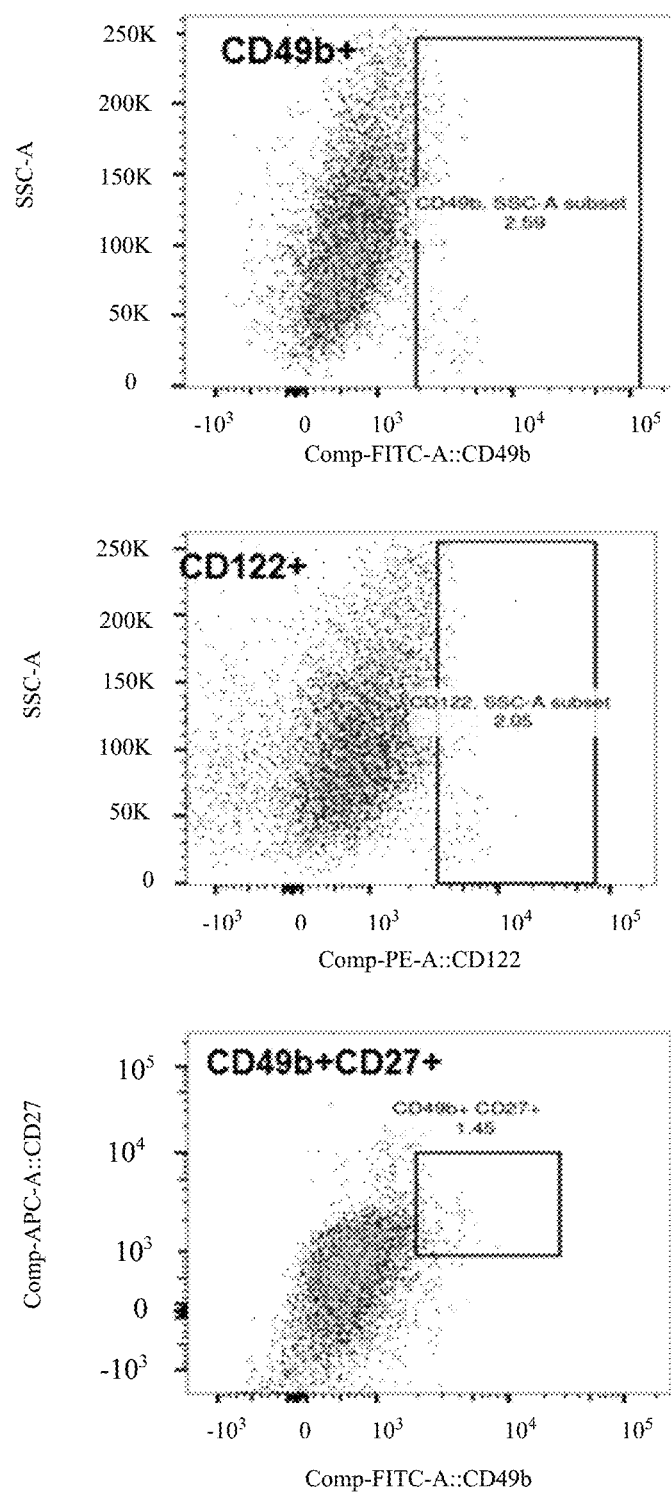
FIG. 16A and FIG. 16B provides FACS analyses, depicting the effect of IL-15-ABD treatment on tumor infiltration lymphocyte populations.
Figure 16B:
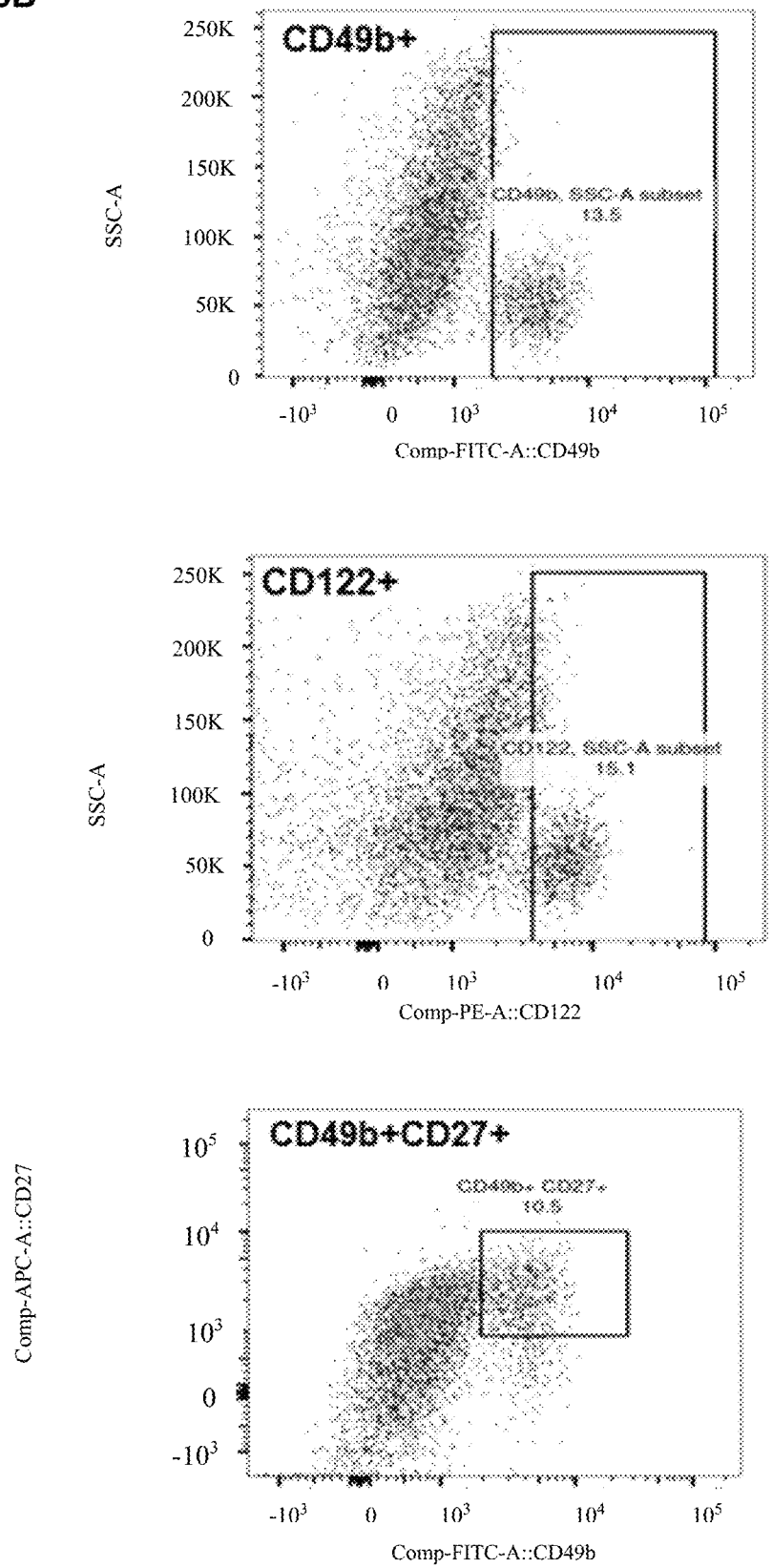

The ability for IL-15 and IL-15-ABD to inhibit tumor growth was assessed using a B16-F10 mouse melanoma model. As summarized in FIG. 14, mice were treated with IL-15, PBS placebo or various doses of IL-15-ABD by IV injection at four different time points, spaced 48 hours apart. As shown in FIG. 16, IL-15-ABD inhibits tumor growth in a dose dependent manner.

FACS analyses were performed to further assess the profile of tumor infiltration lymphocyte populations in IL-15-ABD treated mice from these studies. As shown in FIG. 16, tumors in IL-15-ABD treated mice exhibited an increase in NK cell populations. This data coupled with observations of increased tumor accumulation and retention in IL-15-ABD treated mice, as described above, suggest the ABD enhances the proinflammatory effect of IL-15 within the tumor. The effects of IL-15-ABD treatment on lymphocyte populations in spleens and tumors are summarized in FIGS. 17 and 18. As shown in FIGS. 17 and 18, FACS analysis of lymphocytic populations show a 3-6 fold increases of tumor infiltrating CTL and NK cell populations in tumors of IL-15 ABD treated mice. No significant differences were observed in spleen. Taken altogether, the results of these studies show the tumor immunomodulatory capability of IL-15-ABDs in vivo.

Figure 19A:
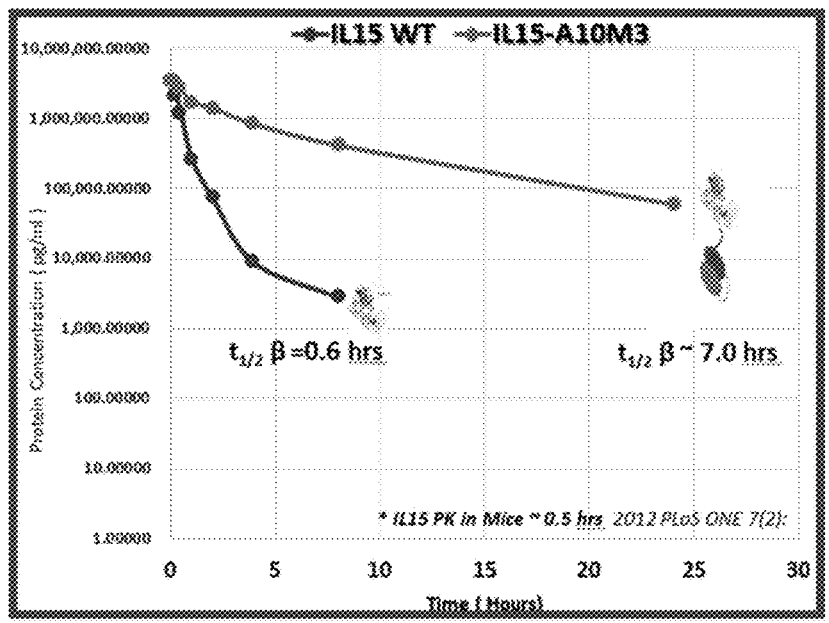
FIG. 19A and FIG. 19B provide results of studies showing the stability of subject IL-15-ABD in a mouse model (A) and in human serum (B), as compared to control IL-15 WT.
Figure 19B:
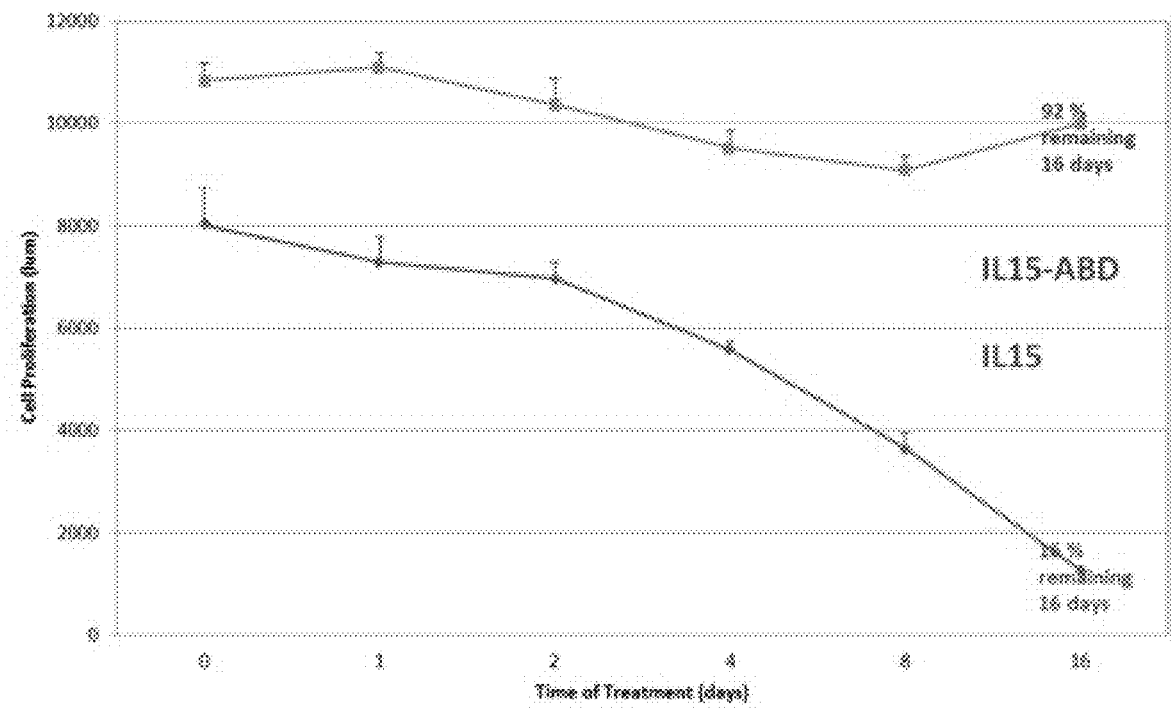

To assess the ability of ABD fusion proteins to increase the half-life of IL-15, C57B mice were injected intravenously with 5 μg of IL-15-ABD or IL-15 alone and serum concentrations of IL-15-ABD and IL-15 were subsequently assessed. As shown in FIG. 20A, IL-15-ABD exhibited a greater PK as compared to IL-15 WT. IL-15 T ½β=0.6 hrs, similar to those reported in the public domain (~0.5 hrs). Study results show ABD extends IL-15 T ½β to ~7.0 hours, which is a ~10× fold increase. IL-15-ABD was also assayed for stability in human serum using a cell based assay. As shown in FIG. 19B, IL-15-ABD was more stable in human serum compared to commercial IL-15 control, without ABD.

Example 4: IL-12-ABD

Figure 21A:
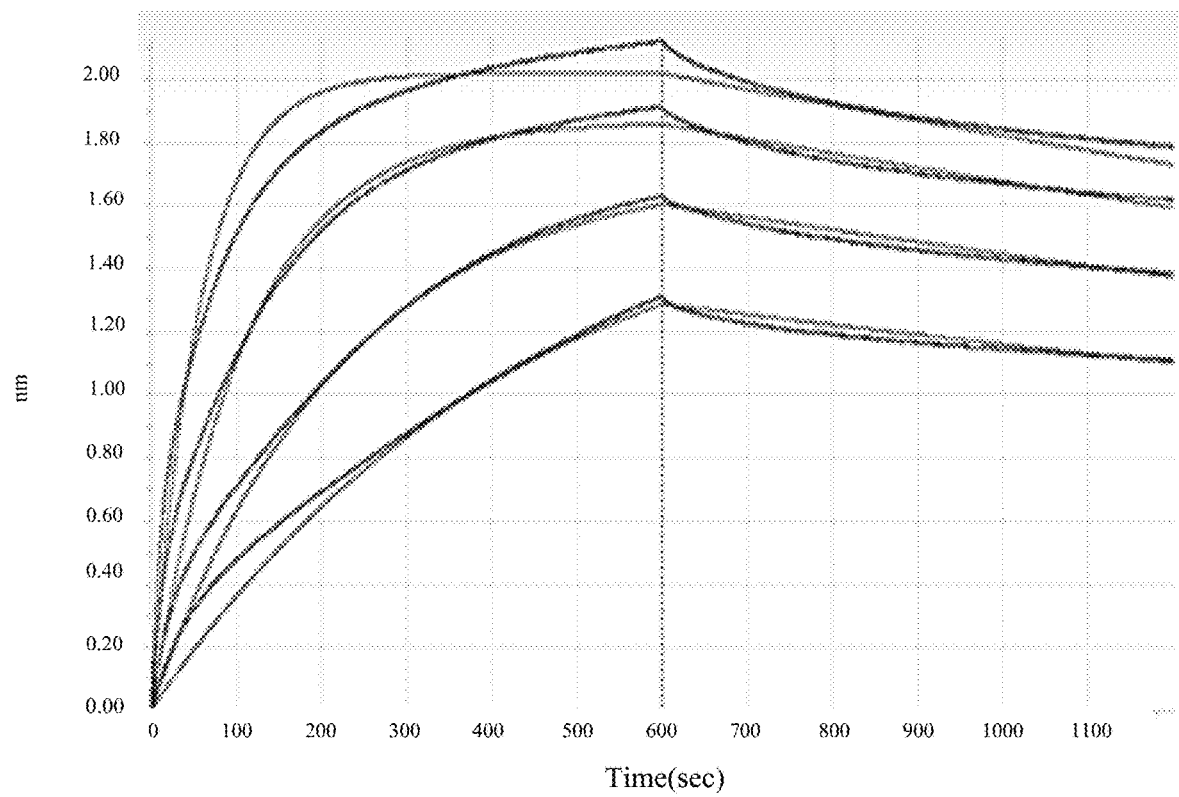
FIG. 21A, FIG. 21B and FIG. 22 are studies showing that subject IL-12-ABD produced from HEK293T cells are biologically active in in vitro assays and cell based assays.
Figure 21B:
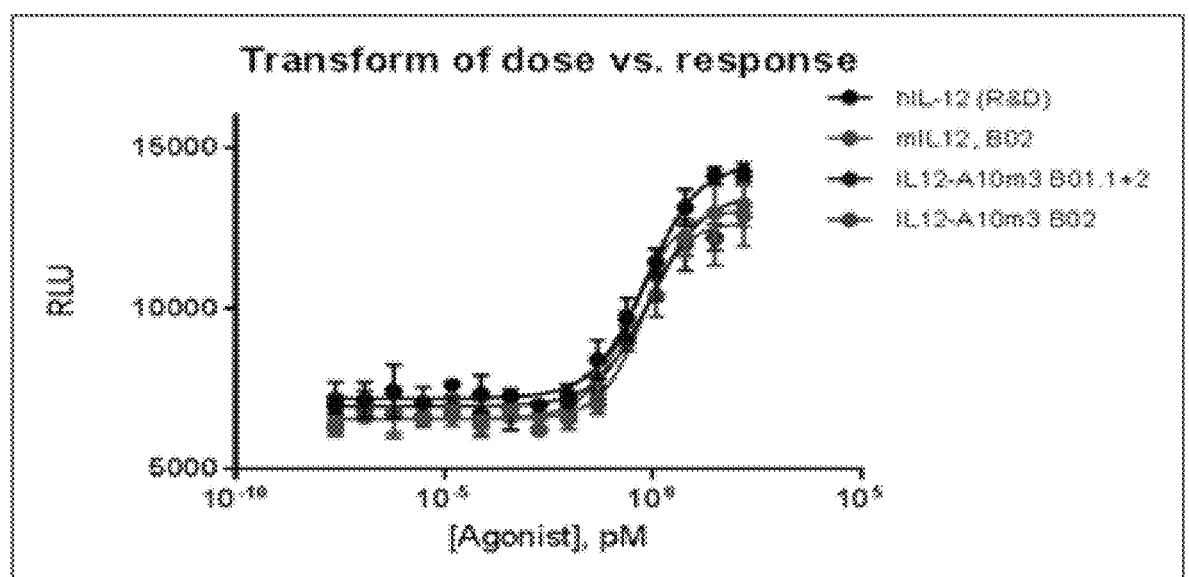
Figure 22:
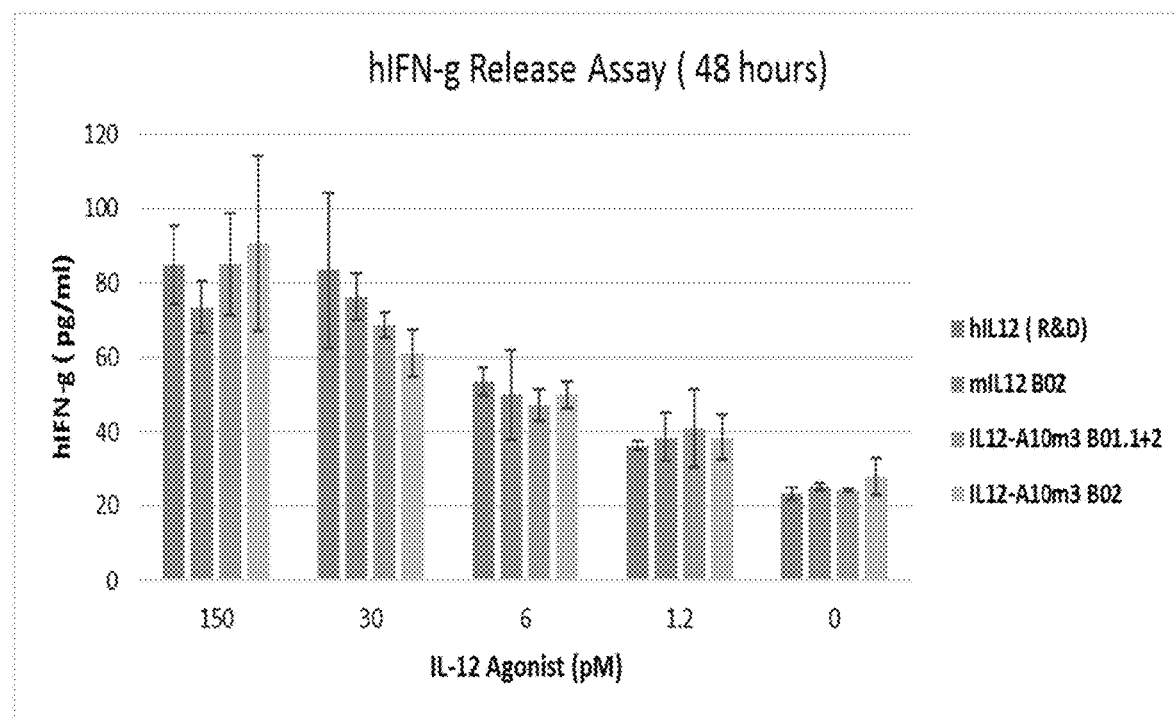
Figure 24A:
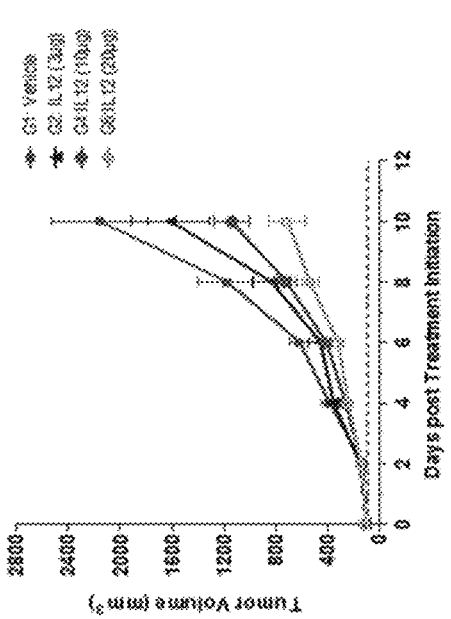
FIG. 24A-FIG. 24C are graphs depicting the tumor growth kinetics of various groups in the in vivo IL-12-ABD/IL-12 studies.
Figure 24B:
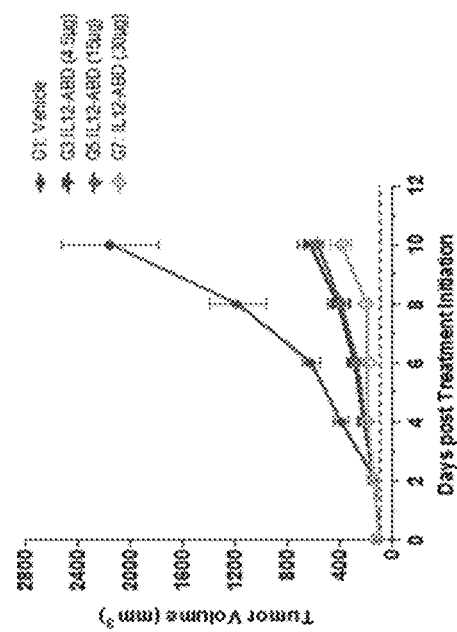
Figure 24C:
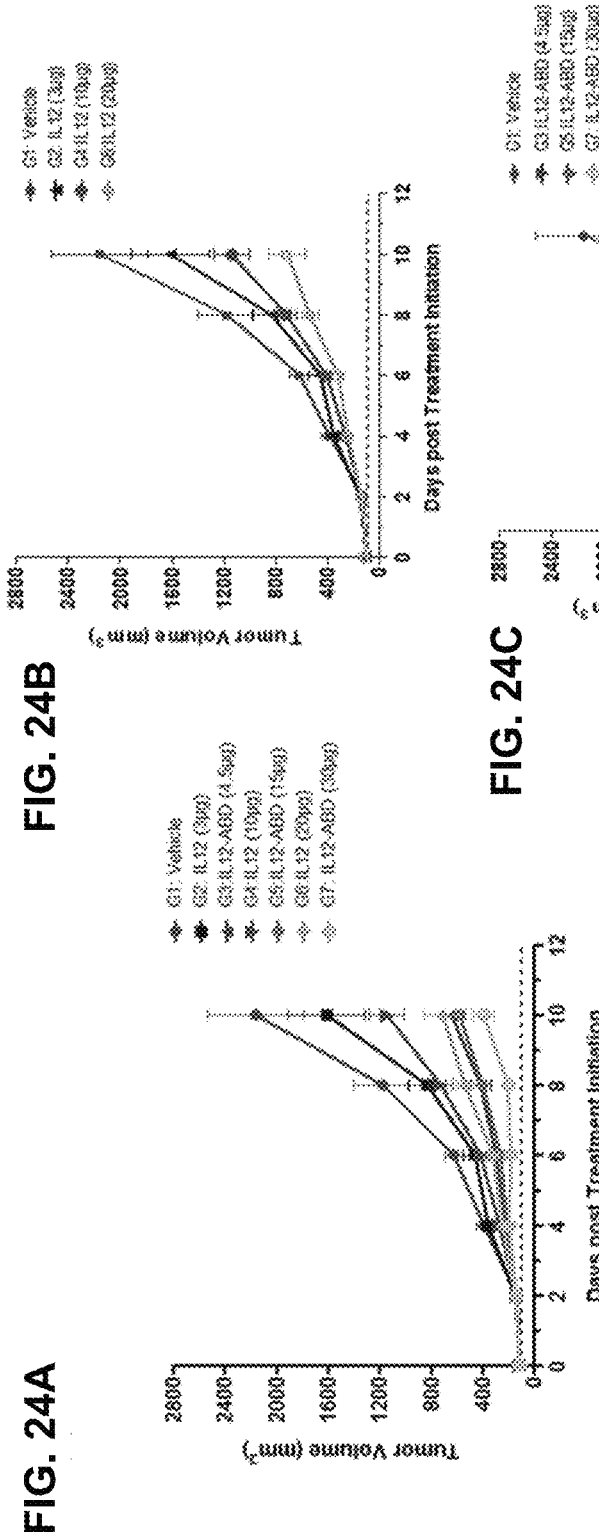
Figure 25:
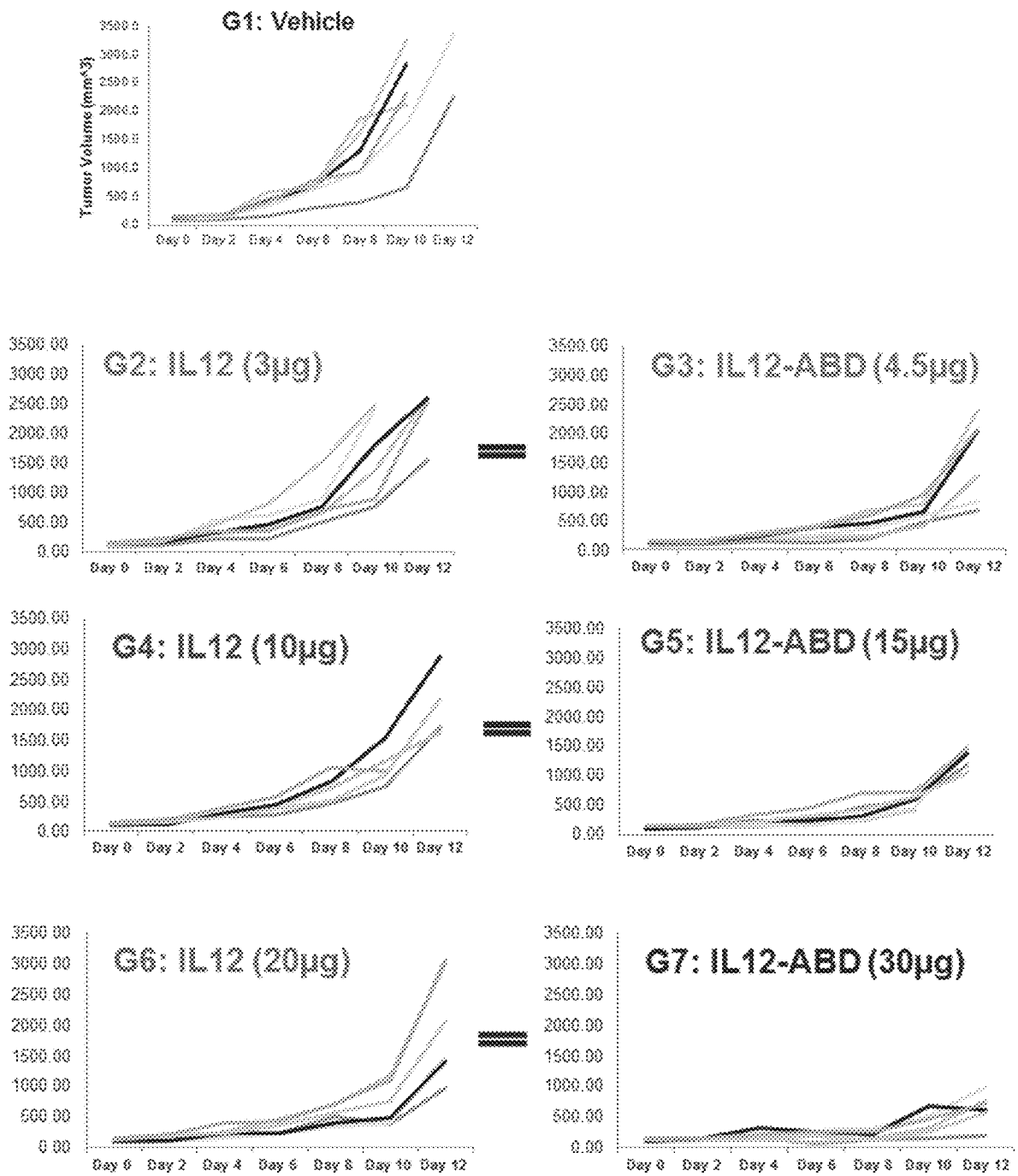
FIG. 25 are graphs depicting the tumor growth kinetics of individual animals in each of the various group of the in vivo IL-12-ABD/IL-12 studies.
Figure 26A:
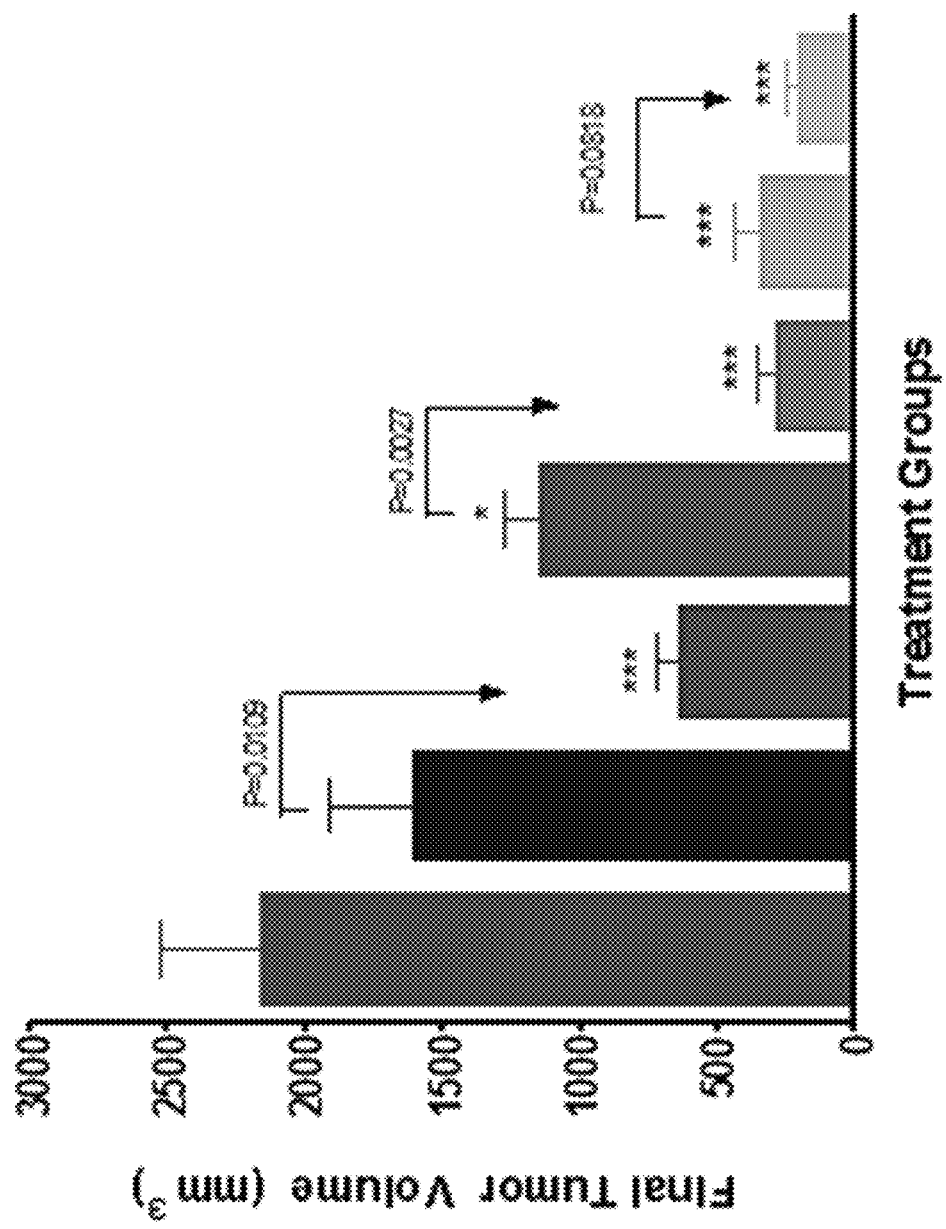
FIG. 26A and FIG. 26B are graphs showing the tumor volumes of various groups in the in vivo IL-12-ABD/IL-12 studies, 10 days post-treatment.
Figure 26B:
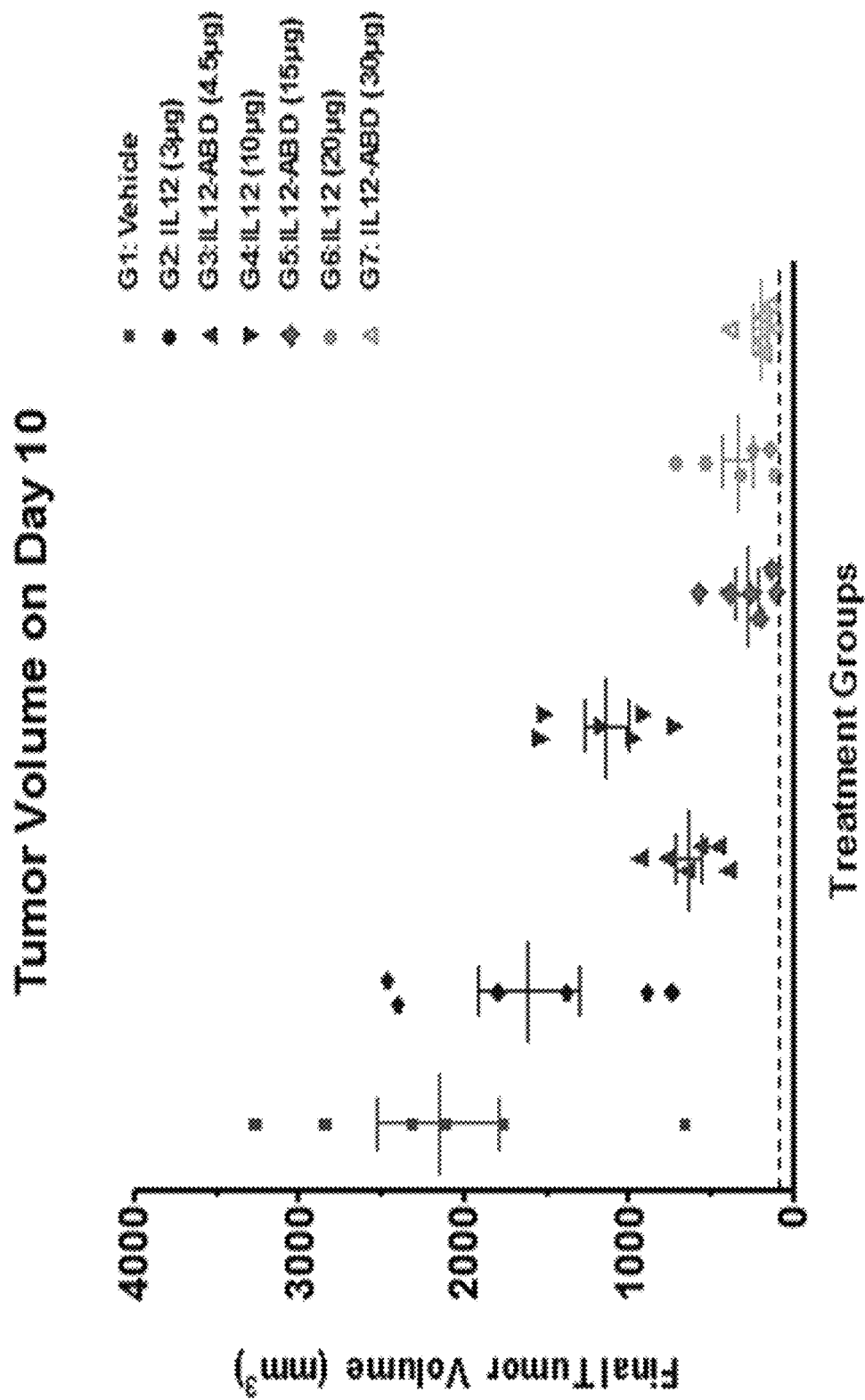

Mouse IL-12 single chain-ABD constructs were made in HEK293T cells and purified by size exclusion chromatograph. IL-12-A10m3 produced from HEK293T cells are fully active in both in vitro assays and cell based assays. As shown in FIG. 21A, IL12-A10m3 is capable of binding to mouse serum albumin, with an equilibrium dissociation constant (KD) of 2.1 nM. IL12-A10m3 produced from HEK293T were also capable of stimulating human PBMC proliferation, comparable to that of in-house produced mouse IL12 and commercial-available mouse IL-12 (R&D) (FIG. 21B). Moreover, IL12-A10m3 produced from HEK293T stimulated secretion of interferon gamma from human PBMC, comparable to that of in-house produced mouse IL-12 and commercial-available mouse IL-12 (R&D) (FIG. 22).

Treatment with IL-12-ABD Reduces Tumor Volume In Vivo.

Figure 27:
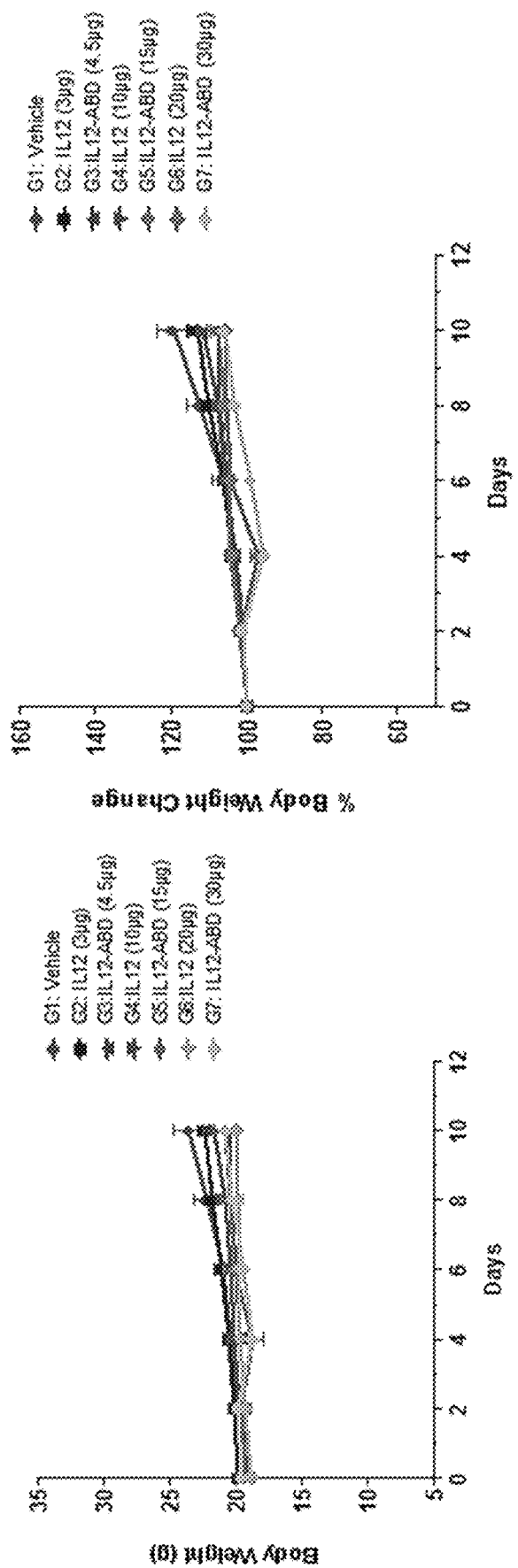
FIG. 27 depicts longitudinal body weight (left) and % body weight (right) measurements in B16-F10 tumor-bearing mice at various time points after treatment with IL-12 or IL-12-ABD.
Figure 28:
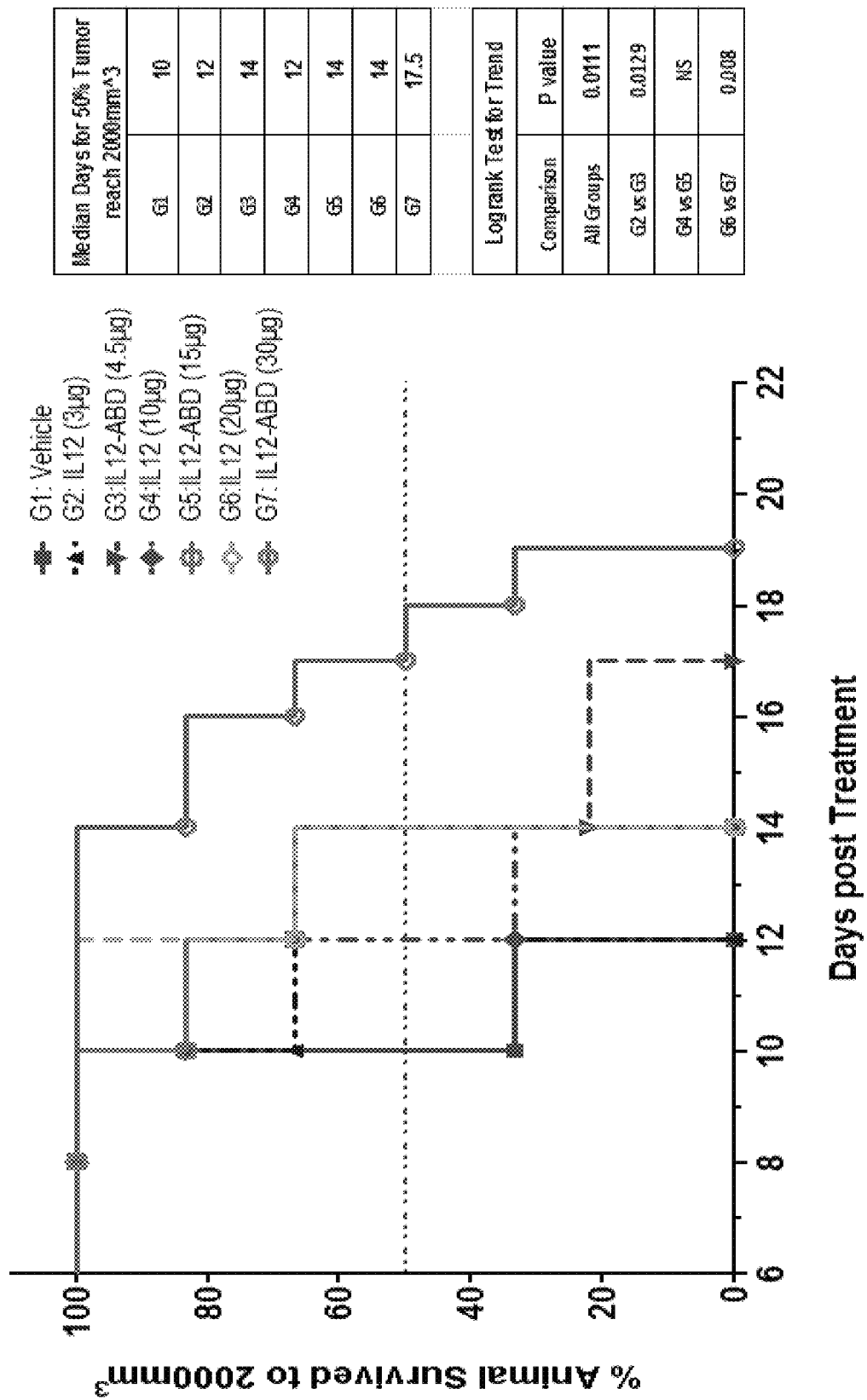
FIG. 28 provides Kalpan-Meier Pseuo-Survival Curves for various groups in the in vivo IL-12-ABD/IL-12 studies.

The ability for IL-12 and IL-12-ABD to inhibit tumor growth was assessed using a B16-F10 mouse melanoma model. As summarized in FIG. 23, mice were treated with either IL-12-ABD or IL-12 at three similar doses by IV injection on day 7 after tumor inoculation (day 0), when tumor volume reached 100 mm$^3$. Tumor growth was monitored every 2 days post treatment for 10 days. PBS placebo served as a control. As shown in FIGS. 24-26 and 28, both IL-12 and IL-12-ABD were able to reduce tumor growh in a dose dependent manner. Moreover, IL-12-ABD was able to reduce tumor volume more effectively compared to IL-12 alone at similarly concentrations (See, e.g., FIG. 26 at 10 days and FIG. 28, median days for 50% tumors to reach 2000 mm$^3$). Longitudinal body mass measurements of mice from these studies show minimal changes in weight across all IL-12-ABD treatment groups (FIG. 27). Lack of observed significant changes in mass, suggest a lack of IL-12-ABD toxicity in treatment groups over the 12 day post treatment course.

Figure 29:
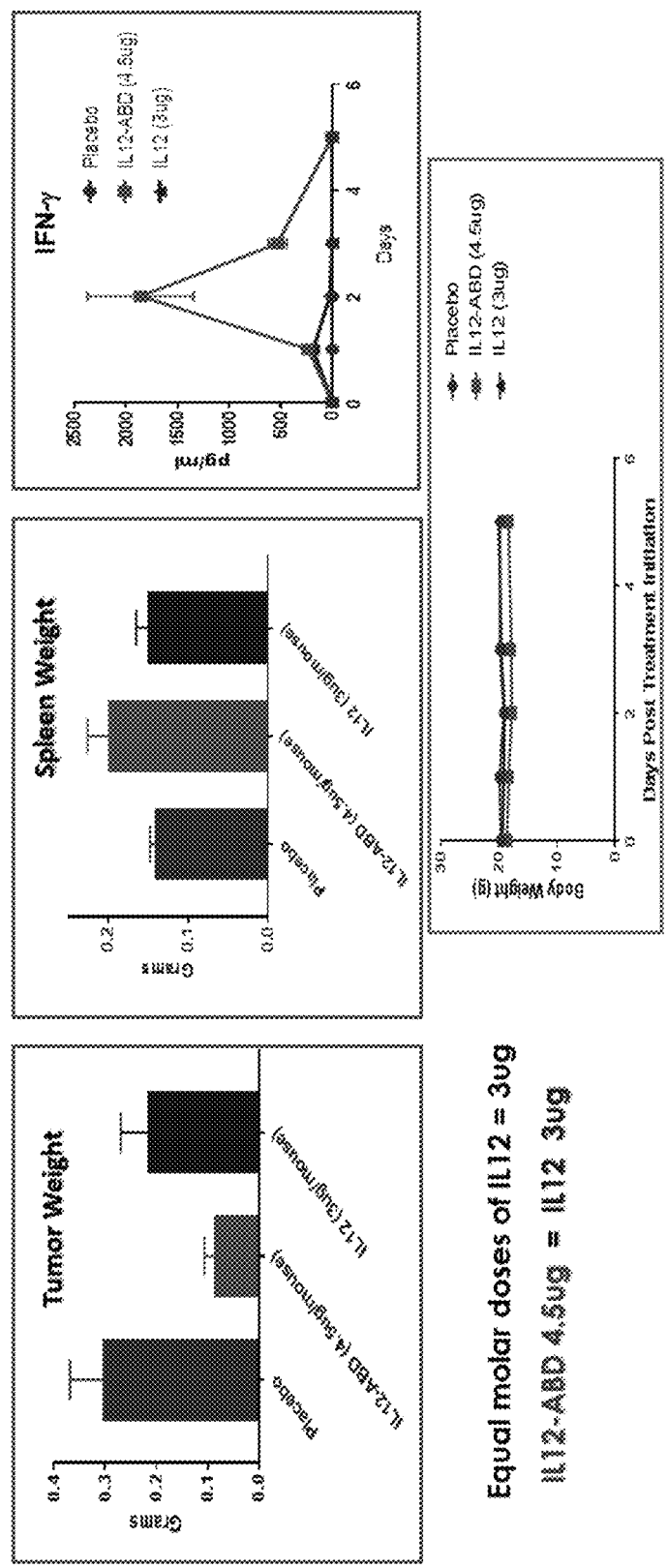
FIG. 29 depicts a summary of studies comparing the pharmacodynamic effects of a single dose of IL-12-ABD versus IL-12 on B16-F10 tumor-bearing mice at five days. Comparisons of tumor weight, spleen weight, serum IFN-γ and body weight are shown.

Further characterization of the pharmacodynamic effects of a single dose of IL-12-ABD (4.5 μg IL-12-ABD, same molar dose as 3 μg IL-12 control) in B16-F10 tumor-bearing mice after 5 days demonstrated that IL-12-ABD exhibited a similar greater suppression of tumor growth as compared to a similar molar dose of IL-12 control. IL-12-ABD treated mice also exhibited a corresponding increase in immune activation as shown by an increase in spleen weight and IFN-γ, without an effect on mouse bodyweight, as compared to control (FIG. 29).

Figure 30:
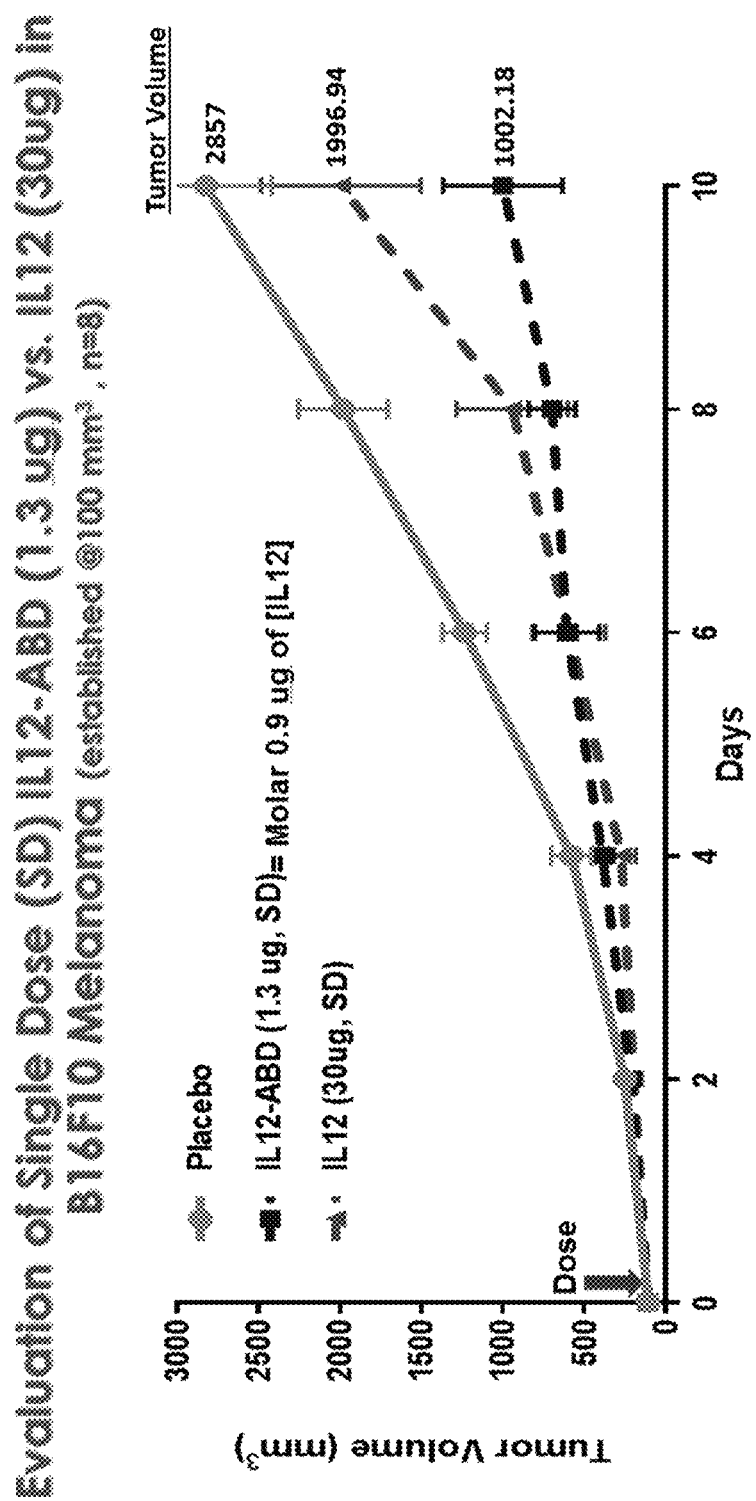
FIG. 30 shows the result of a study comparing tumor volume of B16-F10 tumor-bearing mice at 10 days, injected either with IL-12-ABD (1.3 µg), IL-12 (30 µg), or placebo. IL-12-ABD is administered at a lower molar dose ~30 fold than IL-12 in this study.
Figure 31A:
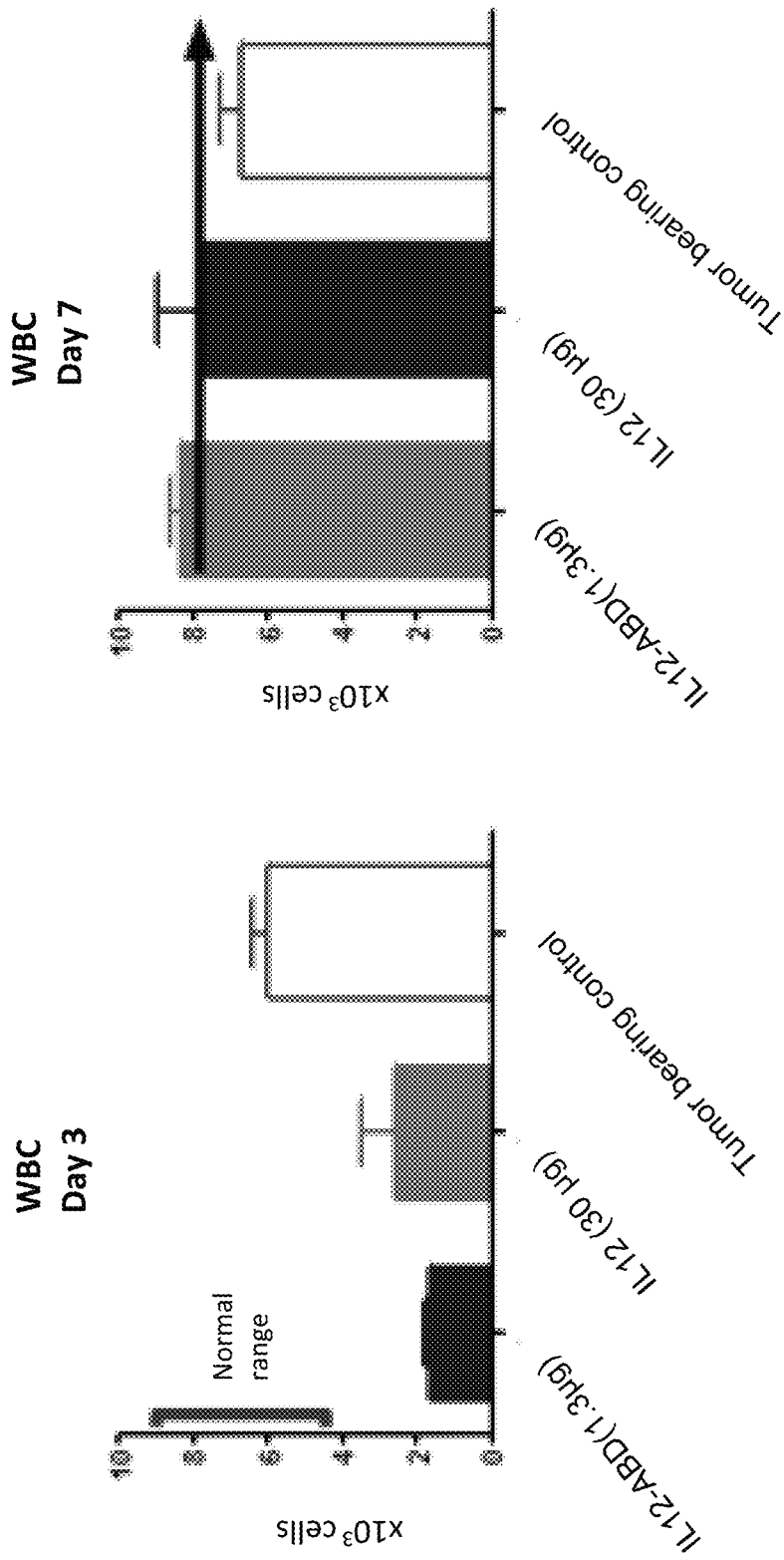
Figure 31C:
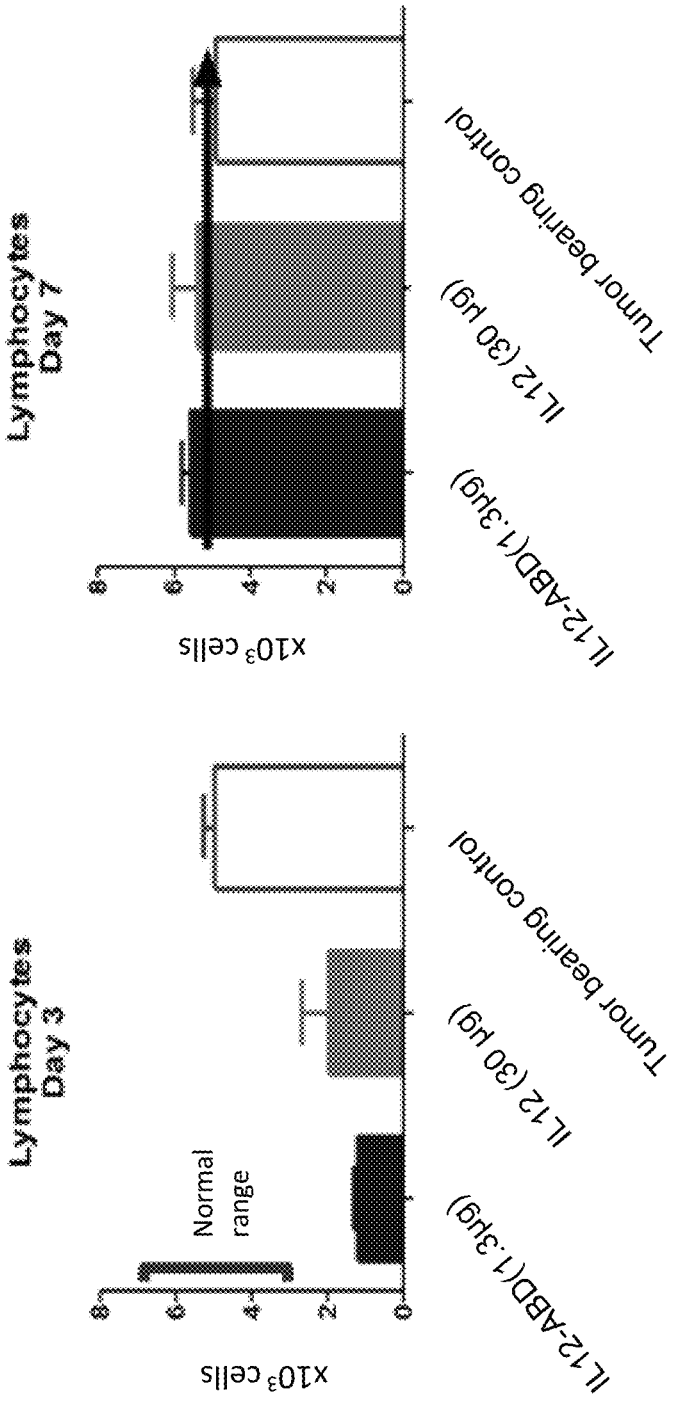
Figure 31D:
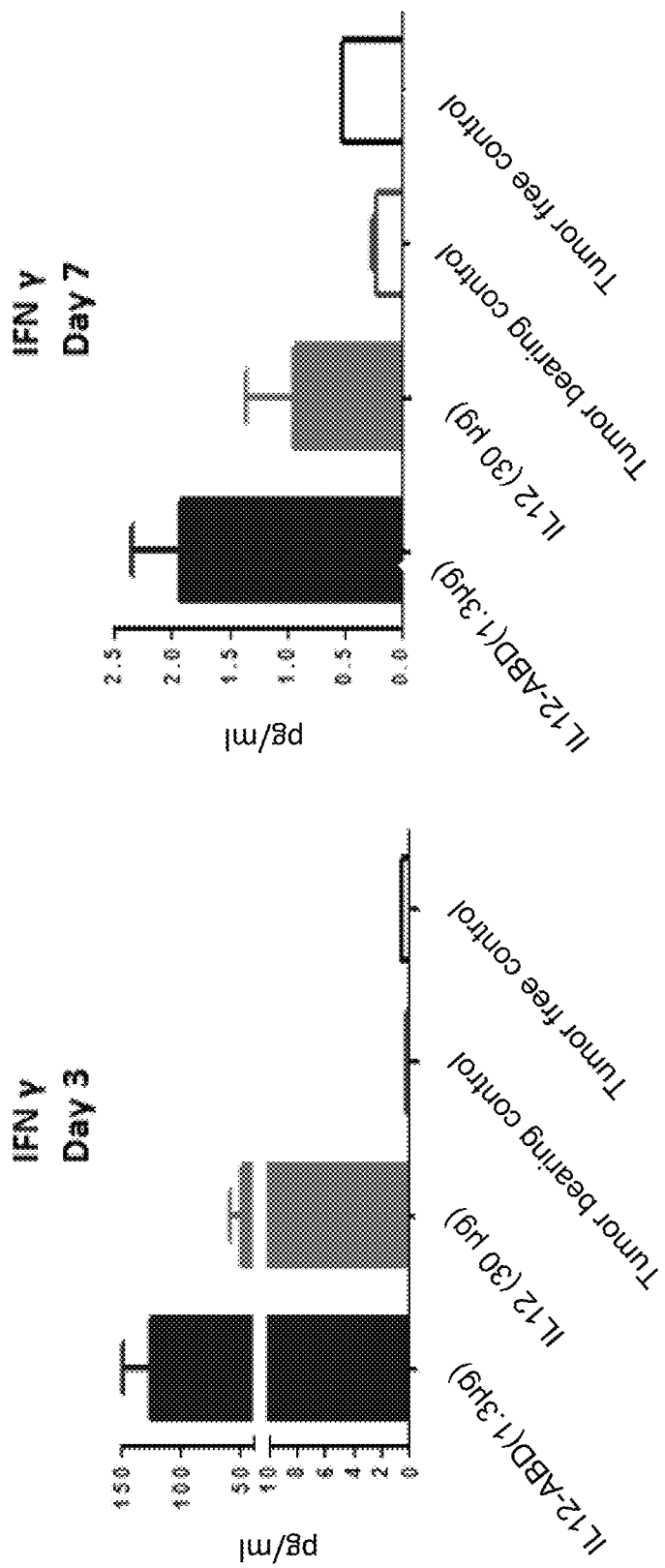

FIG. 30 further shows the result of a study comparing tumor volume of B16-F10 tumor-bearing mice at 10 days, injected either with IL-12-ABD (1.3 μg), IL-12 (30 μg), or placebo. Although IL-12 (1 μg) and IL-12-ABD (1.3 μg) are molar equivalent and have the same bioactivity in vitro, IL-12-ABD is ~30+ fold more potent than IL-12 in vivo (compare results at day 10 in FIG. 30, 1.3 μg IL-12-ABD>30 μg IL-12). FIG. 31 further depicts the hematopoietic effects of IL-12-ABD and IL-12 in mice from the study depicted in FIG. 30 at 3 and 7 days. As shown in FIG. 31, mice treated with IL-12-ABD exhibited a transient lowering of WBC, neutrophils and lymphocytes on day 3 as compared to IL-12 treated mice and placebo control. Such cell populations, however, returned to normal by day 7. Further, IFN-γ levels in mice treated with IL-12-ABD were higher at days 3 and 7, as compared to mice treated with IL-12 and control.

Evaluation of Anti-Tumor Effects of IL-12-ABD or IL-12 in Combination with Anti-PD-1 Antibody In Vivo.

Figure 32:
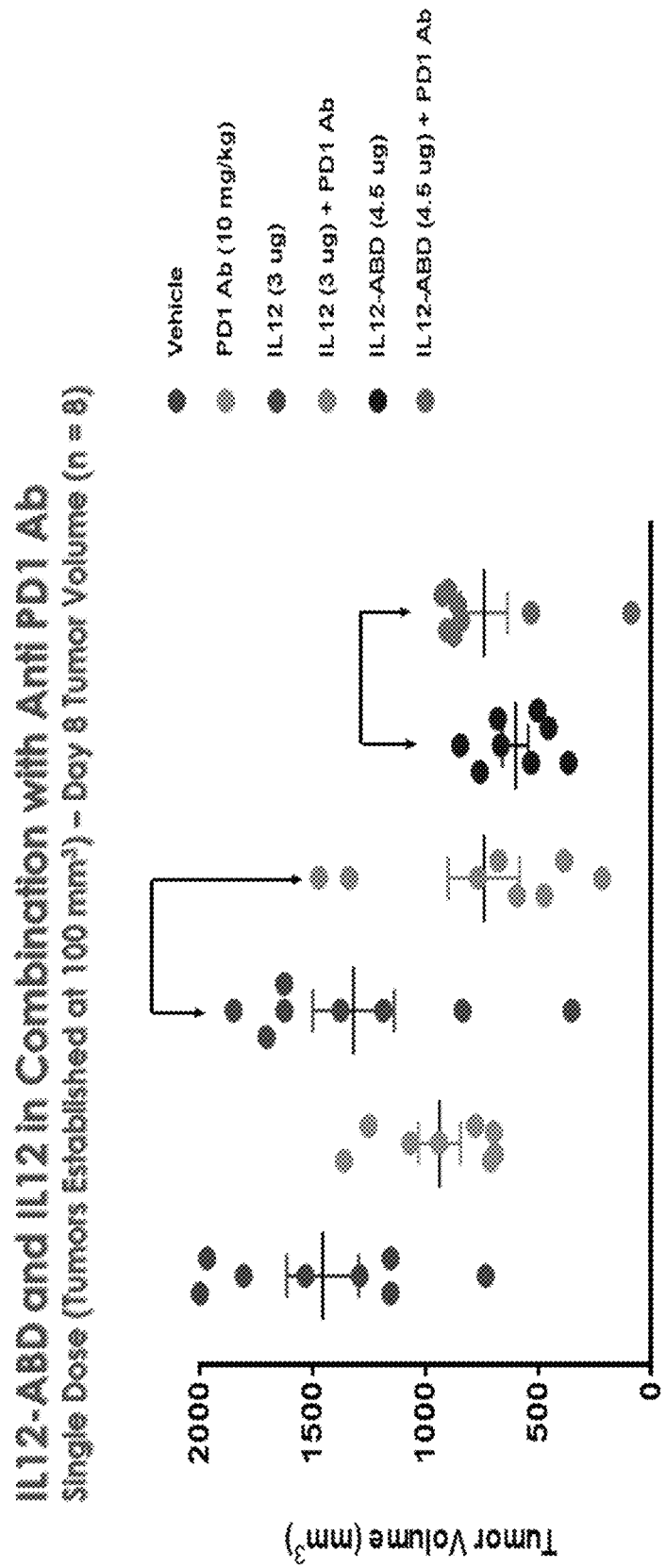
FIG. 32 depicts a study, showing the effect of single dose combination therapies using IL-12-ABD or IL-12 with anti-PD-1 antibodies on tumor growth in B16-F10 tumor-bearing mice.

The effect of single dose combination therapies using IL-12-ABD or IL-12 with anti-PD-1 antibodies was assessed in B16-F10 tumor-bearing mice at 8 days (FIG. 32).

Animals (7-10 weeks old) were assigned into 8 groups (8 animals per group) 10 days after B16-F10 tumor cell inoculation (2×10$^4$ cell/mouse). Animals were assigned based on the tumor volume. At the time of assignment, the average tumor volume per group was 100 mm$^3$. On day 0 (when tumors reached 100 mm$^3$) each group was given an I.V. single dose of either PBS (Placebo), IL12-ABD (1.5 ug, 5 ug, 15 ug) or IL15-ABD-IL12 (1.7 ug, 6 ug, 17 ug).

Groups were examined for body weight, tumor volume and pseudo survivability. Body weights were measured prior to tumor inoculation and at time of tumor measurements. Tumor size was measured every 2 days in two dimensions using a caliper, and the volume expressed in mm³ using the formula: V=0.5×a×b² where a and b are the long and short diameters of the tumor. The study was conducted as pseudo-survival; each mouse was euthanized when its tumor reached 2000 mm³ or when determined to be moribund.

Figure 33:
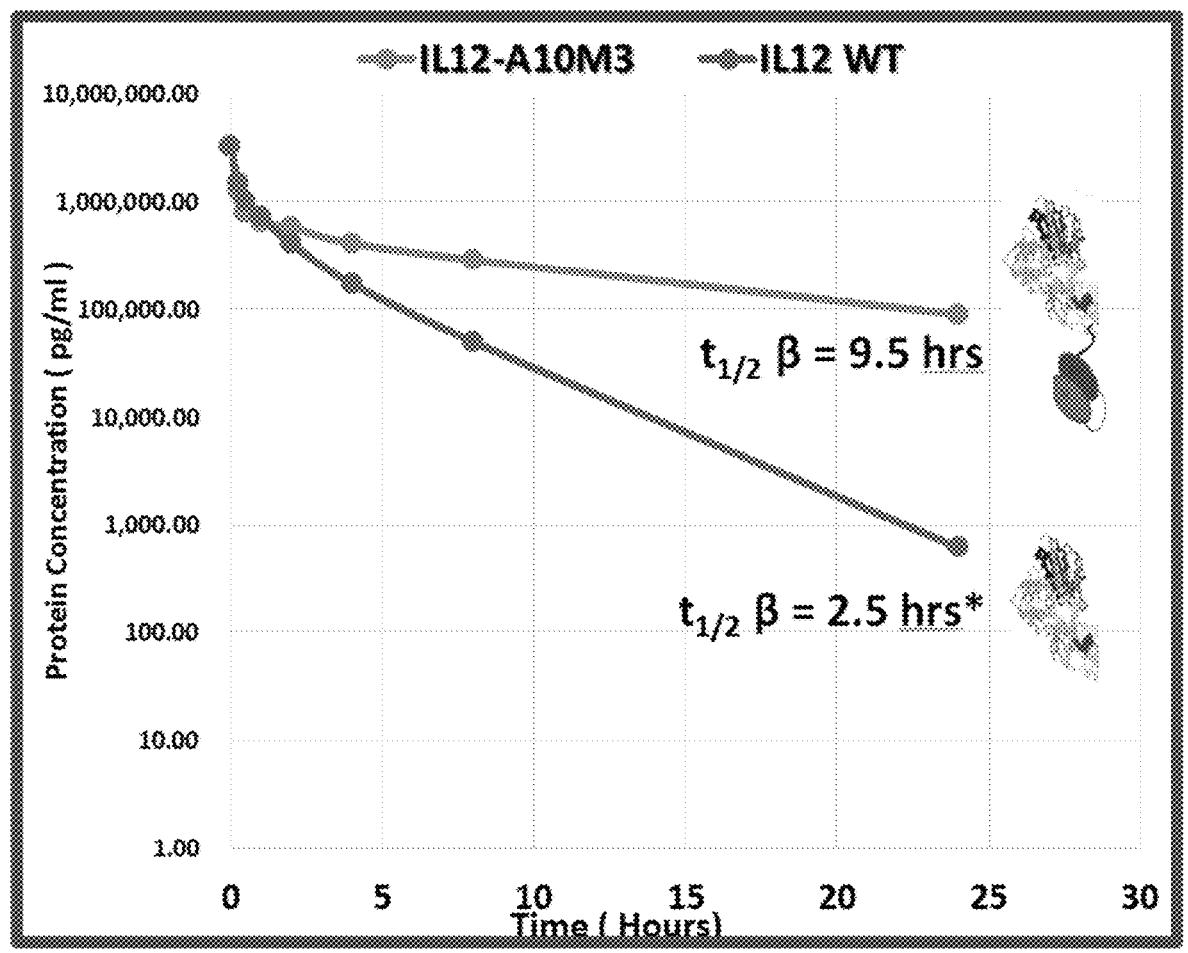
FIG. 33 depicts the results of a serum analysis, showing an increase in PK for IL12-ABD over IL-12 WT.

As shown in FIG. 33, IL-12-ABD was more effective than treatment with either anti-PD-1 or the molar equivalent dose of recombinant IL-12. Moreover, IL-12-ABD was as effective as the combination of recombinant IL-12 and anti-PD-1 treatment. Interestingly, the addition of anti-PD-1 Ab to recombinant IL-12 improved the efficacy of either treatment alone, whereas, anti-PD-1 treatment provided no further benefit to IL-12-ABD To assess the ability of ABD fusion proteins to increase the half-life of IL-12, C57B mice were injected intravenously with 5 μg of IL-12-ABD or IL-12 alone and serum concentrations of IL-12-ABD and IL-12 were assessed. As shown in FIG. 33, IL-12-ABD exhibited a higher PK than IL-12 WT. IL-12 T ½β=2.5 hrs, similar to those reported in the public domain (~3.5 hrs). Study results show ABD extends IL-12 T ½β to 9.5 hours, a ~4× fold increase.

Example 5: Bispecific IL-15-ABD-IL-12

Figure 35A:
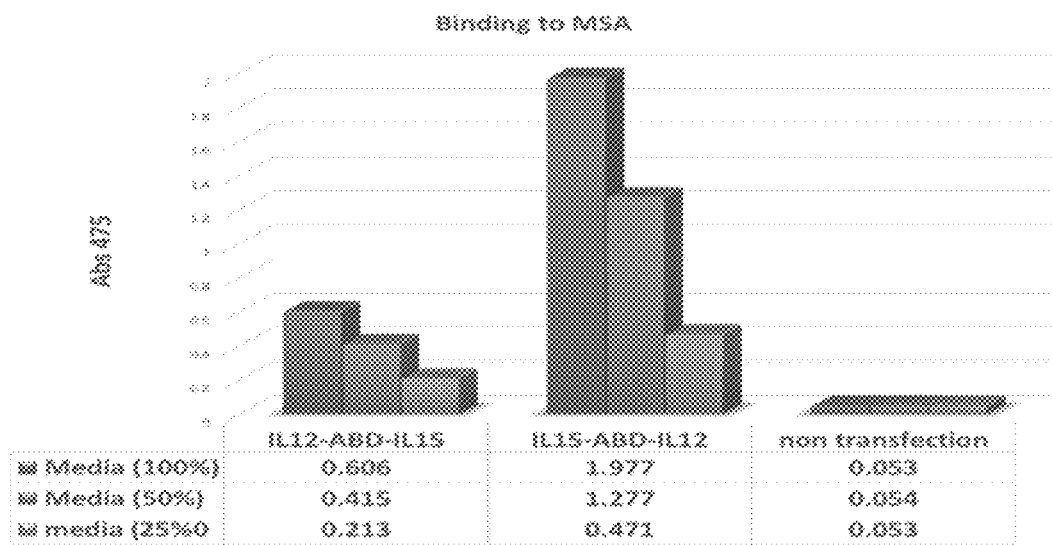
FIG. 35A and FIG. 35B shows binding activities of both hIL-15 (K86R)-A10m3-mIL-12sc and mIL-12sc-A10m3-hIL-15 (K86R) to MSA (A), IL-15 receptor alpha and IL-12 receptor beta2 (B), as confirmed by ELISA.
Figure 35B:
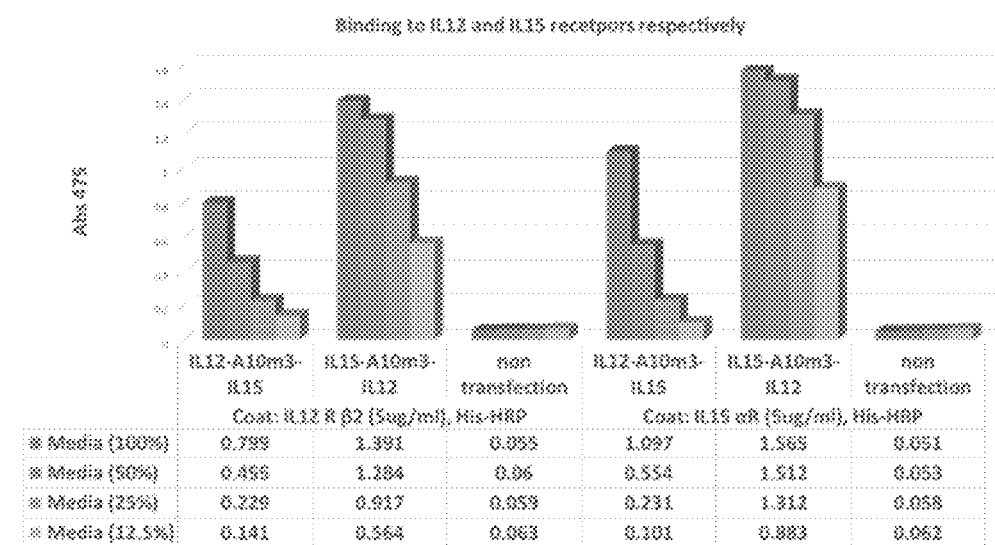

IL-15-ABD-IL-12, hIL15 (K86R/N112A)-A10m3-mIL-12sc and mIL-12sc-A10m3-hIL15 (K86R/N112A) constructs were made in HEK293T cells and purified by size exclusion chromatograph. The sequences of these constructs are depicted in FIG. 34. The ability of hIL15 (K86R/N112A)-A10m3-mIL-12sc and mIL-12sc-A10m3-hIL15 (K86R/N112A) constructs to bind MSA, IL12 receptor beta 2 and IL-15 receptor alpha were assessed by ELISA. As shown in FIG. 35, both IL-15-ABD-IL-12 constructs were able to bind to MSA in a dose dependent manner in cell culture media. Further, both bispecific constructs were able to bind to IL12 receptor beta2 and IL15 receptor alpha in a dose dependent manner in cell culture media. As shown in FIG. 35, IL-12/IL-15-ABDs having the orientation, for N-terminus to C-terminus, IL-15-ABD-IL-12, exhibited better antigen binding as compared to IL-12-ABD-IL-15. Additional bispecifics that include IL-15 and IL-12 are disclosed in FIG. 36.

Assessment of IL-15-ABD-IL-12 for IL-12 and IL-15 Activity

IL-15-ABD-IL-12 was further assessed for IL-12 and IL-15 activity (FIGS. 37 and 38).

Figure 37A:
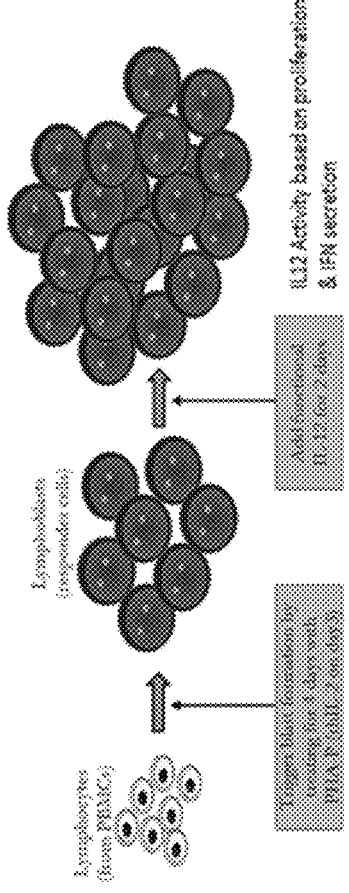
FIG. 37A, FIG. 37B, FIG. 37C, FIG. 38A and FIG. 38B depict the results of experiments showing that IL-15-ABD-IL-12 described herein exhibit both IL-12 (FIG. 39) and IL-15 (FIG. 40) activity.
Figure 38A:
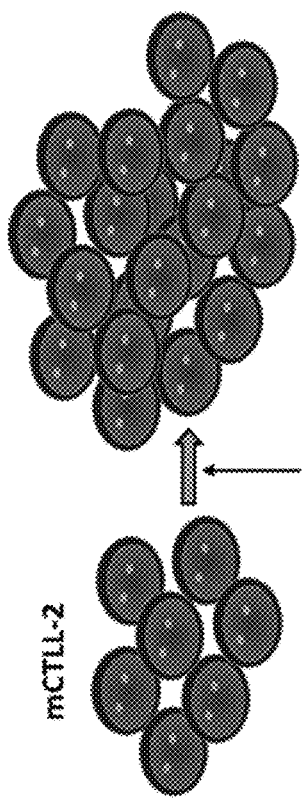

To assess IL-12 activity, lymphocytes from PBMCs were triggered undergo blast formation by treatment with PHA-P for four days and rhIL-2 on the third day. Lymphoblasts were then treated with either IL-15-ABD-IL-12 or IL-12 control for two days and IL-12 activity was assessed, based on lymphoblast proliferation and IFN-γ secretion (FIG. 37A). IL-15 activity was assessed using a CTLL-2 cytotoxic T lymphocyte proliferation assay (FIG. 38A).

Figure 37B:
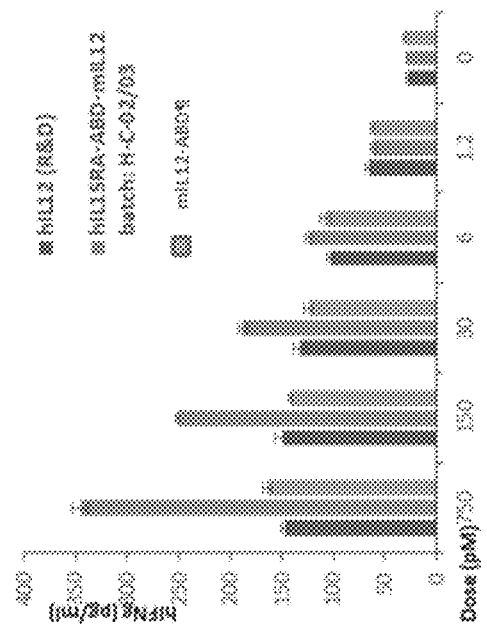
Figure 37C:
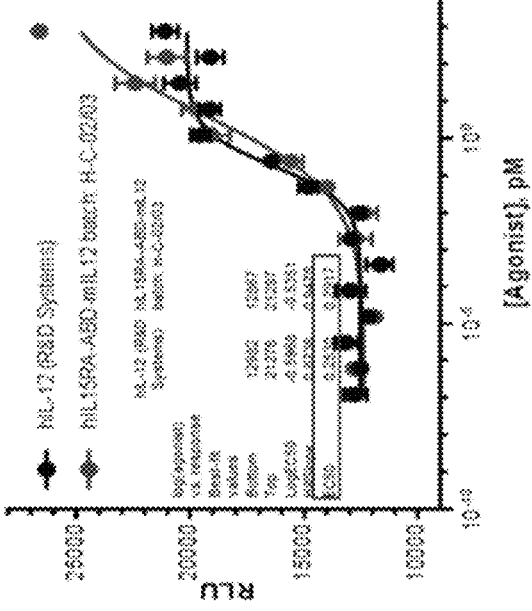
Figure 38B:
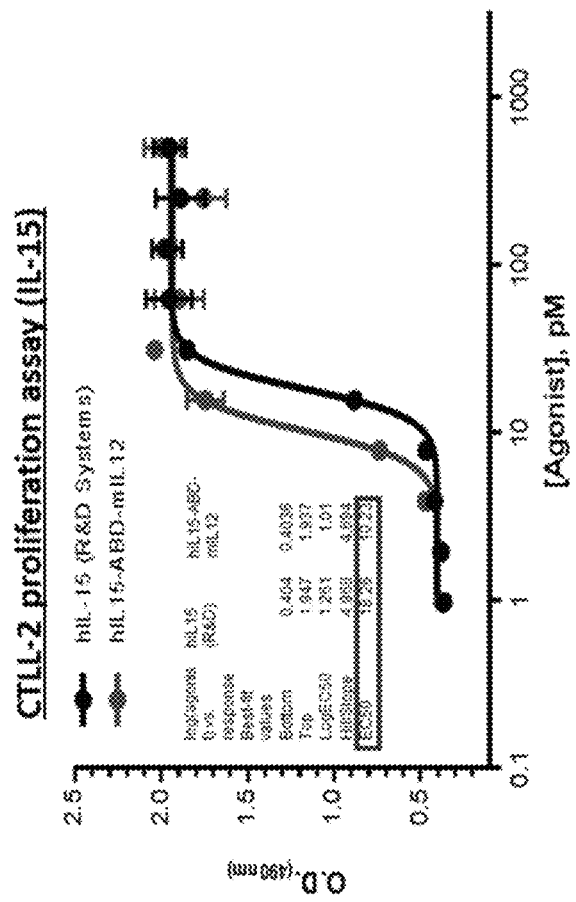

As shown in FIG. 37, IL-15-ABD-IL-12 exhibited IL-12 activity as assess by lymphoblast proliferation (FIG. 37B) and IFN-γ secretion (FIG. 37C). Moreover, IL-15-ABD-IL-12 exhibited IL-15 in the CTLL-2 proliferation assay (FIG. 38B). As such, subject IL-15-ABD-IL-12 exhibited both IL-12 and IL-15 bioactivity.

Anti-Tumor Effects of IL-15-ABD-IL-12 in a B 16-F 10 Mouse Melanoma Model

Without being bound by any particular theory of operation it is believed that IL-15/IL-12 ABDs provide synergistic biological activity. In particular, IL-12 increases IL-15 alpha receptor, IFN-γ. NK/T cells, and TH1 immunity, while downregulating Treg cells. IL-15 increases IL-12 beta 1 receptor, and NK cells, while reducing CD8 cell memory loss.

Figure 39:
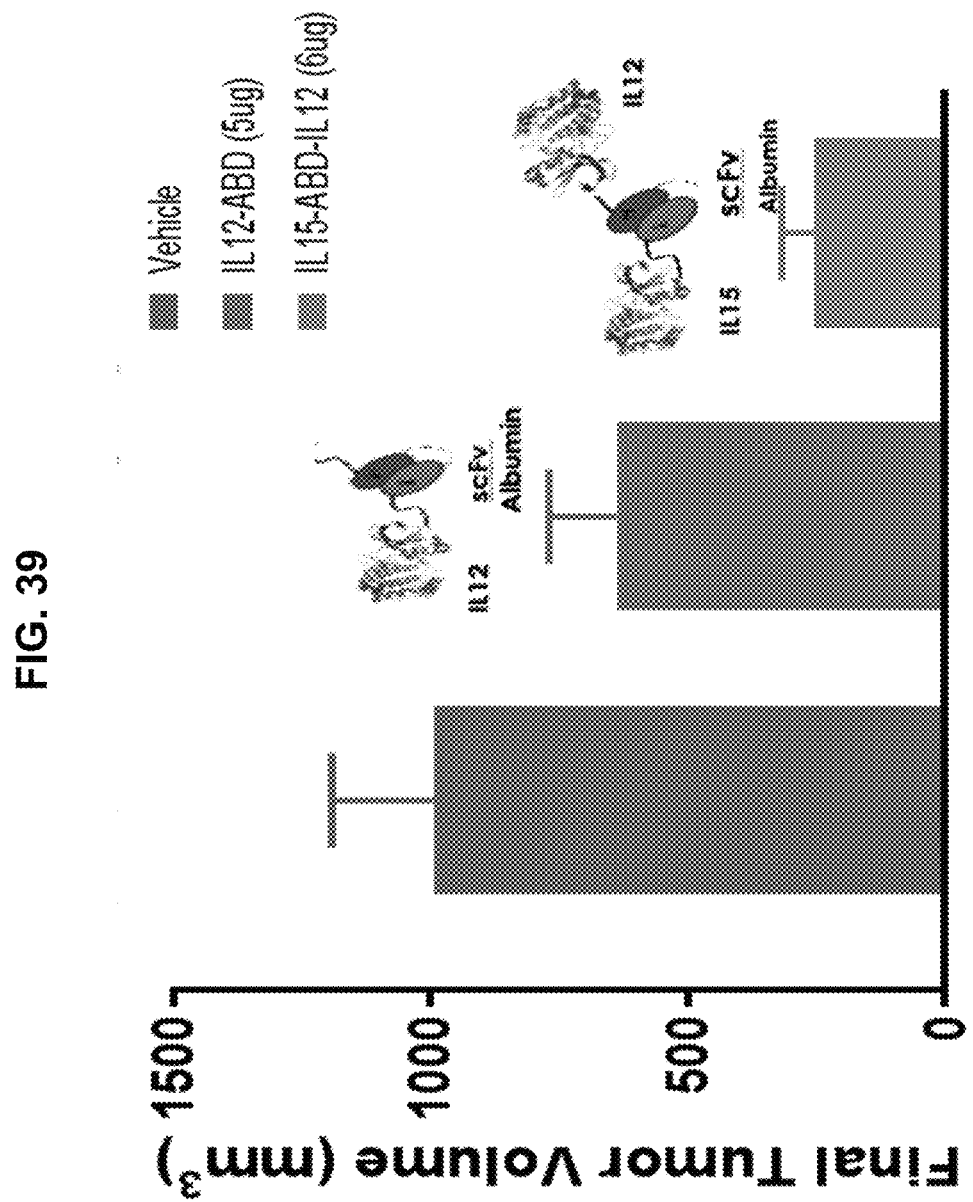
FIG. 39 depicts the results of a study, showing that IL-15-ABD-IL-12 described herein exhibited superior activity as compared to IL-12-ABD alone.

The anti-tumor effects and pseudo-survivability of IL-12-ABD to IL15-ABD-IL12 was assessed using in B16-F10 mouse melanoma model (FIG. 39).

Animals (7-10 weeks old) were assigned into 8 groups (8 animals per group) 10 days after B16-F10 tumor cell inoculation (2×10⁴ cell/mouse). Animals were assigned based on the tumor volume. At the time of assignment, the average tumor volume per group was 100 mm³). On day 0 (when tumors reached 100 mm³) each group was given an I.V. single dose of either PBS (Placebo) or molar does equivalents of IL12-ABD (1.5 ug, 5 ug, 15 ug) or IL15-ABD-IL12 (1.7 ug, 6 ug, 17 ug).

As shown in FIG. 39, IL-15-ABD-IL-12 was superior in anti-tumor activity as compared to IL-12-ABD in the B16-F10 mouse model at equal molar concentration. Other similar in-vivo studies show that free IL-12 (5 ug) in combination with 1-15 (1 ug) is less than 50% as potent as IL-15-ABD-IL-12 (bug) (data not shown).

Example 6: Anti-TGFβ-ABD

After biopanning and screening conducted using surface plasmon resonance technology, anti-hTGFβ1 binding domains were identified: 1A10, 1F11, 2H6, 4B9, 4C10, 4D9, 4G3, 4G6, 4H4, 4H7, and 6H11. These clones exhibited cross reactivity to hTGFβ2, 3 and mTGFβ1 and with potential inhibition of the binding of the hTGFβ1 to its receptor II. The clones were subsequently selected for purification as scFvs and further characterization The scFvs were screened for cross-reactivity to mouse and human TGFβ-1 using standard ELISA techniques. Binding ELISAs show that 2H6, 4G3, 4H7, 4B9, 4D9 & 6H11 have good cross-reactivity against both mTGFβ-1 and hTGFβ-1.

Binding & blocking ELISA was performed to determine whether the anti-TGFβ-1 scFvs were able to bind TGFβ-1 and block its interaction with TGFβR-II. 2H6, 4G3, 4H7, 4B9 & 4D9 all show good blocking efficacy and inhibition of mTGFβ & mTGFβR-II interaction.

Several of these anti-TGFβ-1 scFvs were tested for ability to interfere with TGFβ-1 bioactivity. The sequences of anti-TGFβ-1 scFvs 4H7 and 4D9 are shown in FIGS. 40A and B.

Blockade of TGFβ1-Induced Expansion of CD4⁺Foxp3⁺ Regulatory T Cells

Regulatory T cells (Tregs) are able to influence the homeostasis of the immune system. Such Treg are essential for maintaining self-tolerance as defects can lead to severe autoimmune diseases. In cancer, tumor cells are able to secret cytokines that affect immune system homeostasis. In particular, tumor cells may secrete TGFβ, which then can affect the number of circulating Tregs. It has been previously demonstrated that exposure to TGFβ1 leads to an expansion of CD4⁺Foxp3⁺ Treg subsets from CD4⁺Foxp3⁻ T cells. These induced Tregs are then able to contribute to the induction of a T cell anergic response by inhibiting the activation of tumor antigen specific cytotoxic CD8⁺ T cells.

Figure 41:
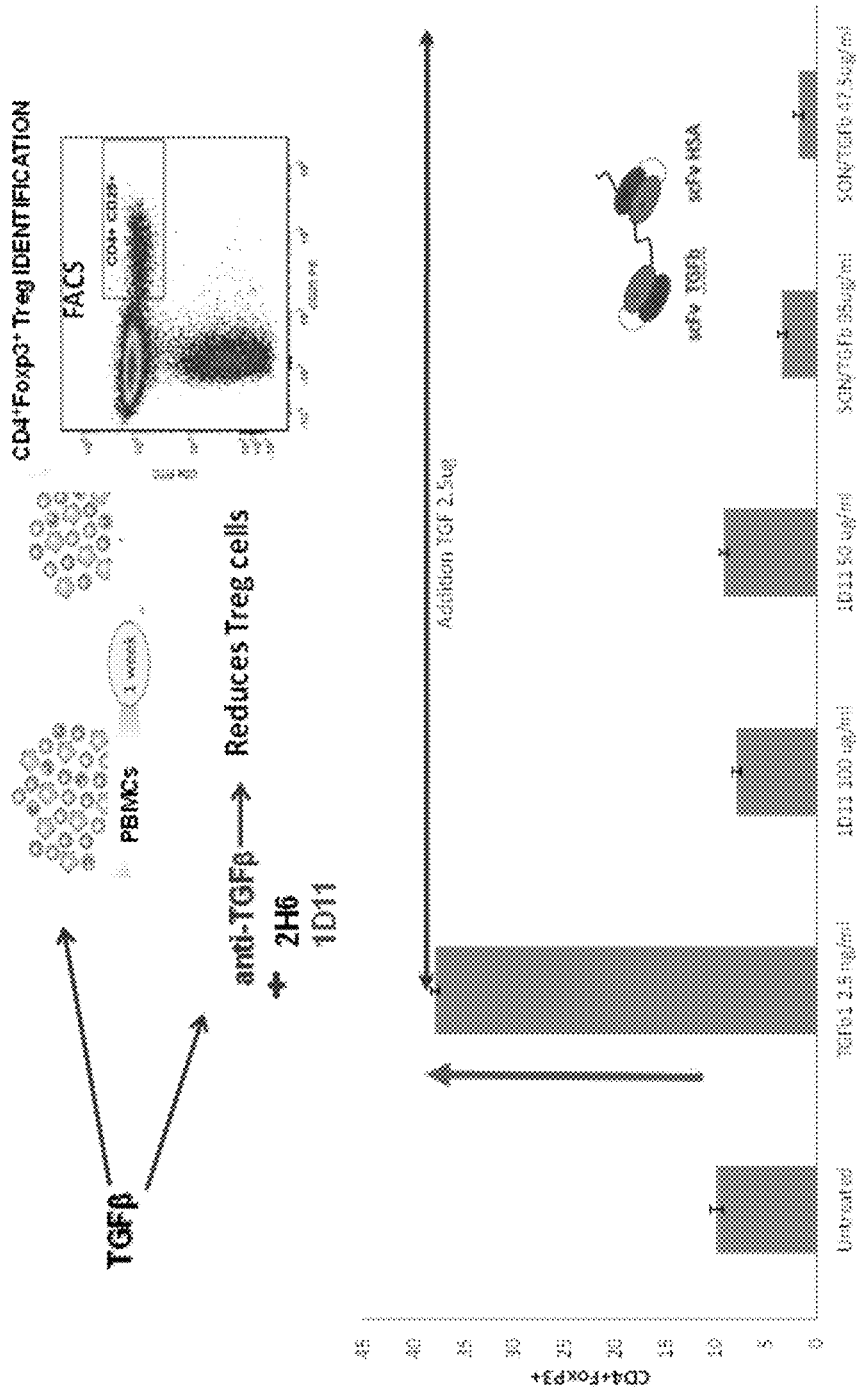
FIG. 41 depicts the results of a study, showing that TGFβ scFvs described herein are capable of blocking TGFβ1 induced Treg (CD4+Foxp3+) expansion.

As shown in FIG. 41, recombinant TGFβ1 is capable of stimulating the expansion of CD4⁺Foxp3⁺ Tregs from a mixed T cell population isolated from healthy human donor PBMCs. TGFβ blockade with anti-TGFβ 1D11 antibody or the TGF-β1 scFv 2H6, 4H7, and 4D9, however, all significantly inhibit the TGFβ induced expansion of CD4+Foxp3+ Tregs also in a dose dependent manner. Thus, such TGFβ1scFvs are useful for reducing TReg expansion in cancers.

Blockade of TGFβ1-Induced Epithelial-to-Mesenchymal Transition (EMT)

Figure 42A:
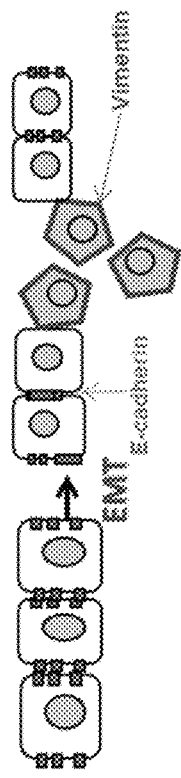
FIG. 42A, FIG. 42B AND FIG. 43 show that TGF-β blockade reverses TGF-β1-induced epithelial-to-mesenchymal transition (FIG. 44) and migration (FIG. 45).

Exposure to TGFβ is known to induce epithelial-to-mesenchymal transition. During this process, epithelial cells transdifferentiate from an organized, polarized and tightly connected epithelial sheet of cells with cobblestone morphology into disorganized and motile cells that appear mesenchymal in morphology. During EMT, the invasive capacity of the cells is activated and thereby enhances the tumorigenic ability of the cells. E-cadherin is a commonly used marker of epithelial cells, and is localized to the adherens junctions between epithelial cells. Loss of E-cadherin is a strong marker of EMT that is indicative of the transdifferentiation process. (FIG. 42A). Additionally, vimentin is associated with highly motile cells. Thus, the induction of vimentin expression in cells is also indicative of increased motility and increased localized invasion in vivo.

Figure 42B:
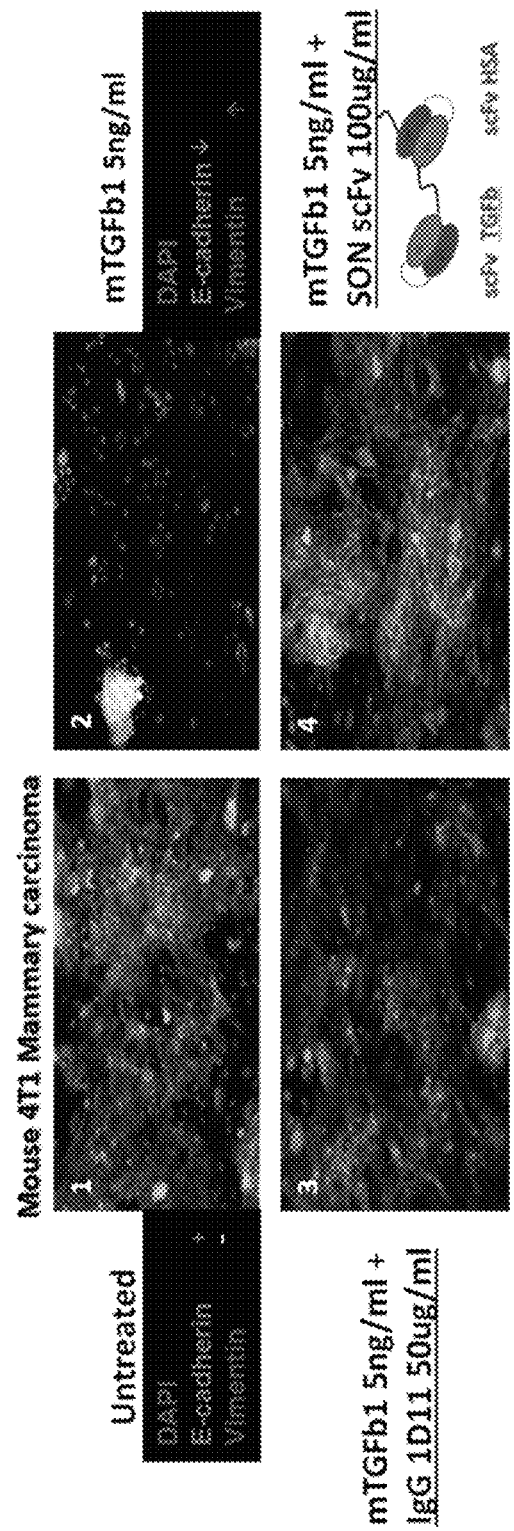
Figure 43:
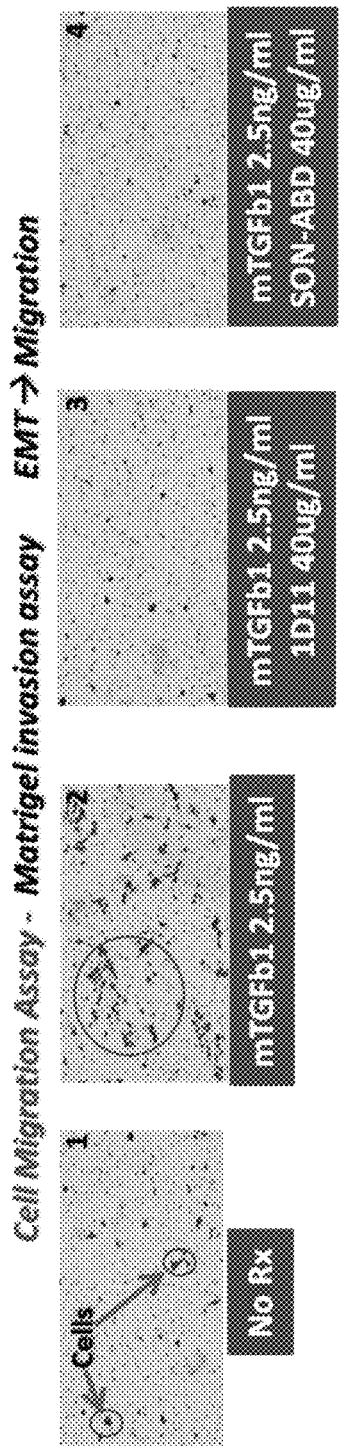

As shown in FIGS. 42 and 43, TGF-β blockade by anti-TGFβ 1D11 antibody or the TGF-β1 scFv reverses TGF-β1-induced epithelial-to-mesenchymal transition (FIG. 42) and migration (FIG. 43). Mouse 4T1 cells were cultured in growth media supplemented with TGF-β1 (panel 2); TGF-β1 and 1D11 (panel 3); or TGF-β1 and anti-TGF-β1 scFv (panel 4), then fixed and stained with E-cadherin antibody (green) and vimentin antibody (purple). Nuclei were counterstained with DAPI (blue). Treatment with TGF-β1 induced loss of E-cadherin from cell-cell junctions and increased expression of vimentin. This effect is reversed by the addition of 1D11 or subject anti-TGF-β1 scFv described herein (FIG. 42 panels 3 and 4). Moreover, the anti-TGF-β1 scFv described herein is capable of blocking TGF-β1-mediated carcinoma cell migration (FIG. 43).

Neutralization of TGFβ1-Induced Smad Activation

The TGFβ superfamily consists of pleiotropic cytokines that regulate various biological processes including cell proliferation, differentiation, migration, cell survival, angiogenesis, wound healing and immune surveillance. In humans, the predominant isoform is TGFβ1, which is expressed in various tissue types. TGFβ inhibits the proliferation of most normal epithelial cells. Additionally, during the early stages of cancers of epithelial origin, TGFβ functions as a cell growth inhibitor. Thus, during cancer initiation, TGFβ acts as a tumor suppressor. However, during later stages of cancer progression, tumor cells become resistant to the growth inhibitory effects of TGFβ, and TGFβ takes on a tumor promoter role. Indeed, TGFβ1 has been shown to be overexpressed in various tumors. Activation of the TGFβ pathway occurs through the binding of TGFβ ligand to the type II TGFβ receptor (TβRII), which then induces an association and oligomerization between TβRII and TβRI. When this oligomer forms, Smad2 and Smad3 are recruited and phosphorylated by TβRI. Phosphorylated Smad2 or Smad3 then bind to Smad4 in the cytoplasm, and this complex translocates to the nucleus where it interacts with the promoter region and activate transcription of target genes. Thus, the activation of the TGFβ pathway is measurable by the rapid phosphorylation of Smad2 after addition of TGFβ to serum starved cells. However, effective blockade of TGFβ will inhibit Smad2 phosphorylation. Here, the absence of Smad2 phosphorylation can be used as a measure of effective blockade of TGFβ by the subject anti-TGFβ scFv constructs.

Using serum-starved human (FIG. 44A) or mouse cells (FIG. 44B), it was determined that addition of human recombinant TGFβ1 (FIG. 44A) or mouse TGF-β1, -β2 and -β3 (FIG. 44B) induced Smad2 phosphorylation. Such phosphorylation is reduced in a dose dependent manner when the TGFβ is preincubated with control anti-TGFβ1D11 antibody or the TGF-β1 scFv constructs 2H6, 4H7, and 4D9. These data suggest that the 2H6, 4H7 and 4D9 scFv constructs are able to sequester TGFβ1 and inhibit its interaction with TβRII/TβRI, thereby inhibiting the TGFβ activation cascade during late stage cancer.

4D9 Anti-TGFβ-1-ABD

Figure 45B:
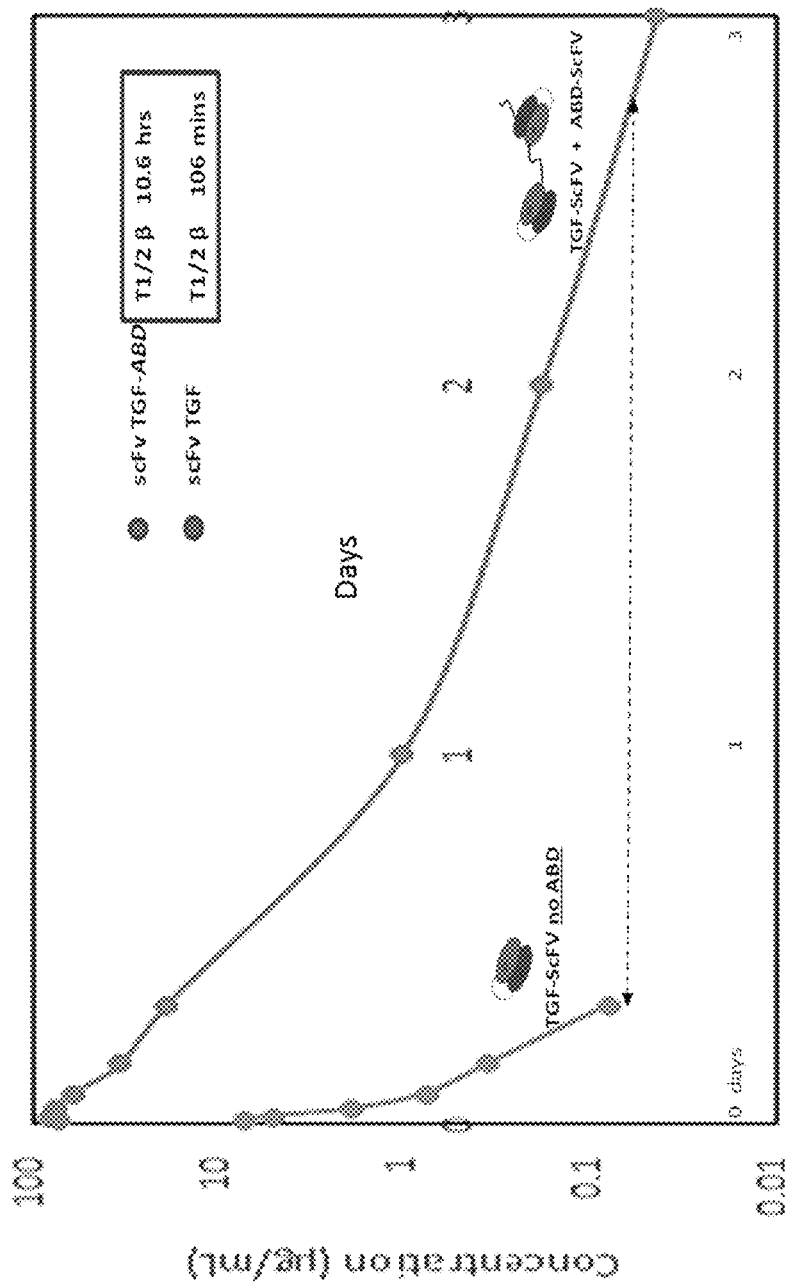
FIG. 45B provides a summary of a study, showing that anti-TGFβ-1-ABD extends the anti-TGF-β-1 scFv.

The sequences of exemplary TGF-β1 scFv-ABD constructs (4D9M-A6m and 4H7M-A6m), are shown in FIG. 45A. As shown in FIG. 45B, anti-TGFβ-1-ABD extended the anti-TGFβ-1 scFv T ½β from 106 minutes to 10.6 hours.

Figure 46:
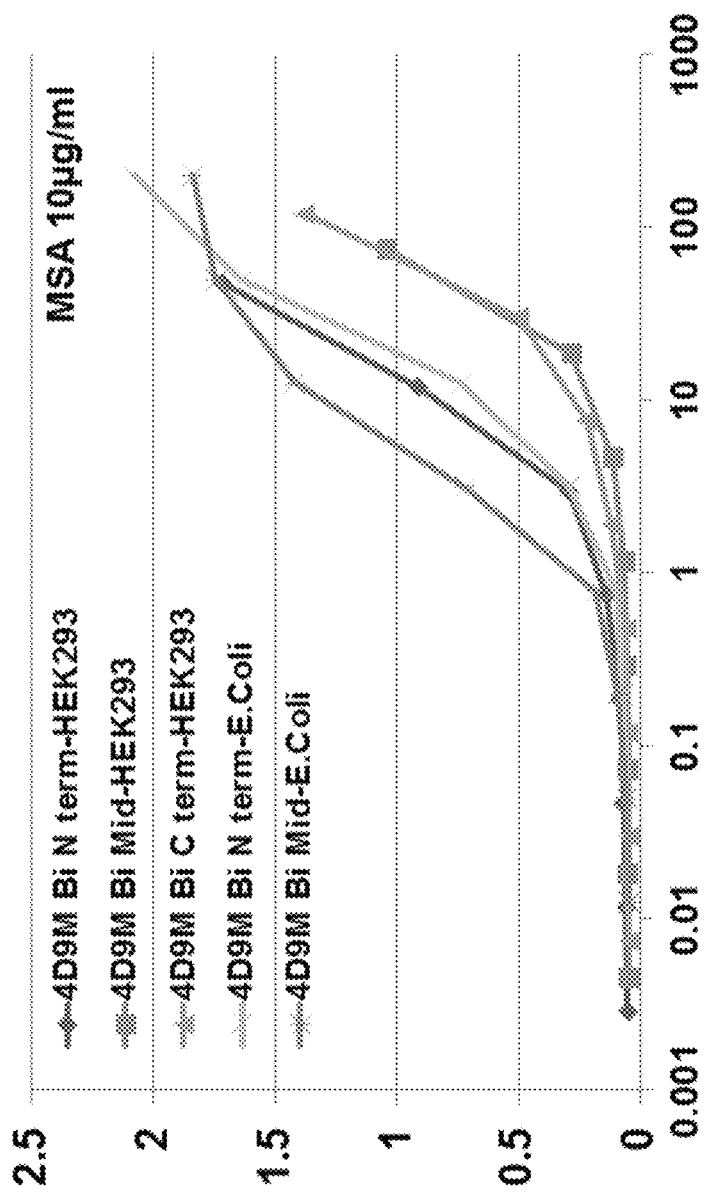
FIG. 46 provides a summary of a study, showing that various anti-TGF-β1 scFv-ABDs (bivalent for TGF-β1) produced in E. Coli or mammalian (HEK) cells are capable of binding to mouse serum albumin.
Figure 47:
FIG. 47 provides the summary of a studying, showing that TGFβ-1 mediated inhibition of T cell proliferation was reversed (i.e., increase T cell proliferation) by exemplary TGF-β1 scFv-ABD constructs (4D9M-A6m and 4H7-A6m).

Anti-TGF-β1 scFv-ABDs (bivalent for TGF-β1) produced in E. coli and HEK cells were assessed for binding to mouse serum albumin (FIG. 47). Three different orientations of the constructs were assessed: two anti-TGF-β1 scFvs attached to the N terminal of the ABD ("Bi N Term"); two anti-TGF-β1 scFvs attached to the C terminal of the ABD ("Bi C Term); or one anti-TGF-β1 scFv attached to each of the N terminal and C terminal of the ABD ("Bi Mid"). As shown in FIG. 46, all constructs exhibited binding to mouse serum albumin. With respect to constructs produced in E. coli, Bi Mid exhibited better binding to MSA than the N Term orientation. With respect to constructs produced in HEK cells, the Bi N Term orientation exhibited better binding to MSA than either the Bi Mid or Bi C term orientation.

As shown in FIG. 47, TGFβ-1 mediated inhibition of T cell proliferation was reversed (i.e., increase T cell proliferation) by such constructs (FIG. 46B). Further, 4D9M-ABD has been shown to block human TGFβ-1 and human TGFβ-3 binding with cognate receptors (data not shown).

All cited references are herein expressly incorporated by reference in their entirety.

Whereas particular embodiments of the invention have been described above for purposes of illustration, it will be appreciated by those skilled in the art that numerous variations of the details may be made without departing from the invention as described in the appended claims.

What is claimed is:

1. An IL-12 albumin binding domain fusion protein comprising the amino acid sequence of SEQ ID NO: 280.

2. A nucleic acid encoding the IL-12 albumin binding domain fusion protein of claim 1.

3. An expression vector comprising the nucleic acid of claim 2.

4. A host cell comprising the nucleic acid of claim 2 or the expression vector of claim 3.

5. A method of making the IL-12 albumin binding domain fusion protein comprising culturing the host cell of claim 4 under conditions wherein the IL-12 albumin binding domain fusion protein is expressed, and recovering the IL-12 albumin binding domain fusion protein.

* * * * *

SEQUENCE LISTING

<160> NUMBER OF SEQ ID NOS: 310

<210> SEQ ID NO 1
<211> LENGTH: 122
<212> TYPE: PRT
<213> ORGANISM: Artificial Sequence
<220> FEATURE:
<223> OTHER INFORMATION: Variable heavy (vh) chain

<400> SEQUENCE: 1

Glu Val Gln Leu Val Glu Ser Gly Gly Leu Ile Gln Pro Gly Arg
1               5                   10                  15

Ser Leu Arg Leu Ser Cys Ala Ala Ser Gly Ile Thr Phe Asp Asp Tyr
            20                  25                  30

Val Met His Trp Val Arg Gln Ala Pro Gly Lys Gly Leu Glu Trp Val
        35                  40                  45

Ala Gly Ile Ser Ser Asn Ser Gly Tyr Ile Gly Tyr Ala Asp Ser Val
    50                  55                  60

Arg Gly Arg Phe Thr Ile Ser Arg Asp Asn Ala Lys Asn Ser Leu Phe
65                  70                  75                  80

Leu Gln Met Asn Arg Leu Arg Pro Glu Asp Thr Ala Leu Tyr Tyr Cys
                85                  90                  95

Val Lys Gly Leu Tyr Ser Asn Pro Arg Gly Gly Ala Phe Asp Ile Trp
            100                 105                 110

Gly Gln Gly Thr Met Val Thr Val Ser Ser
        115                 120

<210> SEQ ID NO 2
<211> LENGTH: 8
<212> TYPE: PRT
<213> ORGANISM: Artificial Sequence
<220> FEATURE:
<223> OTHER INFORMATION: vhCDR1

<400> SEQUENCE: 2

Gly Ile Thr Phe Asp Asp Tyr Val
1               5

<210> SEQ ID NO 3
<211> LENGTH: 8
<212> TYPE: PRT
<213> ORGANISM: Artificial Sequence
<220> FEATURE:
<223> OTHER INFORMATION: vhCDR2

<400> SEQUENCE: 3

Ile Ser Ser Asn Ser Gly Tyr Ile
1               5

<210> SEQ ID NO 4
<211> LENGTH: 15
<212> TYPE: PRT
<213> ORGANISM: Artificial Sequence
<220> FEATURE:
<223> OTHER INFORMATION: vhCDR3

<400> SEQUENCE: 4

Val Lys Gly Leu Tyr Ser Asn Pro Arg Gly Gly Ala Phe Asp Ile
1               5                   10                  15

<210> SEQ ID NO 5
<211> LENGTH: 110
<212> TYPE: PRT
<213> ORGANISM: Artificial Sequence
<220> FEATURE:
<223> OTHER INFORMATION: Variable light (vl) chain

<400> SEQUENCE: 5

Ser Tyr Val Leu Thr Gln Pro Pro Ser Val Ser Val Ala Pro Gly Gln
1               5                   10                  15

```
Thr Ala Thr Ile Thr Cys Gly Gly Asn Ile Gly Thr Lys Ser Val
                20                  25                  30

His Trp Tyr Gln Gln Lys Pro Gly Gln Ala Pro Val Leu Val Val Tyr
            35                  40                  45

Ala Asp Ser Asp Arg Pro Ser Gly Ile Pro Glu Arg Val Ser Gly Ser
 50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Arg Ser Asp His
                85                  90                  95

Leu Trp Val Phe Gly Gly Gly Thr Lys Leu Thr Val Leu Gly
            100                 105                 110

<210> SEQ ID NO 6
<211> LENGTH: 6
<212> TYPE: PRT
<213> ORGANISM: Artificial Sequence
<220> FEATURE:
<223> OTHER INFORMATION: vlCDR1

<400> SEQUENCE: 6

Asn Ile Gly Thr Lys Ser
1               5

<210> SEQ ID NO 7
<211> LENGTH: 3
<212> TYPE: PRT
<213> ORGANISM: Artificial Sequence
<220> FEATURE:
<223> OTHER INFORMATION: vlCDR2

<400> SEQUENCE: 7

Ala Asp Ser
1

<210> SEQ ID NO 8
<211> LENGTH: 12
<212> TYPE: PRT
<213> ORGANISM: Artificial Sequence
<220> FEATURE:
<223> OTHER INFORMATION: vlCDR3

<400> SEQUENCE: 8

Gln Val Trp Asp Ser Arg Ser Asp His Leu Trp Val
1               5                   10

<210> SEQ ID NO 9
<211> LENGTH: 122
<212> TYPE: PRT
<213> ORGANISM: Artificial Sequence
<220> FEATURE:
<223> OTHER INFORMATION: Variable heavy (vh) chain

<400> SEQUENCE: 9

Glu Val Gln Leu Val Glu Ser Gly Gly Gly Leu Ile Gln Pro Gly Arg
1               5                   10                  15

Ser Leu Arg Leu Ser Cys Ala Ala Ser Gly Ile Thr Phe Asp Asp His
                20                  25                  30

Val Met His Trp Val Arg Gln Ala Pro Gly Lys Gly Leu Glu Trp Val
            35                  40                  45

Ala Gly Ile Ser Ser Asn Ser Gly Tyr Ile Gly Tyr Ala Asp Ser Val
 50                  55                  60
```

```
Lys Gly Arg Phe Thr Ile Ser Arg Asp Asn Ala Lys Asn Ser Leu Tyr
 65                  70                  75                  80

Leu Gln Met Asn Arg Leu Arg Ala Glu Asp Thr Ala Val Tyr Tyr Cys
                 85                  90                  95

Val Lys Gly Leu Tyr Ser Asn Pro Arg Gly Gly Ala Phe Asp Ile Trp
            100                 105                 110

Gly Gln Gly Thr Met Val Thr Val Ser Ser
        115                 120
```

<210> SEQ ID NO 10
<211> LENGTH: 8
<212> TYPE: PRT
<213> ORGANISM: Artificial Sequence
<220> FEATURE:
<223> OTHER INFORMATION: vhCDR1

<400> SEQUENCE: 10

```
Gly Ile Thr Phe Asp Asp His Val
1               5
```

<210> SEQ ID NO 11
<211> LENGTH: 8
<212> TYPE: PRT
<213> ORGANISM: Artificial Sequence
<220> FEATURE:
<223> OTHER INFORMATION: vhCDR2

<400> SEQUENCE: 11

```
Ile Ser Ser Asn Ser Gly Tyr Ile
1               5
```

<210> SEQ ID NO 12
<211> LENGTH: 15
<212> TYPE: PRT
<213> ORGANISM: Artificial Sequence
<220> FEATURE:
<223> OTHER INFORMATION: vhCDR3

<400> SEQUENCE: 12

```
Val Lys Gly Leu Tyr Ser Asn Pro Arg Gly Gly Ala Phe Asp Ile
1               5                   10                  15
```

<210> SEQ ID NO 13
<211> LENGTH: 110
<212> TYPE: PRT
<213> ORGANISM: Artificial Sequence
<220> FEATURE:
<223> OTHER INFORMATION: Variable light (vl) chain

<400> SEQUENCE: 13

```
Ser Tyr Val Leu Thr Gln Pro Pro Ser Val Ser Val Ala Pro Gly Gln
1               5                   10                  15

Thr Ala Thr Ile Thr Cys Gly Gly Asn Asn Ile Gly Thr Lys Ser Val
             20                  25                  30

His Trp Tyr Gln Gln Lys Pro Gly Gln Ala Pro Val Leu Val Val Tyr
         35                  40                  45

Ala Asp Ser Asp Arg Pro Ser Gly Ile Pro Glu Arg Val Ser Gly Ser
     50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Arg Ser Asp His
                 85                  90                  95
```

```
Leu Trp Val Phe Gly Gly Gly Thr Lys Leu Thr Val Leu Gly
            100                 105                 110
```

```
<210> SEQ ID NO 14
<211> LENGTH: 6
<212> TYPE: PRT
<213> ORGANISM: Artificial Sequence
<220> FEATURE:
<223> OTHER INFORMATION: vlCDR1

<400> SEQUENCE: 14

Asn Ile Gly Thr Lys Ser
1               5
```

```
<210> SEQ ID NO 15
<211> LENGTH: 3
<212> TYPE: PRT
<213> ORGANISM: Artificial Sequence
<220> FEATURE:
<223> OTHER INFORMATION: vlCDR2

<400> SEQUENCE: 15

Ala Asp Ser
1
```

```
<210> SEQ ID NO 16
<211> LENGTH: 12
<212> TYPE: PRT
<213> ORGANISM: Artificial Sequence
<220> FEATURE:
<223> OTHER INFORMATION: vlCDR3

<400> SEQUENCE: 16

Gln Val Trp Asp Ser Arg Ser Asp His Leu Trp Val
1               5                   10
```

```
<210> SEQ ID NO 17
<211> LENGTH: 122
<212> TYPE: PRT
<213> ORGANISM: Artificial Sequence
<220> FEATURE:
<223> OTHER INFORMATION: Variable heavy (vh) chain

<400> SEQUENCE: 17

Glu Val Gln Leu Val Glu Ser Gly Gly Gly Leu Ile Gln Pro Gly Arg
1               5                   10                  15

Ser Leu Arg Leu Ser Cys Ala Ala Ser Gly Ile Thr Phe Asp Asp Tyr
            20                  25                  30

Ala Met His Trp Val Arg Gln Ala Pro Gly Lys Gly Leu Glu Trp Val
        35                  40                  45

Ala Gly Ile Ser Ser Asn Ser Gly Tyr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Arg Leu Arg Ala Glu Asp Thr Ala Val Tyr Tyr Cys
                85                  90                  95

Val Lys Gly Leu Tyr Ser Asn Pro Arg Gly Gly Ala Phe Asp Ile Trp
            100                 105                 110

Gly Gln Gly Thr Met Val Thr Val Ser Ser
        115                 120
```

```
<210> SEQ ID NO 18
<211> LENGTH: 8
```

```
<212> TYPE: PRT
<213> ORGANISM: Artificial Sequence
<220> FEATURE:
<223> OTHER INFORMATION: vhCDR1

<400> SEQUENCE: 18

Gly Ile Thr Phe Asp Asp Tyr Ala
1               5

<210> SEQ ID NO 19
<211> LENGTH: 8
<212> TYPE: PRT
<213> ORGANISM: Artificial Sequence
<220> FEATURE:
<223> OTHER INFORMATION: vhCDR2

<400> SEQUENCE: 19

Ile Ser Ser Asn Ser Gly Tyr Ile
1               5

<210> SEQ ID NO 20
<211> LENGTH: 15
<212> TYPE: PRT
<213> ORGANISM: Artificial Sequence
<220> FEATURE:
<223> OTHER INFORMATION: vhCDR3

<400> SEQUENCE: 20

Val Lys Gly Leu Tyr Ser Asn Pro Arg Gly Gly Ala Phe Asp Ile
1               5                   10                  15

<210> SEQ ID NO 21
<211> LENGTH: 110
<212> TYPE: PRT
<213> ORGANISM: Artificial Sequence
<220> FEATURE:
<223> OTHER INFORMATION: Variable light (vl) chain

<400> SEQUENCE: 21

Ser Tyr Val Leu Thr Gln Pro Pro Ser Val Ser Val Ala Pro Gly Gln
1               5                   10                  15

Thr Ala Thr Ile Thr Cys Gly Gly Asn Asn Ile Gly Thr Lys Ser Val
            20                  25                  30

His Trp Tyr Gln Gln Lys Pro Gly Gln Ala Pro Val Leu Val Val Tyr
        35                  40                  45

Ala Asp Ser Asp Arg Pro Ser Gly Ile Pro Glu Arg Val Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Arg Ser Asp His
                85                  90                  95

Leu Trp Val Phe Gly Gly Gly Thr Lys Leu Thr Val Leu Gly
            100                 105                 110

<210> SEQ ID NO 22
<211> LENGTH: 6
<212> TYPE: PRT
<213> ORGANISM: Artificial Sequence
<220> FEATURE:
<223> OTHER INFORMATION: vlCDR1

<400> SEQUENCE: 22

Asn Ile Gly Thr Lys Ser
1               5
```

<210> SEQ ID NO 23
<211> LENGTH: 3
<212> TYPE: PRT
<213> ORGANISM: Artificial Sequence
<220> FEATURE:
<223> OTHER INFORMATION: vlCDR2

<400> SEQUENCE: 23

Ala Asp Ser
1

<210> SEQ ID NO 24
<211> LENGTH: 12
<212> TYPE: PRT
<213> ORGANISM: Artificial Sequence
<220> FEATURE:
<223> OTHER INFORMATION: vlCDR3

<400> SEQUENCE: 24

Gln Val Trp Asp Ser Arg Ser Asp His Leu Trp Val
1               5                   10

<210> SEQ ID NO 25
<211> LENGTH: 122
<212> TYPE: PRT
<213> ORGANISM: Artificial Sequence
<220> FEATURE:
<223> OTHER INFORMATION: Variable heavy (vh) chain

<400> SEQUENCE: 25

Glu Val Gln Leu Val Glu Ser Gly Gly Gly Leu Ile Gln Pro Gly Arg
1               5                   10                  15

Ser Leu Arg Leu Ser Cys Ala Ala Ser Gly Ile Thr Phe Asp Asp Ala
            20                  25                  30

Val Met His Trp Val Arg Gln Ala Pro Gly Lys Gly Leu Glu Trp Val
        35                  40                  45

Ala Gly Ile Ser Ser Asn Ser Gly Tyr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Arg Leu Arg Ala Glu Asp Thr Ala Val Tyr Tyr Cys
                85                  90                  95

Val Lys Gly Leu Tyr Ser Asn Pro Arg Gly Gly Ala Phe Asp Ile Trp
            100                 105                 110

Gly Gln Gly Thr Met Val Thr Val Ser Ser
        115                 120

<210> SEQ ID NO 26
<211> LENGTH: 8
<212> TYPE: PRT
<213> ORGANISM: Artificial Sequence
<220> FEATURE:
<223> OTHER INFORMATION: vhCDR1

<400> SEQUENCE: 26

Gly Ile Thr Phe Asp Asp Ala Val
1               5

<210> SEQ ID NO 27
<211> LENGTH: 8
<212> TYPE: PRT
<213> ORGANISM: Artificial Sequence

```
<220> FEATURE:
<223> OTHER INFORMATION: vhCDR2

<400> SEQUENCE: 27

Ile Ser Ser Asn Ser Gly Tyr Ile
1               5

<210> SEQ ID NO 28
<211> LENGTH: 15
<212> TYPE: PRT
<213> ORGANISM: Artificial Sequence
<220> FEATURE:
<223> OTHER INFORMATION: vhCDR3

<400> SEQUENCE: 28

Val Lys Gly Leu Tyr Ser Asn Pro Arg Gly Gly Ala Phe Asp Ile
1               5                   10                  15

<210> SEQ ID NO 29
<211> LENGTH: 110
<212> TYPE: PRT
<213> ORGANISM: Artificial Sequence
<220> FEATURE:
<223> OTHER INFORMATION: Variable light (vl) chain

<400> SEQUENCE: 29

Ser Tyr Val Leu Thr Gln Pro Pro Ser Val Ser Val Ala Pro Gly Gln
1               5                   10                  15

Thr Ala Thr Ile Thr Cys Gly Gly Asn Asn Ile Gly Thr Lys Ser Val
                20                  25                  30

His Trp Tyr Gln Gln Lys Pro Gly Gln Ala Pro Val Leu Val Val Tyr
            35                  40                  45

Ala Asp Ser Asp Arg Pro Ser Gly Ile Pro Glu Arg Val Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Arg Ser Asp His
                85                  90                  95

Leu Trp Val Phe Gly Gly Gly Thr Lys Leu Thr Val Leu Gly
            100                 105                 110

<210> SEQ ID NO 30
<211> LENGTH: 6
<212> TYPE: PRT
<213> ORGANISM: Artificial Sequence
<220> FEATURE:
<223> OTHER INFORMATION: vlCDR1

<400> SEQUENCE: 30

Asn Ile Gly Thr Lys Ser
1               5

<210> SEQ ID NO 31
<211> LENGTH: 3
<212> TYPE: PRT
<213> ORGANISM: Artificial Sequence
<220> FEATURE:
<223> OTHER INFORMATION: vlCDR2

<400> SEQUENCE: 31

Ala Asp Ser
1
```

```
<210> SEQ ID NO 32
<211> LENGTH: 12
<212> TYPE: PRT
<213> ORGANISM: Artificial Sequence
<220> FEATURE:
<223> OTHER INFORMATION: vlCDR3

<400> SEQUENCE: 32

Gln Val Trp Asp Ser Arg Ser Asp His Leu Trp Val
1               5                   10

<210> SEQ ID NO 33
<211> LENGTH: 119
<212> TYPE: PRT
<213> ORGANISM: Artificial Sequence
<220> FEATURE:
<223> OTHER INFORMATION: Variable heavy (vh) chain

<400> SEQUENCE: 33

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asn Ser Tyr
            20                  25                  30

Trp Ile Gly Trp Val Arg Gln Met Pro Gly Lys Gly Leu Glu Trp Met
        35                  40                  45

Ala Ile Ile Tyr Pro Gly Asp Ser Asp Thr Arg Tyr Ser Pro Ser Phe
    50                  55                  60

Gln Gly Gln Val Thr Phe Ser Val Asp Lys Ser Ile Asn Thr Ala Tyr
65                  70                  75                  80

Leu Val Trp Thr Ser Leu Lys Ala Ser Asp Thr Ala Ile Tyr Tyr Cys
                85                  90                  95

Ala Arg Gln Arg Trp Gly Ser Ser Phe Asp Leu Trp Gly Gln Gly
            100                 105                 110

Thr Leu Val Thr Val Ser Ser
        115

<210> SEQ ID NO 34
<211> LENGTH: 8
<212> TYPE: PRT
<213> ORGANISM: Artificial Sequence
<220> FEATURE:
<223> OTHER INFORMATION: vhCDR1

<400> SEQUENCE: 34

Gly Tyr Ser Phe Asn Ser Tyr Trp
1               5

<210> SEQ ID NO 35
<211> LENGTH: 8
<212> TYPE: PRT
<213> ORGANISM: Artificial Sequence
<220> FEATURE:
<223> OTHER INFORMATION: vhCDR2

<400> SEQUENCE: 35

Ile Tyr Pro Gly Asp Ser Asp Thr
1               5

<210> SEQ ID NO 36
<211> LENGTH: 12
<212> TYPE: PRT
<213> ORGANISM: Artificial Sequence
<220> FEATURE:
<223> OTHER INFORMATION: vhCDR3
```

<400> SEQUENCE: 36

Ala Arg Gln Arg Trp Gly Ser Ser Ser Phe Asp Leu
1               5                   10

<210> SEQ ID NO 37
<211> LENGTH: 111
<212> TYPE: PRT
<213> ORGANISM: Artificial Sequence
<220> FEATURE:
<223> OTHER INFORMATION: Variable light (vl) chain

<400> SEQUENCE: 37

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Glu Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Gly Gly Thr Gln Leu Thr Val Leu Gly
            100                 105                 110

<210> SEQ ID NO 38
<211> LENGTH: 8
<212> TYPE: PRT
<213> ORGANISM: Artificial Sequence
<220> FEATURE:
<223> OTHER INFORMATION: vlCDR1

<400> SEQUENCE: 38

Ser Ser Asn Ile Gly Asn Asn Tyr
1               5

<210> SEQ ID NO 39
<211> LENGTH: 3
<212> TYPE: PRT
<213> ORGANISM: Artificial Sequence
<220> FEATURE:
<223> OTHER INFORMATION: vlCDR2

<400> SEQUENCE: 39

Glu Asn Asn
1

<210> SEQ ID NO 40
<211> LENGTH: 11
<212> TYPE: PRT
<213> ORGANISM: Artificial Sequence
<220> FEATURE:
<223> OTHER INFORMATION: vlCDR3

<400> SEQUENCE: 40

Gly Thr Trp Asp Ser Ser Leu Ser Ala Gly Val
1               5                   10

<210> SEQ ID NO 41
<211> LENGTH: 119

<212> TYPE: PRT
<213> ORGANISM: Artificial Sequence
<220> FEATURE:
<223> OTHER INFORMATION: Variable heavy (vh) chain

<400> SEQUENCE: 41

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asn Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Phe Ser Val Asp Lys Ser Ile Asn Thr Ala Tyr
65                  70                  75                  80

Leu Gln Trp Ser Ser Leu Lys Ala Ser Asp Ala Ala Met Tyr Tyr Cys
                85                  90                  95

Ala Arg Gln Arg Trp Gly Ser Ser Ser Phe Asp Ala Trp Gly Gln Gly
            100                 105                 110

Thr Leu Val Thr Val Ser Ser
        115

<210> SEQ ID NO 42
<211> LENGTH: 8
<212> TYPE: PRT
<213> ORGANISM: Artificial Sequence
<220> FEATURE:
<223> OTHER INFORMATION: vhCDR1

<400> SEQUENCE: 42

Gly Tyr Ser Phe Asn Ser Tyr Trp
1               5

<210> SEQ ID NO 43
<211> LENGTH: 8
<212> TYPE: PRT
<213> ORGANISM: Artificial Sequence
<220> FEATURE:
<223> OTHER INFORMATION: vhCDR2

<400> SEQUENCE: 43

Ile Tyr Pro Gly Asp Ser Asp Thr
1               5

<210> SEQ ID NO 44
<211> LENGTH: 12
<212> TYPE: PRT
<213> ORGANISM: Artificial Sequence
<220> FEATURE:
<223> OTHER INFORMATION: vhCDR3

<400> SEQUENCE: 44

Ala Arg Gln Arg Trp Gly Ser Ser Ser Phe Asp Ala
1               5                   10

<210> SEQ ID NO 45
<211> LENGTH: 111
<212> TYPE: PRT
<213> ORGANISM: Artificial Sequence
<220> FEATURE:
<223> OTHER INFORMATION: Variable light (vl) chain

<400> SEQUENCE: 45

Gln Ser Val Leu Thr Gln Pro Pro Ser Val Ala Ala Pro Gly Gln
1               5                   10                  15

Lys Val Thr Ile Ser Cys Ser Gly Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Glu Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Gly Gly Thr Gln Leu Thr Val Leu Gly
            100                 105                 110

<210> SEQ ID NO 46
<211> LENGTH: 8
<212> TYPE: PRT
<213> ORGANISM: Artificial Sequence
<220> FEATURE:
<223> OTHER INFORMATION: vlCDR1

<400> SEQUENCE: 46

Ser Ser Asn Ile Gly Asn Asn Tyr
1               5

<210> SEQ ID NO 47
<211> LENGTH: 3
<212> TYPE: PRT
<213> ORGANISM: Artificial Sequence
<220> FEATURE:
<223> OTHER INFORMATION: vlCDR2

<400> SEQUENCE: 47

Glu Asn Asn
1

<210> SEQ ID NO 48
<211> LENGTH: 11
<212> TYPE: PRT
<213> ORGANISM: Artificial Sequence
<220> FEATURE:
<223> OTHER INFORMATION: vlCDR3

<400> SEQUENCE: 48

Gly Thr Trp Asp Ser Ser Leu Ser Ala Gly Val
1               5                   10

<210> SEQ ID NO 49
<211> LENGTH: 119
<212> TYPE: PRT
<213> ORGANISM: Artificial Sequence
<220> FEATURE:
<223> OTHER INFORMATION: Variable heavy (vh) chain

<400> SEQUENCE: 49

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

```
Gly Ile Ile Tyr Pro Gly Asp Ser Asp Thr Arg Tyr Ser Pro Ser Phe
            50                  55                  60
Glu Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                 85                  90                  95
Ala Arg Leu His Gly Val Val Ser Arg Gly Asp Tyr Trp Gly Gln Gly
            100                 105                 110
Thr Leu Val Thr Val Ser Ser
            115
```

```
<210> SEQ ID NO 50
<211> LENGTH: 8
<212> TYPE: PRT
<213> ORGANISM: Artificial Sequence
<220> FEATURE:
<223> OTHER INFORMATION: vhCDR1

<400> SEQUENCE: 50

Gly Tyr Ser Phe Thr Ser Tyr Trp
1               5
```

```
<210> SEQ ID NO 51
<211> LENGTH: 8
<212> TYPE: PRT
<213> ORGANISM: Artificial Sequence
<220> FEATURE:
<223> OTHER INFORMATION: vhCDR2

<400> SEQUENCE: 51

Ile Tyr Pro Gly Asp Ser Asp Thr
1               5
```

```
<210> SEQ ID NO 52
<211> LENGTH: 12
<212> TYPE: PRT
<213> ORGANISM: Artificial Sequence
<220> FEATURE:
<223> OTHER INFORMATION: vhCDR3

<400> SEQUENCE: 52

Ala Arg Leu His Gly Val Val Ser Arg Gly Asp Tyr
1               5                   10
```

```
<210> SEQ ID NO 53
<211> LENGTH: 112
<212> TYPE: PRT
<213> ORGANISM: Artificial Sequence
<220> FEATURE:
<223> OTHER INFORMATION: Variable light (vl) chain

<400> SEQUENCE: 53

Gln Ser Ala Leu Thr Gln Pro Ala Ser Val Ser Gly Ser Pro Gly Gln
1               5                   10                  15
Ser Ile Thr Ile Ser Cys Ser Gly Ile Ser Ser Leu Ala Gly Ser Tyr
                20                  25                  30
Asn Leu Val Ser Trp Tyr Gln Gln Tyr Pro Gly Lys Ala Pro Lys Leu
            35                  40                  45
Ile Ile Tyr Glu Val Thr Lys Arg Pro Ser Gly Val Ser Asn Arg Phe
        50                  55                  60
Ser Gly Ser Lys Ser Gly Asn Thr Ala Ser Leu Thr Ile Ser Gly Leu
 65                  70                  75                  80
```

Gln Ala Asp Asp Glu Ala Glu Tyr Ser Cys Ser Ser Tyr Ala Gly Arg
            85                  90                  95

Asn Ala Val Ala Val Phe Gly Gly Gly Thr Gln Leu Thr Val Leu Gly
            100                 105                 110

<210> SEQ ID NO 54
<211> LENGTH: 9
<212> TYPE: PRT
<213> ORGANISM: Artificial Sequence
<220> FEATURE:
<223> OTHER INFORMATION: vlCDR1

<400> SEQUENCE: 54

Ser Ser Leu Ala Gly Ser Tyr Asn Leu
1               5

<210> SEQ ID NO 55
<211> LENGTH: 3
<212> TYPE: PRT
<213> ORGANISM: Artificial Sequence
<220> FEATURE:
<223> OTHER INFORMATION: vlCDR2

<400> SEQUENCE: 55

Glu Val Thr
1

<210> SEQ ID NO 56
<211> LENGTH: 11
<212> TYPE: PRT
<213> ORGANISM: Artificial Sequence
<220> FEATURE:
<223> OTHER INFORMATION: vlCDR3

<400> SEQUENCE: 56

Ser Ser Tyr Ala Gly Arg Asn Ala Val Ala Val
1               5                   10

<210> SEQ ID NO 57
<211> LENGTH: 119
<212> TYPE: PRT
<213> ORGANISM: Artificial Sequence
<220> FEATURE:
<223> OTHER INFORMATION: Variable heavy (vh) chain

<400> SEQUENCE: 57

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Glu Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Ala Tyr Tyr Cys
            85                  90                  95

Ala Arg Leu His Gly Val Val Ser Arg Gly Asp Tyr Trp Gly Gln Gly
            100                 105                 110

Thr Leu Val Thr Val Ser Ser
            115

<210> SEQ ID NO 58
<211> LENGTH: 8
<212> TYPE: PRT
<213> ORGANISM: Artificial Sequence
<220> FEATURE:
<223> OTHER INFORMATION: vhCDR1

<400> SEQUENCE: 58

Gly Tyr Ser Phe Thr Ser Tyr Trp
1               5

<210> SEQ ID NO 59
<211> LENGTH: 8
<212> TYPE: PRT
<213> ORGANISM: Artificial Sequence
<220> FEATURE:
<223> OTHER INFORMATION: vhCDR2

<400> SEQUENCE: 59

Ile Tyr Pro Gly Asp Ser Asp Thr
1               5

<210> SEQ ID NO 60
<211> LENGTH: 12
<212> TYPE: PRT
<213> ORGANISM: Artificial Sequence
<220> FEATURE:
<223> OTHER INFORMATION: vhCDR3

<400> SEQUENCE: 60

Ala Arg Leu His Gly Val Val Ser Arg Gly Asp Tyr
1               5                   10

<210> SEQ ID NO 61
<211> LENGTH: 112
<212> TYPE: PRT
<213> ORGANISM: Artificial Sequence
<220> FEATURE:
<223> OTHER INFORMATION: Variable light (vl) chain

<400> SEQUENCE: 61

Gln Ser Ala Leu Thr Gln Pro Ala Ser Val Ser Gly Ser Pro Gly Gln
1               5                   10                  15

Ser Ile Thr Ile Ser Cys Ser Gly Ile Ser Ser Leu Ala Gly Ser Tyr
            20                  25                  30

Asn Leu Val Ser Trp Tyr Gln Gln Tyr Pro Gly Lys Ala Pro Lys Leu
        35                  40                  45

Ile Ile Tyr Glu Val Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Asp Asp Glu Ala Glu Tyr Ser Cys Ser Ser Tyr Ala Gly Arg
                85                  90                  95

Asn Ala Val Ala Val Phe Gly Gly Gly Thr Gln Leu Thr Val Leu Gly
            100                 105                 110

<210> SEQ ID NO 62
<211> LENGTH: 9
<212> TYPE: PRT
<213> ORGANISM: Artificial Sequence
<220> FEATURE:
<223> OTHER INFORMATION: vlCDR1

```
<400> SEQUENCE: 62

Ser Ser Leu Ala Gly Ser Tyr Asn Leu
1               5

<210> SEQ ID NO 63
<211> LENGTH: 3
<212> TYPE: PRT
<213> ORGANISM: Artificial Sequence
<220> FEATURE:
<223> OTHER INFORMATION: vlCDR2

<400> SEQUENCE: 63

Glu Val Thr
1

<210> SEQ ID NO 64
<211> LENGTH: 11
<212> TYPE: PRT
<213> ORGANISM: Artificial Sequence
<220> FEATURE:
<223> OTHER INFORMATION: vlCDR3

<400> SEQUENCE: 64

Ser Ser Tyr Ala Gly Arg Asn Ala Val Ala Val
1               5                   10

<210> SEQ ID NO 65
<211> LENGTH: 122
<212> TYPE: PRT
<213> ORGANISM: Artificial Sequence
<220> FEATURE:
<223> OTHER INFORMATION: Variable heavy (vh) chain

<400> SEQUENCE: 65

Glu Val Gln Leu Val Glu Thr Gly Gly Gly Val Val Arg Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Ser
65                  70                  75                  80

Leu Gln Met Asn Ser Leu Arg Ala Glu Asp Thr Ala Val Tyr Tyr Cys
                85                  90                  95

Ala Lys Ser Ser Gly Trp Tyr Pro Tyr Tyr Tyr Gly Met Asp Val Trp
            100                 105                 110

Gly Gln Gly Thr Thr Val Thr Val Ser Ser
        115                 120

<210> SEQ ID NO 66
<211> LENGTH: 8
<212> TYPE: PRT
<213> ORGANISM: Artificial Sequence
<220> FEATURE:
<223> OTHER INFORMATION: vhCDR1

<400> SEQUENCE: 66

Gly Phe Thr Phe Ser Ser Tyr Ala
1               5
```

```
<210> SEQ ID NO 67
<211> LENGTH: 8
<212> TYPE: PRT
<213> ORGANISM: Artificial Sequence
<220> FEATURE:
<223> OTHER INFORMATION: vhCDR2

<400> SEQUENCE: 67

Ile Ser Gly Ser Gly Gly Ser Thr
1               5

<210> SEQ ID NO 68
<211> LENGTH: 15
<212> TYPE: PRT
<213> ORGANISM: Artificial Sequence
<220> FEATURE:
<223> OTHER INFORMATION: vhCDR3

<400> SEQUENCE: 68

Ala Lys Ser Ser Gly Trp Tyr Pro Tyr Tyr Tyr Gly Met Asp Val
1               5                   10                  15

<210> SEQ ID NO 69
<211> LENGTH: 107
<212> TYPE: PRT
<213> ORGANISM: Artificial Sequence
<220> FEATURE:
<223> OTHER INFORMATION: Variable light (vl) chain

<400> SEQUENCE: 69

Ser Tyr Glu Leu Met Gln Pro Pro Ser Val Ser Val Ser Pro Gly Gln
1               5                   10                  15

Thr Ala Arg Ile Thr Cys Ser Gly Asn Asn Leu Gly Asp Lys Tyr Thr
            20                  25                  30

Ser Trp Tyr Gln His Lys Pro Gly Gln Ser Pro Val Met Val Ile Tyr
        35                  40                  45

Gln Asp Thr Lys Arg Pro Ser Gly Ile Ala Glu Arg Phe Ser Gly Ser
    50                  55                  60

Asn Ser Gly Asn Thr Ala Thr Leu Thr Ile Ser Gly Thr Gln Ala Leu
65                  70                  75                  80

Asp Glu Ala Asp Tyr Tyr Cys Gln Ala Trp Asp Gly Thr Ala Val
                85                  90                  95

Phe Gly Gly Gly Thr Gln Leu Thr Val Leu Gly
            100                 105

<210> SEQ ID NO 70
<211> LENGTH: 6
<212> TYPE: PRT
<213> ORGANISM: Artificial Sequence
<220> FEATURE:
<223> OTHER INFORMATION: vlCDR1

<400> SEQUENCE: 70

Asn Leu Gly Asp Lys Tyr
1               5

<210> SEQ ID NO 71
<211> LENGTH: 3
<212> TYPE: PRT
<213> ORGANISM: Artificial Sequence
<220> FEATURE:
<223> OTHER INFORMATION: vlCDR2

<400> SEQUENCE: 71
```

Gln Asp Thr
1

<210> SEQ ID NO 72
<211> LENGTH: 9
<212> TYPE: PRT
<213> ORGANISM: Artificial Sequence
<220> FEATURE:
<223> OTHER INFORMATION: vlCDR3

<400> SEQUENCE: 72

Gln Ala Trp Asp Thr Gly Thr Ala Val
1               5

<210> SEQ ID NO 73
<211> LENGTH: 122
<212> TYPE: PRT
<213> ORGANISM: Artificial Sequence
<220> FEATURE:
<223> OTHER INFORMATION: Variable heavy (vh) chain

<400> SEQUENCE: 73

Glu Val Gln Leu Val Glu Thr Gly Gly Gly Val Val Arg Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Ser
65                  70                  75                  80

Leu Gln Met Asn Ser Leu Arg Ala Glu Asp Thr Ala Ala Tyr Tyr Cys
                85                  90                  95

Ala Lys Ser Ser Gly Trp Tyr Pro Tyr Tyr Gly Met Asp Val Trp
            100                 105                 110

Gly Gln Gly Thr Thr Val Thr Val Ser Ser
        115                 120

<210> SEQ ID NO 74
<211> LENGTH: 8
<212> TYPE: PRT
<213> ORGANISM: Artificial Sequence
<220> FEATURE:
<223> OTHER INFORMATION: vhCDR1

<400> SEQUENCE: 74

Gly Phe Thr Phe Ser Ser Tyr Ala
1               5

<210> SEQ ID NO 75
<211> LENGTH: 8
<212> TYPE: PRT
<213> ORGANISM: Artificial Sequence
<220> FEATURE:
<223> OTHER INFORMATION: vhCDR2

<400> SEQUENCE: 75

Ile Ser Gly Ser Gly Gly Ser Thr
1               5

<210> SEQ ID NO 76
<211> LENGTH: 15

```
<212> TYPE: PRT
<213> ORGANISM: Artificial Sequence
<220> FEATURE:
<223> OTHER INFORMATION: vhCDR3

<400> SEQUENCE: 76

Ala Lys Ser Ser Gly Trp Tyr Pro Tyr Tyr Tyr Gly Met Asp Val
1               5                   10                  15

<210> SEQ ID NO 77
<211> LENGTH: 107
<212> TYPE: PRT
<213> ORGANISM: Artificial Sequence
<220> FEATURE:
<223> OTHER INFORMATION: Variable light (vl) chain

<400> SEQUENCE: 77

Ser Tyr Glu Leu Met Gln Pro Pro Ser Val Ser Val Ser Pro Gly Gln
1               5                   10                  15

Thr Ala Arg Ile Thr Cys Ser Gly Asn Asn Leu Gly Asp Lys Tyr Thr
            20                  25                  30

Ser Trp Tyr Gln His Lys Pro Gly Gln Ser Pro Val Met Val Ile Tyr
        35                  40                  45

Gln Asp Thr Lys Arg Pro Ser Gly Ile Ala Glu Arg Phe Ser Gly Ser
    50                  55                  60

Asn Ser Gly Asn Thr Ala Thr Leu Thr Ile Ser Gly Thr Gln Ala Leu
65                  70                  75                  80

Asp Glu Ala Asp Tyr Tyr Cys Gln Ala Trp Asp Thr Gly Thr Ala Val
                85                  90                  95

Phe Gly Gly Gly Thr Gln Leu Thr Val Leu Gly
            100                 105

<210> SEQ ID NO 78
<211> LENGTH: 6
<212> TYPE: PRT
<213> ORGANISM: Artificial Sequence
<220> FEATURE:
<223> OTHER INFORMATION: vlCDR1

<400> SEQUENCE: 78

Asn Leu Gly Asp Lys Tyr
1               5

<210> SEQ ID NO 79
<211> LENGTH: 3
<212> TYPE: PRT
<213> ORGANISM: Artificial Sequence
<220> FEATURE:
<223> OTHER INFORMATION: vlCDR2

<400> SEQUENCE: 79

Gln Asp Thr
1

<210> SEQ ID NO 80
<211> LENGTH: 9
<212> TYPE: PRT
<213> ORGANISM: Artificial Sequence
<220> FEATURE:
<223> OTHER INFORMATION: vlCDR3

<400> SEQUENCE: 80

Gln Ala Trp Asp Thr Gly Thr Ala Val
1               5
```

```
<210> SEQ ID NO 81
<211> LENGTH: 119
<212> TYPE: PRT
<213> ORGANISM: Artificial Sequence
<220> FEATURE:
<223> OTHER INFORMATION: Variable heavy (vh) chain

<400> SEQUENCE: 81

Glu Val Gln Leu Val Gln Ser Gly Ala Glu Val Lys Lys Pro Gly Glu
1               5                   10                  15

Ser Leu Lys Ile Ser Cys Gln Ala Phe Gly Tyr Asn Phe Asn Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Ser Thr Val Thr Lys Ser Phe Asp Ile Trp Gly Gln Gly
            100                 105                 110

Thr Met Val Thr Val Ser Ser
        115

<210> SEQ ID NO 82
<211> LENGTH: 8
<212> TYPE: PRT
<213> ORGANISM: Artificial Sequence
<220> FEATURE:
<223> OTHER INFORMATION: vhCDR1

<400> SEQUENCE: 82

Gly Tyr Asn Phe Asn Asn Tyr Trp
1               5

<210> SEQ ID NO 83
<211> LENGTH: 8
<212> TYPE: PRT
<213> ORGANISM: Artificial Sequence
<220> FEATURE:
<223> OTHER INFORMATION: vhCDR2

<400> SEQUENCE: 83

Ile Tyr Pro Gly Asp Ser Asp Thr
1               5

<210> SEQ ID NO 84
<211> LENGTH: 12
<212> TYPE: PRT
<213> ORGANISM: Artificial Sequence
<220> FEATURE:
<223> OTHER INFORMATION: vhCDR3

<400> SEQUENCE: 84

Ala Arg Arg Ser Thr Val Thr Lys Ser Phe Asp Ile
1               5                   10

<210> SEQ ID NO 85
<211> LENGTH: 111
<212> TYPE: PRT
<213> ORGANISM: Artificial Sequence
```

```
<220> FEATURE:
<223> OTHER INFORMATION: Variable light (vl) chain

<400> SEQUENCE: 85

Gln Ala Gly Leu Thr Gln Pro Pro Ser Val Ser Lys Gly Leu Arg Gln
1               5                   10                  15

Thr Ala Thr Leu Thr Cys Thr Gly Asn Ser Asn Val Gly Lys Gln
            20                  25                  30

Gly Ala Ala Trp Leu Gln Gln His Gln Gly His Pro Pro Lys Leu Leu
        35                  40                  45

Ser Tyr Ser Ser Ile Asn Arg Pro Val Gly Ile Ser Glu Arg Phe Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Trp Asp Ser Ser Leu
                85                  90                  95

Ser Ala Trp Val Phe Gly Gly Gly Thr Lys Leu Thr Val Leu Gly
            100                 105                 110

<210> SEQ ID NO 86
<211> LENGTH: 8
<212> TYPE: PRT
<213> ORGANISM: Artificial Sequence
<220> FEATURE:
<223> OTHER INFORMATION: vlCDR1

<400> SEQUENCE: 86

Ser Asn Asn Val Gly Lys Gln Gly
1               5

<210> SEQ ID NO 87
<211> LENGTH: 3
<212> TYPE: PRT
<213> ORGANISM: Artificial Sequence
<220> FEATURE:
<223> OTHER INFORMATION: vlCDR2

<400> SEQUENCE: 87

Ser Ser Ile
1

<210> SEQ ID NO 88
<211> LENGTH: 11
<212> TYPE: PRT
<213> ORGANISM: Artificial Sequence
<220> FEATURE:
<223> OTHER INFORMATION: vlCDR3

<400> SEQUENCE: 88

Ser Ala Trp Asp Ser Ser Leu Ser Ala Trp Val
1               5                   10

<210> SEQ ID NO 89
<211> LENGTH: 130
<212> TYPE: PRT
<213> ORGANISM: Artificial Sequence
<220> FEATURE:
<223> OTHER INFORMATION: Variable heavy (vh) chain

<400> SEQUENCE: 89

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
```

```
                20                  25                  30
Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Ser Ala Trp Ser Ser Gly Trp Ser Thr Leu Arg Tyr
            100                 105                 110

Tyr Tyr Tyr Gly Met Asp Val Trp Gly Gln Gly Thr Thr Val Thr Val
        115                 120                 125

Ser Ser
    130

<210> SEQ ID NO 90
<211> LENGTH: 10
<212> TYPE: PRT
<213> ORGANISM: Artificial Sequence
<220> FEATURE:
<223> OTHER INFORMATION: vhCDR1

<400> SEQUENCE: 90

Gly Gly Ser Ile Ser Ser Ser Ser Tyr Tyr
1               5                   10

<210> SEQ ID NO 91
<211> LENGTH: 7
<212> TYPE: PRT
<213> ORGANISM: Artificial Sequence
<220> FEATURE:
<223> OTHER INFORMATION: vhCDR2

<400> SEQUENCE: 91

Ile Tyr Tyr Ser Gly Ser Thr
1               5

<210> SEQ ID NO 92
<211> LENGTH: 22
<212> TYPE: PRT
<213> ORGANISM: Artificial Sequence
<220> FEATURE:
<223> OTHER INFORMATION: vhCDR3

<400> SEQUENCE: 92

Ala Arg Arg Ser Ala Trp Ser Ser Gly Trp Ser Thr Leu Arg Tyr Tyr
1               5                   10                  15

Tyr Tyr Gly Met Asp Val
            20

<210> SEQ ID NO 93
<211> LENGTH: 109
<212> TYPE: PRT
<213> ORGANISM: Artificial Sequence
<220> FEATURE:
<223> OTHER INFORMATION: Variable light (vl) chain

<400> SEQUENCE: 93

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ala Thr Tyr
```

```
                    20                  25                  30

Leu Ala Trp Tyr Gln Gln Asn Pro Gly Gln Ala Pro Arg Leu Leu Ile
            35                  40                  45

Tyr Asp Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Glu Arg Ser Asn Trp Ser Arg
                85                  90                  95

Leu Thr Phe Gly Gly Gly Thr Lys Val Glu Ile Lys Arg
                100                 105
```

<210> SEQ ID NO 94
<211> LENGTH: 6
<212> TYPE: PRT
<213> ORGANISM: Artificial Sequence
<220> FEATURE:
<223> OTHER INFORMATION: vlCDR1

<400> SEQUENCE: 94

```
Gln Ser Ile Ala Thr Tyr
1               5
```

<210> SEQ ID NO 95
<211> LENGTH: 3
<212> TYPE: PRT
<213> ORGANISM: Artificial Sequence
<220> FEATURE:
<223> OTHER INFORMATION: vlCDR2

<400> SEQUENCE: 95

```
Asp Ala Ser
1
```

<210> SEQ ID NO 96
<211> LENGTH: 10
<212> TYPE: PRT
<213> ORGANISM: Artificial Sequence
<220> FEATURE:
<223> OTHER INFORMATION: vlCDR3

<400> SEQUENCE: 96

```
Gln Glu Arg Ser Asn Trp Ser Arg Leu Thr
1               5                   10
```

<210> SEQ ID NO 97
<211> LENGTH: 119
<212> TYPE: PRT
<213> ORGANISM: Artificial Sequence
<220> FEATURE:
<223> OTHER INFORMATION: Variable heavy (vh) chain

<400> SEQUENCE: 97

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Pro Gly Arg Gly Leu Glu Trp Leu
            35                  40                  45

Ala Ile Ile Tyr Pro Gly Asp Ser Asp Thr Arg Tyr Ser Pro Ser Phe
    50                  55                  60

Glu Gly Gln Val Thr Ile Ser Ala Asp Lys Ser Ile Ser Thr Ala Tyr
```

```
                65                  70                  75                  80
Leu Gln Trp Ser Ser Leu Lys Ala Ser Asp Thr Ala Met Tyr Tyr Cys
                    85                  90                  95

Ala Arg Leu His Gly Val Val Ser Arg Gly Asp Tyr Trp Gly Gln Gly
            100                 105                 110

Thr Leu Val Thr Val Ser Ser
        115

<210> SEQ ID NO 98
<211> LENGTH: 8
<212> TYPE: PRT
<213> ORGANISM: Artificial Sequence
<220> FEATURE:
<223> OTHER INFORMATION: vhCDR1

<400> SEQUENCE: 98

Gly Tyr Ser Phe Thr Asn Tyr Trp
1               5

<210> SEQ ID NO 99
<211> LENGTH: 8
<212> TYPE: PRT
<213> ORGANISM: Artificial Sequence
<220> FEATURE:
<223> OTHER INFORMATION: vhCDR2

<400> SEQUENCE: 99

Ile Tyr Pro Gly Asp Ser Asp Thr
1               5

<210> SEQ ID NO 100
<211> LENGTH: 12
<212> TYPE: PRT
<213> ORGANISM: Artificial Sequence
<220> FEATURE:
<223> OTHER INFORMATION: vhCDR3

<400> SEQUENCE: 100

Ala Arg Leu His Gly Val Val Ser Arg Gly Asp Tyr
1               5                   10

<210> SEQ ID NO 101
<211> LENGTH: 112
<212> TYPE: PRT
<213> ORGANISM: Artificial Sequence
<220> FEATURE:
<223> OTHER INFORMATION: Variable light (vl) chain

<400> SEQUENCE: 101

Gln Ser Ala Leu Thr Gln Pro Ala Ser Val Ser Gly Ser Pro Gly Gln
1               5                   10                  15

Ser Ile Thr Ile Ser Cys Ser Gly Ile Ser Ser Leu Ala Gly Ser Tyr
            20                  25                  30

Asn Leu Val Ser Trp Tyr Gln Gln Tyr Pro Gly Lys Ala Pro Lys Leu
        35                  40                  45

Ile Ile Tyr Glu Val Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Asp Asp Glu Ala Glu Tyr Ser Cys Ser Ser Tyr Ala Gly Arg
                85                  90                  95

Asn Ala Val Ala Val Phe Gly Gly Gly Thr Gln Leu Thr Val Leu Gly
```

<210> SEQ ID NO 102
<211> LENGTH: 9
<212> TYPE: PRT
<213> ORGANISM: Artificial Sequence
<220> FEATURE:
<223> OTHER INFORMATION: vlCDR1

<400> SEQUENCE: 102

Ser Ser Leu Ala Gly Ser Tyr Asn Leu
1               5

<210> SEQ ID NO 103
<211> LENGTH: 3
<212> TYPE: PRT
<213> ORGANISM: Artificial Sequence
<220> FEATURE:
<223> OTHER INFORMATION: vlCDR2

<400> SEQUENCE: 103

Glu Val Thr
1

<210> SEQ ID NO 104
<211> LENGTH: 11
<212> TYPE: PRT
<213> ORGANISM: Artificial Sequence
<220> FEATURE:
<223> OTHER INFORMATION: vlCDR3

<400> SEQUENCE: 104

Ser Ser Tyr Ala Gly Arg Asn Ala Val Ala Val
1               5                   10

<210> SEQ ID NO 105
<211> LENGTH: 119
<212> TYPE: PRT
<213> ORGANISM: Artificial Sequence
<220> FEATURE:
<223> OTHER INFORMATION: Variable heavy (vh) chain

<400> SEQUENCE: 105

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Trp Ile Gly Trp Val Arg Gln Met Pro Gly Glu Gly Leu Glu Trp Met
            35                  40                  45

Gly Ile Ile Tyr Pro Gly Asp Ser Asp Thr Arg Tyr Ser Pro Ser Phe
        50                  55                  60

Glu Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Gly Val Val Ser Arg Gly Asp Tyr Trp Gly Gln Gly
            100                 105                 110

Thr Leu Val Thr Val Ser Ser
        115

<210> SEQ ID NO 106
<211> LENGTH: 8
<212> TYPE: PRT

```
<213> ORGANISM: Artificial Sequence
<220> FEATURE:
<223> OTHER INFORMATION: vhCDR1

<400> SEQUENCE: 106

Gly Tyr Ser Phe Thr Asn Tyr Trp
1               5

<210> SEQ ID NO 107
<211> LENGTH: 8
<212> TYPE: PRT
<213> ORGANISM: Artificial Sequence
<220> FEATURE:
<223> OTHER INFORMATION: vhCDR2

<400> SEQUENCE: 107

Ile Tyr Pro Gly Asp Ser Asp Thr
1               5

<210> SEQ ID NO 108
<211> LENGTH: 12
<212> TYPE: PRT
<213> ORGANISM: Artificial Sequence
<220> FEATURE:
<223> OTHER INFORMATION: vhCDR3

<400> SEQUENCE: 108

Ala Arg Leu His Gly Val Val Ser Arg Gly Asp Tyr
1               5                   10

<210> SEQ ID NO 109
<211> LENGTH: 112
<212> TYPE: PRT
<213> ORGANISM: Artificial Sequence
<220> FEATURE:
<223> OTHER INFORMATION: Variable light (vl) chain

<400> SEQUENCE: 109

Gln Ser Ala Leu Thr Gln Pro Ala Ser Val Ser Gly Ser Pro Gly Gln
1               5                   10                  15

Ser Ile Thr Ile Ser Cys Ser Gly Ile Ser Ser Leu Ala Gly Ser Tyr
            20                  25                  30

Asn Leu Val Ser Trp Tyr Gln Gln Tyr Pro Gly Lys Ala Pro Lys Leu
        35                  40                  45

Ile Ile Tyr Glu Val Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Asp Asp Glu Ala Glu Tyr Ser Cys Ser Ser Tyr Ala Gly Arg
                85                  90                  95

Asn Ala Val Ala Val Phe Gly Gly Gly Thr Gln Leu Thr Val Leu Gly
            100                 105                 110

<210> SEQ ID NO 110
<211> LENGTH: 9
<212> TYPE: PRT
<213> ORGANISM: Artificial Sequence
<220> FEATURE:
<223> OTHER INFORMATION: vlCDR1

<400> SEQUENCE: 110

Ser Ser Leu Ala Gly Ser Tyr Asn Leu
1               5
```

```
<210> SEQ ID NO 111
<211> LENGTH: 3
<212> TYPE: PRT
<213> ORGANISM: Artificial Sequence
<220> FEATURE:
<223> OTHER INFORMATION: vlCDR2

<400> SEQUENCE: 111

Glu Val Thr
1

<210> SEQ ID NO 112
<211> LENGTH: 11
<212> TYPE: PRT
<213> ORGANISM: Artificial Sequence
<220> FEATURE:
<223> OTHER INFORMATION: vlCDR3

<400> SEQUENCE: 112

Ser Ser Tyr Ala Gly Arg Asn Ala Val Ala Val
1               5                   10

<210> SEQ ID NO 113
<211> LENGTH: 119
<212> TYPE: PRT
<213> ORGANISM: Artificial Sequence
<220> FEATURE:
<223> OTHER INFORMATION: Variable heavy (vh) chain

<400> SEQUENCE: 113

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Glu Gly Leu Glu Trp Met
        35                  40                  45

Gly Ile Ile Tyr Pro Gly Asp Ser Asp Thr Arg Tyr Ser Pro Ser Phe
    50                  55                  60

Glu Gly Gln Val Thr Ile Ser Ala Asp Lys Ser Ile Ser Thr Ala Tyr
65                  70                  75                  80

Leu Gln Trp Asn Ser Leu Lys Ala Ser Asp Thr Ala Met Tyr Tyr Cys
                85                  90                  95

Ala Arg Leu His Gly Val Val Ser Arg Gly Asp Tyr Trp Gly Gln Gly
            100                 105                 110

Thr Leu Val Thr Val Ser Ser
        115

<210> SEQ ID NO 114
<211> LENGTH: 8
<212> TYPE: PRT
<213> ORGANISM: Artificial Sequence
<220> FEATURE:
<223> OTHER INFORMATION: vhCDR1

<400> SEQUENCE: 114

Gly Tyr Ser Phe Thr Asn Tyr Trp
1               5

<210> SEQ ID NO 115
<211> LENGTH: 8
<212> TYPE: PRT
<213> ORGANISM: Artificial Sequence
<220> FEATURE:
```

```
<223> OTHER INFORMATION: vhCDR2

<400> SEQUENCE: 115

Ile Tyr Pro Gly Asp Ser Asp Thr
1               5

<210> SEQ ID NO 116
<211> LENGTH: 12
<212> TYPE: PRT
<213> ORGANISM: Artificial Sequence
<220> FEATURE:
<223> OTHER INFORMATION: vhCDR3

<400> SEQUENCE: 116

Ala Arg Leu His Gly Val Val Ser Arg Gly Asp Tyr
1               5                   10

<210> SEQ ID NO 117
<211> LENGTH: 112
<212> TYPE: PRT
<213> ORGANISM: Artificial Sequence
<220> FEATURE:
<223> OTHER INFORMATION: Variable light (vl) chain

<400> SEQUENCE: 117

Gln Ser Ala Leu Thr Gln Pro Ala Ser Val Ser Gly Ser Pro Gly Gln
1               5                   10                  15

Ser Ile Thr Ile Ser Cys Ser Gly Ile Ser Ser Leu Ala Gly Ser Tyr
            20                  25                  30

Asn Leu Val Ser Trp Tyr Gln Gln Tyr Pro Gly Lys Ala Pro Lys Leu
        35                  40                  45

Ile Ile Tyr Glu Val Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Asp Asp Glu Ala Glu Tyr Ser Cys Ser Ser Tyr Ala Gly Arg
                85                  90                  95

Asn Ala Val Ala Val Phe Gly Gly Gly Thr Gln Leu Thr Val Leu Gly
            100                 105                 110

<210> SEQ ID NO 118
<211> LENGTH: 9
<212> TYPE: PRT
<213> ORGANISM: Artificial Sequence
<220> FEATURE:
<223> OTHER INFORMATION: vlCDR1

<400> SEQUENCE: 118

Ser Ser Leu Ala Gly Ser Tyr Asn Leu
1               5

<210> SEQ ID NO 119
<211> LENGTH: 3
<212> TYPE: PRT
<213> ORGANISM: Artificial Sequence
<220> FEATURE:
<223> OTHER INFORMATION: vlCDR2

<400> SEQUENCE: 119

Glu Val Thr
1

<210> SEQ ID NO 120
```

```
<211> LENGTH: 11
<212> TYPE: PRT
<213> ORGANISM: Artificial Sequence
<220> FEATURE:
<223> OTHER INFORMATION: vlCDR3

<400> SEQUENCE: 120

Ser Ser Tyr Ala Gly Arg Asn Ala Val Ala Val
1               5                   10

<210> SEQ ID NO 121
<211> LENGTH: 122
<212> TYPE: PRT
<213> ORGANISM: Artificial Sequence
<220> FEATURE:
<223> OTHER INFORMATION: Variable heavy (vh) chain

<400> SEQUENCE: 121

Glu Val Gln Leu Val Glu Thr Gly Gly Gly Val Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Ser Gly Ser Ser Asn Ser Ile Tyr Tyr Ala Asp Ser Val
    50                  55                  60

Lys Gly Arg Phe Thr Ile Ala Arg Asp Asn Ala Lys Asn Thr Leu Phe
65                  70                  75                  80

Leu Gln Val Asn Ser Leu Arg Ala Glu Asp Thr Ala Val Tyr Tyr Cys
                85                  90                  95

Ala Arg His His Gly Arg Leu Tyr Tyr Tyr Gly Met Asp Val Trp
            100                 105                 110

Gly Gln Gly Thr Thr Val Thr Val Ser Ser
            115                 120

<210> SEQ ID NO 122
<211> LENGTH: 8
<212> TYPE: PRT
<213> ORGANISM: Artificial Sequence
<220> FEATURE:
<223> OTHER INFORMATION: vhCDR1

<400> SEQUENCE: 122

Gly Phe Thr Phe Ser Asn Tyr Ala
1               5

<210> SEQ ID NO 123
<211> LENGTH: 8
<212> TYPE: PRT
<213> ORGANISM: Artificial Sequence
<220> FEATURE:
<223> OTHER INFORMATION: vhCDR2

<400> SEQUENCE: 123

Ile Ser Gly Ser Ser Asn Ser Ile
1               5

<210> SEQ ID NO 124
<211> LENGTH: 15
<212> TYPE: PRT
<213> ORGANISM: Artificial Sequence
<220> FEATURE:
<223> OTHER INFORMATION: vhCDR3
```

```
<400> SEQUENCE: 124

Ala Arg His His Gly Arg Leu Tyr Tyr Tyr Gly Met Asp Val
1               5                   10                  15

<210> SEQ ID NO 125
<211> LENGTH: 107
<212> TYPE: PRT
<213> ORGANISM: Artificial Sequence
<220> FEATURE:
<223> OTHER INFORMATION: Variable light (vl) chain

<400> SEQUENCE: 125

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Glu Lys Tyr Ala
                20                  25                  30

Ser Trp Tyr Gln Gln Lys Pro Gly Gln Ser Pro Val Met Val Ile Tyr
            35                  40                  45

Gln Asp Arg Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Thr Thr Pro Gly
                    85                  90                  95

Phe Gly Gly Gly Thr Lys Val Thr Val Leu Gly
            100                 105

<210> SEQ ID NO 126
<211> LENGTH: 6
<212> TYPE: PRT
<213> ORGANISM: Artificial Sequence
<220> FEATURE:
<223> OTHER INFORMATION: vlCDR1

<400> SEQUENCE: 126

Lys Leu Gly Glu Lys Tyr
1               5

<210> SEQ ID NO 127
<211> LENGTH: 3
<212> TYPE: PRT
<213> ORGANISM: Artificial Sequence
<220> FEATURE:
<223> OTHER INFORMATION: vlCDR2

<400> SEQUENCE: 127

Gln Asp Arg
1

<210> SEQ ID NO 128
<211> LENGTH: 9
<212> TYPE: PRT
<213> ORGANISM: Artificial Sequence
<220> FEATURE:
<223> OTHER INFORMATION: vlCDR3

<400> SEQUENCE: 128

Gln Ala Trp Asp Thr Thr Thr Pro Gly
1               5

<210> SEQ ID NO 129
<211> LENGTH: 122
<212> TYPE: PRT
```

<213> ORGANISM: Artificial Sequence
<220> FEATURE:
<223> OTHER INFORMATION: Variable heavy (vh) chain

<400> SEQUENCE: 129

Glu Val Gln Leu Val Glu Ser Gly Gly Gly Leu Ile Gln Pro Gly Arg
1               5                   10                  15

Ser Leu Arg Leu Ser Cys Ala Ala Ser Gly Ile Thr Phe Asp Asp Tyr
            20                  25                  30

Val Met His Trp Val Arg Gln Ala Pro Gly Lys Gly Leu Glu Trp Val
        35                  40                  45

Ala Gly Ile Ser Ser Asn Ser Gly Tyr Ile Tyr Ala Asp Ser Val
    50                  55                  60

Arg Gly Arg Phe Thr Ile Ser Arg Asp Asn Ala Lys Asn Thr Leu Phe
65                  70                  75                  80

Leu Gln Val Asn Arg Leu Arg Pro Glu Asp Thr Ala Val Tyr Tyr Cys
                85                  90                  95

Ala Arg His His Gly Arg Leu Tyr Tyr Tyr Gly Met Asp Val Trp
            100                 105                 110

Gly Gln Gly Thr Thr Val Thr Val Ser Ser
        115                 120

<210> SEQ ID NO 130
<211> LENGTH: 8
<212> TYPE: PRT
<213> ORGANISM: Artificial Sequence
<220> FEATURE:
<223> OTHER INFORMATION: vhCDR1

<400> SEQUENCE: 130

Gly Ile Thr Phe Asp Asp Tyr Val
1               5

<210> SEQ ID NO 131
<211> LENGTH: 8
<212> TYPE: PRT
<213> ORGANISM: Artificial Sequence
<220> FEATURE:
<223> OTHER INFORMATION: vhCDR2

<400> SEQUENCE: 131

Ile Ser Ser Asn Ser Gly Tyr Ile
1               5

<210> SEQ ID NO 132
<211> LENGTH: 15
<212> TYPE: PRT
<213> ORGANISM: Artificial Sequence
<220> FEATURE:
<223> OTHER INFORMATION: vhCDR3

<400> SEQUENCE: 132

Ala Arg His His Gly Arg Leu Tyr Tyr Tyr Gly Met Asp Val
1               5                   10                  15

<210> SEQ ID NO 133
<211> LENGTH: 107
<212> TYPE: PRT
<213> ORGANISM: Artificial Sequence
<220> FEATURE:
<223> OTHER INFORMATION: Variable light (vl) chain

<400> SEQUENCE: 133

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Glu Lys Tyr Ala
            20                  25                  30

Ser Trp Tyr Gln Gln Lys Pro Gly Gln Ser Pro Val Met Val Ile Tyr
        35                  40                  45

Gln Asp Arg Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Thr Thr Thr Pro Gly
                85                  90                  95

Phe Gly Gly Gly Thr Lys Val Thr Val Leu Gly
            100                 105
```

<210> SEQ ID NO 134
<211> LENGTH: 6
<212> TYPE: PRT
<213> ORGANISM: Artificial Sequence
<220> FEATURE:
<223> OTHER INFORMATION: vlCDR1

<400> SEQUENCE: 134

```
Lys Leu Gly Glu Lys Tyr
1               5
```

<210> SEQ ID NO 135
<211> LENGTH: 3
<212> TYPE: PRT
<213> ORGANISM: Artificial Sequence
<220> FEATURE:
<223> OTHER INFORMATION: vlCDR2

<400> SEQUENCE: 135

```
Gln Asp Arg
1
```

<210> SEQ ID NO 136
<211> LENGTH: 9
<212> TYPE: PRT
<213> ORGANISM: Artificial Sequence
<220> FEATURE:
<223> OTHER INFORMATION: vlCDR3

<400> SEQUENCE: 136

```
Gln Ala Trp Asp Thr Thr Thr Pro Gly
1               5
```

<210> SEQ ID NO 137
<211> LENGTH: 119
<212> TYPE: PRT
<213> ORGANISM: Artificial Sequence
<220> FEATURE:
<223> OTHER INFORMATION: Variable heavy (vh) chain

<400> SEQUENCE: 137

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Ser Tyr
            20                  25                  30

Trp Ile Gly Trp Val Arg Gln Met Pro Gly Lys Gly Leu Glu Trp Met
        35                  40                  45
```

```
Gly Ile Ile Tyr Pro Gly Asp Ser Asp Thr Arg Tyr Ser Pro Ser Phe
        50                  55                  60

Glu Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Gly Val Val Ser Arg Gly Asp Tyr Trp Gly Gln Gly
            100                 105                 110

Thr Leu Val Thr Val Ser Ser
            115

<210> SEQ ID NO 138
<211> LENGTH: 8
<212> TYPE: PRT
<213> ORGANISM: Artificial Sequence
<220> FEATURE:
<223> OTHER INFORMATION: vhCDR1

<400> SEQUENCE: 138

Gly Tyr Ser Phe Ser Ser Tyr Trp
1               5

<210> SEQ ID NO 139
<211> LENGTH: 8
<212> TYPE: PRT
<213> ORGANISM: Artificial Sequence
<220> FEATURE:
<223> OTHER INFORMATION: vhCDR2

<400> SEQUENCE: 139

Ile Tyr Pro Gly Asp Ser Asp Thr
1               5

<210> SEQ ID NO 140
<211> LENGTH: 12
<212> TYPE: PRT
<213> ORGANISM: Artificial Sequence
<220> FEATURE:
<223> OTHER INFORMATION: vhCDR3

<400> SEQUENCE: 140

Ala Arg Leu His Gly Val Val Ser Arg Gly Asp Tyr
1               5                   10

<210> SEQ ID NO 141
<211> LENGTH: 112
<212> TYPE: PRT
<213> ORGANISM: Artificial Sequence
<220> FEATURE:
<223> OTHER INFORMATION: Variable light (vl) chain

<400> SEQUENCE: 141

Gln Ser Ala Leu Thr Gln Pro Ala Ser Val Ser Gly Ser Pro Gly Gln
1               5                   10                  15

Ser Ile Thr Ile Ser Cys Ser Gly Ile Ser Ser Leu Ala Gly Ser Tyr
                20                  25                  30

Asn Leu Val Ser Trp Tyr Gln Gln Tyr Pro Gly Lys Ala Pro Lys Leu
            35                  40                  45

Ile Ile Tyr Glu Val Thr Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80
```

```
Gln Ala Asp Asp Glu Ala Glu Tyr Ser Cys Ser Ser Tyr Ala Gly Arg
                85                  90                  95

Asn Ala Val Ala Val Phe Gly Gly Gly Thr Gln Leu Thr Val Leu Gly
            100                 105                 110
```

<210> SEQ ID NO 142
<211> LENGTH: 9
<212> TYPE: PRT
<213> ORGANISM: Artificial Sequence
<220> FEATURE:
<223> OTHER INFORMATION: vlCDR1

<400> SEQUENCE: 142

```
Ser Ser Leu Ala Gly Ser Tyr Asn Leu
1               5
```

<210> SEQ ID NO 143
<211> LENGTH: 3
<212> TYPE: PRT
<213> ORGANISM: Artificial Sequence
<220> FEATURE:
<223> OTHER INFORMATION: vlCDR2

<400> SEQUENCE: 143

```
Glu Val Thr
1
```

<210> SEQ ID NO 144
<211> LENGTH: 11
<212> TYPE: PRT
<213> ORGANISM: Artificial Sequence
<220> FEATURE:
<223> OTHER INFORMATION: vlCDR3

<400> SEQUENCE: 144

```
Ser Ser Tyr Ala Gly Arg Asn Ala Val Ala Val
1               5                   10
```

<210> SEQ ID NO 145
<211> LENGTH: 119
<212> TYPE: PRT
<213> ORGANISM: Artificial Sequence
<220> FEATURE:
<223> OTHER INFORMATION: Variable heavy (vh) chain

<400> SEQUENCE: 145

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Asn Ser Tyr
            20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Thr Arg Tyr Gly Pro Pro Phe
    50                  55                  60

Lys Gly Gln Ala Thr Ile Ser Ala Asp Lys Ser Ile Asn Thr Ala Tyr
65                  70                  75                  80

Leu Gln Trp Ser Ser Leu Arg Pro Ser Asp Thr Ala Ile Tyr Tyr Cys
                85                  90                  95

Ala Arg Leu Val Gly Glu Gly Arg Ser Ile Gln Tyr Trp Gly Gln Gly
            100                 105                 110

Thr Leu Val Thr Val Ser Ser
        115
```

<210> SEQ ID NO 146
<211> LENGTH: 8
<212> TYPE: PRT
<213> ORGANISM: Artificial Sequence
<220> FEATURE:
<223> OTHER INFORMATION: vhCDR1

<400> SEQUENCE: 146

Gly Tyr Asn Phe Asn Ser Tyr Trp
1               5

<210> SEQ ID NO 147
<211> LENGTH: 8
<212> TYPE: PRT
<213> ORGANISM: Artificial Sequence
<220> FEATURE:
<223> OTHER INFORMATION: vhCDR2

<400> SEQUENCE: 147

Ile Tyr Pro Gly Asp Ser Asp Thr
1               5

<210> SEQ ID NO 148
<211> LENGTH: 12
<212> TYPE: PRT
<213> ORGANISM: Artificial Sequence
<220> FEATURE:
<223> OTHER INFORMATION: vhCDR3

<400> SEQUENCE: 148

Ala Arg Leu Val Gly Glu Gly Arg Ser Ile Gln Tyr
1               5                   10

<210> SEQ ID NO 149
<211> LENGTH: 117
<212> TYPE: PRT
<213> ORGANISM: Artificial Sequence
<220> FEATURE:
<223> OTHER INFORMATION: Variable light (vl) chain

<400> SEQUENCE: 149

Gln Pro Val Leu Thr Gln Pro Pro Ser Ala Ser Ala Ser Leu Gly Ala
1               5                   10                  15

Ser Val Thr Leu Thr Cys Thr Leu Thr Ser Gly Tyr Arg Asn Tyr Lys
                20                  25                  30

Val Asp Trp Tyr Gln Gln Arg Pro Gly Lys Gly Pro Arg Phe Val Met
            35                  40                  45

Arg Val Gly Thr Gly Gly Ile Val Gly Ser Lys Gly Asp Gly Ile Pro
        50                  55                  60

Asp Arg Phe Ser Ala Leu Gly Ser Gly Leu Asn Arg Tyr Leu Thr Ile
65                  70                  75                  80

Lys Asp Ile Gln Glu Glu Asp Glu Ser Asp Tyr Tyr Cys Gly Ala Asp
                85                  90                  95

Tyr Gly Ser Gly Ser Asn Phe Leu Val Val Phe Gly Gly Gly Thr Lys
                100                 105                 110

Leu Thr Val Leu Gly
        115

<210> SEQ ID NO 150
<211> LENGTH: 7
<212> TYPE: PRT
<213> ORGANISM: Artificial Sequence
<220> FEATURE:

<223> OTHER INFORMATION: vlCDR1

<400> SEQUENCE: 150

Ser Gly Tyr Arg Asn Tyr Lys
1               5

<210> SEQ ID NO 151
<211> LENGTH: 8
<212> TYPE: PRT
<213> ORGANISM: Artificial Sequence
<220> FEATURE:
<223> OTHER INFORMATION: vlCDR2

<400> SEQUENCE: 151

Val Gly Thr Gly Gly Ile Val Gly
1               5

<210> SEQ ID NO 152
<211> LENGTH: 13
<212> TYPE: PRT
<213> ORGANISM: Artificial Sequence
<220> FEATURE:
<223> OTHER INFORMATION: vlCDR3

<400> SEQUENCE: 152

Gly Ala Asp Tyr Gly Ser Gly Ser Asn Phe Leu Val Val
1               5                   10

<210> SEQ ID NO 153
<211> LENGTH: 119
<212> TYPE: PRT
<213> ORGANISM: Artificial Sequence
<220> FEATURE:
<223> OTHER INFORMATION: Variable heavy (vh) chain

<400> SEQUENCE: 153

Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Asp Phe Thr Arg Tyr
                20                  25                  30

Trp Ile Val Trp Val Arg Gln Met Pro Gly Lys Gly Leu Glu Tyr Met
            35                  40                  45

Gly Ile Ile Tyr Pro Gly Asp Ser Asp Thr Arg Tyr Gly Pro Pro Phe
        50                  55                  60

Lys Gly Gln Ala Thr Ile Ser Ala Asp Lys Ser Ile Asn Thr Ala Tyr
65                  70                  75                  80

Leu Gln Trp Ser Ser Leu Arg Pro Ser Asp Thr Ala Ile Tyr Tyr Cys
                85                  90                  95

Ala Arg Leu Val Gly Glu Gly Arg Ser Ile Gln Tyr Trp Gly Gln Gly
            100                 105                 110

Thr Leu Val Thr Val Ser Ser
        115

<210> SEQ ID NO 154
<211> LENGTH: 8
<212> TYPE: PRT
<213> ORGANISM: Artificial Sequence
<220> FEATURE:
<223> OTHER INFORMATION: vhCDR1

<400> SEQUENCE: 154

Gly Tyr Asp Phe Thr Arg Tyr Trp
1               5

<210> SEQ ID NO 155
<211> LENGTH: 8
<212> TYPE: PRT
<213> ORGANISM: Artificial Sequence
<220> FEATURE:
<223> OTHER INFORMATION: vhCDR2

<400> SEQUENCE: 155

Ile Tyr Pro Gly Asp Ser Asp Thr
1               5

<210> SEQ ID NO 156
<211> LENGTH: 12
<212> TYPE: PRT
<213> ORGANISM: Artificial Sequence
<220> FEATURE:
<223> OTHER INFORMATION: vhCDR3

<400> SEQUENCE: 156

Ala Arg Leu Val Gly Glu Gly Arg Ser Ile Gln Tyr
1               5                   10

<210> SEQ ID NO 157
<211> LENGTH: 117
<212> TYPE: PRT
<213> ORGANISM: Artificial Sequence
<220> FEATURE:
<223> OTHER INFORMATION: Variable light (vl) chain

<400> SEQUENCE: 157

Gln Pro Val Leu Thr Gln Pro Pro Ser Ala Ser Ala Ser Leu Gly Ala
1               5                   10                  15

Ser Val Thr Leu Thr Cys Thr Leu Thr Ser Gly Tyr Arg Asn Tyr Lys
            20                  25                  30

Val Asp Trp Tyr Gln Gln Arg Pro Gly Lys Gly Pro Arg Phe Val Met
        35                  40                  45

Arg Val Gly Thr Gly Gly Ile Val Gly Ser Lys Gly Asp Gly Ile Pro
    50                  55                  60

Asp Arg Phe Ser Ala Leu Gly Ser Gly Leu Asn Arg Tyr Leu Thr Ile
65                  70                  75                  80

Lys Asp Ile Gln Glu Glu Asp Glu Ser Asp Tyr Tyr Cys Gly Ala Asp
                85                  90                  95

Tyr Gly Ser Gly Ser Asn Phe Leu Val Val Phe Gly Gly Gly Thr Lys
            100                 105                 110

Val Thr Val Leu Gly
        115

<210> SEQ ID NO 158
<211> LENGTH: 7
<212> TYPE: PRT
<213> ORGANISM: Artificial Sequence
<220> FEATURE:
<223> OTHER INFORMATION: vlCDR1

<400> SEQUENCE: 158

Ser Gly Tyr Arg Asn Tyr Lys
1               5

<210> SEQ ID NO 159
<211> LENGTH: 8
<212> TYPE: PRT
<213> ORGANISM: Artificial Sequence

```
<220> FEATURE:
<223> OTHER INFORMATION: vlCDR2

<400> SEQUENCE: 159

Val Gly Thr Gly Gly Ile Val Gly
1               5

<210> SEQ ID NO 160
<211> LENGTH: 13
<212> TYPE: PRT
<213> ORGANISM: Artificial Sequence
<220> FEATURE:
<223> OTHER INFORMATION: vlCDR3

<400> SEQUENCE: 160

Gly Ala Asp Tyr Gly Ser Gly Ser Asn Phe Leu Val Val
1               5                   10

<210> SEQ ID NO 161
<211> LENGTH: 119
<212> TYPE: PRT
<213> ORGANISM: Artificial Sequence
<220> FEATURE:
<223> OTHER INFORMATION: Variable heavy (vh) chain

<400> SEQUENCE: 161

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Arg Ser
                20                  25                  30

Trp Ile Ala Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Glu Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Gly Val Val Ser Arg Gly Asp Tyr Trp Gly Gln Gly
            100                 105                 110

Thr Leu Val Thr Val Ser Ser
        115

<210> SEQ ID NO 162
<211> LENGTH: 8
<212> TYPE: PRT
<213> ORGANISM: Artificial Sequence
<220> FEATURE:
<223> OTHER INFORMATION: vhCDR1

<400> SEQUENCE: 162

Gly Tyr Ser Phe Thr Arg Ser Trp
1               5

<210> SEQ ID NO 163
<211> LENGTH: 8
<212> TYPE: PRT
<213> ORGANISM: Artificial Sequence
<220> FEATURE:
<223> OTHER INFORMATION: vhCDR2

<400> SEQUENCE: 163

Ile Tyr Pro Gly Asp Ser Asp Thr
```

<210> SEQ ID NO 164
<211> LENGTH: 12
<212> TYPE: PRT
<213> ORGANISM: Artificial Sequence
<220> FEATURE:
<223> OTHER INFORMATION: vhCDR3

<400> SEQUENCE: 164

Ala Arg Leu His Gly Val Val Ser Arg Gly Asp Tyr
1               5                   10

<210> SEQ ID NO 165
<211> LENGTH: 112
<212> TYPE: PRT
<213> ORGANISM: Artificial Sequence
<220> FEATURE:
<223> OTHER INFORMATION: Variable light (vl) chain

<400> SEQUENCE: 165

Gln Ser Ala Leu Thr Gln Pro Ala Ser Val Ser Gly Ser Pro Gly Gln
1               5                   10                  15

Ser Ile Thr Ile Ser Cys Ser Gly Ile Ser Ser Leu Ala Gly Ser Tyr
            20                  25                  30

Asn Leu Val Ser Trp Tyr Gln Gln Tyr Pro Gly Lys Ala Pro Lys Leu
        35                  40                  45

Ile Ile Tyr Glu Val Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Asp Asp Glu Ala Glu Tyr Ser Cys Ser Ser Tyr Ala Gly Arg
                85                  90                  95

Asn Ala Val Ala Val Phe Gly Gly Gly Thr Gln Leu Thr Val Leu Gly
            100                 105                 110

<210> SEQ ID NO 166
<211> LENGTH: 9
<212> TYPE: PRT
<213> ORGANISM: Artificial Sequence
<220> FEATURE:
<223> OTHER INFORMATION: vlCDR1

<400> SEQUENCE: 166

Ser Ser Leu Ala Gly Ser Tyr Asn Leu
1               5

<210> SEQ ID NO 167
<211> LENGTH: 3
<212> TYPE: PRT
<213> ORGANISM: Artificial Sequence
<220> FEATURE:
<223> OTHER INFORMATION: vlCDR2

<400> SEQUENCE: 167

Glu Val Thr
1

<210> SEQ ID NO 168
<211> LENGTH: 11
<212> TYPE: PRT
<213> ORGANISM: Artificial Sequence
<220> FEATURE:
<223> OTHER INFORMATION: vlCDR3

<400> SEQUENCE: 168

Ser Ser Tyr Ala Gly Arg Asn Ala Val Ala Val
1               5                   10

<210> SEQ ID NO 169
<211> LENGTH: 119
<212> TYPE: PRT
<213> ORGANISM: Artificial Sequence
<220> FEATURE:
<223> OTHER INFORMATION: Variable heavy (vh) chain

<400> SEQUENCE: 169

Glu Val Gln Leu Val Gln Ser Gly Ala Glu Val Lys Lys Pro Gly Glu
1               5                   10                  15

Ser Pro Lys Ile Ser Cys Lys Gly Ser Gly Tyr Ser Phe Thr Asn Tyr
                20                  25                  30

Trp Ile Gly Trp Val Arg Gln Met Pro Gly Glu Gly Leu Glu Trp Met
            35                  40                  45

Gly Ile Ile Tyr Pro Gly Asp Ser Asp Thr Arg Tyr Ser Pro Ser Phe
        50                  55                  60

Glu Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Gly Val Val Ser Arg Gly Asp Tyr Trp Gly Gln Gly
            100                 105                 110

Thr Leu Val Thr Val Ser Ser
        115

<210> SEQ ID NO 170
<211> LENGTH: 8
<212> TYPE: PRT
<213> ORGANISM: Artificial Sequence
<220> FEATURE:
<223> OTHER INFORMATION: vhCDR1

<400> SEQUENCE: 170

Gly Tyr Ser Phe Thr Asn Tyr Trp
1               5

<210> SEQ ID NO 171
<211> LENGTH: 8
<212> TYPE: PRT
<213> ORGANISM: Artificial Sequence
<220> FEATURE:
<223> OTHER INFORMATION: vhCDR2

<400> SEQUENCE: 171

Ile Tyr Pro Gly Asp Ser Asp Thr
1               5

<210> SEQ ID NO 172
<211> LENGTH: 12
<212> TYPE: PRT
<213> ORGANISM: Artificial Sequence
<220> FEATURE:
<223> OTHER INFORMATION: vhCDR3

<400> SEQUENCE: 172

Ala Arg Leu His Gly Val Val Ser Arg Gly Asp Tyr
1               5                   10

<210> SEQ ID NO 173
<211> LENGTH: 112
<212> TYPE: PRT
<213> ORGANISM: Artificial Sequence
<220> FEATURE:
<223> OTHER INFORMATION: Variable light (vl) chain

<400> SEQUENCE: 173

Gln Ser Ala Leu Thr Gln Pro Ala Ser Val Ser Gly Ser Pro Gly Gln
1               5                   10                  15

Ser Ile Thr Ile Ser Cys Ser Gly Ile Ser Ser Leu Ala Gly Ser Tyr
            20                  25                  30

Asn Leu Val Ser Trp Tyr Gln Gln Tyr Pro Gly Lys Ala Pro Lys Leu
        35                  40                  45

Ile Ile Tyr Glu Val Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Asp Asp Glu Ala Glu Tyr Ser Cys Ser Ser Tyr Ala Gly Arg
                85                  90                  95

Asn Ala Val Ala Val Phe Gly Gly Gly Thr Gln Leu Thr Val Leu Gly
            100                 105                 110

<210> SEQ ID NO 174
<211> LENGTH: 9
<212> TYPE: PRT
<213> ORGANISM: Artificial Sequence
<220> FEATURE:
<223> OTHER INFORMATION: vlCDR1

<400> SEQUENCE: 174

Ser Ser Leu Ala Gly Ser Tyr Asn Leu
1               5

<210> SEQ ID NO 175
<211> LENGTH: 3
<212> TYPE: PRT
<213> ORGANISM: Artificial Sequence
<220> FEATURE:
<223> OTHER INFORMATION: vlCDR2

<400> SEQUENCE: 175

Glu Val Thr
1

<210> SEQ ID NO 176
<211> LENGTH: 11
<212> TYPE: PRT
<213> ORGANISM: Artificial Sequence
<220> FEATURE:
<223> OTHER INFORMATION: vlCDR3

<400> SEQUENCE: 176

Ser Ser Tyr Ala Gly Arg Asn Ala Val Ala Val
1               5                   10

<210> SEQ ID NO 177
<211> LENGTH: 122
<212> TYPE: PRT
<213> ORGANISM: Artificial Sequence
<220> FEATURE:
<223> OTHER INFORMATION: Variable heavy (vh) chain

<400> SEQUENCE: 177

Glu Val Gln Leu Val Glu Thr Gly Gly Gly Val Val Arg Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Ser
65                  70                  75                  80

Leu Gln Met Asn Ser Leu Arg Ala Glu Asp Thr Ala Val Tyr Tyr Cys
                85                  90                  95

Ala Lys Ser Ser Gly Trp Tyr Pro Tyr Tyr Gly Met Asp Val Trp
            100                 105                 110

Gly Gln Gly Thr Thr Val Thr Val Ser Ser
        115                 120

<210> SEQ ID NO 178
<211> LENGTH: 8
<212> TYPE: PRT
<213> ORGANISM: Artificial Sequence
<220> FEATURE:
<223> OTHER INFORMATION: vhCDR1

<400> SEQUENCE: 178

Gly Phe Thr Phe Asp Asp Tyr Ala
1               5

<210> SEQ ID NO 179
<211> LENGTH: 8
<212> TYPE: PRT
<213> ORGANISM: Artificial Sequence
<220> FEATURE:
<223> OTHER INFORMATION: vhCDR2

<400> SEQUENCE: 179

Ile Ser Gly Ser Gly Gly Ser Thr
1               5

<210> SEQ ID NO 180
<211> LENGTH: 15
<212> TYPE: PRT
<213> ORGANISM: Artificial Sequence
<220> FEATURE:
<223> OTHER INFORMATION: vhCDR3

<400> SEQUENCE: 180

Ala Lys Ser Ser Gly Trp Tyr Pro Tyr Tyr Gly Met Asp Val
1               5                   10                  15

<210> SEQ ID NO 181
<211> LENGTH: 107
<212> TYPE: PRT
<213> ORGANISM: Artificial Sequence
<220> FEATURE:
<223> OTHER INFORMATION: Variable light (vl) chain

<400> SEQUENCE: 181

Ser Tyr Glu Leu Met Gln Pro Pro Ser Val Ser Val Ser Pro Gly Gln
1               5                   10                  15

Thr Ala Arg Ile Thr Cys Ser Gly Asn Asn Leu Gly Asp Lys Tyr Thr
            20                  25                  30

-continued

```
Ser Trp Tyr Gln His Lys Pro Gly Gln Ser Pro Val Met Val Ile Tyr
        35                  40                  45

Gln Asp Thr Lys Arg Pro Ser Gly Ile Ala Glu Arg Phe Ser Gly Ser
50                  55                  60

Asn Ser Gly Asn Thr Ala Thr Leu Thr Ile Ser Gly Thr Gln Ala Leu
65                  70                  75                  80

Asp Glu Ala Asp Tyr Tyr Cys Gln Ala Trp Asp Thr Gly Thr Ala Val
                85                  90                  95

Phe Gly Gly Gly Thr Gln Leu Thr Val Leu Gly
                100                 105

<210> SEQ ID NO 182
<211> LENGTH: 6
<212> TYPE: PRT
<213> ORGANISM: Artificial Sequence
<220> FEATURE:
<223> OTHER INFORMATION: vlCDR1

<400> SEQUENCE: 182

Asn Leu Gly Asp Lys Tyr
1               5

<210> SEQ ID NO 183
<211> LENGTH: 3
<212> TYPE: PRT
<213> ORGANISM: Artificial Sequence
<220> FEATURE:
<223> OTHER INFORMATION: vlCDR2

<400> SEQUENCE: 183

Gln Asp Thr
1

<210> SEQ ID NO 184
<211> LENGTH: 9
<212> TYPE: PRT
<213> ORGANISM: Artificial Sequence
<220> FEATURE:
<223> OTHER INFORMATION: vlCDR3

<400> SEQUENCE: 184

Gln Ala Trp Asp Thr Gly Thr Ala Val
1               5

<210> SEQ ID NO 185
<211> LENGTH: 122
<212> TYPE: PRT
<213> ORGANISM: Artificial Sequence
<220> FEATURE:
<223> OTHER INFORMATION: Variable heavy (vh) chain

<400> SEQUENCE: 185

Glu Val Gln Leu Val Glu Thr Gly Gly Gly Val Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Ser Gly Ser Ser Gly Ser Ile Gly Tyr Ala Asp Ser Val
    50                  55                  60

Lys Gly Arg Phe Thr Ile Ala Arg Asp Asn Ala Lys Asn Thr Leu Phe
65                  70                  75                  80
```

```
Leu Gln Val Asn Ser Leu Arg Ala Glu Asp Thr Ala Leu Tyr Tyr Cys
                85                  90                  95

Ala Arg His His Gly Arg Leu Tyr Tyr Tyr Tyr Gly Met Asp Val Trp
            100                 105                 110

Gly Gln Gly Thr Thr Val Thr Val Ser Ser
        115                 120

<210> SEQ ID NO 186
<211> LENGTH: 8
<212> TYPE: PRT
<213> ORGANISM: Artificial Sequence
<220> FEATURE:
<223> OTHER INFORMATION: vhCDR1

<400> SEQUENCE: 186

Gly Phe Thr Phe Ser Asn Tyr Ala
1               5

<210> SEQ ID NO 187
<211> LENGTH: 8
<212> TYPE: PRT
<213> ORGANISM: Artificial Sequence
<220> FEATURE:
<223> OTHER INFORMATION: vhCDR2

<400> SEQUENCE: 187

Ile Ser Gly Ser Ser Gly Ser Ile
1               5

<210> SEQ ID NO 188
<211> LENGTH: 15
<212> TYPE: PRT
<213> ORGANISM: Artificial Sequence
<220> FEATURE:
<223> OTHER INFORMATION: vhCDR3

<400> SEQUENCE: 188

Ala Arg His His Gly Arg Leu Tyr Tyr Tyr Tyr Gly Met Asp Val
1               5                   10                  15

<210> SEQ ID NO 189
<211> LENGTH: 108
<212> TYPE: PRT
<213> ORGANISM: Artificial Sequence
<220> FEATURE:
<223> OTHER INFORMATION: Variable light (vl) chain

<400> SEQUENCE: 189

Ser Tyr Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Thr Val
                85                  90                  95

Val Phe Gly Gly Gly Thr Lys Leu Thr Val Leu Gly
                100                 105
```

<210> SEQ ID NO 190
<211> LENGTH: 6
<212> TYPE: PRT
<213> ORGANISM: Artificial Sequence
<220> FEATURE:
<223> OTHER INFORMATION: vlCDR1

<400> SEQUENCE: 190

Ser Leu Arg Ser Tyr Tyr
1               5

<210> SEQ ID NO 191
<211> LENGTH: 3
<212> TYPE: PRT
<213> ORGANISM: Artificial Sequence
<220> FEATURE:
<223> OTHER INFORMATION: vlCDR2

<400> SEQUENCE: 191

Gly Lys Asn
1

<210> SEQ ID NO 192
<211> LENGTH: 10
<212> TYPE: PRT
<213> ORGANISM: Artificial Sequence
<220> FEATURE:
<223> OTHER INFORMATION: vlCDR3

<400> SEQUENCE: 192

Asn Ser Arg Asp Ser Ser Gly Thr Val Val
1               5                   10

<210> SEQ ID NO 193
<211> LENGTH: 122
<212> TYPE: PRT
<213> ORGANISM: Artificial Sequence
<220> FEATURE:
<223> OTHER INFORMATION: Variable heavy (vh) chain

<400> SEQUENCE: 193

Glu Val Gln Leu Val Glu Thr Gly Gly Gly Val Val Arg Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Lys Asn Thr Leu Ser
65                  70                  75                  80

Leu Gln Met Asn Ser Leu Arg Ala Glu Asp Thr Ala Val Tyr Tyr Cys
                85                  90                  95

Ala Lys Ser Ser Gly Trp Tyr Pro Tyr Tyr Tyr Gly Met Asp Val Trp
            100                 105                 110

Gly Gln Gly Thr Thr Val Thr Val Ser Ser
        115                 120

<210> SEQ ID NO 194
<211> LENGTH: 8
<212> TYPE: PRT
<213> ORGANISM: Artificial Sequence

```
<220> FEATURE:
<223> OTHER INFORMATION: vhCDR1

<400> SEQUENCE: 194

Gly Tyr Ser Phe Thr Ser Tyr Trp
1               5

<210> SEQ ID NO 195
<211> LENGTH: 8
<212> TYPE: PRT
<213> ORGANISM: Artificial Sequence
<220> FEATURE:
<223> OTHER INFORMATION: vhCDR2

<400> SEQUENCE: 195

Ile Tyr Pro Gly Asp Ser Asp Thr
1               5

<210> SEQ ID NO 196
<211> LENGTH: 15
<212> TYPE: PRT
<213> ORGANISM: Artificial Sequence
<220> FEATURE:
<223> OTHER INFORMATION: vhCDR3

<400> SEQUENCE: 196

Val Lys Gly Leu Tyr Ser Asn Pro Arg Gly Gly Ala Phe Asp Ile
1               5                   10                  15

<210> SEQ ID NO 197
<211> LENGTH: 110
<212> TYPE: PRT
<213> ORGANISM: Artificial Sequence
<220> FEATURE:
<223> OTHER INFORMATION: Variable light (vl) chain

<400> SEQUENCE: 197

Ser Tyr Glu Leu Met Gln Pro Pro Ser Val Ser Val Ser Pro Gly Gln
1               5                   10                  15

Thr Ala Arg Ile Thr Cys Ser Gly Asn Asn Leu Gly Asp Lys Tyr Thr
                20                  25                  30

Ser Trp Tyr Gln His Lys Pro Gly Gln Ser Pro Val Met Val Ile Tyr
            35                  40                  45

Gln Asp Thr Lys Arg Pro Ser Gly Ile Ala Glu Arg Phe Ser Gly Ser
        50                  55                  60

Asn Ser Gly Asn Thr Ala Thr Leu Thr Ile Ser Gly Thr Gln Ala Leu
65                  70                  75                  80

Asp Glu Ala Asp Tyr Tyr Cys Gln Ala Trp Asp Thr Gly Thr Ala Val
                85                  90                  95

Phe Gly Gly Gly Thr Gln Leu Thr Val Leu Gly Leu Gly
            100                 105                 110

<210> SEQ ID NO 198
<211> LENGTH: 6
<212> TYPE: PRT
<213> ORGANISM: Artificial Sequence
<220> FEATURE:
<223> OTHER INFORMATION: vlCDR1

<400> SEQUENCE: 198

Asn Leu Gly Asp Lys Tyr
1               5
```

```
<210> SEQ ID NO 199
<211> LENGTH: 3
<212> TYPE: PRT
<213> ORGANISM: Artificial Sequence
<220> FEATURE:
<223> OTHER INFORMATION: vlCDR2

<400> SEQUENCE: 199

Gln Asp Thr
1

<210> SEQ ID NO 200
<211> LENGTH: 9
<212> TYPE: PRT
<213> ORGANISM: Artificial Sequence
<220> FEATURE:
<223> OTHER INFORMATION: vlCDR3

<400> SEQUENCE: 200

Gln Ala Trp Asp Thr Gly Thr Ala Val
1               5

<210> SEQ ID NO 201
<211> LENGTH: 253
<212> TYPE: PRT
<213> ORGANISM: Artificial Sequence
<220> FEATURE:
<223> OTHER INFORMATION: A10m3 amino acid sequence

<400> SEQUENCE: 201

Glu Val Gln Leu Val Glu Ser Gly Gly Gly Leu Ile Gln Pro Gly Arg
1               5                   10                  15

Ser Leu Arg Leu Ser Cys Ala Ala Ser Gly Ile Thr Phe Asp Asp Ala
            20                  25                  30

Val Met His Trp Val Arg Gln Ala Pro Gly Lys Gly Leu Glu Trp Val
        35                  40                  45

Ala Gly Ile Ser Ser Asn Ser Gly Tyr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Arg Leu Arg Ala Glu Asp Thr Ala Val Tyr Tyr Cys
                85                  90                  95

Val Lys Gly Leu Tyr Ser Asn Pro Arg Gly Ala Phe Asp Ile Trp
            100                 105                 110

Gly Gln Gly Thr Met Val Thr Val Ser Ser Ala Ser Thr Gly Gly Gly
        115                 120                 125

Gly Ser Gly Gly Gly Gly Ser Gly Gly Gly Ser Val His Ser Ser
    130                 135                 140

Tyr Val Leu Thr Gln Pro Pro Ser Val Ser Ala Pro Gly Gln Thr
145                 150                 155                 160

Ala Thr Ile Thr Cys Gly Gly Asn Asn Ile Gly Thr Lys Ser Val His
                165                 170                 175

Trp Tyr Gln Gln Lys Pro Gly Gln Ala Pro Val Leu Val Val Tyr Ala
            180                 185                 190

Asp Ser Asp Arg Pro Ser Gly Ile Pro Glu Arg Val Ser Gly Ser Asn
        195                 200                 205

Ser Gly Asn Thr Ala Thr Leu Thr Ile Ser Arg Val Glu Ala Gly Asp
    210                 215                 220

Glu Ala Asp Tyr Tyr Cys Gln Val Trp Asp Ser Arg Ser Asp His Leu
225                 230                 235                 240
```

```
Trp Val Phe Gly Gly Gly Thr Lys Leu Thr Val Leu Gly
                245                 250
```

<210> SEQ ID NO 202
<211> LENGTH: 125
<212> TYPE: PRT
<213> ORGANISM: Artificial Sequence
<220> FEATURE:
<223> OTHER INFORMATION: Variable heavy chain

<400> SEQUENCE: 202

```
Glu Val Gln Leu Val Glu Ser Gly Gly Gly Leu Ile Gln Pro Gly Arg
1               5                   10                  15

Ser Leu Arg Leu Ser Cys Ala Ala Ser Gly Ile Thr Phe Asp Asp Ala
            20                  25                  30

Val Met His Trp Val Arg Gln Ala Pro Gly Lys Gly Leu Glu Trp Val
        35                  40                  45

Ala Gly Ile Ser Ser Asn Ser Gly Tyr Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Arg Leu Arg Ala Glu Asp Thr Ala Val Tyr Tyr Cys
                85                  90                  95

Val Lys Gly Leu Tyr Ser Asn Pro Arg Gly Ala Phe Asp Ile Trp
            100                 105                 110

Gly Gln Gly Thr Met Val Thr Val Ser Ser Ala Ser Thr
            115                 120                 125
```

<210> SEQ ID NO 203
<211> LENGTH: 113
<212> TYPE: PRT
<213> ORGANISM: Artificial Sequence
<220> FEATURE:
<223> OTHER INFORMATION: Variable light chain

<400> SEQUENCE: 203

```
Val His Ser Ser Tyr Val Leu Thr Gln Pro Pro Ser Val Ser Val Ala
1               5                   10                  15

Pro Gly Gln Thr Ala Thr Ile Thr Cys Gly Gly Asn Asn Ile Gly Thr
            20                  25                  30

Lys Ser Val His Trp Tyr Gln Gln Lys Pro Gly Gln Ala Pro Val Leu
        35                  40                  45

Val Val Tyr Ala Asp Ser Asp Arg Pro Ser Gly Ile Pro Glu Arg Val
    50                  55                  60

Ser Gly Ser Asn Ser Gly Asn Thr Ala Thr Leu Thr Ile Ser Arg Val
65                  70                  75                  80

Glu Ala Gly Asp Glu Ala Asp Tyr Tyr Cys Gln Val Trp Asp Ser Arg
                85                  90                  95

Ser Asp His Leu Trp Val Phe Gly Gly Gly Thr Lys Leu Thr Val Leu
            100                 105                 110

Gly
```

<210> SEQ ID NO 204
<211> LENGTH: 114
<212> TYPE: PRT
<213> ORGANISM: Artificial Sequence
<220> FEATURE:
<223> OTHER INFORMATION: Parental IL15

-continued

<400> SEQUENCE: 204

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 205
<211> LENGTH: 114
<212> TYPE: PRT
<213> ORGANISM: Artificial Sequence
<220> FEATURE:
<223> OTHER INFORMATION: IL15 K86A

<400> SEQUENCE: 205

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Ala Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 206
<211> LENGTH: 114
<212> TYPE: PRT
<213> ORGANISM: Artificial Sequence
<220> FEATURE:
<223> OTHER INFORMATION: IL15 K86R

<400> SEQUENCE: 206

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

```
Asn Leu Ile Ile Leu Ala Asn Ser Leu Ser Ser Asn Gly Asn Val
 65                  70                  75                  80

Thr Glu Ser Gly Cys Arg Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser

<210> SEQ ID NO 207
<211> LENGTH: 114
<212> TYPE: PRT
<213> ORGANISM: Artificial Sequence
<220> FEATURE:
<223> OTHER INFORMATION: IL15 N112A

<400> SEQUENCE: 207

Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
                 20                  25                  30

Pro Ser Cys Lys Val Thr Ala Met Lys Cys Phe Leu Leu Glu Leu Gln
             35                  40                  45

Val Ile Ser Leu Glu Ser Gly Asp Ala Ser Ile His Asp Thr Val Glu
 50                  55                  60

Asn Leu Ile Ile Leu Ala Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Ala
            100                 105                 110

Thr Ser

<210> SEQ ID NO 208
<211> LENGTH: 114
<212> TYPE: PRT
<213> ORGANISM: Artificial Sequence
<220> FEATURE:
<223> OTHER INFORMATION: IL15 N112S

<400> SEQUENCE: 208

Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
                 20                  25                  30

Pro Ser Cys Lys Val Thr Ala Met Lys Cys Phe Leu Leu Glu Leu Gln
             35                  40                  45

Val Ile Ser Leu Glu Ser Gly Asp Ala Ser Ile His Asp Thr Val Glu
 50                  55                  60

Asn Leu Ile Ile Leu Ala Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Ser
            100                 105                 110

Thr Ser
```

-continued

```
<210> SEQ ID NO 209
<211> LENGTH: 114
<212> TYPE: PRT
<213> ORGANISM: Artificial Sequence
<220> FEATURE:
<223> OTHER INFORMATION: IL15 N112Q

<400> SEQUENCE: 209

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Gln
            100                 105                 110

Thr Ser

<210> SEQ ID NO 210
<211> LENGTH: 114
<212> TYPE: PRT
<213> ORGANISM: Artificial Sequence
<220> FEATURE:
<223> OTHER INFORMATION: IL15 K86R/N112A

<400> SEQUENCE: 210

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Arg Glu Cys Glu Glu Leu Glu Glu Lys Asn Ile
                85                  90                  95

Lys Glu Phe Leu Gln Ser Phe Val His Ile Val Gln Met Phe Ile Ala
            100                 105                 110

Thr Ser

<210> SEQ ID NO 211
<211> LENGTH: 392
<212> TYPE: PRT
<213> ORGANISM: Artificial Sequence
<220> FEATURE:
<223> OTHER INFORMATION: Parental IL15-A10m3

<400> SEQUENCE: 211

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
```

```
                20                  25                  30
Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Ser Gly Gly Gly Ser Gly Gly Gly Gly
            115                 120                 125

Ser Gly Gly Gly Ser Gly Gly Gly Ser Glu Val Gln Leu Val
            130                 135                 140

Glu Ser Gly Gly Gly Leu Ile Gln Pro Gly Arg Ser Leu Arg Leu Ser
145                 150                 155                 160

Cys Ala Ala Ser Gly Ile Thr Phe Asp Asp Ala Val Met His Trp Val
                165                 170                 175

Arg Gln Ala Pro Gly Lys Gly Leu Glu Trp Val Ala Gly Ile Ser Ser
            180                 185                 190

Asn Ser Gly Tyr Ile Gly Tyr Ala Asp Ser Val Lys Gly Arg Phe Thr
            195                 200                 205

Ile Ser Arg Asp Asn Ala Lys Asn Ser Leu Tyr Leu Gln Met Asn Arg
            210                 215                 220

Leu Arg Ala Glu Asp Thr Ala Val Tyr Tyr Cys Val Lys Gly Leu Tyr
225                 230                 235                 240

Ser Asn Pro Arg Gly Gly Ala Phe Asp Ile Trp Gly Gln Gly Thr Met
                245                 250                 255

Val Thr Val Ser Ser Ala Ser Thr Gly Gly Gly Gly Ser Gly Gly Gly
            260                 265                 270

Gly Ser Gly Gly Gly Gly Ser Val His Ser Ser Tyr Val Leu Thr Gln
            275                 280                 285

Pro Pro Ser Val Ser Val Ala Pro Gly Gln Thr Ala Thr Ile Thr Cys
            290                 295                 300

Gly Gly Asn Asn Ile Gly Thr Lys Ser Val His Trp Tyr Gln Gln Lys
305                 310                 315                 320

Pro Gly Gln Ala Pro Val Leu Val Val Tyr Ala Asp Ser Asp Arg Pro
                325                 330                 335

Ser Gly Ile Pro Glu Arg Val Ser Gly Ser Asn Ser Gly Asn Thr Ala
            340                 345                 350

Thr Leu Thr Ile Ser Arg Val Glu Ala Gly Asp Glu Ala Asp Tyr Tyr
            355                 360                 365

Cys Gln Val Trp Asp Ser Arg Ser Asp His Leu Trp Val Phe Gly Gly
            370                 375                 380

Gly Thr Lys Leu Thr Val Leu Gly
385                 390

<210> SEQ ID NO 212
<211> LENGTH: 392
<212> TYPE: PRT
<213> ORGANISM: Artificial Sequence
<220> FEATURE:
<223> OTHER INFORMATION: IL15 K86A -A10m3 K86A
```

<400> SEQUENCE: 212

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Ala Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Gly Ser Gly Gly Gly Ser Gly Gly Gly Gly
            115                 120                 125

Ser Gly Gly Gly Gly Ser Gly Gly Gly Ser Glu Val Gln Leu Val
    130                 135                 140

Glu Ser Gly Gly Gly Leu Ile Gln Pro Gly Arg Ser Leu Arg Leu Ser
145                 150                 155                 160

Cys Ala Ala Ser Gly Ile Thr Phe Asp Asp Ala Val Met His Trp Val
                165                 170                 175

Arg Gln Ala Pro Gly Lys Gly Leu Glu Trp Val Ala Gly Ile Ser Ser
            180                 185                 190

Asn Ser Gly Tyr Ile Gly Tyr Ala Asp Ser Val Lys Gly Arg Phe Thr
        195                 200                 205

Ile Ser Arg Asp Asn Ala Lys Asn Ser Leu Tyr Leu Gln Met Asn Arg
    210                 215                 220

Leu Arg Ala Glu Asp Thr Ala Val Tyr Tyr Cys Val Lys Gly Leu Tyr
225                 230                 235                 240

Ser Asn Pro Arg Gly Gly Ala Phe Asp Ile Trp Gly Gln Gly Thr Met
                245                 250                 255

Val Thr Val Ser Ser Ala Ser Thr Gly Gly Gly Ser Gly Gly Gly
            260                 265                 270

Gly Ser Gly Gly Gly Gly Ser Val His Ser Ser Tyr Val Leu Thr Gln
    275                 280                 285

Pro Pro Ser Val Ser Val Ala Pro Gly Gln Thr Ala Thr Ile Thr Cys
290                 295                 300

Gly Gly Asn Asn Ile Gly Thr Lys Ser Val His Trp Tyr Gln Gln Lys
305                 310                 315                 320

Pro Gly Gln Ala Pro Val Leu Val Val Tyr Ala Asp Ser Asp Arg Pro
                325                 330                 335

Ser Gly Ile Pro Glu Arg Val Ser Gly Ser Asn Ser Gly Asn Thr Ala
            340                 345                 350

Thr Leu Thr Ile Ser Arg Val Glu Ala Gly Asp Glu Ala Asp Tyr Tyr
        355                 360                 365

Cys Gln Val Trp Asp Ser Arg Ser Asp His Leu Trp Val Phe Gly Gly
    370                 375                 380

Gly Thr Lys Leu Thr Val Leu Gly
385                 390

<210> SEQ ID NO 213

<211> LENGTH: 392
<212> TYPE: PRT
<213> ORGANISM: Artificial Sequence
<220> FEATURE:
<223> OTHER INFORMATION: IL15 K86R -A10m3

<400> SEQUENCE: 213

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Arg Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Gly Ser Gly Gly Gly Gly Ser Gly Gly Gly Gly
        115                 120                 125

Ser Gly Gly Gly Gly Ser Gly Gly Gly Gly Ser Glu Val Gln Leu Val
    130                 135                 140

Glu Ser Gly Gly Gly Leu Ile Gln Pro Gly Arg Ser Leu Arg Leu Ser
145                 150                 155                 160

Cys Ala Ala Ser Gly Ile Thr Phe Asp Asp Ala Val Met His Trp Val
                165                 170                 175

Arg Gln Ala Pro Gly Lys Gly Leu Glu Trp Val Ala Gly Ile Ser Ser
            180                 185                 190

Asn Ser Gly Tyr Ile Gly Tyr Ala Asp Ser Val Lys Gly Arg Phe Thr
        195                 200                 205

Ile Ser Arg Asp Asn Ala Lys Asn Ser Leu Tyr Leu Gln Met Asn Arg
    210                 215                 220

Leu Arg Ala Glu Asp Thr Ala Val Tyr Tyr Cys Val Lys Gly Leu Tyr
225                 230                 235                 240

Ser Asn Pro Arg Gly Gly Ala Phe Asp Ile Trp Gly Gln Gly Thr Met
                245                 250                 255

Val Thr Val Ser Ser Ala Ser Thr Gly Gly Gly Gly Ser Gly Gly Gly
            260                 265                 270

Gly Ser Gly Gly Gly Gly Ser Val His Ser Ser Tyr Val Leu Thr Gln
        275                 280                 285

Pro Pro Ser Val Ser Val Ala Pro Gly Gln Thr Ala Thr Ile Thr Cys
    290                 295                 300

Gly Gly Asn Asn Ile Gly Thr Lys Ser Val His Trp Tyr Gln Gln Lys
305                 310                 315                 320

Pro Gly Gln Ala Pro Val Leu Val Val Tyr Ala Asp Ser Asp Arg Pro
                325                 330                 335

Ser Gly Ile Pro Glu Arg Val Ser Gly Ser Asn Ser Gly Asn Thr Ala
            340                 345                 350

Thr Leu Thr Ile Ser Arg Val Glu Ala Gly Asp Glu Ala Asp Tyr Tyr
        355                 360                 365

Cys Gln Val Trp Asp Ser Arg Ser Asp His Leu Trp Val Phe Gly Gly
    370                 375                 380
```

```
Gly Thr Lys Leu Thr Val Leu Gly
385                 390
```

<210> SEQ ID NO 214
<211> LENGTH: 392
<212> TYPE: PRT
<213> ORGANISM: Artificial Sequence
<220> FEATURE:
<223> OTHER INFORMATION: IL15R K86R/ N112A -A10m3

<400> SEQUENCE: 214

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Arg Glu Cys Glu Glu Leu Glu Glu Lys Asn Ile
                85                  90                  95

Lys Glu Phe Leu Gln Ser Phe Val His Ile Val Gln Met Phe Ile Ala
            100                 105                 110

Thr Ser Gly Gly Gly Gly Ser Gly Gly Gly Gly Ser Gly Gly Gly Gly
        115                 120                 125

Ser Gly Gly Gly Gly Ser Gly Gly Gly Gly Ser Glu Val Gln Leu Val
    130                 135                 140

Glu Ser Gly Gly Gly Leu Ile Gln Pro Gly Arg Ser Leu Arg Leu Ser
145                 150                 155                 160

Cys Ala Ala Ser Gly Ile Thr Phe Asp Asp Ala Val Met His Trp Val
                165                 170                 175

Arg Gln Ala Pro Gly Lys Gly Leu Glu Trp Val Ala Gly Ile Ser Ser
            180                 185                 190

Asn Ser Gly Tyr Ile Gly Tyr Ala Asp Ser Val Lys Gly Arg Phe Thr
        195                 200                 205

Ile Ser Arg Asp Asn Ala Lys Asn Ser Leu Tyr Leu Gln Met Asn Arg
    210                 215                 220

Leu Arg Ala Glu Asp Thr Ala Val Tyr Tyr Cys Val Lys Gly Leu Tyr
225                 230                 235                 240

Ser Asn Pro Arg Gly Gly Ala Phe Asp Ile Trp Gly Gln Gly Thr Met
                245                 250                 255

Val Thr Val Ser Ser Ala Ser Thr Gly Gly Gly Ser Gly Gly Gly Gly
            260                 265                 270

Gly Ser Gly Gly Gly Ser Val His Ser Ser Tyr Val Leu Thr Gln
        275                 280                 285

Pro Pro Ser Val Ser Val Ala Pro Gly Gln Thr Ala Thr Ile Thr Cys
    290                 295                 300

Gly Gly Asn Asn Ile Gly Thr Lys Ser Val His Trp Tyr Gln Gln Lys
305                 310                 315                 320

Pro Gly Gln Ala Pro Val Leu Val Val Tyr Ala Asp Ser Asp Arg Pro
                325                 330                 335

Ser Gly Ile Pro Glu Arg Val Ser Gly Ser Asn Ser Gly Asn Thr Ala
            340                 345                 350
```

-continued

```
Thr Leu Thr Ile Ser Arg Val Glu Ala Gly Asp Glu Ala Asp Tyr Tyr
        355                 360                 365

Cys Gln Val Trp Asp Ser Arg Ser Asp His Leu Trp Val Phe Gly Gly
    370                 375                 380

Gly Thr Lys Leu Thr Val Leu Gly
385                 390

<210> SEQ ID NO 215
<211> LENGTH: 38
<212> TYPE: PRT
<213> ORGANISM: Artificial Sequence
<220> FEATURE:
<223> OTHER INFORMATION: IL-15 ubiquitination sites

<400> SEQUENCE: 215

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr
        35

<210> SEQ ID NO 216
<211> LENGTH: 38
<212> TYPE: PRT
<213> ORGANISM: Artificial Sequence
<220> FEATURE:
<223> OTHER INFORMATION: IL-15 ubiquintination sites

<400> SEQUENCE: 216

Ala Met Lys Cys Phe Leu Leu Glu Leu Gln Val Ile Ser Leu Glu Ser
1               5                   10                  15

Gly Asp Ala Ser Ile His Asp Thr Val Glu Asn Leu Ile Ile Leu Ala
            20                  25                  30

Asn Asn Ser Leu Ser Ser
        35

<210> SEQ ID NO 217
<211> LENGTH: 38
<212> TYPE: PRT
<213> ORGANISM: Artificial Sequence
<220> FEATURE:
<223> OTHER INFORMATION: IL-15 ubiquitination sites

<400> SEQUENCE: 217

Asn Gly Asn Val Thr Glu Ser Gly Cys Lys Glu Cys Glu Glu Leu Glu
1               5                   10                  15

Glu Lys Asn Ile Lys Glu Phe Leu Gln Ser Phe Val His Ile Val Gln
            20                  25                  30

Met Phe Ile Asn Thr Ser
        35

<210> SEQ ID NO 218
<211> LENGTH: 799
<212> TYPE: PRT
<213> ORGANISM: Artificial Sequence
<220> FEATURE:
<223> OTHER INFORMATION: mIL12sc-A10m3

<400> SEQUENCE: 218

Met Trp Glu Leu Glu Lys Asp Val Tyr Val Val Glu Val Asp Trp Thr
1               5                   10                  15
```

```
Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
290                 295                 300

Ala Cys Val Pro Cys Arg Val Arg Ser Gly Gly Gly Ser Gly Gly
305                 310                 315                 320

Gly Gly Ser Gly Gly Gly Ser Arg Val Ile Pro Val Ser Gly Pro
                325                 330                 335

Ala Arg Cys Leu Ser Gln Ser Arg Asn Leu Leu Lys Thr Thr Asp Asp
        340                 345                 350

Met Val Lys Thr Ala Arg Glu Lys Leu Lys His Tyr Ser Cys Thr Ala
    355                 360                 365

Glu Asp Ile Asp His Glu Asp Ile Thr Arg Asp Gln Thr Ser Thr Leu
        370                 375                 380

Lys Thr Cys Leu Pro Leu Glu Leu His Lys Asn Glu Ser Cys Leu Ala
385                 390                 395                 400

Thr Arg Glu Thr Ser Ser Thr Thr Arg Gly Ser Cys Leu Pro Pro Gln
                405                 410                 415

Lys Thr Ser Leu Met Met Thr Leu Cys Leu Gly Ser Ile Tyr Glu Asp
            420                 425                 430
```

```
Leu Lys Met Tyr Gln Thr Glu Phe Gln Ala Ile Asn Ala Ala Leu Gln
            435                 440                 445
Asn His Asn His Gln Gln Ile Ile Leu Asp Lys Gly Met Leu Val Ala
450                 455                 460
Ile Asp Glu Leu Met Gln Ser Leu Asn His Asn Gly Glu Thr Leu Arg
465                 470                 475                 480
Gln Lys Pro Pro Val Gly Glu Ala Asp Pro Tyr Arg Val Lys Met Lys
                485                 490                 495
Leu Cys Ile Leu Leu His Ala Phe Ser Thr Arg Val Val Thr Ile Asn
            500                 505                 510
Arg Val Met Gly Tyr Leu Ser Ser Ala Gly Gly Gly Ser Gly Gly
        515                 520                 525
Gly Gly Ser Gly Gly Gly Ser Gly Gly Gly Ser Gly Gly Gly
    530                 535                 540
Gly Ser Glu Val Gln Leu Val Glu Ser Gly Gly Leu Ile Gln Pro
545                 550                 555                 560
Gly Arg Ser Leu Arg Leu Ser Cys Ala Ala Ser Gly Ile Thr Phe Asp
                565                 570                 575
Asp Ala Val Met His Trp Val Arg Gln Ala Pro Gly Lys Gly Leu Glu
            580                 585                 590
Trp Val Ala Gly Ile Ser Ser Asn Ser Gly Tyr Ile Gly Tyr Ala Asp
        595                 600                 605
Ser Val Lys Gly Arg Phe Thr Ile Ser Arg Asp Asn Ala Lys Asn Ser
    610                 615                 620
Leu Tyr Leu Gln Met Asn Arg Leu Arg Ala Glu Asp Thr Ala Val Tyr
625                 630                 635                 640
Tyr Cys Val Lys Gly Leu Tyr Ser Asn Pro Arg Gly Gly Ala Phe Asp
                645                 650                 655
Ile Trp Gly Gln Gly Thr Met Val Thr Val Ser Ser Ala Ser Thr Gly
            660                 665                 670
Gly Gly Gly Ser Gly Gly Gly Gly Ser Gly Gly Gly Ser Val His
        675                 680                 685
Ser Ser Tyr Val Leu Thr Gln Pro Pro Ser Val Ser Val Ala Pro Gly
    690                 695                 700
Gln Thr Ala Thr Ile Thr Cys Gly Gly Asn Asn Ile Gly Thr Lys Ser
705                 710                 715                 720
Val His Trp Tyr Gln Gln Lys Pro Gly Gln Ala Pro Val Leu Val Val
                725                 730                 735
Tyr Ala Asp Ser Asp Arg Pro Ser Gly Ile Pro Glu Arg Val Ser Gly
            740                 745                 750
Ser Asn Ser Gly Asn Thr Ala Thr Leu Thr Ile Ser Arg Val Glu Ala
        755                 760                 765
Gly Asp Glu Ala Asp Tyr Tyr Cys Gln Val Trp Asp Ser Arg Ser Asp
    770                 775                 780
His Leu Trp Val Phe Gly Gly Thr Lys Leu Thr Val Leu Gly
785                 790                 795

<210> SEQ ID NO 219
<211> LENGTH: 788
<212> TYPE: PRT
<213> ORGANISM: Artificial Sequence
<220> FEATURE:
<223> OTHER INFORMATION: Human IL-12sc-A10m3

<400> SEQUENCE: 219
```

-continued

```
Ile Trp Glu Leu Lys Lys Asp Val Tyr Val Glu Leu Asp Trp Tyr
 1               5                  10                 15

Pro Asp Ala Pro Gly Glu Met Val Val Leu Thr Cys Asp Thr Pro Glu
                20                  25                  30

Glu Asp Gly Ile Thr Trp Thr Leu Asp Gln Ser Ser Glu Val Leu Gly
            35                  40                  45

Ser Gly Lys Thr Leu Thr Ile Gln Val Lys Glu Phe Gly Asp Ala Gly
 50                  55                  60

Gln Tyr Thr Cys His Lys Gly Gly Glu Val Leu Ser His Ser Leu Leu
 65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
            115                 120                 125

Asp Leu Thr Phe Ser Val Lys Ser Ser Arg Gly Ser Ser Asp Pro Gln
            130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
                180                 185                 190

Val His Lys Leu Lys Tyr Glu Asn Tyr Thr Ser Ser Phe Phe Ile Arg
                195                 200                 205

Asp Ile Ile Lys Pro Asp Pro Pro Lys Asn Leu Gln Leu Lys Pro Leu
            210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
            275                 280                 285

Gln Asp Arg Tyr Tyr Ser Ser Ser Trp Ser Glu Trp Ala Ser Val Pro
            290                 295                 300

Cys Ser Gly Gly Gly Gly Gly Ser Arg Asn Leu Pro Val Ala Thr
305                 310                 315                 320

Pro Asp Pro Gly Met Phe Pro Cys Leu His His Ser Gln Asn Leu Leu
                325                 330                 335

Arg Ala Val Ser Asn Met Leu Gln Lys Ala Arg Gln Thr Leu Glu Phe
                340                 345                 350

Tyr Pro Cys Thr Ser Glu Glu Ile Asp His Glu Asp Ile Thr Lys Asp
            355                 360                 365

Lys Thr Ser Thr Val Glu Ala Cys Leu Pro Leu Glu Leu Thr Lys Asn
            370                 375                 380

Glu Ser Cys Leu Asn Ser Arg Glu Thr Ser Phe Ile Thr Asn Gly Ser
385                 390                 395                 400

Cys Leu Ala Ser Arg Lys Thr Ser Phe Met Met Ala Leu Cys Leu Ser
                405                 410                 415

Ser Ile Tyr Glu Asp Leu Lys Met Tyr Gln Val Glu Phe Lys Thr Met
```

```
                420             425             430
Asn Ala Lys Leu Leu Met Asp Pro Lys Arg Gln Ile Phe Leu Asp Gln
            435                 440                 445
Asn Met Leu Ala Val Ile Asp Glu Leu Met Gln Ala Leu Asn Phe Asn
450                 455                 460
Ser Glu Thr Val Pro Gln Lys Ser Ser Leu Glu Glu Pro Asp Phe Tyr
465                 470                 475                 480
Lys Thr Lys Ile Lys Leu Cys Ile Leu Leu His Ala Phe Arg Ile Arg
            485                 490                 495
Ala Val Thr Ile Asp Arg Val Thr Ser Tyr Leu Asn Ala Ser Gly Gly
            500                 505                 510
Gly Gly Ser Gly Gly Gly Gly Ser Gly Gly Gly Gly Ser Gly Gly Gly
            515                 520                 525
Gly Ser Gly Gly Gly Gly Ser Glu Val Gln Leu Val Glu Ser Gly Gly
            530                 535                 540
Gly Leu Ile Gln Pro Gly Arg Ser Leu Arg Leu Ser Cys Ala Ala Ser
545                 550                 555                 560
Gly Ile Thr Phe Asp Asp Ala Val Met His Trp Val Arg Gln Ala Pro
            565                 570                 575
Gly Lys Gly Leu Glu Trp Val Ala Gly Ile Ser Ser Asn Ser Gly Tyr
            580                 585                 590
Ile Gly Tyr Ala Asp Ser Val Lys Gly Arg Phe Thr Ile Ser Arg Asp
            595                 600                 605
Asn Ala Lys Asn Ser Leu Tyr Leu Gln Met Asn Arg Leu Arg Ala Glu
            610                 615                 620
Asp Thr Ala Val Tyr Tyr Cys Val Lys Gly Leu Tyr Ser Asn Pro Arg
625                 630                 635                 640
Gly Gly Ala Phe Asp Ile Trp Gly Gln Gly Thr Met Val Thr Val Ser
            645                 650                 655
Ser Ala Ser Thr Gly Gly Gly Gly Ser Gly Gly Gly Gly Ser Gly Gly
            660                 665                 670
Gly Gly Ser Val His Ser Ser Tyr Val Leu Thr Gln Pro Pro Ser Val
            675                 680                 685
Ser Val Ala Pro Gly Gln Thr Ala Thr Ile Thr Cys Gly Gly Asn Asn
            690                 695                 700
Ile Gly Thr Lys Ser Val His Trp Tyr Gln Gln Lys Pro Gly Gln Ala
705                 710                 715                 720
Pro Val Leu Val Val Tyr Ala Asp Ser Asp Arg Pro Ser Gly Ile Pro
            725                 730                 735
Glu Arg Val Ser Gly Ser Asn Ser Gly Asn Thr Ala Thr Leu Thr Ile
            740                 745                 750
Ser Arg Val Glu Ala Gly Asp Glu Ala Asp Tyr Tyr Cys Gln Val Trp
            755                 760                 765
Asp Ser Arg Ser Asp His Leu Trp Val Phe Gly Gly Gly Thr Lys Leu
            770                 775                 780
Thr Val Leu Gly
785

<210> SEQ ID NO 220
<211> LENGTH: 938
<212> TYPE: PRT
<213> ORGANISM: Artificial Sequence
<220> FEATURE:
<223> OTHER INFORMATION: hIL15RA-A10m3-mIL-12sc
```

<400> SEQUENCE: 220

```
Asn Trp Val Asn Val Ile Ser Asp Leu Lys Lys Ile Glu Asp Leu Ile
1               5                   10                  15
Gln Ser Met His Ile Asp Ala Thr Leu Tyr Thr Glu Ser Asp Val His
                20                  25                  30
Pro Ser Cys Lys Val Thr Ala Met Lys Cys Phe Leu Leu Glu Leu Gln
            35                  40                  45
Val Ile Ser Leu Glu Ser Gly Asp Ala Ser Ile His Asp Thr Val Glu
    50                  55                  60
Asn Leu Ile Ile Leu Ala Asn Asn Ser Leu Ser Ser Asn Gly Asn Val
65                  70                  75                  80
Thr Glu Ser Gly Cys Arg Glu Cys Glu Glu Leu Glu Glu Lys Asn Ile
                85                  90                  95
Lys Glu Phe Leu Gln Ser Phe Val His Ile Val Gln Met Phe Ile Ala
            100                 105                 110
Thr Ser Gly Gly Gly Gly Ser Gly Gly Gly Gly Ser Gly Gly Gly Gly
    115                 120                 125
Ser Gly Gly Gly Gly Ser Gly Gly Gly Gly Ser Glu Val Gln Leu Val
130                 135                 140
Glu Ser Gly Gly Gly Leu Ile Gln Pro Gly Arg Ser Leu Arg Leu Ser
145                 150                 155                 160
Cys Ala Ala Ser Gly Ile Thr Phe Asp Asp Ala Val Met His Trp Val
                165                 170                 175
Arg Gln Ala Pro Gly Lys Gly Leu Glu Trp Val Ala Gly Ile Ser Ser
            180                 185                 190
Asn Ser Gly Tyr Ile Gly Tyr Ala Asp Ser Val Lys Gly Arg Phe Thr
    195                 200                 205
Ile Ser Arg Asp Asn Ala Lys Asn Ser Leu Tyr Leu Gln Met Asn Arg
210                 215                 220
Leu Arg Ala Glu Asp Thr Ala Val Tyr Tyr Cys Val Lys Gly Leu Tyr
225                 230                 235                 240
Ser Asn Pro Arg Gly Gly Ala Phe Asp Ile Trp Gly Gln Gly Thr Met
                245                 250                 255
Val Thr Val Ser Ser Ala Ser Thr Gly Gly Gly Ser Gly Gly Gly
            260                 265                 270
Gly Ser Gly Gly Gly Ser Val His Ser Ser Tyr Val Leu Thr Gln
    275                 280                 285
Pro Pro Ser Val Ser Val Ala Pro Gly Gln Thr Ala Thr Ile Thr Cys
290                 295                 300
Gly Gly Asn Asn Ile Gly Thr Lys Ser Val His Trp Tyr Gln Gln Lys
305                 310                 315                 320
Pro Gly Gln Ala Pro Val Leu Val Val Tyr Ala Asp Ser Asp Arg Pro
                325                 330                 335
Ser Gly Ile Pro Glu Arg Val Ser Gly Ser Asn Ser Gly Asn Thr Ala
            340                 345                 350
Thr Leu Thr Ile Ser Arg Val Glu Ala Gly Asp Glu Ala Asp Tyr Tyr
    355                 360                 365
Cys Gln Val Trp Asp Ser Arg Ser Asp His Leu Trp Val Phe Gly Gly
370                 375                 380
Gly Thr Lys Leu Thr Val Leu Gly Gly Gly Gly Ser Gly Gly Gly
385                 390                 395                 400
Gly Ser Gly Gly Gly Gly Ser Gly Gly Gly Gly Ser Gly Gly Gly Gly
                405                 410                 415
```

-continued

```
Ser Met Trp Glu Leu Glu Lys Asp Val Tyr Val Glu Val Asp Trp
        420                 425                 430

Thr Pro Asp Ala Pro Gly Glu Thr Val Asn Leu Thr Cys Asp Thr Pro
        435                 440                 445

Glu Glu Asp Asp Ile Thr Trp Thr Ser Asp Gln Arg His Gly Val Ile
        450                 455                 460

Gly Ser Gly Lys Thr Leu Thr Ile Thr Val Lys Glu Phe Leu Asp Ala
465                 470                 475                 480

Gly Gln Tyr Thr Cys His Lys Gly Gly Glu Thr Leu Ser His Ser His
                485                 490                 495

Leu Leu Leu His Lys Lys Glu Asn Gly Ile Trp Ser Thr Glu Ile Leu
            500                 505                 510

Lys Asn Phe Lys Asn Lys Thr Phe Leu Lys Cys Glu Ala Pro Asn Tyr
            515                 520                 525

Ser Gly Arg Phe Thr Cys Ser Trp Leu Val Gln Arg Asn Met Asp Leu
        530                 535                 540

Lys Phe Asn Ile Lys Ser Ser Ser Ser Pro Asp Ser Arg Ala Val
545                 550                 555                 560

Thr Cys Gly Met Ala Ser Leu Ser Ala Glu Lys Val Thr Leu Asp Gln
                565                 570                 575

Arg Asp Tyr Glu Lys Tyr Ser Val Ser Cys Gln Glu Asp Val Thr Cys
            580                 585                 590

Pro Thr Ala Glu Glu Thr Leu Pro Ile Glu Leu Ala Leu Glu Ala Arg
        595                 600                 605

Gln Gln Asn Lys Tyr Glu Asn Tyr Ser Thr Ser Phe Phe Ile Arg Asp
        610                 615                 620

Ile Ile Lys Pro Asp Pro Pro Lys Asn Leu Gln Met Lys Pro Leu Lys
625                 630                 635                 640

Asn Ser Gln Val Glu Val Ser Trp Glu Tyr Pro Asp Ser Trp Ser Thr
                645                 650                 655

Pro His Ser Tyr Phe Ser Leu Lys Phe Phe Val Arg Ile Gln Arg Lys
            660                 665                 670

Lys Glu Lys Met Lys Glu Thr Glu Glu Gly Cys Asn Gln Lys Gly Ala
        675                 680                 685

Phe Leu Val Glu Lys Thr Ser Thr Glu Val Gln Cys Lys Gly Gly Asn
        690                 695                 700

Val Cys Val Gln Ala Gln Asp Arg Tyr Tyr Asn Ser Ser Cys Ser Lys
705                 710                 715                 720

Trp Ala Cys Val Pro Cys Arg Val Arg Ser Gly Gly Gly Ser Gly
                725                 730                 735

Gly Gly Gly Ser Gly Gly Gly Ser Arg Val Ile Pro Val Ser Gly
            740                 745                 750

Pro Ala Arg Cys Leu Ser Gln Ser Arg Asn Leu Leu Lys Thr Thr Asp
        755                 760                 765

Asp Met Val Lys Thr Ala Arg Glu Lys Leu Lys His Tyr Ser Cys Thr
        770                 775                 780

Ala Glu Asp Ile Asp His Glu Asp Ile Thr Arg Asp Gln Thr Ser Thr
785                 790                 795                 800

Leu Lys Thr Cys Leu Pro Leu Glu Leu His Lys Asn Glu Ser Cys Leu
                805                 810                 815

Ala Thr Arg Glu Thr Ser Ser Thr Thr Arg Gly Ser Cys Leu Pro Pro
            820                 825                 830
```

Gln Lys Thr Ser Leu Met Met Thr Leu Cys Leu Gly Ser Ile Tyr Glu
835                 840                 845

Asp Leu Lys Met Tyr Gln Thr Glu Phe Gln Ala Ile Asn Ala Ala Leu
850                 855                 860

Gln Asn His Asn His Gln Gln Ile Ile Leu Asp Lys Gly Met Leu Val
865                 870                 875                 880

Ala Ile Asp Glu Leu Met Gln Ser Leu Asn His Asn Gly Glu Thr Leu
                885                 890                 895

Arg Gln Lys Pro Pro Val Gly Glu Ala Asp Pro Tyr Arg Val Lys Met
                900                 905                 910

Lys Leu Cys Ile Leu Leu His Ala Phe Ser Thr Arg Val Val Thr Ile
                915                 920                 925

Asn Arg Val Met Gly Tyr Leu Ser Ser Ala
                930                 935

<210> SEQ ID NO 221
<211> LENGTH: 938
<212> TYPE: PRT
<213> ORGANISM: Artificial Sequence
<220> FEATURE:
<223> OTHER INFORMATION: mIL-12sc-A10m3-hIL15R

<400> SEQUENCE: 221

Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
                20                  25                  30

Glu Asp Asp Ile Thr Trp Thr Ser Asp Gln Arg His Gly Val Ile Gly
            35                  40                  45

Ser Gly Lys Thr Leu Thr Ile Thr Val Lys Glu Phe Leu Asp Ala Gly
        50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
                100                 105                 110

Gly Arg Phe Thr Cys Ser Trp Leu Val Gln Arg Asn Met Asp Leu Lys
            115                 120                 125

Phe Asn Ile Lys Ser Ser Ser Ser Pro Asp Ser Arg Ala Val Thr
        130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
                180                 185                 190

Gln Asn Lys Tyr Glu Asn Tyr Ser Thr Ser Phe Phe Ile Arg Asp Ile
            195                 200                 205

Ile Lys Pro Asp Pro Pro Lys Asn Leu Gln Met Lys Pro Leu Lys Asn
        210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

```
Glu Lys Met Lys Glu Thr Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser Gly Gly Gly Ser Gly Gly
305             310                 315                 320

Gly Gly Ser Gly Gly Gly Ser Arg Val Ile Pro Val Ser Gly Pro
            325                 330                 335

Ala Arg Cys Leu Ser Gln Ser Arg Asn Leu Leu Lys Thr Thr Asp Asp
            340                 345                 350

Met Val Lys Thr Ala Arg Glu Lys Leu Lys His Tyr Ser Cys Thr Ala
            355                 360                 365

Glu Asp Ile Asp His Glu Asp Ile Thr Arg Asp Gln Thr Ser Thr Leu
    370                 375                 380

Lys Thr Cys Leu Pro Leu Glu Leu His Lys Asn Glu Ser Cys Leu Ala
385                 390                 395                 400

Thr Arg Glu Thr Ser Ser Thr Thr Arg Gly Ser Cys Leu Pro Pro Gln
                405                 410                 415

Lys Thr Ser Leu Met Met Thr Leu Cys Leu Gly Ser Ile Tyr Glu Asp
            420                 425                 430

Leu Lys Met Tyr Gln Thr Glu Phe Gln Ala Ile Asn Ala Ala Leu Gln
        435                 440                 445

Asn His Asn His Gln Gln Ile Ile Leu Asp Lys Gly Met Leu Val Ala
    450                 455                 460

Ile Asp Glu Leu Met Gln Ser Leu Asn His Asn Gly Glu Thr Leu Arg
465                 470                 475                 480

Gln Lys Pro Pro Val Gly Glu Ala Asp Pro Tyr Arg Val Lys Met Lys
                485                 490                 495

Leu Cys Ile Leu Leu His Ala Phe Ser Thr Arg Val Val Thr Ile Asn
            500                 505                 510

Arg Val Met Gly Tyr Leu Ser Ser Ala Gly Gly Gly Ser Gly Gly
        515                 520                 525

Gly Gly Ser Gly Gly Gly Ser Gly Gly Gly Ser Gly Gly Gly
    530                 535                 540

Gly Ser Glu Val Gln Leu Val Glu Ser Gly Gly Leu Ile Gln Pro
545                 550                 555                 560

Gly Arg Ser Leu Arg Leu Ser Cys Ala Ala Ser Gly Ile Thr Phe Asp
                565                 570                 575

Asp Ala Val Met His Trp Val Arg Gln Ala Pro Gly Lys Gly Leu Glu
            580                 585                 590

Trp Val Ala Gly Ile Ser Ser Asn Ser Gly Tyr Ile Gly Tyr Ala Asp
        595                 600                 605

Ser Val Lys Gly Arg Phe Thr Ile Ser Arg Asp Asn Ala Lys Asn Ser
    610                 615                 620

Leu Tyr Leu Gln Met Asn Arg Leu Arg Ala Glu Asp Thr Ala Val Tyr
625                 630                 635                 640

Tyr Cys Val Lys Gly Leu Tyr Ser Asn Pro Arg Gly Gly Ala Phe Asp
                645                 650                 655

Ile Trp Gly Gln Gly Thr Met Val Thr Val Ser Ser Ala Ser Thr Gly
            660                 665                 670

Gly Gly Gly Ser Gly Gly Gly Gly Ser Gly Gly Gly Gly Ser Val His
```

```
            675                 680                 685
Ser Ser Tyr Val Leu Thr Gln Pro Pro Ser Val Ser Val Ala Pro Gly
        690                 695                 700

Gln Thr Ala Thr Ile Thr Cys Gly Gly Asn Asn Ile Gly Thr Lys Ser
705                 710                 715                 720

Val His Trp Tyr Gln Gln Lys Pro Gly Gln Ala Pro Val Leu Val Val
                725                 730                 735

Tyr Ala Asp Ser Asp Arg Pro Ser Gly Ile Pro Glu Arg Val Ser Gly
            740                 745                 750

Ser Asn Ser Gly Asn Thr Ala Thr Leu Thr Ile Ser Arg Val Glu Ala
        755                 760                 765

Gly Asp Glu Ala Asp Tyr Tyr Cys Gln Val Trp Asp Ser Arg Ser Asp
    770                 775                 780

His Leu Trp Val Phe Gly Gly Gly Thr Lys Leu Thr Val Leu Gly Gly
785                 790                 795                 800

Gly Gly Gly Ser Gly Gly Gly Gly Ser Gly Gly Gly Gly Ser Gly Gly
                805                 810                 815

Gly Gly Ser Gly Gly Gly Gly Ser Asn Trp Val Asn Val Ile Ser Asp
            820                 825                 830

Leu Lys Lys Ile Glu Asp Leu Ile Gln Ser Met His Ile Asp Ala Thr
        835                 840                 845

Leu Tyr Thr Glu Ser Asp Val His Pro Ser Cys Lys Val Thr Ala Met
    850                 855                 860

Lys Cys Phe Leu Leu Glu Leu Gln Val Ile Ser Leu Glu Ser Gly Asp
865                 870                 875                 880

Ala Ser Ile His Asp Thr Val Glu Asn Leu Ile Ile Leu Ala Asn Asn
                885                 890                 895

Ser Leu Ser Ser Asn Gly Asn Val Thr Glu Ser Gly Cys Arg Glu Cys
            900                 905                 910

Glu Glu Leu Glu Glu Lys Asn Ile Lys Glu Phe Leu Gln Ser Phe Val
        915                 920                 925

His Ile Val Gln Met Phe Ile Asn Thr Ser
    930                 935

<210> SEQ ID NO 222
<211> LENGTH: 938
<212> TYPE: PRT
<213> ORGANISM: Artificial Sequence
<220> FEATURE:
<223> OTHER INFORMATION: mIL-12sc-A10m3-hIL15RA

<400> SEQUENCE: 222

Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
```

-continued

```
                100                 105                 110
Gly Arg Phe Thr Cys Ser Trp Leu Val Gln Arg Asn Met Asp Leu Lys
            115                 120                 125

Phe Asn Ile Lys Ser Ser Ser Ser Pro Asp Ser Arg Ala Val Thr
        130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
        210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
        290                 295                 300

Ala Cys Val Pro Cys Arg Val Arg Ser Gly Gly Gly Ser Gly Gly
305                 310                 315                 320

Gly Gly Ser Gly Gly Gly Ser Arg Val Ile Pro Val Ser Gly Pro
                325                 330                 335

Ala Arg Cys Leu Ser Gln Ser Arg Asn Leu Leu Lys Thr Thr Asp Asp
            340                 345                 350

Met Val Lys Thr Ala Arg Glu Lys Leu Lys His Tyr Ser Cys Thr Ala
        355                 360                 365

Glu Asp Ile Asp His Glu Asp Ile Thr Arg Asp Gln Thr Ser Thr Leu
        370                 375                 380

Lys Thr Cys Leu Pro Leu Glu Leu His Lys Asn Glu Ser Cys Leu Ala
385                 390                 395                 400

Thr Arg Glu Thr Ser Ser Thr Thr Arg Gly Ser Cys Leu Pro Pro Gln
                405                 410                 415

Lys Thr Ser Leu Met Met Thr Leu Cys Leu Gly Ser Ile Tyr Glu Asp
            420                 425                 430

Leu Lys Met Tyr Gln Thr Glu Phe Gln Ala Ile Asn Ala Ala Leu Gln
        435                 440                 445

Asn His Asn His Gln Gln Ile Ile Leu Asp Lys Gly Met Leu Val Ala
        450                 455                 460

Ile Asp Glu Leu Met Gln Ser Leu Asn His Asn Gly Glu Thr Leu Arg
465                 470                 475                 480

Gln Lys Pro Pro Val Gly Glu Ala Asp Pro Tyr Arg Val Lys Met Lys
                485                 490                 495

Leu Cys Ile Leu Leu His Ala Phe Ser Thr Arg Val Val Thr Ile Asn
            500                 505                 510

Arg Val Met Gly Tyr Leu Ser Ser Ala Gly Gly Gly Gly Ser Gly Gly
        515                 520                 525
```

-continued

Gly Gly Ser Gly Gly Gly Ser Gly Gly Gly Ser Gly Gly
    530             535             540

Gly Ser Glu Val Gln Leu Val Glu Ser Gly Gly Leu Ile Gln Pro
545                 550                 555                 560

Gly Arg Ser Leu Arg Leu Ser Cys Ala Ala Ser Gly Ile Thr Phe Asp
                565                 570                 575

Asp Ala Val Met His Trp Val Arg Gln Ala Pro Gly Lys Gly Leu Glu
                580                 585                 590

Trp Val Ala Gly Ile Ser Ser Asn Ser Gly Tyr Ile Gly Tyr Ala Asp
            595                 600                 605

Ser Val Lys Gly Arg Phe Thr Ile Ser Arg Asp Asn Ala Lys Asn Ser
    610                 615                 620

Leu Tyr Leu Gln Met Asn Arg Leu Arg Ala Glu Asp Thr Ala Val Tyr
625                 630                 635                 640

Tyr Cys Val Lys Gly Leu Tyr Ser Asn Pro Arg Gly Gly Ala Phe Asp
                645                 650                 655

Ile Trp Gly Gln Gly Thr Met Val Thr Val Ser Ser Ala Ser Thr Gly
            660                 665                 670

Gly Gly Gly Ser Gly Gly Gly Ser Gly Gly Gly Ser Val His
    675                 680                 685

Ser Ser Tyr Val Leu Thr Gln Pro Pro Ser Val Ser Val Ala Pro Gly
690                 695                 700

Gln Thr Ala Thr Ile Thr Cys Gly Gly Asn Asn Ile Gly Thr Lys Ser
705                 710                 715                 720

Val His Trp Tyr Gln Gln Lys Pro Gly Gln Ala Pro Val Leu Val Val
                725                 730                 735

Tyr Ala Asp Ser Asp Arg Pro Ser Gly Ile Pro Glu Arg Val Ser Gly
                740                 745                 750

Ser Asn Ser Gly Asn Thr Ala Thr Leu Thr Ile Ser Arg Val Glu Ala
            755                 760                 765

Gly Asp Glu Ala Asp Tyr Tyr Cys Gln Val Trp Asp Ser Arg Ser Asp
    770                 775                 780

His Leu Trp Val Phe Gly Gly Gly Thr Lys Leu Thr Val Leu Gly Gly
785                 790                 795                 800

Gly Gly Gly Ser Gly Gly Gly Ser Gly Gly Gly Ser Gly Gly
                805                 810                 815

Gly Gly Ser Gly Gly Gly Ser Asn Trp Val Asn Val Ile Ser Asp
            820                 825                 830

Leu Lys Lys Ile Glu Asp Leu Ile Gln Ser Met His Ile Asp Ala Thr
    835                 840                 845

Leu Tyr Thr Glu Ser Asp Val His Pro Ser Cys Lys Val Thr Ala Met
850                 855                 860

Lys Cys Phe Leu Leu Glu Leu Gln Val Ile Ser Leu Glu Ser Gly Asp
865                 870                 875                 880

Ala Ser Ile His Asp Thr Val Glu Asn Leu Ile Ile Leu Ala Asn Asn
                885                 890                 895

Ser Leu Ser Ser Asn Gly Asn Val Thr Glu Ser Gly Cys Arg Glu Cys
            900                 905                 910

Glu Glu Leu Glu Glu Lys Asn Ile Lys Glu Phe Leu Gln Ser Phe Val
    915                 920                 925

His Ile Val Gln Met Phe Ile Ala Thr Ser
    930                 935

```
<210> SEQ ID NO 223
<211> LENGTH: 927
<212> TYPE: PRT
<213> ORGANISM: Artificial Sequence
<220> FEATURE:
<223> OTHER INFORMATION: hIL15RA-A10m3-hIL-12sc

<400> SEQUENCE: 223
```

| | | | | | | | | | | | | | | | |
|---|---|---|---|---|---|---|---|---|---|---|---|---|---|---|---|
| Asn | Trp | Val | Asn | Val | Ile | Ser | Asp | Leu | Lys | Lys | Ile | Glu | Asp | Leu | Ile |
| 1 | | | | 5 | | | | | 10 | | | | | 15 | |
| Gln | Ser | Met | His | Ile | Asp | Ala | Thr | Leu | Tyr | Thr | Glu | Ser | Asp | Val | His |
| | | | 20 | | | | | 25 | | | | | 30 | | |
| Pro | Ser | Cys | Lys | Val | Thr | Ala | Met | Lys | Cys | Phe | Leu | Leu | Glu | Leu | Gln |
| | | | 35 | | | | | 40 | | | | | 45 | | |
| Val | Ile | Ser | Leu | Glu | Ser | Gly | Asp | Ala | Ser | Ile | His | Asp | Thr | Val | Glu |
| | 50 | | | | | 55 | | | | | 60 | | | | |
| Asn | Leu | Ile | Ile | Leu | Ala | Asn | Asn | Ser | Leu | Ser | Ser | Asn | Gly | Asn | Val |
| 65 | | | | | 70 | | | | | 75 | | | | | 80 |
| Thr | Glu | Ser | Gly | Cys | Arg | Glu | Cys | Glu | Glu | Leu | Glu | Glu | Lys | Asn | Ile |
| | | | | 85 | | | | | 90 | | | | | 95 | |
| Lys | Glu | Phe | Leu | Gln | Ser | Phe | Val | His | Ile | Val | Gln | Met | Phe | Ile | Ala |
| | | | 100 | | | | | 105 | | | | | 110 | | |
| Thr | Ser | Gly | Gly | Gly | Gly | Ser | Gly | Gly | Gly | Gly | Ser | Gly | Gly | Gly | Gly |
| | | | 115 | | | | | 120 | | | | | 125 | | |
| Ser | Gly | Gly | Gly | Gly | Ser | Gly | Gly | Gly | Gly | Ser | Glu | Val | Gln | Leu | Val |
| | 130 | | | | | 135 | | | | | 140 | | | | |
| Glu | Ser | Gly | Gly | Gly | Leu | Ile | Gln | Pro | Gly | Arg | Ser | Leu | Arg | Leu | Ser |
| 145 | | | | | 150 | | | | | 155 | | | | | 160 |
| Cys | Ala | Ala | Ser | Gly | Ile | Thr | Phe | Asp | Asp | Ala | Val | Met | His | Trp | Val |
| | | | | 165 | | | | | 170 | | | | | 175 | |
| Arg | Gln | Ala | Pro | Gly | Lys | Gly | Leu | Glu | Trp | Val | Ala | Gly | Ile | Ser | Ser |
| | | | 180 | | | | | 185 | | | | | 190 | | |
| Asn | Ser | Gly | Tyr | Ile | Gly | Tyr | Ala | Asp | Ser | Val | Lys | Gly | Arg | Phe | Thr |
| | | | | 195 | | | | | 200 | | | | | 205 | |
| Ile | Ser | Arg | Asp | Asn | Ala | Lys | Asn | Ser | Leu | Tyr | Leu | Gln | Met | Asn | Arg |
| | 210 | | | | | 215 | | | | | 220 | | | | |
| Leu | Arg | Ala | Glu | Asp | Thr | Ala | Val | Tyr | Tyr | Cys | Val | Lys | Gly | Leu | Tyr |
| 225 | | | | | 230 | | | | | 235 | | | | | 240 |
| Ser | Asn | Pro | Arg | Gly | Gly | Ala | Phe | Asp | Ile | Trp | Gly | Gln | Gly | Thr | Met |
| | | | | 245 | | | | | 250 | | | | | 255 | |
| Val | Thr | Val | Ser | Ser | Ala | Ser | Thr | Gly | Gly | Gly | Ser | Gly | Gly | Gly | Gly |
| | | | 260 | | | | | 265 | | | | | 270 | | |
| Gly | Ser | Gly | Gly | Gly | Ser | Val | His | Ser | Ser | Tyr | Val | Leu | Thr | Gln |
| | | | 275 | | | | | 280 | | | | | 285 | | |
| Pro | Pro | Ser | Val | Ser | Val | Ala | Pro | Gly | Gln | Thr | Ala | Thr | Ile | Thr | Cys |
| | 290 | | | | | 295 | | | | | 300 | | | | |
| Gly | Gly | Asn | Asn | Ile | Gly | Thr | Lys | Ser | Val | His | Trp | Tyr | Gln | Gln | Lys |
| 305 | | | | | 310 | | | | | 315 | | | | | 320 |
| Pro | Gly | Gln | Ala | Pro | Val | Leu | Val | Val | Tyr | Ala | Asp | Ser | Asp | Arg | Pro |
| | | | | 325 | | | | | 330 | | | | | 335 | |
| Ser | Gly | Ile | Pro | Glu | Arg | Val | Ser | Gly | Ser | Asn | Ser | Gly | Asn | Thr | Ala |
| | | | 340 | | | | | 345 | | | | | 350 | | |
| Thr | Leu | Thr | Ile | Ser | Arg | Val | Glu | Ala | Gly | Asp | Glu | Ala | Asp | Tyr | Tyr |
| | | | | 355 | | | | | 360 | | | | | 365 | |

```
Cys Gln Val Trp Asp Ser Arg Ser Asp His Leu Trp Val Phe Gly Gly
    370                 375                 380
Gly Thr Lys Leu Thr Val Leu Gly Gly Gly Gly Ser Gly Gly Gly
385                 390                 395                 400
Gly Ser Gly Gly Gly Ser Gly Gly Gly Ser Gly Gly Gly
                405                 410                 415
Ser Ile Trp Glu Leu Lys Lys Asp Val Tyr Val Val Glu Leu Asp Trp
            420                 425                 430
Tyr Pro Asp Ala Pro Gly Glu Met Val Val Leu Thr Cys Asp Thr Pro
            435                 440                 445
Glu Glu Asp Gly Ile Thr Trp Thr Leu Asp Gln Ser Ser Glu Val Leu
    450                 455                 460
Gly Ser Gly Lys Thr Leu Thr Ile Gln Val Lys Glu Phe Gly Asp Ala
465                 470                 475                 480
Gly Gln Tyr Thr Cys His Lys Gly Gly Glu Val Leu Ser His Ser Leu
            485                 490                 495
Leu Leu Leu His Lys Lys Glu Asp Gly Ile Trp Ser Thr Asp Ile Leu
            500                 505                 510
Lys Asp Gln Lys Glu Pro Lys Asn Lys Thr Phe Leu Arg Cys Glu Ala
    515                 520                 525
Lys Asn Tyr Ser Gly Arg Phe Thr Cys Trp Trp Leu Thr Thr Ile Ser
    530                 535                 540
Thr Asp Leu Thr Phe Ser Val Lys Ser Ser Arg Gly Ser Ser Asp Pro
545                 550                 555                 560
Gln Gly Val Thr Cys Gly Ala Ala Thr Leu Ser Ala Glu Arg Val Arg
            565                 570                 575
Gly Asp Asn Lys Glu Tyr Glu Tyr Ser Val Glu Cys Gln Glu Asp Ser
            580                 585                 590
Ala Cys Pro Ala Ala Glu Glu Ser Leu Pro Ile Glu Val Met Val Asp
    595                 600                 605
Ala Val His Lys Leu Lys Tyr Glu Asn Tyr Thr Ser Ser Phe Phe Ile
    610                 615                 620
Arg Asp Ile Ile Lys Pro Asp Pro Pro Lys Asn Leu Gln Leu Lys Pro
625                 630                 635                 640
Leu Lys Asn Ser Arg Gln Val Glu Val Ser Trp Glu Tyr Pro Asp Thr
            645                 650                 655
Trp Ser Thr Pro His Ser Tyr Phe Ser Leu Thr Phe Cys Val Gln Val
            660                 665                 670
Gln Gly Lys Ser Lys Arg Glu Lys Lys Asp Arg Val Phe Thr Asp Lys
    675                 680                 685
Thr Ser Ala Thr Val Ile Cys Arg Lys Asn Ala Ser Ile Ser Val Arg
    690                 695                 700
Ala Gln Asp Arg Tyr Tyr Ser Ser Ser Trp Ser Glu Trp Ala Ser Val
705                 710                 715                 720
Pro Cys Ser Gly Gly Gly Gly Gly Ser Arg Asn Leu Pro Val Ala
            725                 730                 735
Thr Pro Asp Pro Gly Met Phe Pro Cys Leu His His Ser Gln Asn Leu
            740                 745                 750
Leu Arg Ala Val Ser Asn Met Leu Gln Lys Ala Arg Gln Thr Leu Glu
            755                 760                 765
Phe Tyr Pro Cys Thr Ser Glu Glu Ile Asp His Glu Asp Ile Thr Lys
    770                 775                 780
Asp Lys Thr Ser Thr Val Glu Ala Cys Leu Pro Leu Glu Leu Thr Lys
```

```
            785                 790                 795                 800
Asn Glu Ser Cys Leu Asn Ser Arg Glu Thr Ser Phe Ile Thr Asn Gly
                    805                 810                 815

Ser Cys Leu Ala Ser Arg Lys Thr Ser Phe Met Met Ala Leu Cys Leu
                820                 825                 830

Ser Ser Ile Tyr Glu Asp Leu Lys Met Tyr Gln Val Glu Phe Lys Thr
            835                 840                 845

Met Asn Ala Lys Leu Leu Met Asp Pro Lys Arg Gln Ile Phe Leu Asp
850                 855                 860

Gln Asn Met Leu Ala Val Ile Asp Glu Leu Met Gln Ala Leu Asn Phe
865                 870                 875                 880

Asn Ser Glu Thr Val Pro Gln Lys Ser Ser Leu Glu Glu Pro Asp Phe
                885                 890                 895

Tyr Lys Thr Lys Ile Lys Leu Cys Ile Leu Leu His Ala Phe Arg Ile
            900                 905                 910

Arg Ala Val Thr Ile Asp Arg Val Thr Ser Tyr Leu Asn Ala Ser
                915                 920                 925

<210> SEQ ID NO 224
<211> LENGTH: 927
<212> TYPE: PRT
<213> ORGANISM: Artificial Sequence
<220> FEATURE:
<223> OTHER INFORMATION: Human IL-12sc-A10m3-hIL15R

<400> SEQUENCE: 224

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
                20                  25                  30

Glu Asp Gly Ile Thr Trp Thr Leu Asp Gln Ser Ser Glu Val Leu Gly
            35                  40                  45

Ser Gly Lys Thr Leu Thr Ile Gln Val Lys Glu Phe Gly Asp Ala Gly
        50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
```

-continued

```
                225                 230                 235                 240
            Ser Thr Pro His Ser Tyr Phe Ser Leu Thr Phe Cys Val Gln Val Gln
                            245                 250                 255
            Gly Lys Ser Lys Arg Glu Lys Lys Asp Arg Val Phe Thr Asp Lys Thr
                            260                 265                 270
            Ser Ala Thr Val Ile Cys Arg Lys Asn Ala Ser Ile Ser Val Arg Ala
                            275                 280                 285
            Gln Asp Arg Tyr Tyr Ser Ser Ser Trp Ser Glu Trp Ala Ser Val Pro
                            290                 295                 300
            Cys Ser Gly Gly Gly Gly Gly Ser Arg Asn Leu Pro Val Ala Thr
            305                 310                 315                 320
            Pro Asp Pro Gly Met Phe Pro Cys Leu His His Ser Gln Asn Leu Leu
                            325                 330                 335
            Arg Ala Val Ser Asn Met Leu Gln Lys Ala Arg Gln Thr Leu Glu Phe
                            340                 345                 350
            Tyr Pro Cys Thr Ser Glu Glu Ile Asp His Glu Asp Ile Thr Lys Asp
                            355                 360                 365
            Lys Thr Ser Thr Val Glu Ala Cys Leu Pro Leu Glu Leu Thr Lys Asn
                            370                 375                 380
            Glu Ser Cys Leu Asn Ser Arg Glu Thr Ser Phe Ile Thr Asn Gly Ser
            385                 390                 395                 400
            Cys Leu Ala Ser Arg Lys Thr Ser Phe Met Met Ala Leu Cys Leu Ser
                            405                 410                 415
            Ser Ile Tyr Glu Asp Leu Lys Met Tyr Gln Val Glu Phe Lys Thr Met
                            420                 425                 430
            Asn Ala Lys Leu Leu Met Asp Pro Lys Arg Gln Ile Phe Leu Asp Gln
                            435                 440                 445
            Asn Met Leu Ala Val Ile Asp Glu Leu Met Gln Ala Leu Asn Phe Asn
                            450                 455                 460
            Ser Glu Thr Val Pro Gln Lys Ser Ser Leu Glu Glu Pro Asp Phe Tyr
            465                 470                 475                 480
            Lys Thr Lys Ile Lys Leu Cys Ile Leu Leu His Ala Phe Arg Ile Arg
                            485                 490                 495
            Ala Val Thr Ile Asp Arg Val Thr Ser Tyr Leu Asn Ala Ser Gly Gly
                            500                 505                 510
            Gly Gly Ser Gly Gly Gly Gly Ser Gly Gly Gly Gly Ser Gly Gly Gly
                            515                 520                 525
            Gly Ser Gly Gly Gly Gly Ser Glu Val Gln Leu Val Glu Ser Gly Gly
                            530                 535                 540
            Gly Leu Ile Gln Pro Gly Arg Ser Leu Arg Leu Ser Cys Ala Ala Ser
            545                 550                 555                 560
            Gly Ile Thr Phe Asp Asp Ala Val Met His Trp Val Arg Gln Ala Pro
                            565                 570                 575
            Gly Lys Gly Leu Glu Trp Val Ala Gly Ile Ser Ser Asn Ser Gly Tyr
                            580                 585                 590
            Ile Gly Tyr Ala Asp Ser Val Lys Gly Arg Phe Thr Ile Ser Arg Asp
                            595                 600                 605
            Asn Ala Lys Asn Ser Leu Tyr Leu Gln Met Asn Arg Leu Arg Ala Glu
                            610                 615                 620
            Asp Thr Ala Val Tyr Tyr Cys Val Lys Gly Leu Tyr Ser Asn Pro Arg
            625                 630                 635                 640
            Gly Gly Ala Phe Asp Ile Trp Gly Gln Gly Thr Met Val Thr Val Ser
                            645                 650                 655
```

```
Ser Ala Ser Thr Gly Gly Gly Ser Gly Gly Gly Ser Gly Gly
            660                 665                 670

Gly Gly Ser Val His Ser Ser Tyr Val Leu Thr Gln Pro Ser Val
        675                 680                 685

Ser Val Ala Pro Gly Gln Thr Ala Thr Ile Thr Cys Gly Gly Asn Asn
690                 695                 700

Ile Gly Thr Lys Ser Val His Trp Tyr Gln Gln Lys Pro Gly Gln Ala
705                 710                 715                 720

Pro Val Leu Val Val Tyr Ala Asp Ser Asp Arg Pro Ser Gly Ile Pro
                725                 730                 735

Glu Arg Val Ser Gly Ser Asn Ser Gly Asn Thr Ala Thr Leu Thr Ile
                740                 745                 750

Ser Arg Val Glu Ala Gly Asp Glu Ala Asp Tyr Tyr Cys Gln Val Trp
            755                 760                 765

Asp Ser Arg Ser Asp His Leu Trp Val Phe Gly Gly Gly Thr Lys Leu
770                 775                 780

Thr Val Leu Gly Gly Gly Gly Ser Gly Gly Gly Gly Ser Gly Gly
785                 790                 795                 800

Gly Gly Ser Gly Gly Gly Gly Ser Gly Gly Gly Gly Ser Asn Trp Val
            805                 810                 815

Asn Val Ile Ser Asp Leu Lys Lys Ile Glu Asp Leu Ile Gln Ser Met
            820                 825                 830

His Ile Asp Ala Thr Leu Tyr Thr Glu Ser Asp Val His Pro Ser Cys
            835                 840                 845

Lys Val Thr Ala Met Lys Cys Phe Leu Leu Glu Leu Gln Val Ile Ser
        850                 855                 860

Leu Glu Ser Gly Asp Ala Ser Ile His Asp Thr Val Glu Asn Leu Ile
865                 870                 875                 880

Ile Leu Ala Asn Asn Ser Leu Ser Ser Asn Gly Asn Val Thr Glu Ser
                885                 890                 895

Gly Cys Arg Glu Cys Glu Glu Leu Glu Glu Lys Asn Ile Lys Glu Phe
            900                 905                 910

Leu Gln Ser Phe Val His Ile Val Gln Met Phe Ile Asn Thr Ser
            915                 920                 925

<210> SEQ ID NO 225
<211> LENGTH: 927
<212> TYPE: PRT
<213> ORGANISM: Artificial Sequence
<220> FEATURE:
<223> OTHER INFORMATION: Human IL-12sc-A10m3-hIL15RA

<400> SEQUENCE: 225

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95
```

```
Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Gly Ser Arg Asn Leu Pro Val Ala Thr
305                 310                 315                 320

Pro Asp Pro Gly Met Phe Pro Cys Leu His His Ser Gln Asn Leu Leu
                325                 330                 335

Arg Ala Val Ser Asn Met Leu Gln Lys Ala Arg Gln Thr Leu Glu Phe
            340                 345                 350

Tyr Pro Cys Thr Ser Glu Glu Ile Asp His Glu Asp Ile Thr Lys Asp
        355                 360                 365

Lys Thr Ser Thr Val Glu Ala Cys Leu Pro Leu Glu Leu Thr Lys Asn
    370                 375                 380

Glu Ser Cys Leu Asn Ser Arg Glu Thr Ser Phe Ile Thr Asn Gly Ser
385                 390                 395                 400

Cys Leu Ala Ser Arg Lys Thr Ser Phe Met Met Ala Leu Cys Leu Ser
                405                 410                 415

Ser Ile Tyr Glu Asp Leu Lys Met Tyr Gln Val Glu Phe Lys Thr Met
            420                 425                 430

Asn Ala Lys Leu Leu Met Asp Pro Lys Arg Gln Ile Phe Leu Asp Gln
        435                 440                 445

Asn Met Leu Ala Val Ile Asp Glu Leu Met Gln Ala Leu Asn Phe Asn
    450                 455                 460

Ser Glu Thr Val Pro Gln Lys Ser Ser Leu Glu Glu Pro Asp Phe Tyr
465                 470                 475                 480

Lys Thr Lys Ile Lys Leu Cys Ile Leu Leu His Ala Phe Arg Ile Arg
                485                 490                 495

Ala Val Thr Ile Asp Arg Val Thr Ser Tyr Leu Asn Ala Ser Gly Gly
            500                 505                 510
```

```
Gly Gly Ser Gly Gly Gly Ser Gly Gly Gly Ser Gly Gly
            515                 520                 525

Gly Ser Gly Gly Gly Ser Glu Val Gln Leu Val Glu Ser Gly Gly
530                 535                 540

Gly Leu Ile Gln Pro Gly Arg Ser Leu Arg Leu Ser Cys Ala Ala Ser
545                 550                 555                 560

Gly Ile Thr Phe Asp Asp Ala Val Met His Trp Val Arg Gln Ala Pro
                565                 570                 575

Gly Lys Gly Leu Glu Trp Val Ala Gly Ile Ser Ser Asn Ser Gly Tyr
                580                 585                 590

Ile Gly Tyr Ala Asp Ser Val Lys Gly Arg Phe Thr Ile Ser Arg Asp
            595                 600                 605

Asn Ala Lys Asn Ser Leu Tyr Leu Gln Met Asn Arg Leu Arg Ala Glu
            610                 615                 620

Asp Thr Ala Val Tyr Tyr Cys Val Lys Gly Leu Tyr Ser Asn Pro Arg
625                 630                 635                 640

Gly Gly Ala Phe Asp Ile Trp Gly Gln Gly Thr Met Val Thr Val Ser
                645                 650                 655

Ser Ala Ser Thr Gly Gly Gly Gly Ser Gly Gly Gly Gly Ser Gly Gly
                660                 665                 670

Gly Gly Ser Val His Ser Ser Tyr Val Leu Thr Gln Pro Pro Ser Val
            675                 680                 685

Ser Val Ala Pro Gly Gln Thr Ala Thr Ile Thr Cys Gly Gly Asn Asn
            690                 695                 700

Ile Gly Thr Lys Ser Val His Trp Tyr Gln Gln Lys Pro Gly Gln Ala
705                 710                 715                 720

Pro Val Leu Val Val Tyr Ala Asp Ser Asp Arg Pro Ser Gly Ile Pro
                725                 730                 735

Glu Arg Val Ser Gly Ser Asn Ser Gly Asn Thr Ala Thr Leu Thr Ile
                740                 745                 750

Ser Arg Val Glu Ala Gly Asp Glu Ala Asp Tyr Tyr Cys Gln Val Trp
            755                 760                 765

Asp Ser Arg Ser Asp His Leu Trp Val Phe Gly Gly Gly Thr Lys Leu
            770                 775                 780

Thr Val Leu Gly Gly Gly Gly Ser Gly Gly Gly Gly Ser Gly Gly
785                 790                 795                 800

Gly Gly Ser Gly Gly Gly Ser Gly Gly Gly Gly Ser Asn Trp Val
                805                 810                 815

Asn Val Ile Ser Asp Leu Lys Lys Ile Glu Asp Leu Ile Gln Ser Met
            820                 825                 830

His Ile Asp Ala Thr Leu Tyr Thr Glu Ser Asp Val His Pro Ser Cys
            835                 840                 845

Lys Val Thr Ala Met Lys Cys Phe Leu Leu Glu Leu Gln Val Ile Ser
            850                 855                 860

Leu Glu Ser Gly Asp Ala Ser Ile His Asp Thr Val Glu Asn Leu Ile
865                 870                 875                 880

Ile Leu Ala Asn Asn Ser Leu Ser Ser Asn Gly Asn Val Thr Glu Ser
                885                 890                 895

Gly Cys Arg Glu Cys Glu Glu Leu Glu Glu Lys Asn Ile Lys Glu Phe
            900                 905                 910

Leu Gln Ser Phe Val His Ile Val Gln Met Phe Ile Ala Thr Ser
            915                 920                 925
```

<210> SEQ ID NO 226
<211> LENGTH: 131
<212> TYPE: PRT
<213> ORGANISM: Artificial Sequence
<220> FEATURE:
<223> OTHER INFORMATION: Variable heavy (vh) chain

<400> SEQUENCE: 226

```
Gln Val Gln Leu Val Glu Ser Gly Gly Gly Leu Val Lys Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Met Arg Tyr Cys Ser Gly Gly Ser Cys Tyr Pro Tyr Ala
            100                 105                 110

Tyr Tyr Met Asp Val Trp Gly Gln Gly Thr Thr Val Thr Val Ser Ser
        115                 120                 125

Ala Ser Thr
    130
```

<210> SEQ ID NO 227
<211> LENGTH: 115
<212> TYPE: PRT
<213> ORGANISM: Artificial Sequence
<220> FEATURE:
<223> OTHER INFORMATION: Variable light (vl) chain

<400> SEQUENCE: 227

```
Val His Ser Ser Ser Glu Leu Thr Gln Asp Pro Ala Val Ser Val Ala
1               5                   10                  15

Leu Gly Gln Thr Val Arg Ile Thr Cys Gln Gly Asp Ser Leu Arg Ser
            20                  25                  30

Tyr Tyr Ala Ser Trp Tyr Gln Gln Lys Pro Gly Gln Ala Pro Val Leu
        35                  40                  45

Val Ile Tyr Gly Lys Asn Asn Arg Pro Ser Gly Ile Pro Asp Arg Phe
    50                  55                  60

Ser Gly Ser Ser Ser Gly Asn Thr Ala Ser Leu Thr Ile Thr Gly Ala
65                  70                  75                  80

Gln Ala Glu Asp Glu Ala Asp Tyr Tyr Cys Asn Ser Arg Asp Ser Ser
                85                  90                  95

Gly Asn Leu Val Val Phe Gly Gly Gly Thr Lys Leu Thr Val Leu Gly
            100                 105                 110

Leu Gly Gly
    115
```

<210> SEQ ID NO 228
<211> LENGTH: 261
<212> TYPE: PRT
<213> ORGANISM: Artificial Sequence
<220> FEATURE:
<223> OTHER INFORMATION: scFv

<400> SEQUENCE: 228

Gln Val Gln Leu Val Glu Ser Gly Gly Gly Leu Val Lys Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Met Arg Tyr Cys Ser Gly Gly Ser Cys Tyr Pro Tyr Ala
            100                 105                 110

Tyr Tyr Met Asp Val Trp Gly Gln Gly Thr Thr Val Thr Val Ser Ser
        115                 120                 125

Ala Ser Thr Gly Gly Gly Gly Ser Gly Gly Gly Ser Gly Gly Gly
    130                 135                 140

Gly Ser Val His Ser Ser Glu Leu Thr Gln Asp Pro Ala Val Ser
145                 150                 155                 160

Val Ala Leu Gly Gln Thr Val Arg Ile Thr Cys Gln Gly Asp Ser Leu
                165                 170                 175

Arg Ser Tyr Tyr Ala Ser Trp Tyr Gln Gln Lys Pro Gly Gln Ala Pro
            180                 185                 190

Val Leu Val Ile Tyr Gly Lys Asn Asn Arg Pro Ser Gly Ile Pro Asp
        195                 200                 205

Arg Phe Ser Gly Ser Ser Ser Gly Asn Thr Ala Ser Leu Thr Ile Thr
    210                 215                 220

Gly Ala Gln Ala Glu Asp Glu Ala Asp Tyr Tyr Cys Asn Ser Arg Asp
225                 230                 235                 240

Ser Ser Gly Asn Leu Val Val Phe Gly Gly Gly Thr Lys Leu Thr Val
                245                 250                 255

Leu Gly Leu Gly Gly
            260

<210> SEQ ID NO 229
<211> LENGTH: 125
<212> TYPE: PRT
<213> ORGANISM: Artificial Sequence
<220> FEATURE:
<223> OTHER INFORMATION: Variable heavy (vh) chain

<400> SEQUENCE: 229

Val Gln Leu Val Glu Ser Gly Gly Gly Leu Val Gln Pro Gly Gly Ser
1               5                   10                  15

Leu Arg Leu Ser Cys Ala Ala Ser Gly Phe Thr Phe Ser Ser Tyr Ala
            20                  25                  30

Ile Ser Trp Val Arg Gln Ala Pro Gly Lys Gly Leu Glu Trp Val Ser
        35                  40                  45

Ala Ile Ser Gly Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Ala Tyr Tyr Cys Ala
                85                  90                  95

-continued

Lys Glu Ile Ser Gly Ser Tyr Leu Gly Leu Val Ala Phe Asp Ile Trp
                100                 105                 110

Gly Gln Gly Thr Met Val Thr Val Ser Ser Ala Ser Thr
            115                 120                 125

<210> SEQ ID NO 230
<211> LENGTH: 114
<212> TYPE: PRT
<213> ORGANISM: Artificial Sequence
<220> FEATURE:
<223> OTHER INFORMATION: Variable light (vl) chain

<400> SEQUENCE: 230

Val His Ser Ser Tyr Val Leu Thr Gln Pro Leu Ser Val Ser Val Ala
1               5                   10                  15

Pro Gly Gln Thr Ala Arg Met Thr Cys Gly Gly Asp Asn Val Gly Ala
            20                  25                  30

Lys Ser Val His Trp Tyr Gln Gln Lys Pro Gly Gln Ala Pro Val Leu
        35                  40                  45

Leu Ile Tyr Tyr Asp His Asp Arg Pro Ser Gly Ile Pro Glu Arg Phe
    50                  55                  60

Ser Gly Ser Asn Ser Gly Asn Thr Ala Thr Leu Thr Ile Thr Arg Val
65                  70                  75                  80

Glu Ala Gly Asp Glu Ala Asp Tyr Tyr Cys Gln Val Trp Asp Pro Ser
                85                  90                  95

Ser Asp Val Val Phe Gly Gly Gly Thr Gln Leu Thr Val Leu Gly Leu
            100                 105                 110

Gly Gly

<210> SEQ ID NO 231
<211> LENGTH: 255
<212> TYPE: PRT
<213> ORGANISM: Artificial Sequence
<220> FEATURE:
<223> OTHER INFORMATION: scFv

<400> SEQUENCE: 231

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Ile Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Ala Tyr Tyr Cys
                85                  90                  95

Ala Lys Glu Ile Ser Gly Ser Tyr Leu Gly Leu Val Ala Phe Asp Ile
            100                 105                 110

Trp Gly Gln Gly Thr Met Val Thr Val Ser Ser Ala Ser Thr Gly Gly
        115                 120                 125

Gly Gly Ser Gly Gly Gly Gly Ser Gly Gly Gly Gly Ser Val His Ser
    130                 135                 140

Ser Tyr Val Leu Thr Gln Pro Leu Ser Val Ser Val Ala Pro Gly Gln
145                 150                 155                 160

```
Thr Ala Arg Met Thr Cys Gly Gly Asp Asn Val Gly Ala Lys Ser Val
                165                 170                 175

His Trp Tyr Gln Gln Lys Pro Gly Gln Ala Pro Val Leu Leu Ile Tyr
            180                 185                 190

Tyr Asp His Asp Arg Pro Ser Gly Ile Pro Glu Arg Phe Ser Gly Ser
        195                 200                 205

Asn Ser Gly Asn Thr Ala Thr Leu Thr Ile Thr Arg Val Glu Ala Gly
    210                 215                 220

Asp Glu Ala Asp Tyr Tyr Cys Gln Val Trp Asp Ser Ser Asp Val
225                 230                 235                 240

Val Phe Gly Gly Gly Thr Gln Leu Thr Val Leu Gly Leu Gly Gly
                245                 250                 255
```

<210> SEQ ID NO 232
<211> LENGTH: 261
<212> TYPE: PRT
<213> ORGANISM: Artificial Sequence
<220> FEATURE:
<223> OTHER INFORMATION: 4H7m scFv

<400> SEQUENCE: 232

```
Gln Val Gln Leu Val Glu Ser Gly Gly Gly Leu Val Lys Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Met Arg Tyr Cys Ser Gly Gly Ser Cys Tyr Pro Tyr Ala
            100                 105                 110

Tyr Tyr Met Asp Val Trp Gly Gln Gly Thr Thr Val Thr Val Ser Ser
        115                 120                 125

Ala Ser Thr Gly Gly Gly Ser Gly Gly Gly Ser Gly Gly Gly
    130                 135                 140

Gly Ser Val His Ser Ser Glu Leu Thr Gln Asp Pro Ala Val Ser
145                 150                 155                 160

Val Ala Leu Gly Gln Thr Val Arg Ile Thr Cys Gln Gly Asp Ser Leu
                165                 170                 175

Arg Ser Tyr Tyr Ala Ser Trp Tyr Gln Gln Lys Pro Gly Gln Ala Pro
            180                 185                 190

Val Leu Val Ile Tyr Gly Lys Asn Asn Arg Pro Ser Gly Ile Pro Asp
        195                 200                 205

Arg Phe Ser Gly Ser Ser Ser Gly Asn Thr Ala Ser Leu Thr Ile Thr
    210                 215                 220

Gly Ala Gln Ala Glu Asp Glu Ala Asp Tyr Tyr Cys Asn Ser Arg Asp
225                 230                 235                 240

Ser Ser Gly Asn Leu Val Val Phe Gly Gly Gly Thr Lys Leu Thr Val
                245                 250                 255

Leu Gly Leu Gly Gly
            260
```

<210> SEQ ID NO 233
<211> LENGTH: 537
<212> TYPE: PRT
<213> ORGANISM: Artificial Sequence
<220> FEATURE:
<223> OTHER INFORMATION: 4H7m scFV-A6m

<400> SEQUENCE: 233

```
Gln Val Gln Leu Val Glu Ser Gly Gly Gly Leu Val Lys Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Met Arg Tyr Cys Ser Gly Ser Cys Tyr Pro Tyr Ala
            100                 105                 110

Tyr Tyr Met Asp Val Trp Gly Gln Gly Thr Thr Val Thr Val Ser Ser
        115                 120                 125

Ala Ser Thr Gly Gly Gly Gly Ser Gly Gly Gly Gly Ser Gly Gly Gly
    130                 135                 140

Gly Ser Val His Ser Ser Glu Leu Thr Gln Asp Pro Ala Val Ser
145                 150                 155                 160

Val Ala Leu Gly Gln Thr Val Arg Ile Thr Cys Gln Gly Asp Ser Leu
                165                 170                 175

Arg Ser Tyr Tyr Ala Ser Trp Tyr Gln Gln Lys Pro Gly Gln Ala Pro
            180                 185                 190

Val Leu Val Ile Tyr Gly Lys Asn Asn Arg Pro Ser Gly Ile Pro Asp
        195                 200                 205

Arg Phe Ser Gly Ser Ser Ser Gly Asn Thr Ala Ser Leu Thr Ile Thr
    210                 215                 220

Gly Ala Gln Ala Glu Asp Glu Ala Asp Tyr Tyr Cys Asn Ser Arg Asp
225                 230                 235                 240

Ser Ser Gly Asn Leu Val Val Phe Gly Gly Gly Thr Lys Leu Thr Val
                245                 250                 255

Leu Gly Leu Gly Gly Gly Gly Gly Ser Gly Gly Gly Gly Ser Gly
            260                 265                 270

Gly Gly Gly Ser Gly Gly Gly Gly Ser Gly Gly Gly Gly Ser Glu Val
        275                 280                 285

Gln Leu Val Gln Ser Gly Ala Glu Val Lys Lys Pro Gly Glu Ser Leu
    290                 295                 300

Lys Ile Ser Cys Lys Gly Ser Gly Tyr Ser Phe Asn Ser Tyr Trp Ile
305                 310                 315                 320

Gly Trp Val Arg Gln Met Pro Gly Lys Gly Leu Glu Trp Met Gly Ile
                325                 330                 335

Ile Tyr Pro Gly Asp Ser Asp Thr Arg Tyr Ser Pro Ser Phe Gln Gly
            340                 345                 350

Gln Val Thr Phe Ser Val Asp Lys Ser Ile Asn Thr Ala Tyr Leu Gln
        355                 360                 365
```

-continued

```
Trp Ser Ser Leu Lys Ala Ser Asp Ala Ala Met Tyr Tyr Cys Ala Arg
            370                 375                 380

Gln Arg Trp Gly Ser Ser Phe Asp Ala Trp Gly Gln Gly Thr Leu
385                 390                 395                 400

Val Thr Val Ser Ser Ala Ser Thr Gly Gly Gly Ser Gly Gly Gly
                405                 410                 415

Gly Ser Gly Gly Gly Gly Ser Val His Ser Gln Ser Val Leu Thr Gln
            420                 425                 430

Pro Pro Ser Val Ser Ala Ala Pro Gly Gln Lys Val Thr Ile Ser Cys
            435                 440                 445

Ser Gly Ser Ser Ser Asn Ile Gly Asn Asn Tyr Val Ser Trp Tyr Gln
    450                 455                 460

Gln Leu Pro Gly Thr Ala Pro Lys Leu Leu Ile Tyr Glu Asn Asn Lys
465                 470                 475                 480

Arg Pro Ser Gly Ile Pro Asp Arg Phe Ser Gly Ser Lys Ser Gly Thr
                485                 490                 495

Ser Ala Thr Leu Gly Ile Thr Gly Leu Gln Thr Gly Asp Glu Ala Asp
            500                 505                 510

Tyr Tyr Cys Gly Thr Trp Asp Ser Ser Leu Ser Ala Gly Val Phe Gly
            515                 520                 525

Gly Gly Thr Gln Leu Thr Val Leu Gly
    530                 535
```

<210> SEQ ID NO 234
<211> LENGTH: 255
<212> TYPE: PRT
<213> ORGANISM: Artificial Sequence
<220> FEATURE:
<223> OTHER INFORMATION: 4D9m scFV

<400> SEQUENCE: 234

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Ile Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ala Tyr Tyr Cys
                85                  90                  95

Ala Lys Glu Ile Ser Gly Ser Tyr Leu Gly Leu Val Ala Phe Asp Ile
            100                 105                 110

Trp Gly Gln Gly Thr Met Val Thr Val Ser Ser Ala Ser Thr Gly Gly
        115                 120                 125

Gly Gly Ser Gly Gly Gly Gly Ser Gly Gly Gly Gly Ser Val His Ser
    130                 135                 140

Ser Tyr Val Leu Thr Gln Pro Leu Ser Val Ser Val Ala Pro Gly Gln
145                 150                 155                 160

Thr Ala Arg Met Thr Cys Gly Gly Asp Asn Val Gly Ala Lys Ser Val
                165                 170                 175

His Trp Tyr Gln Gln Lys Pro Gly Gln Ala Pro Val Leu Leu Ile Tyr
            180                 185                 190
```

Tyr Asp His Asp Arg Pro Ser Gly Ile Pro Glu Arg Phe Ser Gly Ser
            195                 200                 205

Asn Ser Gly Asn Thr Ala Thr Leu Thr Ile Thr Arg Val Glu Ala Gly
    210                 215                 220

Asp Glu Ala Asp Tyr Tyr Cys Gln Val Trp Asp Pro Ser Ser Asp Val
225                 230                 235                 240

Val Phe Gly Gly Gly Thr Gln Leu Thr Val Leu Gly Leu Gly
                245                 250                 255

<210> SEQ ID NO 235
<211> LENGTH: 126
<212> TYPE: PRT
<213> ORGANISM: Artificial Sequence
<220> FEATURE:
<223> OTHER INFORMATION: VH

<400> SEQUENCE: 235

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Ile Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ala Tyr Tyr Cys
                85                  90                  95

Ala Lys Glu Ile Ser Gly Ser Tyr Leu Gly Leu Val Ala Phe Asp Ile
            100                 105                 110

Trp Gly Gln Gly Thr Met Val Thr Val Ser Ser Ala Ser Thr
        115                 120                 125

<210> SEQ ID NO 236
<211> LENGTH: 8
<212> TYPE: PRT
<213> ORGANISM: Artificial Sequence
<220> FEATURE:
<223> OTHER INFORMATION: vhCDR1

<400> SEQUENCE: 236

Gly Phe Thr Phe Ser Ser Tyr Ala
1               5

<210> SEQ ID NO 237
<211> LENGTH: 7
<212> TYPE: PRT
<213> ORGANISM: Artificial Sequence
<220> FEATURE:
<223> OTHER INFORMATION: vhCDR2

<400> SEQUENCE: 237

Ser Gly Ser Gly Gly Ser Thr
1               5

<210> SEQ ID NO 238
<211> LENGTH: 24
<212> TYPE: PRT
<213> ORGANISM: Artificial Sequence
<220> FEATURE:

<223> OTHER INFORMATION: vhCDR3

<400> SEQUENCE: 238

Ala Glu Asp Thr Ala Ala Tyr Tyr Cys Ala Lys Glu Ile Ser Gly Ser
1               5                   10                  15

Tyr Leu Gly Leu Val Ala Phe Asp
            20

<210> SEQ ID NO 239
<211> LENGTH: 114
<212> TYPE: PRT
<213> ORGANISM: Artificial Sequence
<220> FEATURE:
<223> OTHER INFORMATION: VL

<400> SEQUENCE: 239

Val His Ser Ser Tyr Val Leu Thr Gln Pro Leu Ser Val Ser Val Ala
1               5                   10                  15

Pro Gly Gln Thr Ala Arg Met Thr Cys Gly Gly Asp Asn Val Gly Ala
            20                  25                  30

Lys Ser Val His Trp Tyr Gln Gln Lys Pro Gly Gln Ala Pro Val Leu
        35                  40                  45

Leu Ile Tyr Tyr Asp His Asp Arg Pro Ser Gly Ile Pro Glu Arg Phe
    50                  55                  60

Ser Gly Ser Asn Ser Gly Asn Thr Ala Thr Leu Thr Ile Thr Arg Val
65                  70                  75                  80

Glu Ala Gly Asp Glu Ala Asp Tyr Tyr Cys Gln Val Trp Asp Pro Ser
                85                  90                  95

Ser Asp Val Val Phe Gly Gly Gly Thr Gln Leu Thr Val Leu Gly Leu
            100                 105                 110

Gly Gly

<210> SEQ ID NO 240
<211> LENGTH: 6
<212> TYPE: PRT
<213> ORGANISM: Artificial Sequence
<220> FEATURE:
<223> OTHER INFORMATION: vlCDR1

<400> SEQUENCE: 240

Asn Val Gly Ala Lys Ser
1               5

<210> SEQ ID NO 241
<211> LENGTH: 3
<212> TYPE: PRT
<213> ORGANISM: Artificial Sequence
<220> FEATURE:
<223> OTHER INFORMATION: vlCDR2

<400> SEQUENCE: 241

Tyr Asp His
1

<210> SEQ ID NO 242
<211> LENGTH: 10
<212> TYPE: PRT
<213> ORGANISM: Artificial Sequence
<220> FEATURE:
<223> OTHER INFORMATION: vlCDR3

<400> SEQUENCE: 242

Gln Val Trp Asp Pro Ser Ser Asp Val Val
1               5                   10

<210> SEQ ID NO 243
<211> LENGTH: 531
<212> TYPE: PRT
<213> ORGANISM: Artificial Sequence
<220> FEATURE:
<223> OTHER INFORMATION: 4D9m scFV-A6m

<400> SEQUENCE: 243

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Ile Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ala Tyr Tyr Cys
                85                  90                  95

Ala Lys Glu Ile Ser Gly Ser Tyr Leu Gly Leu Val Ala Phe Asp Ile
            100                 105                 110

Trp Gly Gln Gly Thr Met Val Thr Val Ser Ser Ala Ser Thr Gly Gly
        115                 120                 125

Gly Gly Ser Gly Gly Gly Ser Gly Gly Gly Ser Val His Ser
    130                 135                 140

Ser Tyr Val Leu Thr Gln Pro Leu Ser Val Ser Val Ala Pro Gly Gln
145                 150                 155                 160

Thr Ala Arg Met Thr Cys Gly Gly Asp Asn Val Gly Ala Lys Ser Val
                165                 170                 175

His Trp Tyr Gln Gln Lys Pro Gly Gln Ala Pro Val Leu Leu Ile Tyr
            180                 185                 190

Tyr Asp His Asp Arg Pro Ser Gly Ile Pro Glu Arg Phe Ser Gly Ser
        195                 200                 205

Asn Ser Gly Asn Thr Ala Thr Leu Thr Ile Thr Arg Val Glu Ala Gly
    210                 215                 220

Asp Glu Ala Asp Tyr Tyr Cys Gln Val Trp Asp Pro Ser Ser Asp Val
225                 230                 235                 240

Val Phe Gly Gly Gly Thr Gln Leu Thr Val Leu Gly Leu Gly Gly Gly
                245                 250                 255

Gly Gly Gly Ser Gly Gly Gly Ser Gly Gly Gly Ser Gly Gly
            260                 265                 270

Gly Gly Ser Gly Gly Gly Gly Ser Glu Val Gln Leu Val Gln Ser Gly
        275                 280                 285

Ala Glu Val Lys Lys Pro Gly Glu Ser Leu Lys Ile Ser Cys Lys Gly
    290                 295                 300

Ser Gly Tyr Ser Phe Asn Ser Tyr Trp Ile Gly Trp Val Arg Gln Met
305                 310                 315                 320

Pro Gly Lys Gly Leu Glu Trp Met Gly Ile Ile Tyr Pro Gly Asp Ser
                325                 330                 335

Asp Thr Arg Tyr Ser Pro Ser Phe Gln Gly Gln Val Thr Phe Ser Val
            340                 345                 350

```
Asp Lys Ser Ile Asn Thr Ala Tyr Leu Gln Trp Ser Leu Lys Ala
        355                 360                 365

Ser Asp Ala Ala Met Tyr Tyr Cys Ala Arg Gln Arg Trp Gly Ser Ser
    370                 375                 380

Ser Phe Asp Ala Trp Gly Gln Gly Thr Leu Val Thr Val Ser Ser Ala
385                 390                 395                 400

Ser Thr Gly Gly Gly Gly Ser Gly Gly Gly Ser Gly Gly Gly Gly
                405                 410                 415

Ser Val His Ser Gln Ser Val Leu Thr Gln Pro Pro Ser Val Ser Ala
        420                 425                 430

Ala Pro Gly Gln Lys Val Thr Ile Ser Cys Ser Gly Ser Ser Ser Asn
    435                 440                 445

Ile Gly Asn Asn Tyr Val Ser Trp Tyr Gln Gln Leu Pro Gly Thr Ala
    450                 455                 460

Pro Lys Leu Leu Ile Tyr Glu Asn Asn Lys Arg Pro Ser Gly Ile Pro
465                 470                 475                 480

Asp Arg Phe Ser Gly Ser Lys Ser Gly Thr Ser Ala Thr Leu Gly Ile
                485                 490                 495

Thr Gly Leu Gln Thr Gly Asp Glu Ala Asp Tyr Tyr Cys Gly Thr Trp
        500                 505                 510

Asp Ser Ser Leu Ser Ala Gly Val Phe Gly Gly Gly Thr Gln Leu Thr
            515                 520                 525

Val Leu Gly
    530

<210> SEQ ID NO 244
<211> LENGTH: 15
<212> TYPE: PRT
<213> ORGANISM: Artificial Sequence
<220> FEATURE:
<223> OTHER INFORMATION: Gly-Ser 15

<400> SEQUENCE: 244

Gly Gly Gly Gly Ser Gly Gly Gly Ser Gly Gly Gly Gly Ser
1               5                   10                  15

<210> SEQ ID NO 245
<211> LENGTH: 18
<212> TYPE: PRT
<213> ORGANISM: Artificial Sequence
<220> FEATURE:
<223> OTHER INFORMATION: Whitlow linker

<400> SEQUENCE: 245

Gly Ser Thr Ser Gly Ser Gly Lys Pro Gly Ser Gly Glu Gly Ser Thr
1               5                   10                  15

Lys Gly

<210> SEQ ID NO 246
<211> LENGTH: 14
<212> TYPE: PRT
<213> ORGANISM: Artificial Sequence
<220> FEATURE:
<223> OTHER INFORMATION: 6paxA_1(+A)

<400> SEQUENCE: 246

Ile Arg Pro Arg Ala Ile Gly Gly Ser Lys Pro Arg Val Ala
1               5                   10

<210> SEQ ID NO 247
```

<211> LENGTH: 15
<212> TYPE: PRT
<213> ORGANISM: Artificial Sequence
<220> FEATURE:
<223> OTHER INFORMATION: +B

<400> SEQUENCE: 247

Gly Lys Gly Gly Ser Gly Lys Gly Gly Ser Gly Lys Gly Gly Ser
1               5                   10                  15

<210> SEQ ID NO 248
<211> LENGTH: 15
<212> TYPE: PRT
<213> ORGANISM: Artificial Sequence
<220> FEATURE:
<223> OTHER INFORMATION: +C

<400> SEQUENCE: 248

Gly Gly Lys Gly Ser Gly Gly Lys Gly Ser Gly Gly Lys Gly Ser
1               5                   10                  15

<210> SEQ ID NO 249
<211> LENGTH: 15
<212> TYPE: PRT
<213> ORGANISM: Artificial Sequence
<220> FEATURE:
<223> OTHER INFORMATION: +D

<400> SEQUENCE: 249

Gly Gly Gly Lys Ser Gly Gly Gly Lys Ser Gly Gly Gly Lys Ser
1               5                   10                  15

<210> SEQ ID NO 250
<211> LENGTH: 15
<212> TYPE: PRT
<213> ORGANISM: Artificial Sequence
<220> FEATURE:
<223> OTHER INFORMATION: +E

<400> SEQUENCE: 250

Gly Lys Gly Lys Ser Gly Lys Gly Lys Ser Gly Lys Gly Lys Ser
1               5                   10                  15

<210> SEQ ID NO 251
<211> LENGTH: 15
<212> TYPE: PRT
<213> ORGANISM: Artificial Sequence
<220> FEATURE:
<223> OTHER INFORMATION: +F

<400> SEQUENCE: 251

Gly Gly Gly Lys Ser Gly Gly Lys Gly Ser Gly Lys Gly Gly Ser
1               5                   10                  15

<210> SEQ ID NO 252
<211> LENGTH: 15
<212> TYPE: PRT
<213> ORGANISM: Artificial Sequence
<220> FEATURE:
<223> OTHER INFORMATION: +G

<400> SEQUENCE: 252

Gly Lys Pro Gly Ser Gly Lys Pro Gly Ser Gly Lys Pro Gly Ser
1               5                   10                  15

<210> SEQ ID NO 253
<211> LENGTH: 20

```
<212> TYPE: PRT
<213> ORGANISM: Artificial Sequence
<220> FEATURE:
<223> OTHER INFORMATION: +H

<400> SEQUENCE: 253

Gly Lys Pro Gly Ser Gly Lys Pro Gly Ser Gly Lys Pro Gly Ser Gly
1               5                   10                  15

Lys Pro Gly Ser
            20

<210> SEQ ID NO 254
<211> LENGTH: 20
<212> TYPE: PRT
<213> ORGANISM: Artificial Sequence
<220> FEATURE:
<223> OTHER INFORMATION: +I

<400> SEQUENCE: 254

Gly Lys Gly Lys Ser Gly Lys Gly Lys Ser Gly Lys Gly Lys Ser Gly
1               5                   10                  15

Lys Gly Lys Ser
            20

<210> SEQ ID NO 255
<211> LENGTH: 20
<212> TYPE: PRT
<213> ORGANISM: Artificial Sequence
<220> FEATURE:
<223> OTHER INFORMATION: Gly-Ser 15

<400> SEQUENCE: 255

Gly Gly Gly Gly Ser Gly Gly Gly Gly Ser Gly Gly Gly Gly Ser Gly
1               5                   10                  15

Gly Gly Gly Ser
            20

<210> SEQ ID NO 256
<211> LENGTH: 14
<212> TYPE: PRT
<213> ORGANISM: Artificial Sequence
<220> FEATURE:
<223> OTHER INFORMATION: 3hsc_2(-A)

<400> SEQUENCE: 256

Ser Thr Ala Gly Asp Thr His Leu Gly Gly Glu Asp Phe Asp
1               5                   10

<210> SEQ ID NO 257
<211> LENGTH: 15
<212> TYPE: PRT
<213> ORGANISM: Artificial Sequence
<220> FEATURE:
<223> OTHER INFORMATION: -B

<400> SEQUENCE: 257

Gly Glu Gly Gly Ser Gly Glu Gly Gly Ser Gly Glu Gly Gly Ser
1               5                   10                  15

<210> SEQ ID NO 258
<211> LENGTH: 15
<212> TYPE: PRT
<213> ORGANISM: Artificial Sequence
<220> FEATURE:
<223> OTHER INFORMATION: -C
```

```
<400> SEQUENCE: 258

Gly Gly Glu Gly Ser Gly Gly Glu Gly Ser Gly Gly Glu Gly Ser
1               5                   10                  15

<210> SEQ ID NO 259
<211> LENGTH: 15
<212> TYPE: PRT
<213> ORGANISM: Artificial Sequence
<220> FEATURE:
<223> OTHER INFORMATION: -D

<400> SEQUENCE: 259

Gly Gly Gly Glu Ser Gly Gly Gly Glu Ser Gly Gly Gly Glu Ser
1               5                   10                  15

<210> SEQ ID NO 260
<211> LENGTH: 15
<212> TYPE: PRT
<213> ORGANISM: Artificial Sequence
<220> FEATURE:
<223> OTHER INFORMATION: -E

<400> SEQUENCE: 260

Gly Glu Gly Glu Ser Gly Glu Gly Glu Ser Gly Glu Gly Glu Ser
1               5                   10                  15

<210> SEQ ID NO 261
<211> LENGTH: 15
<212> TYPE: PRT
<213> ORGANISM: Artificial Sequence
<220> FEATURE:
<223> OTHER INFORMATION: -F

<400> SEQUENCE: 261

Gly Gly Gly Glu Ser Gly Gly Glu Gly Ser Gly Glu Gly Gly Ser
1               5                   10                  15

<210> SEQ ID NO 262
<211> LENGTH: 20
<212> TYPE: PRT
<213> ORGANISM: Artificial Sequence
<220> FEATURE:
<223> OTHER INFORMATION: -G

<400> SEQUENCE: 262

Gly Glu Gly Glu Ser Gly Glu Gly Glu Ser Gly Glu Gly Glu Ser Gly
1               5                   10                  15

Glu Gly Glu Ser
            20

<210> SEQ ID NO 263
<211> LENGTH: 15
<212> TYPE: PRT
<213> ORGANISM: Artificial Sequence
<220> FEATURE:
<223> OTHER INFORMATION: Additional linkers

<400> SEQUENCE: 263

Gly Gly Gly Gly Ser Gly Gly Gly Gly Ser Gly Gly Gly Gly Ser
1               5                   10                  15

<210> SEQ ID NO 264
<211> LENGTH: 20
<212> TYPE: PRT
<213> ORGANISM: Artificial Sequence
<220> FEATURE:
```

```
<223> OTHER INFORMATION: Additional linker

<400> SEQUENCE: 264

Gly Gly Gly Gly Ser Gly Gly Gly Ser Gly Gly Gly Ser Gly
1               5                   10                  15

Gly Gly Gly Ser
            20

<210> SEQ ID NO 265
<211> LENGTH: 18
<212> TYPE: PRT
<213> ORGANISM: Artificial Sequence
<220> FEATURE:
<223> OTHER INFORMATION: Additional linker

<400> SEQUENCE: 265

Gly Ser Thr Ser Gly Ser Gly Lys Pro Gly Ser Gly Glu Gly Ser Thr
1               5                   10                  15

Lys Gly

<210> SEQ ID NO 266
<211> LENGTH: 19
<212> TYPE: PRT
<213> ORGANISM: Artificial Sequence
<220> FEATURE:
<223> OTHER INFORMATION: Additional linker

<400> SEQUENCE: 266

Pro Arg Gly Ala Ser Lys Ser Gly Ser Ala Ser Gln Thr Gly Ser Ala
1               5                   10                  15

Pro Gly Ser

<210> SEQ ID NO 267
<211> LENGTH: 19
<212> TYPE: PRT
<213> ORGANISM: Artificial Sequence
<220> FEATURE:
<223> OTHER INFORMATION: Additional linker

<400> SEQUENCE: 267

Gly Thr Ala Ala Ala Gly Ala Gly Ala Ala Gly Gly Ala Ala Ala Gly
1               5                   10                  15

Ala Ala Gly

<210> SEQ ID NO 268
<211> LENGTH: 19
<212> TYPE: PRT
<213> ORGANISM: Artificial Sequence
<220> FEATURE:
<223> OTHER INFORMATION: Artificial linker

<400> SEQUENCE: 268

Gly Thr Ser Gly Ser Ser Gly Ser Gly Ser Gly Gly Ser Gly Ser Gly
1               5                   10                  15

Gly Gly Gly

<210> SEQ ID NO 269
<211> LENGTH: 20
<212> TYPE: PRT
<213> ORGANISM: Artificial Sequence
<220> FEATURE:
<223> OTHER INFORMATION: Additional linker

<400> SEQUENCE: 269
```

```
Gly Lys Pro Gly Ser Gly Lys Pro Gly Ser Gly Lys Pro Gly Ser Gly
1               5                   10                  15

Lys Pro Gly Ser
            20

<210> SEQ ID NO 270
<211> LENGTH: 7
<212> TYPE: PRT
<213> ORGANISM: Artificial Sequence
<220> FEATURE:
<223> OTHER INFORMATION: Additional linker

<400> SEQUENCE: 270

Gly Gly Gly Gly Gly Gly Ser
1               5

<210> SEQ ID NO 271
<211> LENGTH: 133
<212> TYPE: PRT
<213> ORGANISM: Artificial Sequence
<220> FEATURE:
<223> OTHER INFORMATION: Human hIL-2

<400> SEQUENCE: 271

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 272
<211> LENGTH: 411
<212> TYPE: PRT
<213> ORGANISM: Artificial Sequence
<220> FEATURE:
<223> OTHER INFORMATION: Human hIL-2-A10m3

<400> SEQUENCE: 272

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60
```

```
Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Gly Gly Gly Ser Gly
    130                 135                 140

Gly Gly Gly Ser Gly Gly Gly Ser Gly Gly Gly Ser Glu Val
145                 150                 155                 160

Gln Leu Val Glu Ser Gly Gly Leu Ile Gln Pro Gly Arg Ser Leu
                165                 170                 175

Arg Leu Ser Cys Ala Ala Ser Gly Ile Thr Phe Asp Asp Ala Val Met
                180                 185                 190

His Trp Val Arg Gln Ala Pro Gly Lys Gly Leu Glu Trp Val Ala Gly
        195                 200                 205

Ile Ser Ser Asn Ser Gly Tyr Ile Gly Tyr Ala Asp Ser Val Lys Gly
    210                 215                 220

Arg Phe Thr Ile Ser Arg Asp Asn Ala Lys Asn Ser Leu Tyr Leu Gln
225                 230                 235                 240

Met Asn Arg Leu Arg Ala Glu Asp Thr Ala Val Tyr Tyr Cys Val Lys
                245                 250                 255

Gly Leu Tyr Ser Asn Pro Arg Gly Gly Ala Phe Asp Ile Trp Gly Gln
                260                 265                 270

Gly Thr Met Val Thr Val Ser Ser Ala Ser Thr Gly Gly Gly Gly Ser
        275                 280                 285

Gly Gly Gly Gly Ser Gly Gly Gly Ser Val His Ser Ser Tyr Val
        290                 295                 300

Leu Thr Gln Pro Pro Ser Val Ser Val Ala Pro Gly Gln Thr Ala Thr
305                 310                 315                 320

Ile Thr Cys Gly Gly Asn Asn Ile Gly Thr Lys Ser Val His Trp Tyr
        325                 330                 335

Gln Gln Lys Pro Gly Gln Ala Pro Val Leu Val Val Tyr Ala Asp Ser
            340                 345                 350

Asp Arg Pro Ser Gly Ile Pro Glu Arg Val Ser Gly Ser Asn Ser Gly
                355                 360                 365

Asn Thr Ala Thr Leu Thr Ile Ser Arg Val Glu Ala Gly Asp Glu Ala
        370                 375                 380

Asp Tyr Tyr Cys Gln Val Trp Asp Ser Arg Ser Asp His Leu Trp Val
385                 390                 395                 400

Phe Gly Gly Gly Thr Lys Leu Thr Val Leu Gly
                405                 410

<210> SEQ ID NO 273
<211> LENGTH: 149
<212> TYPE: PRT
<213> ORGANISM: Artificial Sequence
<220> FEATURE:
<223> OTHER INFORMATION: Mouse mIL-2

<400> SEQUENCE: 273

Ala Pro Thr Ser Ser Ser Thr Ser Ser Ser Thr Ala Glu Ala Gln Gln
 1               5                  10                  15
```

```
Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
             35                  40                  45

Lys Leu Pro Arg Met Leu Thr Phe Lys Phe Tyr Leu Pro Lys Gln Ala
 50                      55                  60

Thr Glu Leu Lys Asp Leu Gln Cys Leu Glu Asp Glu Leu Gly Pro Leu
 65                  70                  75                  80

Arg His Val Leu Asp Leu Thr Gln Ser Lys Ser Phe Gln Leu Glu Asp
                 85                  90                  95

Ala Glu Asn Phe Ile Ser Asn Ile Arg Val Thr Val Val Lys Leu Lys
                100                 105                 110

Gly Ser Asp Asn Thr Phe Glu Cys Gln Phe Asp Asp Glu Ser Ala Thr
            115                 120                 125

Val Val Asp Phe Leu Arg Arg Trp Ile Ala Phe Cys Gln Ser Ile Ile
        130                 135                 140

Ser Thr Ser Pro Gln
145
```

<210> SEQ ID NO 274
<211> LENGTH: 427
<212> TYPE: PRT
<213> ORGANISM: Artificial Sequence
<220> FEATURE:
<223> OTHER INFORMATION: Mouse mIL2-A10m3

<400> SEQUENCE: 274

```
Ala Pro Thr Ser Ser Thr Ser Ser Ser Thr Ala Glu Ala Gln Gln
 1               5                  10                  15

Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
             35                  40                  45

Lys Leu Pro Arg Met Leu Thr Phe Lys Phe Tyr Leu Pro Lys Gln Ala
 50                      55                  60

Thr Glu Leu Lys Asp Leu Gln Cys Leu Glu Asp Glu Leu Gly Pro Leu
 65                  70                  75                  80

Arg His Val Leu Asp Leu Thr Gln Ser Lys Ser Phe Gln Leu Glu Asp
                 85                  90                  95

Ala Glu Asn Phe Ile Ser Asn Ile Arg Val Thr Val Val Lys Leu Lys
                100                 105                 110

Gly Ser Asp Asn Thr Phe Glu Cys Gln Phe Asp Asp Glu Ser Ala Thr
            115                 120                 125

Val Val Asp Phe Leu Arg Arg Trp Ile Ala Phe Cys Gln Ser Ile Ile
        130                 135                 140

Ser Thr Ser Pro Gln Gly Gly Gly Gly Ser Gly Gly Gly Ser Gly
145                 150                 155                 160

Gly Gly Gly Ser Gly Gly Gly Ser Gly Gly Gly Ser Glu Val
                165                 170                 175

Gln Leu Val Glu Ser Gly Gly Gly Leu Ile Gln Pro Gly Arg Ser Leu
            180                 185                 190

Arg Leu Ser Cys Ala Ala Ser Gly Ile Thr Phe Asp Asp Ala Val Met
                195                 200                 205

His Trp Val Arg Gln Ala Pro Gly Lys Gly Leu Glu Trp Val Ala Gly
        210                 215                 220
```

```
Ile Ser Ser Asn Ser Gly Tyr Ile Gly Tyr Ala Asp Ser Val Lys Gly
225                 230                 235                 240

Arg Phe Thr Ile Ser Arg Asp Asn Ala Lys Asn Ser Leu Tyr Leu Gln
                245                 250                 255

Met Asn Arg Leu Arg Ala Glu Asp Thr Ala Val Tyr Tyr Cys Val Lys
            260                 265                 270

Gly Leu Tyr Ser Asn Pro Arg Gly Gly Ala Phe Asp Ile Trp Gly Gln
        275                 280                 285

Gly Thr Met Val Thr Val Ser Ser Ala Ser Thr Gly Gly Gly Gly Ser
    290                 295                 300

Gly Gly Gly Gly Ser Gly Gly Gly Ser Val His Ser Ser Tyr Val
305                 310                 315                 320

Leu Thr Gln Pro Pro Ser Val Ser Val Ala Pro Gly Gln Thr Ala Thr
                325                 330                 335

Ile Thr Cys Gly Gly Asn Asn Ile Gly Thr Lys Ser Val His Trp Tyr
            340                 345                 350

Gln Gln Lys Pro Gly Gln Ala Pro Val Leu Val Val Tyr Ala Asp Ser
        355                 360                 365

Asp Arg Pro Ser Gly Ile Pro Glu Arg Val Ser Gly Ser Asn Ser Gly
370                 375                 380

Asn Thr Ala Thr Leu Thr Ile Ser Arg Val Glu Ala Gly Asp Glu Ala
385                 390                 395                 400

Asp Tyr Tyr Cys Gln Val Trp Asp Ser Arg Ser Asp His Leu Trp Val
                405                 410                 415

Phe Gly Gly Gly Thr Lys Leu Thr Val Leu Gly
                420                 425

<210> SEQ ID NO 275
<211> LENGTH: 152
<212> TYPE: PRT
<213> ORGANISM: Artificial Sequence
<220> FEATURE:
<223> OTHER INFORMATION: Human hIL-7

<400> SEQUENCE: 275

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150
```

<210> SEQ ID NO 276
<211> LENGTH: 430
<212> TYPE: PRT
<213> ORGANISM: Artificial Sequence
<220> FEATURE:
<223> OTHER INFORMATION: Human hIL-7-A10m3

<400> SEQUENCE: 276

```
Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His Gly Gly Gly Ser Gly Gly Gly
145                 150                 155                 160

Gly Ser Gly Gly Gly Gly Ser Gly Gly Gly Gly Ser Gly Gly Gly Gly
                165                 170                 175

Ser Glu Val Gln Leu Val Glu Ser Gly Gly Gly Leu Ile Gln Pro Gly
            180                 185                 190

Arg Ser Leu Arg Leu Ser Cys Ala Ala Ser Gly Ile Thr Phe Asp Asp
        195                 200                 205

Ala Val Met His Trp Val Arg Gln Ala Pro Gly Lys Gly Leu Glu Trp
    210                 215                 220

Val Ala Gly Ile Ser Ser Asn Ser Gly Tyr Ile Gly Tyr Ala Asp Ser
225                 230                 235                 240

Val Lys Gly Arg Phe Thr Ile Ser Arg Asp Asn Ala Lys Asn Ser Leu
                245                 250                 255

Tyr Leu Gln Met Asn Arg Leu Arg Ala Glu Asp Thr Ala Val Tyr Tyr
            260                 265                 270

Cys Val Lys Gly Leu Tyr Ser Asn Pro Arg Gly Gly Ala Phe Asp Ile
        275                 280                 285

Trp Gly Gln Gly Thr Met Val Thr Val Ser Ser Ala Ser Thr Gly Gly
    290                 295                 300

Gly Gly Ser Gly Gly Gly Gly Ser Gly Gly Gly Gly Ser Val His Ser
305                 310                 315                 320

Ser Tyr Val Leu Thr Gln Pro Pro Ser Val Ser Val Ala Pro Gly Gln
                325                 330                 335

Thr Ala Thr Ile Thr Cys Gly Gly Asn Asn Ile Gly Thr Lys Ser Val
            340                 345                 350

His Trp Tyr Gln Gln Lys Pro Gly Gln Ala Pro Val Leu Val Val Tyr
        355                 360                 365
```

```
Ala Asp Ser Asp Arg Pro Ser Gly Ile Pro Glu Arg Val Ser Gly Ser
    370                 375                 380

Asn Ser Gly Asn Thr Ala Thr Leu Thr Ile Ser Arg Val Glu Ala Gly
385                 390                 395                 400

Asp Glu Ala Asp Tyr Tyr Cys Gln Val Trp Asp Ser Arg Ser Asp His
                405                 410                 415

Leu Trp Val Phe Gly Gly Gly Thr Lys Leu Thr Val Leu Gly
                420                 425                 430
```

<210> SEQ ID NO 277
<211> LENGTH: 129
<212> TYPE: PRT
<213> ORGANISM: Artificial Sequence
<220> FEATURE:
<223> OTHER INFORMATION: Mouse mIL-7

<400> SEQUENCE: 277

```
Glu Cys His Ile Lys Asp Lys Glu Gly Lys Ala Tyr Glu Ser Val Leu
1               5                   10                  15

Met Ile Ser Ile Asp Glu Leu Asp Lys Met Thr Gly Thr Asp Ser Asn
                20                  25                  30

Cys Pro Asn Asn Glu Pro Asn Phe Phe Arg Lys His Val Cys Asp Asp
            35                  40                  45

Thr Lys Glu Ala Ala Phe Leu Asn Arg Ala Ala Arg Lys Leu Lys Gln
        50                  55                  60

Phe Leu Lys Met Asn Ile Ser Glu Glu Phe Asn Val His Leu Leu Thr
65                  70                  75                  80

Val Ser Gln Gly Thr Gln Thr Leu Val Asn Cys Thr Ser Lys Glu Glu
                85                  90                  95

Lys Asn Val Lys Glu Gln Lys Lys Asn Asp Ala Cys Phe Leu Lys Arg
            100                 105                 110

Leu Leu Arg Glu Ile Lys Thr Cys Trp Asn Lys Ile Leu Lys Gly Ser
        115                 120                 125

Ile
```

<210> SEQ ID NO 278
<211> LENGTH: 407
<212> TYPE: PRT
<213> ORGANISM: Artificial Sequence
<220> FEATURE:
<223> OTHER INFORMATION: Mouse mIL-7-A10m3

<400> SEQUENCE: 278

```
Glu Cys His Ile Lys Asp Lys Glu Gly Lys Ala Tyr Glu Ser Val Leu
1               5                   10                  15

Met Ile Ser Ile Asp Glu Leu Asp Lys Met Thr Gly Thr Asp Ser Asn
                20                  25                  30

Cys Pro Asn Asn Glu Pro Asn Phe Phe Arg Lys His Val Cys Asp Asp
            35                  40                  45

Thr Lys Glu Ala Ala Phe Leu Asn Arg Ala Ala Arg Lys Leu Lys Gln
        50                  55                  60

Phe Leu Lys Met Asn Ile Ser Glu Glu Phe Asn Val His Leu Leu Thr
65                  70                  75                  80

Val Ser Gln Gly Thr Gln Thr Leu Val Asn Cys Thr Ser Lys Glu Glu
                85                  90                  95

Lys Asn Val Lys Glu Gln Lys Lys Asn Asp Ala Cys Phe Leu Lys Arg
            100                 105                 110
```

-continued

```
Leu Leu Arg Glu Ile Lys Thr Cys Trp Asn Lys Ile Leu Lys Gly Ser
            115                 120                 125

Ile Gly Gly Gly Ser Gly Gly Gly Ser Gly Gly Gly Ser
130                 135                 140

Gly Gly Gly Gly Ser Gly Gly Gly Ser Glu Val Gln Leu Val Glu
145                 150                 155                 160

Ser Gly Gly Gly Leu Ile Gln Pro Gly Arg Ser Leu Arg Leu Ser Cys
                165                 170                 175

Ala Ala Ser Gly Ile Thr Phe Asp Asp Ala Val Met His Trp Val Arg
            180                 185                 190

Gln Ala Pro Gly Lys Gly Leu Glu Trp Val Ala Gly Ile Ser Ser Asn
        195                 200                 205

Ser Gly Tyr Ile Gly Tyr Ala Asp Ser Val Lys Gly Arg Phe Thr Ile
    210                 215                 220

Ser Arg Asp Asn Ala Lys Asn Ser Leu Tyr Leu Gln Met Asn Arg Leu
225                 230                 235                 240

Arg Ala Glu Asp Thr Ala Val Tyr Tyr Cys Val Lys Gly Leu Tyr Ser
                245                 250                 255

Asn Pro Arg Gly Gly Ala Phe Asp Ile Trp Gly Gln Gly Thr Met Val
            260                 265                 270

Thr Val Ser Ser Ala Ser Thr Gly Gly Gly Ser Gly Gly Gly Gly
        275                 280                 285

Ser Gly Gly Gly Gly Ser Val His Ser Ser Tyr Val Leu Thr Gln Pro
290                 295                 300

Pro Ser Val Ser Val Ala Pro Gly Gln Thr Ala Thr Ile Thr Cys Gly
305                 310                 315                 320

Gly Asn Asn Ile Gly Thr Lys Ser Val His Trp Tyr Gln Gln Lys Pro
                325                 330                 335

Gly Gln Ala Pro Val Leu Val Val Tyr Ala Asp Ser Asp Arg Pro Ser
            340                 345                 350

Gly Ile Pro Glu Arg Val Ser Gly Ser Asn Ser Gly Asn Thr Ala Thr
        355                 360                 365

Leu Thr Ile Ser Arg Val Glu Ala Gly Asp Glu Ala Asp Tyr Tyr Cys
    370                 375                 380

Gln Val Trp Asp Ser Arg Ser Asp His Leu Trp Val Phe Gly Gly Gly
385                 390                 395                 400

Thr Lys Leu Thr Val Leu Gly
            405
```

<210> SEQ ID NO 279
<211> LENGTH: 510
<212> TYPE: PRT
<213> ORGANISM: Artificial Sequence
<220> FEATURE:
<223> OTHER INFORMATION: Human hIL-12sc

<400> SEQUENCE: 279

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60
```

```
Gln Tyr Thr Cys His Lys Gly Gly Glu Val Leu Ser His Ser Leu Leu
 65                  70                  75                  80

Leu Leu His Lys Lys Glu Asp Gly Ile Trp Ser Thr Asp Ile Leu Lys
             85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
        130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Gly Ser Arg Asn Leu Pro Val Ala Thr
305                 310                 315                 320

Pro Asp Pro Gly Met Phe Pro Cys Leu His His Ser Gln Asn Leu Leu
                325                 330                 335

Arg Ala Val Ser Asn Met Leu Gln Lys Ala Arg Gln Thr Leu Glu Phe
            340                 345                 350

Tyr Pro Cys Thr Ser Glu Glu Ile Asp His Glu Asp Ile Thr Lys Asp
        355                 360                 365

Lys Thr Ser Thr Val Glu Ala Cys Leu Pro Leu Glu Leu Thr Lys Asn
    370                 375                 380

Glu Ser Cys Leu Asn Ser Arg Glu Thr Ser Phe Ile Thr Asn Gly Ser
385                 390                 395                 400

Cys Leu Ala Ser Arg Lys Thr Ser Phe Met Met Ala Leu Cys Leu Ser
                405                 410                 415

Ser Ile Tyr Glu Asp Leu Lys Met Tyr Gln Val Glu Phe Lys Thr Met
            420                 425                 430

Asn Ala Lys Leu Leu Met Asp Pro Lys Arg Gln Ile Phe Leu Asp Gln
        435                 440                 445

Asn Met Leu Ala Val Ile Asp Glu Leu Met Gln Ala Leu Asn Phe Asn
    450                 455                 460

Ser Glu Thr Val Pro Gln Lys Ser Ser Leu Glu Glu Pro Asp Phe Tyr
465                 470                 475                 480

Lys Thr Lys Ile Lys Leu Cys Ile Leu Leu His Ala Phe Arg Ile Arg
```

```
                        485                 490                 495
Ala Val Thr Ile Asp Arg Val Thr Ser Tyr Leu Asn Ala Ser
                500                 505                 510

<210> SEQ ID NO 280
<211> LENGTH: 788
<212> TYPE: PRT
<213> ORGANISM: Artificial Sequence
<220> FEATURE:
<223> OTHER INFORMATION: Human hIL-12sc-A10m3

<400> SEQUENCE: 280

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Gly Ser Arg Asn Leu Pro Val Ala Thr
305                 310                 315                 320

Pro Asp Pro Gly Met Phe Pro Cys Leu His His Ser Gln Asn Leu Leu
                325                 330                 335

Arg Ala Val Ser Asn Met Leu Gln Lys Ala Arg Gln Thr Leu Glu Phe
```

-continued

```
                340                 345                 350
Tyr Pro Cys Thr Ser Glu Glu Ile Asp His Glu Asp Ile Thr Lys Asp
            355                 360                 365
Lys Thr Ser Thr Val Glu Ala Cys Leu Pro Leu Glu Leu Thr Lys Asn
    370                 375                 380
Glu Ser Cys Leu Asn Ser Arg Glu Thr Ser Phe Ile Thr Asn Gly Ser
385                 390                 395                 400
Cys Leu Ala Ser Arg Lys Thr Ser Phe Met Met Ala Leu Cys Leu Ser
                405                 410                 415
Ser Ile Tyr Glu Asp Leu Lys Met Tyr Gln Val Glu Phe Lys Thr Met
            420                 425                 430
Asn Ala Lys Leu Leu Met Asp Pro Lys Arg Gln Ile Phe Leu Asp Gln
    435                 440                 445
Asn Met Leu Ala Val Ile Asp Glu Leu Met Gln Ala Leu Asn Phe Asn
450                 455                 460
Ser Glu Thr Val Pro Gln Lys Ser Ser Leu Glu Glu Pro Asp Phe Tyr
465                 470                 475                 480
Lys Thr Lys Ile Lys Leu Cys Ile Leu Leu His Ala Phe Arg Ile Arg
                485                 490                 495
Ala Val Thr Ile Asp Arg Val Thr Ser Tyr Leu Asn Ala Ser Gly Gly
            500                 505                 510
Gly Gly Ser Gly Gly Gly Gly Ser Gly Gly Gly Gly Ser Gly Gly Gly
    515                 520                 525
Gly Ser Gly Gly Gly Gly Ser Glu Val Gln Leu Val Glu Ser Gly Gly
530                 535                 540
Gly Leu Ile Gln Pro Gly Arg Ser Leu Arg Leu Ser Cys Ala Ala Ser
545                 550                 555                 560
Gly Ile Thr Phe Asp Asp Ala Val Met His Trp Val Arg Gln Ala Pro
                565                 570                 575
Gly Lys Gly Leu Glu Trp Val Ala Gly Ile Ser Ser Asn Ser Gly Tyr
            580                 585                 590
Ile Gly Tyr Ala Asp Ser Val Lys Gly Arg Phe Thr Ile Ser Arg Asp
    595                 600                 605
Asn Ala Lys Asn Ser Leu Tyr Leu Gln Met Asn Arg Leu Arg Ala Glu
610                 615                 620
Asp Thr Ala Val Tyr Tyr Cys Val Lys Gly Leu Tyr Ser Asn Pro Arg
625                 630                 635                 640
Gly Gly Ala Phe Asp Ile Trp Gly Gln Gly Thr Met Val Thr Val Ser
                645                 650                 655
Ser Ala Ser Thr Gly Gly Gly Ser Gly Gly Gly Ser Gly Gly
            660                 665                 670
Gly Gly Ser Val His Ser Ser Tyr Val Leu Thr Gln Pro Pro Ser Val
    675                 680                 685
Ser Val Ala Pro Gly Gln Thr Ala Thr Ile Thr Cys Gly Gly Asn Asn
690                 695                 700
Ile Gly Thr Lys Ser Val His Trp Tyr Gln Gln Lys Pro Gly Gln Ala
705                 710                 715                 720
Pro Val Leu Val Val Tyr Ala Asp Ser Asp Arg Pro Ser Gly Ile Pro
                725                 730                 735
Glu Arg Val Ser Gly Ser Asn Ser Gly Asn Thr Ala Thr Leu Thr Ile
            740                 745                 750
Ser Arg Val Glu Ala Gly Asp Glu Ala Asp Tyr Tyr Cys Gln Val Trp
    755                 760                 765
```

```
Asp Ser Arg Ser Asp His Leu Trp Val Phe Gly Gly Thr Lys Leu
            770                 775                 780
Thr Val Leu Gly
785

<210> SEQ ID NO 281
<211> LENGTH: 157
<212> TYPE: PRT
<213> ORGANISM: Artificial Sequence
<220> FEATURE:
<223> OTHER INFORMATION: Human hIL-18-A10m3

<400> SEQUENCE: 281

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
                20                  25                  30

Met Thr Asp Ser Asp Cys Arg Asp Asn Ala Pro Arg Thr Ile Phe Ile
            35                  40                  45

Ile Ser Met Tyr Lys Asp Ser Gln Pro Arg Gly Met Ala Val Thr Ile
        50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155

<210> SEQ ID NO 282
<211> LENGTH: 435
<212> TYPE: PRT
<213> ORGANISM: Artificial Sequence
<220> FEATURE:
<223> OTHER INFORMATION: Human hIL-18-A10m3

<400> SEQUENCE: 282

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
                20                  25                  30

Met Thr Asp Ser Asp Cys Arg Asp Asn Ala Pro Arg Thr Ile Phe Ile
            35                  40                  45

Ile Ser Met Tyr Lys Asp Ser Gln Pro Arg Gly Met Ala Val Thr Ile
        50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
```

```
                115                 120                 125
Lys Glu Arg Asp Leu Phe Lys Leu Ile Leu Lys Lys Glu Asp Glu Leu
        130                 135                 140

Gly Asp Arg Ser Ile Met Phe Thr Val Gln Asn Glu Asp Gly Gly Gly
145                 150                 155                 160

Gly Ser Gly Gly Gly Gly Ser Gly Gly Gly Ser Gly Gly Gly Gly
                165                 170                 175

Ser Gly Gly Gly Gly Ser Glu Val Gln Leu Val Glu Ser Gly Gly Gly
            180                 185                 190

Leu Ile Gln Pro Gly Arg Ser Leu Arg Leu Ser Cys Ala Ala Ser Gly
            195                 200                 205

Ile Thr Phe Asp Asp Ala Val Met His Trp Val Arg Gln Ala Pro Gly
            210                 215                 220

Lys Gly Leu Glu Trp Val Ala Gly Ile Ser Ser Asn Ser Gly Tyr Ile
225                 230                 235                 240

Gly Tyr Ala Asp Ser Val Lys Gly Arg Phe Thr Ile Ser Arg Asp Asn
                245                 250                 255

Ala Lys Asn Ser Leu Tyr Leu Gln Met Asn Arg Leu Arg Ala Glu Asp
            260                 265                 270

Thr Ala Val Tyr Tyr Cys Val Lys Gly Leu Tyr Ser Asn Pro Arg Gly
            275                 280                 285

Gly Ala Phe Asp Ile Trp Gly Gln Gly Thr Met Val Thr Val Ser Ser
            290                 295                 300

Ala Ser Thr Gly Gly Gly Gly Ser Gly Gly Gly Gly Ser Gly Gly Gly
305                 310                 315                 320

Gly Ser Val His Ser Ser Tyr Val Leu Thr Gln Pro Pro Ser Val Ser
                325                 330                 335

Val Ala Pro Gly Gln Thr Ala Thr Ile Thr Cys Gly Gly Asn Asn Ile
            340                 345                 350

Gly Thr Lys Ser Val His Trp Tyr Gln Gln Lys Pro Gly Gln Ala Pro
            355                 360                 365

Val Leu Val Val Tyr Ala Asp Ser Asp Arg Pro Ser Gly Ile Pro Glu
            370                 375                 380

Arg Val Ser Gly Ser Asn Ser Gly Asn Thr Ala Thr Leu Thr Ile Ser
385                 390                 395                 400

Arg Val Glu Ala Gly Asp Glu Ala Asp Tyr Tyr Cys Gln Val Trp Asp
                405                 410                 415

Ser Arg Ser Asp His Leu Trp Val Phe Gly Gly Gly Thr Lys Leu Thr
            420                 425                 430

Val Leu Gly
        435

<210> SEQ ID NO 283
<211> LENGTH: 435
<212> TYPE: PRT
<213> ORGANISM: Artificial Sequence
<220> FEATURE:
<223> OTHER INFORMATION: Mouse mIL-18-A10m3

<400> SEQUENCE: 283

Asn Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Glu Asp Met
            20                  25                  30

Thr Asp Ile Asp Gln Ser Ala Ser Glu Pro Gln Thr Arg Leu Ile Ile
```

```
                35                  40                  45
Tyr Met Tyr Lys Asp Ser Glu Val Arg Gly Leu Ala Val Thr Leu Ser
 50                  55                  60

Val Lys Asp Ser Lys Met Ser Thr Leu Ser Cys Lys Asn Lys Ile Ile
 65                  70                  75                  80

Ser Phe Glu Glu Met Asp Pro Pro Glu Asn Ile Asp Ile Gln Ser
                 85                  90                  95

Asp Leu Ile Phe Phe Gln Lys Arg Val Pro Gly His Asn Lys Met Glu
                100                 105                 110

Phe Glu Ser Ser Leu Tyr Glu Gly His Phe Leu Ala Cys Gln Lys Glu
                115                 120                 125

Asp Ala Phe Lys Leu Ile Leu Lys Lys Asp Glu Asn Gly Asp
                130                 135                 140

Lys Ser Val Met Phe Thr Leu Thr Asn Leu His Gln Ser Gly Gly Gly
145                 150                 155                 160

Gly Ser Gly Gly Gly Gly Ser Gly Gly Gly Gly Ser Gly Gly Gly Gly
                165                 170                 175

Ser Gly Gly Gly Gly Ser Glu Val Gln Leu Val Glu Ser Gly Gly Gly
                180                 185                 190

Leu Ile Gln Pro Gly Arg Ser Leu Arg Leu Ser Cys Ala Ala Ser Gly
                195                 200                 205

Ile Thr Phe Asp Asp Ala Val Met His Trp Val Arg Gln Ala Pro Gly
210                 215                 220

Lys Gly Leu Glu Trp Val Ala Gly Ile Ser Ser Asn Ser Gly Tyr Ile
225                 230                 235                 240

Gly Tyr Ala Asp Ser Val Lys Gly Arg Phe Thr Ile Ser Arg Asp Asn
                245                 250                 255

Ala Lys Asn Ser Leu Tyr Leu Gln Met Asn Arg Leu Arg Ala Glu Asp
                260                 265                 270

Thr Ala Val Tyr Tyr Cys Val Lys Gly Leu Tyr Ser Asn Pro Arg Gly
                275                 280                 285

Gly Ala Phe Asp Ile Trp Gly Gln Gly Thr Met Val Thr Val Ser Ser
                290                 295                 300

Ala Ser Thr Gly Gly Gly Gly Ser Gly Gly Gly Gly Ser Gly Gly Gly
305                 310                 315                 320

Gly Ser Val His Ser Ser Tyr Val Leu Thr Gln Pro Pro Ser Val Ser
                325                 330                 335

Val Ala Pro Gly Gln Thr Ala Thr Ile Thr Cys Gly Gly Asn Asn Ile
                340                 345                 350

Gly Thr Lys Ser Val His Trp Tyr Gln Gln Lys Pro Gly Gln Ala Pro
                355                 360                 365

Val Leu Val Val Tyr Ala Asp Ser Asp Arg Pro Ser Gly Ile Pro Glu
                370                 375                 380

Arg Val Ser Gly Ser Asn Ser Gly Asn Thr Ala Thr Leu Thr Ile Ser
385                 390                 395                 400

Arg Val Glu Ala Gly Asp Glu Ala Asp Tyr Tyr Cys Gln Val Trp Asp
                405                 410                 415

Ser Arg Ser Asp His Leu Trp Val Phe Gly Gly Gly Thr Lys Leu Thr
                420                 425                 430

Val Leu Gly
        435

<210> SEQ ID NO 284
```

<211> LENGTH: 133
<212> TYPE: PRT
<213> ORGANISM: Artificial Sequence
<220> FEATURE:
<223> OTHER INFORMATION: Human hIL-21

<400> SEQUENCE: 284

```
Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130
```

<210> SEQ ID NO 285
<211> LENGTH: 411
<212> TYPE: PRT
<213> ORGANISM: Artificial Sequence
<220> FEATURE:
<223> OTHER INFORMATION: Human hIL-21-A10m3

<400> SEQUENCE: 285

```
Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Gly Gly Gly Ser Gly Gly Gly Ser Gly
    130                 135                 140

Gly Gly Gly Ser Gly Gly Gly Ser Gly Gly Gly Ser Glu Val
145                 150                 155                 160

Gln Leu Val Glu Ser Gly Gly Leu Ile Gln Pro Gly Arg Ser Leu
            165                 170                 175

Arg Leu Ser Cys Ala Ala Ser Gly Ile Thr Phe Asp Asp Ala Val Met
```

```
                   180                 185                 190
His Trp Val Arg Gln Ala Pro Gly Lys Gly Leu Glu Trp Val Ala Gly
            195                 200                 205
Ile Ser Ser Asn Ser Gly Tyr Ile Gly Tyr Ala Asp Ser Val Lys Gly
            210                 215                 220
Arg Phe Thr Ile Ser Arg Asp Asn Ala Lys Asn Ser Leu Tyr Leu Gln
225                 230                 235                 240
Met Asn Arg Leu Arg Ala Glu Asp Thr Ala Val Tyr Tyr Cys Val Lys
            245                 250                 255
Gly Leu Tyr Ser Asn Pro Arg Gly Gly Ala Phe Asp Ile Trp Gly Gln
            260                 265                 270
Gly Thr Met Val Thr Val Ser Ser Ala Ser Thr Gly Gly Gly Gly Ser
            275                 280                 285
Gly Gly Gly Gly Ser Gly Gly Gly Ser Val His Ser Ser Tyr Val
            290                 295                 300
Leu Thr Gln Pro Pro Ser Val Ser Val Ala Pro Gly Gln Thr Ala Thr
305                 310                 315                 320
Ile Thr Cys Gly Gly Asn Asn Ile Gly Thr Lys Ser Val His Trp Tyr
            325                 330                 335
Gln Gln Lys Pro Gly Gln Ala Pro Val Leu Val Val Tyr Ala Asp Ser
            340                 345                 350
Asp Arg Pro Ser Gly Ile Pro Glu Arg Val Ser Gly Ser Asn Ser Gly
            355                 360                 365
Asn Thr Ala Thr Leu Thr Ile Ser Arg Val Glu Ala Gly Asp Glu Ala
            370                 375                 380
Asp Tyr Tyr Cys Gln Val Trp Asp Ser Arg Ser Asp His Leu Trp Val
385                 390                 395                 400
Phe Gly Gly Gly Thr Lys Leu Thr Val Leu Gly
            405                 410
```

<210> SEQ ID NO 286
<211> LENGTH: 122
<212> TYPE: PRT
<213> ORGANISM: Artificial Sequence
<220> FEATURE:
<223> OTHER INFORMATION: Mouse mIL-21

<400> SEQUENCE: 286

```
Pro Asp Arg Leu Leu Ile Arg Leu Arg His Leu Ile Asp Ile Val Glu
1               5                   10                  15
Gln Leu Lys Ile Tyr Glu Asn Asp Leu Asp Pro Glu Leu Leu Ser Ala
            20                  25                  30
Pro Gln Asp Val Lys Gly His Cys Glu His Ala Ala Phe Ala Cys Phe
            35                  40                  45
Gln Lys Ala Lys Leu Lys Pro Ser Asn Pro Gly Asn Asn Lys Thr Phe
        50                  55                  60
Ile Ile Asp Leu Val Ala Gln Leu Arg Arg Arg Leu Pro Ala Arg Arg
65                  70                  75                  80
Gly Gly Lys Lys Gln Lys His Ile Ala Lys Cys Pro Ser Cys Asp Ser
            85                  90                  95
Tyr Glu Lys Arg Thr Pro Lys Glu Phe Leu Glu Arg Leu Lys Trp Leu
            100                 105                 110
Leu Gln Lys Met Ile His Gln His Leu Ser
            115                 120
```

<210> SEQ ID NO 287
<211> LENGTH: 400
<212> TYPE: PRT
<213> ORGANISM: Artificial Sequence
<220> FEATURE:
<223> OTHER INFORMATION: Mouse mIL-21-A10m3

<400> SEQUENCE: 287

```
Pro Asp Arg Leu Leu Ile Arg Leu Arg His Leu Ile Asp Ile Val Glu
1               5                   10                  15

Gln Leu Lys Ile Tyr Glu Asn Asp Leu Asp Pro Glu Leu Leu Ser Ala
            20                  25                  30

Pro Gln Asp Val Lys Gly His Cys Glu His Ala Ala Phe Ala Cys Phe
        35                  40                  45

Gln Lys Ala Lys Leu Lys Pro Ser Asn Pro Gly Asn Asn Lys Thr Phe
    50                  55                  60

Ile Ile Asp Leu Val Ala Gln Leu Arg Arg Arg Leu Pro Ala Arg Arg
65                  70                  75                  80

Gly Gly Lys Lys Gln Lys His Ile Ala Lys Cys Pro Ser Cys Asp Ser
                85                  90                  95

Tyr Glu Lys Arg Thr Pro Lys Glu Phe Leu Glu Arg Leu Lys Trp Leu
            100                 105                 110

Leu Gln Lys Met Ile His Gln His Leu Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Glu Val Gln Leu Val Glu Ser Gly Gly Gly Leu Ile Gln
145                 150                 155                 160

Pro Gly Arg Ser Leu Arg Leu Ser Cys Ala Ala Ser Gly Ile Thr Phe
                165                 170                 175

Asp Asp Ala Val Met His Trp Val Arg Gln Ala Pro Gly Lys Gly Leu
            180                 185                 190

Glu Trp Val Ala Gly Ile Ser Ser Asn Ser Gly Tyr Ile Gly Tyr Ala
        195                 200                 205

Asp Ser Val Lys Gly Arg Phe Thr Ile Ser Arg Asp Asn Ala Lys Asn
    210                 215                 220

Ser Leu Tyr Leu Gln Met Asn Arg Leu Arg Ala Glu Asp Thr Ala Val
225                 230                 235                 240

Tyr Tyr Cys Val Lys Gly Leu Tyr Ser Asn Pro Arg Gly Gly Ala Phe
                245                 250                 255

Asp Ile Trp Gly Gln Gly Thr Met Val Thr Val Ser Ser Ala Ser Thr
            260                 265                 270

Gly Gly Gly Gly Ser Gly Gly Gly Gly Ser Gly Gly Gly Gly Ser Val
        275                 280                 285

His Ser Ser Tyr Val Leu Thr Gln Pro Pro Ser Val Ser Val Ala Pro
    290                 295                 300

Gly Gln Thr Ala Thr Ile Thr Cys Gly Gly Asn Asn Ile Gly Thr Lys
305                 310                 315                 320

Ser Val His Trp Tyr Gln Gln Lys Pro Gly Gln Ala Pro Val Leu Val
                325                 330                 335

Val Tyr Ala Asp Ser Asp Arg Pro Ser Gly Ile Pro Glu Arg Val Ser
            340                 345                 350

Gly Ser Asn Ser Gly Asn Thr Ala Thr Leu Thr Ile Ser Arg Val Glu
        355                 360                 365

Ala Gly Asp Glu Ala Asp Tyr Tyr Cys Gln Val Trp Asp Ser Arg Ser
```

```
                370                 375                 380
Asp His Leu Trp Val Phe Gly Gly Thr Lys Leu Thr Val Leu Gly
385                 390                 395                 400

<210> SEQ ID NO 288
<211> LENGTH: 209
<212> TYPE: PRT
<213> ORGANISM: Artificial Sequence
<220> FEATURE:
<223> OTHER INFORMATION: Human hIL-27sc

<400> SEQUENCE: 288

Arg Lys Gly Pro Pro Ala Ala Leu Thr Leu Pro Arg Val Gln Cys Arg
1               5                   10                  15

Ala Ser Arg Tyr Pro Ile Ala Val Asp Cys Ser Trp Thr Leu Pro Pro
            20                  25                  30

Ala Pro Asn Ser Thr Ser Pro Val Ser Phe Ile Ala Thr Tyr Arg Leu
        35                  40                  45

Gly Met Ala Ala Arg Gly His Ser Trp Pro Cys Leu Gln Gln Thr Pro
    50                  55                  60

Thr Ser Thr Ser Cys Thr Ile Thr Asp Val Gln Leu Phe Ser Met Ala
65                  70                  75                  80

Pro Tyr Val Leu Asn Val Thr Ala Val His Pro Trp Gly Ser Ser Ser
                85                  90                  95

Ser Phe Val Pro Phe Ile Thr Glu His Ile Ile Lys Pro Asp Pro Pro
            100                 105                 110

Glu Gly Val Arg Leu Ser Pro Leu Ala Glu Arg Gln Leu Gln Val Gln
        115                 120                 125

Trp Glu Pro Pro Gly Ser Trp Pro Phe Pro Glu Ile Phe Ser Leu Lys
    130                 135                 140

Tyr Trp Ile Arg Tyr Lys Arg Gln Gly Ala Ala Arg Phe His Arg Val
145                 150                 155                 160

Gly Pro Ile Glu Ala Thr Ser Phe Ile Leu Arg Ala Val Arg Pro Arg
                165                 170                 175

Ala Arg Tyr Tyr Val Gln Val Ala Ala Gln Asp Leu Thr Asp Tyr Gly
            180                 185                 190

Glu Leu Ser Asp Trp Ser Leu Pro Ala Thr Ala Thr Met Ser Leu Gly
        195                 200                 205

Lys

<210> SEQ ID NO 289
<211> LENGTH: 716
<212> TYPE: PRT
<213> ORGANISM: Artificial Sequence
<220> FEATURE:
<223> OTHER INFORMATION: Human hIL-27sc-A10m3

<400> SEQUENCE: 289

Lys Gly Pro Pro Ala Ala Leu Thr Leu Pro Arg Val Gln Cys Arg Ala
1               5                   10                  15

Ser Arg Tyr Pro Ile Ala Val Asp Cys Ser Trp Thr Leu Pro Pro Ala
            20                  25                  30

Pro Asn Ser Thr Ser Pro Val Ser Phe Ile Ala Thr Tyr Arg Leu Gly
        35                  40                  45

Met Ala Ala Arg Gly His Ser Trp Pro Cys Leu Gln Gln Thr Pro Thr
    50                  55                  60

Ser Thr Ser Cys Thr Ile Thr Asp Val Gln Leu Phe Ser Met Ala Pro
```

-continued

```
                65                  70                  75                  80
        Tyr Val Leu Asn Val Thr Ala Val His Pro Trp Gly Ser Ser Ser Ser
                        85                  90                  95
        Phe Val Pro Phe Ile Thr Glu His Ile Ile Lys Pro Asp Pro Pro Glu
                       100                 105                 110
        Gly Val Arg Leu Ser Pro Leu Ala Glu Arg Gln Leu Gln Val Gln Trp
                       115                 120                 125
        Glu Pro Pro Gly Ser Trp Pro Phe Pro Glu Ile Phe Ser Leu Lys Tyr
                       130                 135                 140
        Trp Ile Arg Tyr Lys Arg Gln Gly Ala Ala Arg Phe His Arg Val Gly
        145                 150                 155                 160
        Pro Ile Glu Ala Thr Ser Phe Ile Leu Arg Ala Val Arg Pro Arg Ala
                       165                 170                 175
        Arg Tyr Tyr Val Gln Val Ala Ala Gln Asp Leu Thr Asp Tyr Gly Glu
                       180                 185                 190
        Leu Ser Asp Trp Ser Leu Pro Ala Thr Ala Thr Met Ser Leu Gly Lys
                       195                 200                 205
        Gly Gly Gly Gly Ser Gly Gly Gly Ser Gly Gly Gly Ser Phe
                       210                 215                 220
        Pro Arg Pro Pro Gly Arg Pro Gln Leu Ser Leu Gln Glu Leu Arg Arg
        225                 230                 235                 240
        Glu Phe Thr Val Ser Leu His Leu Ala Arg Lys Leu Leu Ser Glu Val
                       245                 250                 255
        Arg Gly Gln Ala His Arg Phe Ala Glu Ser His Leu Pro Gly Val Asn
                       260                 265                 270
        Leu Tyr Leu Leu Pro Leu Gly Glu Gln Leu Pro Asp Val Ser Leu Thr
                       275                 280                 285
        Phe Gln Ala Trp Arg Arg Leu Ser Asp Pro Glu Arg Leu Cys Phe Ile
                       290                 295                 300
        Ser Thr Thr Leu Gln Pro Phe His Ala Pro Leu Gly Gly Leu Gly Thr
        305                 310                 315                 320
        Gln Gly Arg Trp Thr Asn Met Glu Arg Met Gln Leu Trp Ala Met Arg
                       325                 330                 335
        Leu Asp Leu Arg Asp Leu Gln Arg His Leu Arg Phe Gln Val Leu Ala
                       340                 345                 350
        Ala Gly Phe Asn Leu Pro Glu Glu Glu Glu Glu Glu Glu Glu Glu Glu
                       355                 360                 365
        Glu Glu Glu Arg Lys Gly Leu Leu Pro Gly Ala Leu Gly Ser Ala Leu
                       370                 375                 380
        Gln Gly Pro Ala Gln Val Ser Trp Pro Gln Leu Leu Ser Thr Tyr Arg
        385                 390                 395                 400
        Leu Leu His Ser Leu Glu Leu Val Leu Ser Arg Ala Val Arg Glu Leu
                       405                 410                 415
        Leu Leu Leu Ser Lys Ala Gly His Ser Val Trp Pro Leu Gly Phe Pro
                       420                 425                 430
        Thr Leu Ser Pro Gln Pro Gly Gly Gly Ser Gly Gly Gly Gly Ser
                       435                 440                 445
        Gly Gly Gly Gly Ser Gly Gly Gly Ser Gly Gly Gly Gly Ser Glu
                       450                 455                 460
        Val Gln Leu Val Glu Ser Gly Gly Gly Leu Ile Gln Pro Gly Arg Ser
        465                 470                 475                 480
        Leu Arg Leu Ser Cys Ala Ala Ser Gly Ile Thr Phe Asp Asp Ala Val
                       485                 490                 495
```

```
Met His Trp Val Arg Gln Ala Pro Gly Lys Gly Leu Glu Trp Val Ala
            500                 505                 510

Gly Ile Ser Ser Asn Ser Gly Tyr Ile Gly Tyr Ala Asp Ser Val Lys
            515                 520                 525

Gly Arg Phe Thr Ile Ser Arg Asp Asn Ala Lys Asn Ser Leu Tyr Leu
530                 535                 540

Gln Met Asn Arg Leu Arg Ala Glu Asp Thr Ala Val Tyr Tyr Cys Val
545                 550                 555                 560

Lys Gly Leu Tyr Ser Asn Pro Arg Gly Gly Ala Phe Asp Ile Trp Gly
            565                 570                 575

Gln Gly Thr Met Val Thr Val Ser Ser Ala Ser Thr Gly Gly Gly Gly
            580                 585                 590

Ser Gly Gly Gly Gly Ser Gly Gly Gly Ser Val His Ser Ser Tyr
            595                 600                 605

Val Leu Thr Gln Pro Pro Ser Val Ser Val Ala Pro Gly Gln Thr Ala
            610                 615                 620

Thr Ile Thr Cys Gly Gly Asn Asn Ile Gly Thr Lys Ser Val His Trp
625                 630                 635                 640

Tyr Gln Gln Lys Pro Gly Gln Ala Pro Val Leu Val Val Tyr Ala Asp
            645                 650                 655

Ser Asp Arg Pro Ser Gly Ile Pro Glu Arg Val Ser Gly Ser Asn Ser
            660                 665                 670

Gly Asn Thr Ala Thr Leu Thr Ile Ser Arg Val Glu Ala Gly Asp Glu
            675                 680                 685

Ala Asp Tyr Tyr Cys Gln Val Trp Asp Ser Arg Ser Asp His Leu Trp
            690                 695                 700

Val Phe Gly Gly Gly Thr Lys Leu Thr Val Leu Gly
705                 710                 715

<210> SEQ ID NO 290
<211> LENGTH: 210
<212> TYPE: PRT
<213> ORGANISM: Artificial Sequence
<220> FEATURE:
<223> OTHER INFORMATION: Mouse mIL-27sc

<400> SEQUENCE: 290

Tyr Thr Glu Thr Ala Leu Val Ala Leu Ser Gln Pro Arg Val Gln Cys
1               5                   10                  15

His Ala Ser Arg Tyr Pro Val Ala Val Asp Cys Ser Trp Thr Pro Leu
            20                  25                  30

Gln Ala Pro Asn Ser Thr Arg Ser Thr Ser Phe Ile Ala Thr Tyr Arg
        35                  40                  45

Leu Gly Val Ala Thr Gln Gln Ser Gln Pro Cys Leu Gln Arg Ser
    50                  55                  60

Pro Gln Ala Ser Arg Cys Thr Ile Pro Asp Val His Leu Phe Ser Thr
65                  70                  75                  80

Val Pro Tyr Met Leu Asn Val Thr Ala Val His Pro Gly Gly Ala Ser
            85                  90                  95

Ser Ser Leu Leu Ala Phe Val Ala Glu Arg Ile Ile Lys Pro Asp Pro
            100                 105                 110

Pro Glu Gly Val Arg Leu Arg Thr Ala Gly Gln Arg Leu Gln Val Leu
        115                 120                 125

Trp His Pro Pro Ala Ser Trp Pro Phe Pro Asp Ile Phe Ser Leu Lys
    130                 135                 140
```

```
Tyr Arg Leu Arg Tyr Arg Arg Gly Ala Ser His Phe Arg Gln Val
145                 150                 155                 160

Gly Pro Ile Glu Ala Thr Thr Phe Thr Leu Arg Asn Ser Lys Pro His
            165                 170                 175

Ala Lys Tyr Cys Ile Gln Val Ser Ala Gln Asp Leu Thr Asp Tyr Gly
            180                 185                 190

Lys Pro Ser Asp Trp Ser Leu Pro Gly Gln Val Glu Ser Ala Pro His
        195                 200                 205

Lys Pro
    210

<210> SEQ ID NO 291
<211> LENGTH: 709
<212> TYPE: PRT
<213> ORGANISM: Artificial Sequence
<220> FEATURE:
<223> OTHER INFORMATION: Mouse mIL-27sc-A10m3

<400> SEQUENCE: 291

Tyr Thr Glu Thr Ala Leu Val Ala Leu Ser Gln Pro Arg Val Gln Cys
1               5                   10                  15

His Ala Ser Arg Tyr Pro Val Ala Val Asp Cys Ser Trp Thr Pro Leu
            20                  25                  30

Gln Ala Pro Asn Ser Thr Arg Ser Thr Ser Phe Ile Ala Thr Tyr Arg
            35                  40                  45

Leu Gly Val Ala Thr Gln Gln Ser Gln Pro Cys Leu Gln Arg Ser
    50                  55                  60

Pro Gln Ala Ser Arg Cys Thr Ile Pro Asp Val His Leu Phe Ser Thr
65                  70                  75                  80

Val Pro Tyr Met Leu Asn Val Thr Ala Val His Pro Gly Gly Ala Ser
                85                  90                  95

Ser Ser Leu Leu Ala Phe Val Ala Glu Arg Ile Ile Lys Pro Asp Pro
            100                 105                 110

Pro Glu Gly Val Arg Leu Arg Thr Ala Gly Gln Arg Leu Gln Val Leu
            115                 120                 125

Trp His Pro Pro Ala Ser Trp Pro Phe Pro Asp Ile Phe Ser Leu Lys
    130                 135                 140

Tyr Arg Leu Arg Tyr Arg Arg Gly Ala Ser His Phe Arg Gln Val
145                 150                 155                 160

Gly Pro Ile Glu Ala Thr Thr Phe Thr Leu Arg Asn Ser Lys Pro His
            165                 170                 175

Ala Lys Tyr Cys Ile Gln Val Ser Ala Gln Asp Leu Thr Asp Tyr Gly
            180                 185                 190

Lys Pro Ser Asp Trp Ser Leu Pro Gly Gln Val Glu Ser Ala Pro His
        195                 200                 205

Lys Pro Gly Gly Gly Gly Ser Gly Gly Gly Ser Gly Gly Gly Gly
    210                 215                 220

Ser Phe Pro Thr Asp Pro Leu Ser Leu Gln Glu Leu Arg Arg Glu Phe
225                 230                 235                 240

Thr Val Ser Leu Tyr Leu Ala Arg Lys Leu Leu Ser Glu Val Gln Gly
                245                 250                 255

Tyr Val His Ser Phe Ala Glu Ser Arg Leu Pro Gly Val Asn Leu Asp
            260                 265                 270

Leu Leu Pro Leu Gly Tyr His Leu Pro Asn Val Ser Leu Thr Phe Gln
    275                 280                 285
```

```
Ala Trp His His Leu Ser Asp Ser Glu Arg Leu Cys Phe Leu Ala Thr
    290                 295                 300
Thr Leu Arg Pro Phe Pro Ala Met Leu Gly Gly Leu Gly Thr Gln Gly
305                 310                 315                 320
Thr Trp Thr Ser Ser Glu Arg Glu Gln Leu Trp Ala Met Arg Leu Asp
                325                 330                 335
Leu Arg Asp Leu His Arg His Leu Arg Phe Gln Val Leu Ala Ala Gly
            340                 345                 350
Phe Lys Cys Ser Lys Glu Glu Asp Lys Glu Glu Glu Glu Glu Glu Glu
        355                 360                 365
Glu Glu Glu Glu Lys Lys Leu Pro Leu Gly Ala Leu Gly Gly Pro Asn
370                 375                 380
Gln Val Ser Ser Gln Val Ser Trp Pro Gln Leu Leu Tyr Thr Tyr Gln
385                 390                 395                 400
Leu Leu His Ser Leu Glu Leu Val Leu Ser Arg Ala Val Arg Asp Leu
            405                 410                 415
Leu Leu Leu Ser Leu Pro Arg Arg Pro Gly Ser Ala Trp Asp Ser Gly
            420                 425                 430
Gly Gly Gly Ser Gly Gly Gly Ser Gly Gly Gly Gly Ser Gly Gly
        435                 440                 445
Gly Gly Ser Gly Gly Gly Ser Glu Val Gln Leu Val Glu Ser Gly
450                 455                 460
Gly Gly Leu Ile Gln Pro Gly Arg Ser Leu Arg Leu Ser Cys Ala Ala
465                 470                 475                 480
Ser Gly Ile Thr Phe Asp Asp Ala Val Met His Trp Val Arg Gln Ala
            485                 490                 495
Pro Gly Lys Gly Leu Glu Trp Val Ala Gly Ile Ser Ser Asn Ser Gly
        500                 505                 510
Tyr Ile Gly Tyr Ala Asp Ser Val Lys Gly Arg Phe Thr Ile Ser Arg
        515                 520                 525
Asp Asn Ala Lys Asn Ser Leu Tyr Leu Gln Met Asn Arg Leu Arg Ala
            530                 535                 540
Glu Asp Thr Ala Val Tyr Tyr Cys Val Lys Gly Leu Tyr Ser Asn Pro
545                 550                 555                 560
Arg Gly Gly Ala Phe Asp Ile Trp Gly Gln Gly Thr Met Val Thr Val
                565                 570                 575
Ser Ser Ala Ser Thr Gly Gly Gly Ser Gly Gly Gly Gly Ser Gly
            580                 585                 590
Gly Gly Ser Val His Ser Ser Tyr Val Leu Thr Gln Pro Pro Ser
        595                 600                 605
Val Ser Val Ala Pro Gly Gln Thr Ala Thr Ile Thr Cys Gly Gly Asn
610                 615                 620
Asn Ile Gly Thr Lys Ser Val His Trp Tyr Gln Gln Lys Pro Gly Gln
625                 630                 635                 640
Ala Pro Val Leu Val Val Tyr Ala Asp Ser Asp Arg Pro Ser Gly Ile
                645                 650                 655
Pro Glu Arg Val Ser Gly Ser Asn Ser Gly Asn Thr Ala Thr Leu Thr
                660                 665                 670
Ile Ser Arg Val Glu Ala Gly Asp Glu Ala Asp Tyr Tyr Cys Gln Val
            675                 680                 685
Trp Asp Ser Arg Ser Asp His Leu Trp Val Phe Gly Gly Gly Thr Lys
690                 695                 700
```

Leu Thr Val Leu Gly
705

<210> SEQ ID NO 292
<211> LENGTH: 144
<212> TYPE: PRT
<213> ORGANISM: Artificial Sequence
<220> FEATURE:
<223> OTHER INFORMATION: Human GM-CSF

<400> SEQUENCE: 292

Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 293
<211> LENGTH: 422
<212> TYPE: PRT
<213> ORGANISM: Artificial Sequence
<220> FEATURE:
<223> OTHER INFORMATION: Human GM-CSF-A10m3

<400> SEQUENCE: 293

Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

Gly Gly Gly Gly Ser Gly Gly Gly Gly Ser Gly Gly Gly

Gly Gly Gly Ser Gly Gly Gly Ser Glu Val Gln Leu Val Glu Ser
            165                 170                 175

Gly Gly Gly Leu Ile Gln Pro Gly Arg Ser Leu Arg Leu Ser Cys Ala
            180                 185                 190

Ala Ser Gly Ile Thr Phe Asp Asp Ala Val Met His Trp Val Arg Gln
            195                 200                 205

Ala Pro Gly Lys Gly Leu Glu Trp Val Ala Gly Ile Ser Ser Asn Ser
210                 215                 220

Gly Tyr Ile Gly Tyr Ala Asp Ser Val Lys Gly Arg Phe Thr Ile Ser
225                 230                 235                 240

Arg Asp Asn Ala Lys Asn Ser Leu Tyr Leu Gln Met Asn Arg Leu Arg
                245                 250                 255

Ala Glu Asp Thr Ala Val Tyr Tyr Cys Val Lys Gly Leu Tyr Ser Asn
            260                 265                 270

Pro Arg Gly Gly Ala Phe Asp Ile Trp Gly Gln Gly Thr Met Val Thr
            275                 280                 285

Val Ser Ser Ala Ser Thr Gly Gly Gly Ser Gly Gly Gly Gly Ser
            290                 295                 300

Gly Gly Gly Ser Val His Ser Ser Tyr Val Leu Thr Gln Pro Pro
305                 310                 315                 320

Ser Val Ser Val Ala Pro Gly Gln Thr Ala Thr Ile Thr Cys Gly Gly
                325                 330                 335

Asn Asn Ile Gly Thr Lys Ser Val His Trp Tyr Gln Gln Lys Pro Gly
            340                 345                 350

Gln Ala Pro Val Leu Val Val Tyr Ala Asp Ser Asp Arg Pro Ser Gly
            355                 360                 365

Ile Pro Glu Arg Val Ser Gly Ser Asn Ser Gly Asn Thr Ala Thr Leu
370                 375                 380

Thr Ile Ser Arg Val Glu Ala Gly Asp Glu Ala Asp Tyr Tyr Cys Gln
385                 390                 395                 400

Val Trp Asp Ser Arg Ser Asp His Leu Trp Val Phe Gly Gly Gly Thr
                405                 410                 415

Lys Leu Thr Val Leu Gly
            420

<210> SEQ ID NO 294
<211> LENGTH: 166
<212> TYPE: PRT
<213> ORGANISM: Artificial Sequence
<220> FEATURE:
<223> OTHER INFORMATION: Human IFN-?

<400> SEQUENCE: 294

Cys Asp Leu Pro Glu Thr His Ser Leu Asp Asn Arg Arg Thr Leu Met
1               5                   10                  15

Leu Leu Ala Gln Met Ser Arg Ile Ser Pro Ser Ser Cys Leu Met Asp
                20                  25                  30

Arg His Asp Phe Gly Phe Pro Gln Glu Glu Phe Asp Gly Asn Gln Phe
            35                  40                  45

Gln Lys Ala Pro Ala Ile Ser Val Leu His Glu Leu Ile Gln Gln Ile
        50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Arg Val Gly Glu Thr Pro Leu Met
                100                 105                 110

Asn Ala Asp Ser Ile Leu Ala Val Lys Lys Tyr Phe Arg Arg Ile Thr
                115                 120                 125

Leu Tyr Leu Thr Glu Lys Lys Tyr Ser Pro Cys Ala Trp Glu Val Val
                130                 135                 140

Arg Ala Glu Ile Met Arg Ser Leu Ser Leu Ser Thr Asn Leu Gln Glu
145                 150                 155                 160

Arg Leu Arg Arg Lys Glu
                165

<210> SEQ ID NO 295
<211> LENGTH: 444
<212> TYPE: PRT
<213> ORGANISM: Artificial Sequence
<220> FEATURE:
<223> OTHER INFORMATION: Human IFN-?-A10m3

<400> SEQUENCE: 295

Cys Asp Leu Pro Glu Thr His Ser Leu Asp Asn Arg Arg Thr Leu Met
1               5                   10                  15

Leu Leu Ala Gln Met Ser Arg Ile Ser Pro Ser Ser Cys Leu Met Asp
                20                  25                  30

Arg His Asp Phe Gly Phe Pro Gln Glu Glu Phe Asp Gly Asn Gln Phe
                35                  40                  45

Gln Lys Ala Pro Ala Ile Ser Val Leu His Glu Leu Ile Gln Gln Ile
            50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Arg Val Gly Glu Thr Pro Leu Met
                100                 105                 110

Asn Ala Asp Ser Ile Leu Ala Val Lys Lys Tyr Phe Arg Arg Ile Thr
                115                 120                 125

Leu Tyr Leu Thr Glu Lys Lys Tyr Ser Pro Cys Ala Trp Glu Val Val
                130                 135                 140

Arg Ala Glu Ile Met Arg Ser Leu Ser Leu Ser Thr Asn Leu Gln Glu
145                 150                 155                 160

Arg Leu Arg Arg Lys Glu Gly Gly Gly Ser Gly Gly Gly Ser
                165                 170                 175

Gly Gly Gly Gly Ser Gly Gly Gly Ser Gly Gly Gly Ser Glu
                180                 185                 190

Val Gln Leu Val Glu Ser Gly Gly Leu Ile Gln Pro Gly Arg Ser
                195                 200                 205

Leu Arg Leu Ser Cys Ala Ala Ser Gly Ile Thr Phe Asp Asp Ala Val
                210                 215                 220

Met His Trp Val Arg Gln Ala Pro Gly Lys Gly Leu Glu Trp Val Ala
225                 230                 235                 240

Gly Ile Ser Ser Asn Ser Gly Tyr Ile Gly Tyr Ala Asp Ser Val Lys
                245                 250                 255

Gly Arg Phe Thr Ile Ser Arg Asp Asn Ala Lys Asn Ser Leu Tyr Leu
                260                 265                 270

Gln Met Asn Arg Leu Arg Ala Glu Asp Thr Ala Val Tyr Tyr Cys Val
                275                 280                 285

```
Lys Gly Leu Tyr Ser Asn Pro Arg Gly Gly Ala Phe Asp Ile Trp Gly
            290                 295                 300

Gln Gly Thr Met Val Thr Val Ser Ser Ala Ser Thr Gly Gly Gly Gly
305                 310                 315                 320

Ser Gly Gly Gly Ser Gly Gly Gly Ser Val His Ser Ser Tyr
                325                 330                 335

Val Leu Thr Gln Pro Pro Ser Val Ser Val Ala Pro Gly Gln Thr Ala
                340                 345                 350

Thr Ile Thr Cys Gly Gly Asn Asn Ile Gly Thr Lys Ser Val His Trp
            355                 360                 365

Tyr Gln Gln Lys Pro Gly Gln Ala Pro Val Leu Val Val Tyr Ala Asp
        370                 375                 380

Ser Asp Arg Pro Ser Gly Ile Pro Glu Arg Val Ser Gly Ser Asn Ser
385                 390                 395                 400

Gly Asn Thr Ala Thr Leu Thr Ile Ser Arg Val Glu Ala Gly Asp Glu
                405                 410                 415

Ala Asp Tyr Tyr Cys Gln Val Trp Asp Ser Arg Ser Asp His Leu Trp
            420                 425                 430

Val Phe Gly Gly Gly Thr Lys Leu Thr Val Leu Gly
            435                 440

<210> SEQ ID NO 296
<211> LENGTH: 118
<212> TYPE: PRT
<213> ORGANISM: Artificial Sequence
<220> FEATURE:
<223> OTHER INFORMATION: Anti-PD-L1 10D12, Variable Heavy Domain

<400> SEQUENCE: 296

Val Gln Leu Val Glu Ser Gly Gly Gly Leu Val Lys Pro Gly Gly Ser
1               5                   10                  15

Leu Arg Leu Ser Cys Ala Ala Ser Gly Phe Thr Phe Ser Asp Tyr Tyr
            20                  25                  30

Met Ser Trp Ile Arg Gln Ala Pro Gly Lys Gly Leu Glu Trp Val Ser
        35                  40                  45

Tyr Ile Ser Ser Ser Gly Ser Thr Ile Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Ser Arg Ser Ser Met Ala Gln His Trp Gly Gln Gly Thr Leu Val Thr
            100                 105                 110

Val Ser Ser Ala Ser Thr
        115

<210> SEQ ID NO 297
<211> LENGTH: 8
<212> TYPE: PRT
<213> ORGANISM: Artificial Sequence
<220> FEATURE:
<223> OTHER INFORMATION: vhCDR1

<400> SEQUENCE: 297

Gly Phe Thr Phe Ser Asp Tyr Tyr
1               5
```

```
<210> SEQ ID NO 298
<211> LENGTH: 8
<212> TYPE: PRT
<213> ORGANISM: Artificial Sequence
<220> FEATURE:
<223> OTHER INFORMATION: vhCDR2

<400> SEQUENCE: 298

Ile Ser Ser Ser Gly Ser Thr Ile
1               5

<210> SEQ ID NO 299
<211> LENGTH: 9
<212> TYPE: PRT
<213> ORGANISM: Artificial Sequence
<220> FEATURE:
<223> OTHER INFORMATION: vhCDR3

<400> SEQUENCE: 299

Ala Ser Arg Ser Ser Met Ala Gln His
1               5

<210> SEQ ID NO 300
<211> LENGTH: 112
<212> TYPE: PRT
<213> ORGANISM: Artificial Sequence
<220> FEATURE:
<223> OTHER INFORMATION: Variable Light Domain

<400> SEQUENCE: 300

Ser Asn Phe Met Leu Thr Gln Pro His Ser Val Ser Glu Ser Pro Gly
1               5                   10                  15

Lys Thr Val Thr Ile Ser Cys Thr Arg Ser Ser Gly Ser Ile Ala Ser
            20                  25                  30

Tyr Tyr Val Gln Trp Tyr Gln Gln Arg Pro Gly Ser Ala Pro Thr Thr
        35                  40                  45

Val Ile Tyr Glu Asp Asn Gln Arg Pro Ser Gly Val Pro Asp Arg Phe
    50                  55                  60

Ser Gly Ser Ile Asp Ser Ser Ser Asn Ser Ala Ser Leu Thr Ile Ser
65                  70                  75                  80

Gly Leu Lys Thr Glu Asp Glu Ala Asp Tyr Tyr Cys Gln Ser Tyr Asp
                85                  90                  95

Ser Asn Asn Gln Val Phe Gly Gly Gly Thr Lys Val Thr Val Leu Gly
            100                 105                 110

<210> SEQ ID NO 301
<211> LENGTH: 8
<212> TYPE: PRT
<213> ORGANISM: Artificial Sequence
<220> FEATURE:
<223> OTHER INFORMATION: vlCDR1

<400> SEQUENCE: 301

Ser Gly Ser Ile Ala Ser Tyr Tyr
1               5

<210> SEQ ID NO 302
<211> LENGTH: 3
<212> TYPE: PRT
<213> ORGANISM: Artificial Sequence
<220> FEATURE:
<223> OTHER INFORMATION: vlCDR2

<400> SEQUENCE: 302
```

Glu Asp Asn
1

<210> SEQ ID NO 303
<211> LENGTH: 9
<212> TYPE: PRT
<213> ORGANISM: Artificial Sequence
<220> FEATURE:
<223> OTHER INFORMATION: vlCDR3

<400> SEQUENCE: 303

Gln Ser Tyr Asp Ser Asn Asn Gln Val
1               5

<210> SEQ ID NO 304
<211> LENGTH: 245
<212> TYPE: PRT
<213> ORGANISM: Artificial Sequence
<220> FEATURE:
<223> OTHER INFORMATION: scFv

<400> SEQUENCE: 304

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Arg Ser Ser Met Ala Gln His Trp Gly Gln Gly Thr Leu Val
            100                 105                 110

Thr Val Ser Ser Ala Ser Thr Gly Gly Gly Gly Ser Gly Gly Gly Gly
        115                 120                 125

Ser Gly Gly Gly Gly Ser Asn Phe Met Leu Thr Gln Pro His Ser Val
    130                 135                 140

Ser Glu Ser Pro Gly Lys Thr Val Thr Ile Ser Cys Thr Arg Ser Ser
145                 150                 155                 160

Gly Ser Ile Ala Ser Tyr Tyr Val Gln Trp Tyr Gln Gln Arg Pro Gly
                165                 170                 175

Ser Ala Pro Thr Thr Val Ile Tyr Glu Asp Asn Gln Arg Pro Ser Gly
            180                 185                 190

Val Pro Asp Arg Phe Ser Gly Ser Ile Asp Ser Ser Asn Ser Ala
        195                 200                 205

Ser Leu Thr Ile Ser Gly Leu Lys Thr Glu Asp Glu Ala Asp Tyr Tyr
    210                 215                 220

Cys Gln Ser Tyr Asp Ser Asn Asn Gln Val Phe Gly Gly Gly Thr Lys
225                 230                 235                 240

Val Thr Val Leu Gly
            245

<210> SEQ ID NO 305
<211> LENGTH: 303
<212> TYPE: PRT
<213> ORGANISM: Artificial Sequence
<220> FEATURE:
<223> OTHER INFORMATION: linker-ABD-linker

<400> SEQUENCE: 305

Gly Gly Gly Gly Ser Gly Gly Gly Ser Gly Gly Gly Ser Gly
1               5                   10                  15

Gly Gly Gly Ser Gly Gly Gly Ser Glu Val Gln Leu Val Glu Ser
                20                  25                  30

Gly Gly Gly Leu Ile Gln Pro Gly Arg Ser Leu Arg Leu Ser Cys Ala
            35                  40                  45

Ala Ser Gly Ile Thr Phe Asp Asp Ala Val Met His Trp Val Arg Gln
        50                  55                  60

Ala Pro Gly Lys Gly Leu Glu Trp Val Ala Gly Ile Ser Ser Asn Ser
65                  70                  75                  80

Gly Tyr Ile Gly Tyr Ala Asp Ser Val Lys Gly Arg Phe Thr Ile Ser
                85                  90                  95

Arg Asp Asn Ala Lys Asn Ser Leu Tyr Leu Gln Met Asn Arg Leu Arg
            100                 105                 110

Ala Glu Asp Thr Ala Val Tyr Tyr Cys Val Lys Gly Leu Tyr Ser Asn
        115                 120                 125

Pro Arg Gly Gly Ala Phe Asp Ile Trp Gly Gln Gly Thr Met Val Thr
130                 135                 140

Val Ser Ser Ala Ser Thr Gly Gly Gly Ser Gly Gly Gly Gly Ser
145                 150                 155                 160

Gly Gly Gly Gly Ser Val His Ser Ser Tyr Val Leu Thr Gln Pro Pro
                165                 170                 175

Ser Val Ser Val Ala Pro Gly Gln Thr Ala Thr Ile Thr Cys Gly Gly
            180                 185                 190

Asn Asn Ile Gly Thr Lys Ser Val His Trp Tyr Gln Gln Lys Pro Gly
        195                 200                 205

Gln Ala Pro Val Leu Val Val Tyr Ala Asp Ser Asp Arg Pro Ser Gly
210                 215                 220

Ile Pro Glu Arg Val Ser Gly Ser Asn Ser Gly Asn Thr Ala Thr Leu
225                 230                 235                 240

Thr Ile Ser Arg Val Glu Ala Gly Asp Glu Ala Asp Tyr Tyr Cys Gln
                245                 250                 255

Val Trp Asp Ser Arg Ser Asp His Leu Trp Val Phe Gly Gly Gly Thr
            260                 265                 270

Lys Leu Thr Val Leu Gly Gly Gly Gly Ser Gly Gly Gly Gly Ser
        275                 280                 285

Gly Gly Gly Gly Ser Gly Gly Gly Ser Gly Gly Gly Ser
    290                 295                 300

<210> SEQ ID NO 306
<211> LENGTH: 303
<212> TYPE: PRT
<213> ORGANISM: Artificial Sequence
<220> FEATURE:
<223> OTHER INFORMATION: linker-ABD-linker

<400> SEQUENCE: 306

Gly Gly Gly Gly Ser Gly Gly Gly Ser Gly Gly Gly Ser Gly
1               5                   10                  15

Gly Gly Gly Ser Gly Gly Gly Ser Glu Val Gln Leu Val Glu Ser
                20                  25                  30

Gly Gly Gly Leu Ile Gln Pro Gly Arg Ser Leu Arg Leu Ser Cys Ala

```
            35                  40                  45
Ala Ser Gly Ile Thr Phe Asp Asp Ala Val Met His Trp Val Arg Gln
 50                  55                  60
Ala Pro Gly Lys Gly Leu Glu Trp Val Ala Gly Ile Ser Ser Asn Ser
 65                  70                  75                  80
Gly Tyr Ile Gly Tyr Ala Asp Ser Val Lys Gly Arg Phe Thr Ile Ser
                     85                  90                  95
Arg Asp Asn Ala Lys Asn Ser Leu Tyr Leu Gln Met Asn Arg Leu Arg
                100                 105                 110
Ala Glu Asp Thr Ala Val Tyr Tyr Cys Val Lys Gly Leu Tyr Ser Asn
                115                 120                 125
Pro Arg Gly Gly Ala Phe Asp Ile Trp Gly Gln Gly Thr Met Val Thr
                130                 135                 140
Val Ser Ser Ala Ser Thr Gly Gly Gly Ser Gly Gly Gly Gly Gly Ser
145                 150                 155                 160
Gly Gly Gly Gly Ser Val His Ser Ser Tyr Val Leu Thr Gln Pro Pro
                    165                 170                 175
Ser Val Ser Val Ala Pro Gly Gln Thr Ala Thr Ile Thr Cys Gly Gly
                180                 185                 190
Asn Asn Ile Gly Thr Lys Ser Val His Trp Tyr Gln Gln Lys Pro Gly
                195                 200                 205
Gln Ala Pro Val Leu Val Val Tyr Ala Asp Ser Asp Arg Pro Ser Gly
210                 215                 220
Ile Pro Glu Arg Val Ser Gly Ser Asn Ser Gly Asn Thr Ala Thr Leu
225                 230                 235                 240
Thr Ile Ser Arg Val Glu Ala Gly Asp Glu Ala Asp Tyr Tyr Cys Gln
                    245                 250                 255
Val Trp Asp Ser Arg Ser Asp His Leu Trp Val Phe Gly Gly Gly Thr
                260                 265                 270
Lys Leu Thr Val Leu Gly Gly Gly Gly Ser Gly Gly Gly Gly Gly Ser
                275                 280                 285
Gly Gly Gly Gly Ser Gly Gly Gly Ser Gly Gly Gly Gly Ser
                290                 295                 300

<210> SEQ ID NO 307
<211> LENGTH: 5
<212> TYPE: PRT
<213> ORGANISM: Artificial Sequence
<220> FEATURE:
<223> OTHER INFORMATION: ABD linker

<400> SEQUENCE: 307

Gly Gly Gly Gly Ser
1               5

<210> SEQ ID NO 308
<211> LENGTH: 2
<212> TYPE: PRT
<213> ORGANISM: Artificial Sequence
<220> FEATURE:
<223> OTHER INFORMATION: Linker

<400> SEQUENCE: 308

Gly Ser
1

<210> SEQ ID NO 309
<211> LENGTH: 5
```

```
<212> TYPE: PRT
<213> ORGANISM: Artificial Sequence
<220> FEATURE:
<223> OTHER INFORMATION: Linker

<400> SEQUENCE: 309

Gly Ser Gly Gly Ser
1               5

<210> SEQ ID NO 310
<211> LENGTH: 4
<212> TYPE: PRT
<213> ORGANISM: Artificial Sequence
<220> FEATURE:
<223> OTHER INFORMATION: Linker

<400> SEQUENCE: 310

Gly Gly Gly Ser
1
```